United States Patent
Kawabata et al.

(10) Patent No.: US 10,234,759 B2
(45) Date of Patent: Mar. 19, 2019

(54) ACTINIC-RAY- OR RADIATION-SENSITIVE RESIN COMPOSITION, ACTINIC-RAY- OR RADIATION-SENSITIVE FILM AND METHOD OF FORMING PATTERN

(71) Applicant: FUJIFILM Corporation, Tokyo (JP)

(72) Inventors: Takeshi Kawabata, Shizuoka-ken (JP); Hiroo Takizawa, Shizuoka-ken (JP); Akinori Shibuya, Shizuoka-ken (JP); Akiyoshi Goto, Shizuoka-ken (JP); Masafumi Kojima, Shizuoka-ken (JP); Keita Kato, Shizuoka-ken (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 14/751,669

(22) Filed: Jun. 26, 2015

(65) Prior Publication Data
US 2015/0338736 A1    Nov. 26, 2015

Related U.S. Application Data

(63) Continuation of application No. PCT/JP2013/085328, filed on Dec. 25, 2013.

(60) Provisional application No. 61/746,442, filed on Dec. 27, 2012.

(30) Foreign Application Priority Data

Dec. 27, 2012 (JP) ................... 2012-284642

(51) Int. Cl.
| | |
|---|---|
| G03F 7/004 | (2006.01) |
| G03F 7/039 | (2006.01) |
| C07D 217/06 | (2006.01) |
| C07D 333/48 | (2006.01) |
| C07D 333/46 | (2006.01) |
| C07D 333/76 | (2006.01) |
| C07D 335/02 | (2006.01) |
| C07D 295/185 | (2006.01) |
| C07D 327/06 | (2006.01) |
| C07C 309/12 | (2006.01) |
| C07C 309/29 | (2006.01) |
| C07C 309/17 | (2006.01) |
| C07C 309/06 | (2006.01) |
| C07C 311/48 | (2006.01) |
| C07C 317/04 | (2006.01) |
| C07C 381/12 | (2006.01) |
| C07J 9/00 | (2006.01) |
| C07J 17/00 | (2006.01) |
| C07J 31/00 | (2006.01) |
| G03F 7/038 | (2006.01) |

(52) U.S. Cl.
CPC .......... *G03F 7/0045* (2013.01); *C07C 309/06* (2013.01); *C07C 309/12* (2013.01); *C07C 309/17* (2013.01); *C07C 309/29* (2013.01); *C07C 311/48* (2013.01); *C07C 317/04* (2013.01); *C07C 381/12* (2013.01); *C07D 217/06* (2013.01); *C07D 295/185* (2013.01); *C07D 327/06* (2013.01); *C07D 333/46* (2013.01); *C07D 333/48* (2013.01); *C07D 333/76* (2013.01); *C07D 335/02* (2013.01); *C07J 9/005* (2013.01); *C07J 17/00* (2013.01); *C07J 31/006* (2013.01); *G03F 7/0397* (2013.01); *C07C 2601/14* (2017.05); *C07C 2603/74* (2017.05); *G03F 7/038* (2013.01); *G03F 7/039* (2013.01)

(58) Field of Classification Search
None
See application file for complete search history.

(56) References Cited

U.S. PATENT DOCUMENTS

| | | | |
|---|---|---|---|
| 8,993,212 B2 | 3/2015 | Takihana et al. | |
| 2010/0136480 A1* | 6/2010 | Motoike | G03F 7/0048 430/270.1 |

(Continued)

FOREIGN PATENT DOCUMENTS

| | | |
|---|---|---|
| JP | 2003-327572 A | 11/2003 |
| JP | 2004-117959 A | 4/2004 |

(Continued)

OTHER PUBLICATIONS

DERWENT English abstract for JP2006-162735 (2006).*

(Continued)

*Primary Examiner* — Sin J Lee
(74) *Attorney, Agent, or Firm* — Sughrue Mion, PLLC

(57) ABSTRACT

Provided is an actinic-ray- or radiation-sensitive resin composition including a resin (A) and any of compounds (B) of general formula (I) below. (In general formula (I), Rf represents a fluorine atom or a monovalent organic group containing at least one fluorine atom; $R_1$ represents a hydrogen atom or a monovalent substituent containing no fluorine atom; $X_1$ represents a monovalent organic group having at least two carbon atoms, or a methyl group in which a substituent other than a fluorine atom is optionally introduced, provided that $X_1$ may be bonded to $R_1$ to thereby form a ring; and Z represents a moiety that when exposed to actinic rays or radiation, is converted to a sulfonic acid group, an imidic acid group or a methide acid group).

(I)

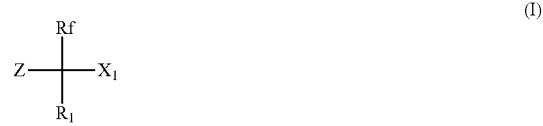

12 Claims, No Drawings

(56) References Cited

U.S. PATENT DOCUMENTS

| | | | |
|---|---|---|---|
| 2012/0107744 A1* | 5/2012 | Utsumi | C07D 307/00 430/283.1 |
| 2012/0289738 A1 | 11/2012 | Hosoi et al. | |
| 2012/0322006 A1* | 12/2012 | Kato | C08F 228/04 430/283.1 |
| 2013/0011619 A1 | 1/2013 | Fujii et al. | |
| 2013/0078579 A1 | 3/2013 | Asano | |
| 2013/0136900 A1 | 5/2013 | Shibuya et al. | |
| 2013/0149644 A1 | 6/2013 | Maruyama | |
| 2013/0209938 A1 | 8/2013 | Takihana et al. | |
| 2013/0295505 A1* | 11/2013 | Maruyama | C08K 5/42 430/270.1 |

FOREIGN PATENT DOCUMENTS

| | | |
|---|---|---|
| JP | 2006-162735 A | 6/2006 |
| JP | 2011-221501 A | 11/2011 |
| JP | 2012-108496 A | 6/2012 |
| JP | 2013-83944 A | 5/2013 |
| JP | 2013-114085 A | 6/2013 |
| KR | 10-2013-0033321 A | 4/2013 |
| WO | 2011/093139 A1 | 8/2011 |
| WO | 2012/023374 A1 | 2/2012 |
| WO | 2012/096264 A1 | 7/2012 |

OTHER PUBLICATIONS

International Preliminary Report on Patentability issued in application No. PCT/JP2013/085328 dated Jul. 9, 2015.
International Search Report for PCT/JP2013/085328 dated Feb. 4, 2014 [PCT/ISA/210].
Written Opinion for PCT/JP2013/085328 dated Feb. 4, 2014 [PCT/ISA/237].
Communication dated Mar. 22, 2016, from the Japanese Patent Office in counterpart application No. 2012-284642.
Communication dated Oct. 6, 2015, issued by the Japan Patent Office in corresponding Japanese Application No. 2012-284642.
Communication dated Jul. 20, 2016 from the Korean Intellectual Property Office in counterpart Application No. 10-2015-7013617.
Communication dated Feb. 17, 2017, from the Intellectual Property Office of Taiwan in counterpart application No. 102148494.

* cited by examiner

ACTINIC-RAY- OR RADIATION-SENSITIVE RESIN COMPOSITION, ACTINIC-RAY- OR RADIATION-SENSITIVE FILM AND METHOD OF FORMING PATTERN

CROSS-REFERENCE TO RELATED APPLICATIONS

This application is a Continuation application of PCT Application No. PCT/JP2013/085328, filed Dec. 25, 2013, and based upon and claiming the benefit of priority from Japanese Patent Application No. 2012-284642, filed Dec. 27, 2012, and claiming the benefit of U.S. Provisional Application No. 61/746,442, filed Dec. 27, 2012, the entire contents of all of which are incorporated herein by reference.

BACKGROUND OF THE INVENTION

1. Field of the Invention

The present invention relates to an actinic-ray- or radiation-sensitive resin composition that when exposed to actinic rays or radiation, reacts to thereby change its properties, and relates to an actinic-ray- or radiation-sensitive film formed from the composition and a method of forming a pattern with the use of the composition. More particularly, the present invention relates to an actinic-ray- or radiation-sensitive resin composition appropriately used in a semiconductor production process for an IC or the like, a circuit board production process for a liquid crystal, a thermal head or the like, other photofabrication processes, a lithographic printing plate and an acid-hardenable composition, and further relates to an actinic-ray- or radiation-sensitive film formed from the composition and a method of forming a pattern with the use of the composition.

2. Description of the Related Art

Heretofore, the microfabrication by lithography using a photoresist composition is performed in the process for manufacturing semiconductor devices, such as an IC and an LSI. In recent years, the formation of an ultrafine pattern in the submicron region or quarter-micron region is increasingly required in accordance with the realization of high integration for integrated circuits. Accordingly, the trend of exposure wavelength toward a short wavelength, for example, from g-rays to i-rays and further to a KrF excimer laser light is seen. To now, an exposure equipment using an ArF excimer laser of 193 nm wavelength as a light source has been developed. Further, the development of a method, known as a liquid-immersion method, in which the space between a projector lens and a sample is filled with a liquid of high refractive index (hereinafter also referred to as an "immersion liquid") has progressed as a technology for enhancing the resolving power. Still further, the development of lithography using electron beams, X-rays, EUV light or the like, aside from the excimer laser light, is now being promoted. Accordingly, chemically amplified resist compositions that effectively respond to various types of radiations and excel in sensitivity and resolution are now being developed, and various compounds are being developed as acid generators being a major constituent thereof.

For example, acid generators capable of generating a perfluorinated alkanesulfonic acid can exhibit a satisfactory acid strength in the reaction of deprotection of a protective group whose deprotection is difficult, so that many thereof are brought into practical use. Further, various compounds having a fluorine content reduced relative to those of such conventional acid generators are proposed.

For example, patent reference 1 points out the problem that acid generators having a high fluorine content, such as a perfluoroalkylsulfonic acid, exhibit an extremely high acid strength, so that, in the leaving reaction of protective group capable of changing a dissolution contrast of resin, unanticipated reactions may occur to result in the occurrence of foreign matter either after the alkali development or at the detachment of the resist. Then, the reference discloses specified fluorinated sulfonic acid salts having a fluorine content reduced for solving the problem.

Further, patent reference 2 discloses specified fluorinated sulfonic acid salts that while reducing the fluorine content thereof to decrease environmental burdens, can exhibit satisfactory acidities as acid generators.

Still further, patent reference 3 discloses specified fluorinated sulfonic acid salts intended to increase the solubility of an alkanesulfonic acid salt having a reduced fluorine content in resist solvents to thereby enhance the resist performance, such as resolution.

PRIOR ART REFERENCE

Patent Reference

Patent reference 1: International Publication No. 2011/093139,

Patent reference 2: Jpn. Pat. Appln. KOKAI Publication No. (hereinafter referred to as JP-A-) 2004-117959, and Patent reference 3: JP-A-2012-108496.

BRIEF SUMMARY OF THE INVENTION

Acid generators exercise greater influence over the resist performances, such as sensitivity, resolving power, roughness characteristic and pattern shape, of chemically amplified resist compositions. There is a demand for the development of an acid generator that while reducing the fluorine content thereof to decrease environmental burdens, can enhance the above performances required for chemically amplified resist compositions.

It is an object of the present invention to provide an actinic-ray- or radiation-sensitive resin composition excelling in the performances required for chemically amplified resist compositions, such as sensitivity, resolving power, roughness characteristic and pattern shape. It is other objects of the present invention to provide an actinic-ray- or radiation-sensitive film therefrom and a method of forming a pattern.

The inventors have conducted extensive and intensive studies with a view toward attaining the above objects. As a result, the present invention has been completed.

The present invention in an aspect thereof is as follows.

[1] An actinic-ray- or radiation-sensitive resin composition comprising a resin (A) and any of compounds (B) of general formula (I) below,

in which

Rf represents a fluorine atom or a monovalent organic group containing at least one fluorine atom;

$R_1$ represents a hydrogen atom or a monovalent substituent containing no fluorine atom;

$X_1$ represents a monovalent organic group having at least two carbon atoms, or a methyl group in which a substituent other than a fluorine atom is optionally introduced, provided that $X_1$ may be bonded to $R_1$ to thereby form a ring; and Z represents a moiety that when exposed to actinic rays or radiation, is converted to a sulfonic acid group, an imidic acid group or a methide acid group.

[2] The actinic-ray- or radiation-sensitive resin composition according to item [1], wherein $X_1$ in general formula (I) above is any of organic groups of general formula (Ia) below,

 (Ia)

in which $L_{11}$ represents a connecting group selected from among —COO—, —OCO—, —CO—, —O—, —S—, —SO—, —$SO_2$—, —NH—, —C(=S)—, —CONR— (R is a hydrogen atom, an alkyl group or a cycloalkyl group), an alkylene group, a cycloalkylene group, an alkenylene group, an alkynylene group, an arylene group and a group comprised of a combination of two or more of these, provided that the connecting group represented by $L_{11}$ contains no fluorine atom, and $X_{11}$ represents a substituent, provided that the any of organic groups of general formula (Ia) as a whole contains at least two carbon atoms.

[3] The actinic-ray- or radiation-sensitive resin composition according to item [1] or [2], wherein Rf in general formula (I) above is a fluorine atom or a perfluoroalkyl group having 1 to 4 carbon atoms.

[4] The actinic-ray- or radiation-sensitive resin composition according to item [1], wherein the compounds (B) of general formula (I) are compounds of general formula (II) below,

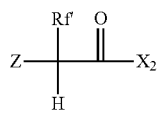 (II)

in which

Rf' represents a fluorine atom or a perfluoroalkyl group having 1 to 4 carbon atoms, $X_2$ represents a monovalent organic group having at least one carbon atom, and Z represents a moiety that when exposed to actinic rays or radiation, is converted to a sulfonic acid group, an imidic acid group or a methide acid group.

[5] The actinic-ray- or radiation-sensitive resin composition according to item [4], wherein $X_2$ in general formula (II) above is either *—$OR_3$ or *—$NR_4R_5$, in which * represents a position of bonding to the carbonyl group in general formula (II) above; $R_3$ represents an alkyl group, a mono- or polycycloalkyl group, an alkenyl group, an oxoalkyl group, an oxocycloalkyl group, an aryl group, an aralkyl group or a lactone group; and each of $R_4$ and $R_5$ independently represents a hydrogen atom, an alkyl group, a mono- or polycycloalkyl group, an alkenyl group, an oxoalkyl group, an oxocycloalkyl group, an aryl group, an aralkyl group or a lactone group, provided that $R_4$ and $R_5$ are not simultaneously hydrogen atoms, and provided that $R_4$ and $R_5$ may be bonded to each other to thereby form a ring structure in cooperation with the nitrogen atom to which $R_4$ and $R_5$ are bonded.

[6] An actinic-ray- or radiation-sensitive film formed from the actinic-ray- or radiation-sensitive resin composition according to any one of items [1] to [5].

[7] A method of forming a pattern, comprising forming an actinic-ray- or radiation-sensitive film from the actinic-ray- or radiation-sensitive resin composition according to any one of items [1] to [5], exposing the actinic-ray- or radiation-sensitive film to actinic rays or radiation, and developing the exposed actinic-ray- or radiation-sensitive film.

[8] Compounds of general formula (IIa) below,

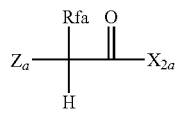 (IIa)

in which

Rfa represents a fluorine atom or $CF_3$;

$X_{2a}$ represents an alkyl group, a cycloalkyl group, an alkoxy group, a cycloalkyloxy group, an aryloxy group, an adamantylmethyloxy group, an adamantylcarbonyl group, an oxocycloalkyl group, an oxocycloalkyloxy group or *—$NR_{4a}R_{5a}$ in which * represents a position of bonding to the carbonyl group in general formula (IIa) above, and in which each of $R_{4a}$ and $R_{5a}$ independently represents an alkyl group or a cycloalkyl group, provided that $R_{4a}$ and $R_{5a}$ may be bonded to each other to thereby form a ring structure in cooperation with the nitrogen atom to which $R_{4a}$ and $R_{5a}$ are bonded; and $Z_a$ represents a moiety that when exposed to actinic rays or radiation, is converted to a sulfonic acid group, an imidic acid group or a methide acid group.

The present invention has made it feasible to provide an actinic-ray- or radiation-sensitive resin composition excelling in the performances required for chemically amplified resist compositions, such as sensitivity, resolving power, roughness characteristic and pattern shape. The present invention has also made it feasible to provide an actinic-ray- or radiation-sensitive film therefrom and a method of forming a pattern.

DETAILED DESCRIPTION OF THE INVENTION

Embodiments of the present invention will be described in detail below.

Herein, the groups and atomic groups for which no statement is made as to substitution or nonsubstitution are to be interpreted as including those containing no substituents and also those containing substituents. For example, the "alkyl groups" for which no statement is made as to substitution or nonsubstitution are to be interpreted as including not only the alkyl groups containing no substituents (unsubstituted alkyl groups) but also the alkyl groups containing substituents (substituted alkyl groups).

Further, herein, the term "actinic rays" or "radiation" means, for example, brightline spectra from a mercury lamp, far ultraviolet represented by an excimer laser, X-rays, soft X-rays such as extreme ultraviolet (EUV) light, or electron beams (EB). The term "light" means actinic rays or radiation. The term "exposure to light" unless otherwise specified means not only irradiation with light, such as light from a mercury lamp, far ultraviolet, X-rays or EUV light, but also lithography using particle beams, such as electron beams and ion beams.

The actinic-ray- or radiation-sensitive resin composition of the present invention (hereinafter also referred to as "the composition of the present invention" or the like) comprises a resin (A) and any of compounds (B) of general formula (I) below.

The resin (A) is a resin whose polarity is changed under the action of an acid. The resin (A) in its one form is a resin containing a group decomposable under the action of an acid, and in its another form is a resin containing a phenolic hydroxyl group.

The composition of the present invention in its one form is used in the formation of a negative pattern, and in its another form is used in the formation of a positive pattern, in accordance with, for example, the method to be described in the section regarding a pattern forming method hereinafter.

Essential components and optional components contained in the composition of the present invention will first be described below.

[1] Acid Generator

[Compounds of General Formula (I)]

The composition of the present invention comprises any of compounds of general formula (I) below (hereinafter also referred to "compounds (B)," "acid generators (B)" or the like).

It is presumed that the incorporation of compounds (B) in the composition of the present invention realizes the uniform distribution of generated acids in the resist film, thereby contributing toward the enhancement of resist performances, such as sensitivity, resolving power, roughness characteristic and pattern shape.

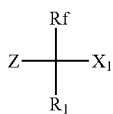

(I)

In general formula (I),

Rf represents a fluorine atom or a monovalent organic group containing at least one fluorine atom;

$R_1$ represents a hydrogen atom or a monovalent substituent containing no fluorine atom;

$X_1$ represents a monovalent organic group having at least two carbon atoms or a methyl group in which a substituent other than a fluorine atom is optionally introduced, provided that $X_1$ may be bonded to $R_1$ to thereby form a ring; and Z represents a moiety that when exposed to actinic rays or radiation, is converted to a sulfonic acid group, an imidic acid group or a methide acid group.

General formula (I) will be described in detail below.

Rf represents a fluorine atom or a monovalent organic group containing at least one fluorine atom.

As the monovalent organic group containing at least one fluorine atom, there can be mentioned, for example, a linear or branched alkyl group having 1 to 10 carbon atoms in which the hydrogen atoms are partially or entirely replaced with a fluorine atom or a fluoroalkyl group. In particular, there can be mentioned $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$, $CH_2CH_2C_4F_9$ or the like.

Rf is preferably a fluorine atom or a perfluoroalkyl group having 1 to 4 carbon atoms, more preferably a fluorine atom or $CF_3$. A fluorine atom is most preferred.

$R_1$ represents a hydrogen atom or a monovalent substituent containing no fluorine atom.

As the monovalent substituent containing no fluorine atom, there can be mentioned, for example, a halogen atom (excluding a fluorine atom), such as a chlorine atom, a bromine atom or an iodine atom; an alkoxy group, such as a methoxy group, an ethoxy group or a tert-butoxy group; an aryloxy group, such as a phenoxy group or a p-tolyloxy group; an alkylthioxy group, such as a methylthioxy group, an ethylthioxy group or a tert-butylthioxy group; an arylthioxy group, such as a phenylthioxy group or a p-tolylthioxy group; an alkoxycarbonyl group, such as a methoxycarbonyl group, a butoxycarbonyl group or an adamantylmethyloxycarbonyl group; an aryloxycarbonyl group, such as a phenoxycarbonyl group; an alkylcarbonyl group or cycloalkylcarbonyl group, such as an acetoxy group, a cyclohexylcarbonyl group or an adamantylcarbonyl group; a linear alkyl group or branched alkyl group, such as a methyl group, an ethyl group, a propyl group, a butyl group, a heptyl group, a hexyl group, a dodecyl group or a 2-ethylhexyl group; an alkenyl group, such as a vinyl group, a propenyl group or a hexenyl group; an acetylene group; an alkynyl group, such as a propynyl group or a hexynyl group; a cycloalkyl group, such as a cyclopentyl group or a cyclohexyl group; an aryl group, such as a phenyl group or a tolyl group; an aralkyl group, such as a benzyl group, a 1-phenylethyl group, a 2-phenylethyl group, a 1-phenylpropyl group, a 2-phenylpropyl group, a 3-phenylpropyl group, a 1-naphthylmethyl group or a 2-naphthylmethyl group; a mono- or polycyclolactone group having 3 to 30 carbon atoms; an oxoalkyl group having 2 to 20 carbon atoms; an oxocycloalkyl group having 6 to 10 carbon atoms; a carbamoyl group; a hydroxyl group; a carboxyl group; a cyano group; a nitro group; or a sulfonic acid group.

$R_1$ is preferably a hydrogen atom, an alkoxy group, an alkoxycarbonyl group, an alkylcarbonyl group, an alkyl group, a hydroxyl group, a carboxyl group, a cyano group or the like. $R_1$ is more preferably a hydrogen atom, an alkoxycarbonyl group, an alkylcarbonyl group or a cyano group, most preferably a hydrogen atom.

When $R_1$ and $X_1$ are bonded to each other to thereby form a ring, the formed ring structure contains no fluorine atom.

As mentioned above, $X_1$ represents a monovalent organic group having at least two carbon atoms or a methyl group in which a substituent other than a fluorine atom is optionally introduced. As the substituent optionally introduced in the methyl group represented by $X_1$, there can be mentioned any of groups set forth above by way of example as the monovalent substituent containing no fluorine atom represented by $R_1$.

In an aspect of the present invention, it is preferred for $X_1$ to be an organic group containing a cyclic structure. The cyclic structure contained in $X_1$ is not particularly limited, which can be an alicyclic group, an aryl group, a heterocyclic group (including not only one exhibiting aromaticity but also one exhibiting no aromaticity; including, for example, a tetrahydropyran ring structure, a lactone ring structure and a sultone ring structure), or the like. It is preferred for the cyclic structure contained in $X_1$ to be a bulky structure. The number of atoms constituting the skeleton of each ring is preferably 7 or greater, more preferably 8 or greater, and further more preferably 10 or greater. From the viewpoint of bulkiness, it is preferred for $X_1$ to contain a polycyclic structure.

The alicyclic group may be monocyclic or polycyclic. As preferred alicyclic groups, there can be mentioned a monocycloalkyl group, such as a cyclopentyl group, a cyclohexyl group or a cyclooctyl group, and a polycycloalkyl group, such as a norbornyl group, a norbornen-1-yl group, a tricyclodecanyl group (for example, a tricyclo[5.2.1.0(2,6)]decanyl group), a tetracyclodecanyl group, a tetracyclododecanyl group or an adamantyl group. An adamantyl group is most preferred. Also, preferred use is made of a nitrogen-atom-containing alicyclic group, such as a piperidine group, a decahydroquinoline group or a decahydroisoquinoline group. Of these, alicyclic groups with a bulky structure having at least 7 carbon atoms, selected from among a norbornyl group, a tricyclodecanyl group, a tetracyclodecanyl group, a tetracyclododecanyl group, an adamantyl group, a decahydroquinoline group and a decahydroisoquinoline group, are preferred from the viewpoint of inhibiting any in-film diffusion in the PEB (post-exposure bake) operation, thereby attaining an enhancement of exposure latitude. Of these, an adamantyl group and a decahydroisoquinoline group are most preferred.

As the aryl groups, there can be mentioned a benzene ring, a naphthalene ring, a phenanthrene ring and an anthracene ring. Of these, naphthalene ensuring a low absorbance is preferred from the viewpoint of the light absorbance at 193 nm.

As the heterocyclic groups, there can be mentioned those derived from a furan ring, a thiophene ring, a benzofuran ring, a benzothiophene ring, a dibenzofuran ring, a dibenzothiophene ring, a pyridine ring and a piperidine ring. Of these, the heterocyclic groups derived from a furan ring, a thiophene ring, a pyridine ring and a piperidine ring are preferred. As other preferred heterocyclic groups, there can be mentioned the following structures (in the formulae, X represents a methylene group or an oxygen atom, and R represents a monovalent organic group).

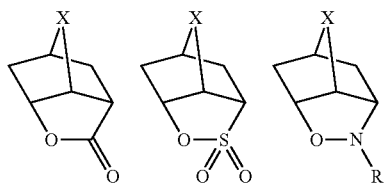

Substituents may be introduced in the above cyclic organic groups. As the substituents, there can be mentioned an alkyl group (any of linear, branched and cyclic forms, preferably having 1 to 12 carbon atoms), an aryl group (preferably having 6 to 14 carbon atoms), a hydroxyl group, an alkoxy group, an ester group, an amido group, a urethane group, a ureido group, a thioether group, a sulfonamido group, a sulfonic ester group and the like.

The carbon as a constituent of the organic group containing a cyclic structure (carbon contributing to ring formation) may be a carbonyl carbon.

When $X_1$ is an organic group containing a cyclic structure, $X_1$ in its one form is preferably a group with the following steroid skeleton.

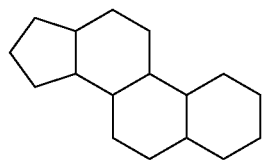 [SMILES: C1CCC2C(C1)CCC1C3CCCC3CCC21]

Further, $X_1$ in its one form is expressed by general formula (Ia) below.

$$-L_{11}-X_{11} \quad \text{(Ia)}$$

In general formula (Ia), $L_{11}$ represents a connecting group, and $X_{11}$ represents a substituent. Any of organic groups of general formula (Ia) as a whole contains at least two carbon atoms.

As the connecting group represented by $L_{11}$, there can be mentioned, for example, —COO—, —OCO—, —CO—, —O—, —S—, —SO—, —SO$_2$—, —NH—, —C(=S)—, —CONR— (R represents a hydrogen atom, an alkyl group (preferably having 1 to 10 carbon atoms) or a cycloalkyl group (preferably having 3 to 20 carbon atoms)), an alkylene group (preferably 1 to 5 carbon atoms), a cycloalkylene group (preferably 3 to 10 carbon atoms), an alkenylene group, an alkynylene group or an arylene group (preferably 6 to 10 carbon atoms). $L_{11}$ may be a combination of two or more of these. The connecting group represented by $L_{11}$ preferably contains no fluorine atom.

In an aspect of the present invention, $L_{11}$ is preferably —COO—, —CO— or —CONH—, more preferably —COO— or —CO—.

In an aspect of the present invention, it is preferred for the substituent represented by $X_{11}$ to be an organic group containing a cyclic structure. The cyclic structure contained in $X_{11}$ is not particularly limited, which can be an alicyclic group, an aryl group, a heterocyclic group (including not only one exhibiting aromaticity but also one exhibiting no aromaticity; including, for example, a tetrahydropyran ring, a lactone ring structure and a sultone ring structure), or the like. It is preferred for the cyclic structure contained in $X_{11}$ to be a bulky structure. The number of atoms constituting the skeleton of each ring is preferably 7 or greater, more preferably 8 or greater, and further more preferably 10 or greater. From the viewpoint of bulkiness, it is preferred for $X_{11}$ to contain a polycyclic structure.

In an aspect of the present invention, as the substituent represented by $X_{11}$, there can be mentioned, for example, $R_3$ or *—$NR_4R_5$, in which * represents a position of bonding to $L_{11}$ in general formula (Ia) above. $R_3$ represents an alkyl group, a mono- or polycycloalkyl group, an alkenyl group, an oxoalkyl group, an oxocycloalkyl group, an aryl group, an aralkyl group, a lactone group or a sultone group. Each of $R_4$ and $R_5$ independently represents a hydrogen atom, an alkyl group, a mono- or polycycloalkyl group, an alkenyl group, an oxoalkyl group, an oxocycloalkyl group, an aryl group, an aralkyl group, a lactone group or a sultone group. $R_4$ and $R_5$ may be bonded to each other to thereby form a ring structure in cooperation with the nitrogen atom to which $R_4$ and $R_5$ are bonded.

Each of the alkyl groups represented by $R_3$, $R_4$ and $R_5$ preferably has 1 to 20 carbon atoms. Each of the mono- or polycycloalkyl groups represented by $R_3$, $R_4$ and $R_5$ preferably has 3 to 20 carbon atoms. Each of the alkenyl groups and oxoalkyl groups represented by $R_3$, $R_4$ and $R_5$ preferably has 2 to 20 carbon atoms. Each of the oxocycloalkyl groups represented by $R_3$, $R_4$ and $R_5$ preferably has 6 to 10 carbon atoms. Each of the aryl groups and aralkyl groups represented by $R_3$, $R_4$ and $R_5$ preferably has 6 to 18 carbon atoms. Each of the lactone groups represented by $R_3$, $R_4$ and $R_5$ preferably has 3 to 30 carbon atoms, which may be monocyclic or polycyclic. Each of the sultone groups represented by $R_3$, $R_4$ and $R_5$ preferably has 3 to 30 carbon atoms, which may be monocyclic or polycyclic. The hydrogen atoms on carbon contained in $R_3$, $R_4$ and $R_5$ may be replaced with substituents.

As a linear alkyl group having 1 to 20 carbon atoms, there can be mentioned, for example, a methyl group, an ethyl group, an n-propyl group, an n-butyl group, an n-pentyl group, an n-hexyl group, an n-heptyl group, an n-octyl group, an n-nonyl group, an n-decyl group or the like. As a substituted alkyl group, there can be mentioned, for example, a linear alkyl group containing a cycloalkyl group, such as a cyclopentylmethyl group, a cyclopentylethyl group, a cyclohexylmethyl group, a cyclohexylethyl group, an adamantylmethyl group, an adamantylethyl group, a norbornylmethyl group, a norbornylethyl group, a camphoroylmethyl group, a camphoroylethyl group or the like.

As a branched alkyl group having 3 to 20 carbon atoms, there can be mentioned, for example, an i-propyl group, a sec-butyl group, an i-butyl group, a t-butyl group or the like.

As a mono- or polycycloalkyl group having 3 to 20 carbon atoms, there can be mentioned, for example, a cyclopentyl group, a cyclohexyl group, an adamantyl group, a norbornyl group, a camphoroyl group or the like. As a substituted mono- or polycycloalkyl group, there can be mentioned, for example, a methylcyclopentyl group, a methylcyclohexyl group, a methyladamantyl group, an ethylcyclopentyl group, an ethylcyclohexyl group, an ethyladamantyl group or the like. Each of the cycloalkyl groups represented by $R_3$, $R_4$ and $R_5$ may contain an ether oxygen atom in its ring structure.

As an alkenyl group having 2 to 20 carbon atoms, there can be mentioned, for example, a vinyl group, a 1-methylethenyl group, an allyl group, a 3-butenyl group, a 1-methylallyl group, a 2-methylallyl group, a 4-pentenyl group, a 5-hexenyl group or the like.

As an oxoalkyl group having 2 to 20 carbon atoms and an oxocycloalkyl group having 2 to 20 carbon atoms, there can be mentioned, for example, a 2-oxo-propyl group, a 2-oxo-butyl group, a 2-oxo-3-methyl-butyl group, a 2-oxo-pentyl group, a 2-oxo-3-methyl-pentyl group, a 2-oxo-4-methyl-pentyl group, a 2-oxo-3-ethyl-pentyl group, a 2-oxo-hexyl group, a 2-oxo-3-methyl-hexyl group, a 2-oxo-4-methyl-hexyl group, a 2-oxo-5-methyl-hexyl group, a 2-oxo-3-ethyl-hexyl group, a 2-oxo-4-ethyl-hexyl group, a 2-oxo-heptyl group, a 2-oxo-3-methyl-heptyl group, a 2-oxo-4-methyl-heptyl group, a 2-oxo-5-methyl-heptyl group, a 2-oxo-6-methyl-heptyl group, a 2-oxo-3-ethyl-heptyl group, a 2-oxo-4-ethyl-heptyl group, a 2-oxo-5-ethyl-heptyl group, a 2-oxo-3-propyl-heptyl group, a 2-oxo-4-propyl-heptyl group, a 2-oxo-octyl group, a 2-oxo-3-methyl-octyl group, a 2-oxo-4-methyl-octyl group, a 2-oxo-5-methyl-octyl group, a 2-oxo-6-methyl-octyl group, a 2-oxo-7-methyl-octyl group, a 2-oxo-3-ethyl-octyl group, a 2-oxo-4-ethyl-octyl group, a 2-oxo-5-ethyl-octyl group, a 2-oxo-cyclopentyl group, a 2-oxo-cyclohexyl group, a 2-oxo-cycloheptyl group, a 2-oxo-cyclopropylmethyl group, a 2-oxo-methylcyclohexyl group, a 2-oxo-cyclohexylmethyl group, a 2-oxo-norbornyl group, a 2-oxo-tricyclo[5.2.1.0$^{2,6}$]decyl group, a 2-cyclo-oxotetracyclo[4.4.0.1$^{2,5}$1$^{7,10}$]dodecyl group, a 2-oxo-bornyl group or the like.

As an aryl group having 6 to 18 carbon atoms, there can be mentioned, for example, a phenyl group, an o-tolyl group, am-tolyl group, a p-tolyl group, a p-hydroxyphenyl group, a p-trifluoromethylphenyl group, a 1-naphthyl group, a 1-anthracenyl group or the like.

As an aralkyl group having 6 to 18 carbon atoms, there can be mentioned, for example, a benzyl group, a 1-phenylethyl group, a 2-phenylethyl group, a 1-phenylpropyl group, a 2-phenylpropyl group, a 3-phenylpropyl group, a 1-naphthylmethyl group, a 2-naphthylmethyl group or the like.

The lactone group having 3 to 30 carbon atoms is a monovalent group resulting from the removal of one hydrogen atom from the corresponding lactone. This lactone may be monocyclic or polycyclic. As such, there can be mentioned, for example, γ-butyrolactone, γ-valerolactone, angelica-lactone, γ-hexalactone, γ-heptalactone, γ-octalactone, γ-nonalactone, 3-methyl-4-octanolide (whisky lactone), γ-decalactone, γ-undecalactone, γ-dodecalactone, γ-jasmolactone (7-decenolactone), δ-hexalactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasmine lactone, cis-jasmone lactone or methyl-γ-decalactone. Further, as the lactone group, there can be mentioned the following. The dotted line shows a position of bonding.

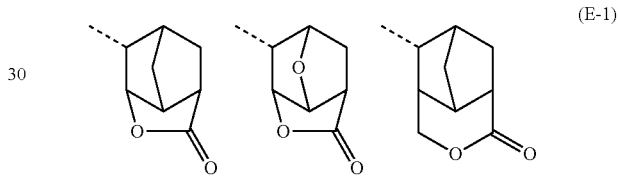

(E-1)

In an aspect of the present invention, it is preferred for $R_3$ to be a bulky functional group. For example, $R_3$ is preferably a group comprising a mono- or polycycloalkyl group having 5 to 10 carbon atoms. As such a group, there can be mentioned, for example, a cyclopentyl group, a cyclohexyl group, an adamantyl group, a methylcyclopentyl group, a methylcyclohexyl group, a methyladamantyl group, an ethylcyclopentyl group, an ethylcyclohexyl group, an ethyladamantyl group, a norbornyl group, a camphoroyl group, a cyclopentylmethyl group, a cyclopentylethyl group, a cyclohexylmethyl group, a cyclohexylethyl group, an adamantylmethyl group, an adamantylethyl group, a norbornylmethyl group, a norbornylethyl group, a camphoroylmethyl group, a camphoroylethyl group or the like. A cyclohexyl group and an adamantyl group are more preferred.

As mentioned above, $R_4$ and $R_5$ may be bonded to each other to thereby form a ring structure in cooperation with the nitrogen atom to which $R_4$ and $R_5$ are bonded. The ring structure preferably has 3 to 18 ring members, and may be monocyclic or polycyclic. The ring structure may further contain a heteroatom, such as a nitrogen atom, an oxygen atom or a sulfur atom, other than the nitrogen atom to which $R_4$ and $R_5$ are bonded.

The ring structure formed by $R_4$ and $R_5$ may be, for example, the following, in which * represents a position of bonding to $L_{11}$ in general formula (Ia).

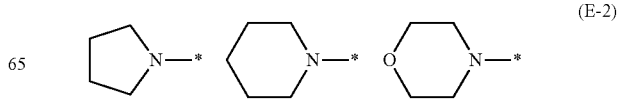

(E-2)

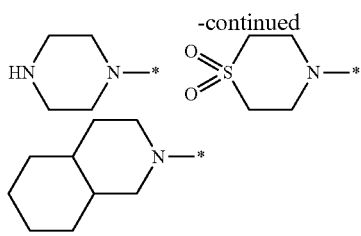

As mentioned above, the hydrogen atoms on carbon contained in $R_3$, $R_4$ and $R_5$ may be replaced with substituents. As the substituents, there can be mentioned, for example, a halogen atom, such as a fluorine atom, a chlorine atom, a bromine atom or an iodine atom, a hydroxyl group, a thiol group, an alkyl group, an aryl group and the like. Further, there can be mentioned organic groups each containing a heteroatom, such as a halogen atom, an oxygen atom, a nitrogen atom, a sulfur atom, a phosphorus atom or a silicon atom. As a still further example, there can be mentioned a ketone group resulting from the replacement of two hydrogen atoms on any identical carbon atom in $R_3$, $R_4$ and $R_5$ mentioned above with an oxygen atom. The number of substituents introduced is not limited within a structurally permitted range.

In an aspect of the present invention, $X_{11}$ has the same meaning as $X_2$ in general formula (II) to be described hereinafter.

In an aspect of the present invention, as preferred monovalent organic groups represented by $X_1$, there can be mentioned an alkoxy group, an alkoxycarbonyl group, an alkylcarbonyl group, an alkylamido group, an alkyl group and the like. Of these, an alkoxycarbonyl group, an alkylcarbonyl group and an alkylamido group are more preferred. An alkoxycarbonyl group is most preferred.

The monovalent organic group represented by $X_1$ may contain a fluorine atom. From the viewpoint of uniform distribution in the resist film, the number of fluorine atoms in the organic group represented by $X_1$ is preferably in the range of 0 to 6, more preferably 0 to 3 and further more preferably 0 to 2. Containing no fluorine atom is most preferred.

Z represents a moiety that when exposed to actinic rays or radiation, is converted to a sulfonic acid group, an imidic acid group or a methide acid group. The moiety represented by Z is preferably an onium salt. The onium salt is preferably a sulfonium salt or an iodonium salt. It is especially preferred for the moiety to have any of the structures of general formulae (ZI) to (ZIII) below.

$$*-\mathrm{SO}_3^{\ominus} \ \mathrm{A}^{\oplus} \quad \text{(ZI)}$$

$$*-Z_1-\overset{\ominus}{\mathrm{N}}-Z_2-Rz_1 \ \mathrm{A}^{\oplus} \quad \text{(ZII)}$$

$$*-Z_3-\overset{\ominus}{\underset{|}{\mathrm{C}}}-Z_4-Rz_2 \ \mathrm{A}^{\oplus} \quad \text{(ZIII)}$$
$$Z_5-Rz_3$$

In general formulae (ZII) and (ZIII), each of $Z_1$, $Z_2$, $Z_3$, $Z_4$ and $Z_5$ independently represents —CO— or —SO$_2$—. From the viewpoint of lowering the pKa value of generated acid, —SO$_2$— is preferred.

Each of $Rz_1$, $Rz_2$ and $Rz_3$ independently represents an alkyl group, a cycloalkyl group, an aryl group or an aralkyl group.

The above alkyl group may be linear or branched. For example, an alkyl group having 1 to 4 carbon atoms, such as a methyl group, an ethyl group, a propyl group or a butyl group, is most preferred.

It is preferred for the cycloalkyl group to be, for example, one having 3 to 10 carbon atoms, such as a cyclobutyl group, a cyclopentyl group or a cyclohexyl group. A cycloalkyl group having 3 to 6 carbon atoms is more preferred.

The aryl group is preferably one having 6 to 18 carbon atoms. An aryl group having 6 to 10 carbon atoms is more preferred. A phenyl group is most preferred.

As a preferred form of the aralkyl group, there can be mentioned one resulting from the bonding of the above aryl group to an alkylene group having 1 to 8 carbon atoms. An aralkyl group resulting from the bonding of the above aryl group to an alkylene group having 1 to 4 carbon atoms is most preferred.

Preferably, each of $Rz_1$, $Rz_2$ and $Rz_3$ in general formulae (ZII) and (ZIII) independently is an alkyl group.

In general formulae (ZI) to (ZIII) above, $A^+$ represents a sulfonium cation or an iodonium cation. It is preferred for $A^+$ to be any of sulfonium cations of general formula (ZX) below or any of iodonium cations of general formula (ZXI) below.

In general formula (ZX) above, each of $R_{201}$, $R_{202}$ and $R_{203}$ independently represents an organic group. Each of the organic groups represented by $R_{201}$, $R_{202}$ and $R_{203}$ has, for example, 1 to 30 carbon atoms, preferably 1 to 20 carbon atoms.

Any two of $R_{201}$ to $R_{203}$ may be bonded to each other to thereby form a ring structure (including a condensed ring), and the ring within the same may contain an oxygen atom, a sulfur atom, an ester bond, an amide bond or a carbonyl group in addition to the sulfur atom in the formula. As a group formed by the mutual bonding of two of $R_{201}$ to $R_{203}$, there can be mentioned an alkylene group (for example, a butylene group or a pentylene group) or the like.

As the organic groups represented by $R_{201}$, $R_{202}$ and $R_{203}$, there can be mentioned, for example, corresponding groups in the groups (ZA-1-1), (ZA-1-2) and (ZA-1-3) to be described below. Corresponding groups in the groups (ZA-1-1) and (ZA-1-3) are most preferred.

First, the groups (ZA-1-1) will be described.

The groups (ZA-1-1) are groups of general formula (ZX) above in which at least one of $R_{201}$ to $R_{203}$ is an aryl group, namely, groups comprising an arylsulfonium as a cation.

All of $R_{201}$ to $R_{203}$ may be aryl groups. Alternatively, $R_{201}$ to $R_{203}$ may be an aryl group in part and an alkyl group or a cycloalkyl group in the remainder.

For example, there can be mentioned groups corresponding to a triarylsulfonium, a diarylalkylsulfonium, an aryldialkylsulfonium, a diarylcycloalkylsulfonium and an aryldicycloalkylsulfonium.

The aryl group in the arylsulfonium is preferably a phenyl group or a naphthyl group. The aryl group may be one with a heterocyclic structure containing an oxygen atom, a nitrogen atom, a sulfur atom or the like. As the heterocyclic structure, there can be mentioned the structure of pyrrole, furan, thiophene, indole, benzofuran, benzothiophene or the like.

When the arylsulfonium contains two or more aryl groups, the two or more aryl groups may be identical to or different from each other.

The alkyl group or cycloalkyl group contained in the arylsulfonium according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

Each of the aryl groups, alkyl groups and cycloalkyl groups represented by $R_{201}$ to $R_{203}$ may contain as a substituent thereof an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are an alkyl group having 1 to 4 carbon atoms and an alkoxy group having 1 to 4 carbon atoms. Each of the substituents may be introduced in any one of the three $R_{201}$ to $R_{203}$, or alternatively may be introduced in all of the three $R_{201}$ to $R_{203}$. When $R_{201}$ to $R_{203}$ represent aryl groups, each of the substituents is preferably introduced in the p-position of the aryl group.

As preferred groups (ZA-1-1), there can be mentioned a triarylsulfonium and any of structures of general formulae (ZA-1-1A) and (ZA-1-1B) below (hereinafter also referred to as "specified cation structures"). When the repeating unit (A) contains any of such specified cation structures, any decomposition product occurring upon exposure to X-rays, electron beams or EUV exhibits a high boiling point, preferably tending to lessen the problem of outgassing.

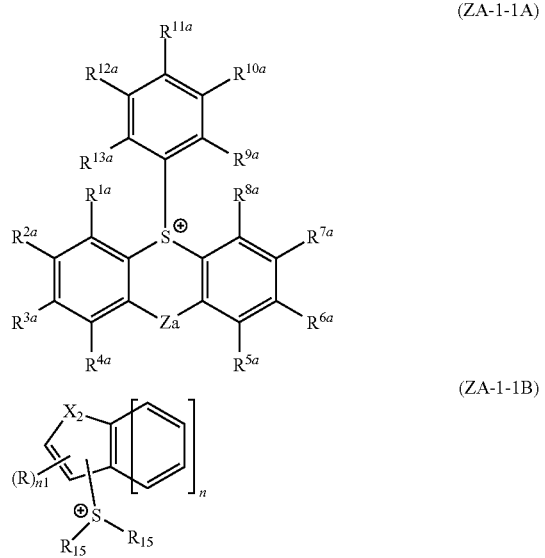

(ZA-1-1A)

(ZA-1-1B)

In general formula (ZA-1-1A), each of $R^{1a}$ to $R^{13a}$ independently represents a hydrogen atom or a substituent.

Preferably, at least one of $R^{1a}$ to $R^{13a}$ is a substituent containing an alcoholic hydroxyl group.

Za represents a single bond or a bivalent connecting group.

The term "alcoholic hydroxyl group" used in the present invention refers to a hydroxyl group bonded to a carbon atom of a chain or cyclic alkyl group.

When $R^{1a}$ to $R^{13a}$ are substituents each containing an alcoholic hydroxyl group, $R^{1a}$ to $R^{13a}$ are expressed by the formula —W—Y. In the formula, Y represents a chain or cyclic alkyl group substituted with a hydroxyl group, and W represents a single bond or a bivalent connecting group.

In general formula (ZA-1-1A), at least one of $R^{1a}$ to $R^{13a}$ contains an alcoholic hydroxyl group. Preferably, at least one of $R^{9a}$ to $R^{13a}$ contains an alcoholic hydroxyl group.

Za represents a single bond or a bivalent connecting group. A substituent may be introduced therein. The substituent is the same as set forth above in connection with $R^{1a}$ to $R^{13a}$. Za is preferably a single bond, an ether group or a thioether group, most preferably a single bond.

Now, general formula (ZA-1-1B) will be described.

In general formula (ZA-1-1B), each of $R_{15}$s independently represents an alkyl group, a cycloalkyl group or a naphthyl group, provided that two $R_{15}$s may be bonded to each other to thereby form a ring.

$X_2$ represents any of —$CR_{21}$=$CR_{22}$—, —$NR_{23}$—, —S— and —O—. Each of $R_{21}$ and $R_{22}$ independently represents a hydrogen atom, an alkyl group, a cycloalkyl group or an aryl group. $R_{23}$ represents a hydrogen atom, an alkyl group, a cycloalkyl group, an aryl group or an acyl group.

R, or each of R's independently, represents a substituent. As the substituent represented by R, there can be mentioned, for example, corresponding groups in general formulae (ZI-1) to (ZI-3) to be described below as preferred forms of general formula (ZA-1-1B).

In the formula, n is an integer of 0 to 3, and n1 is an integer of 0 to 11.

The ring that may be formed by the mutual bonding of two $R_{15}$s is a ring structure formed in cooperation with —S$^+$— shown in formula (ZA-1-1B), preferably a 5-membered ring containing one sulfur atom or a condensed ring containing the same. The condensed ring is preferably one containing one sulfur atom and up to 18 carbon atoms, more preferably any of the ring structures of general formulae (IV-1) to (IV-3) below.

In the formulae, * represents a bonding hand. R represents an arbitrary substituent. As such, there can be mentioned, for example, any of the same substituents that may be introduced in the groups represented by $R_{15}$ and $R_{21}$ to $R_{23}$. In the formulae, n is an integer of 0 to 4, and n2 is an integer of 0 to 3.

(IV-1)

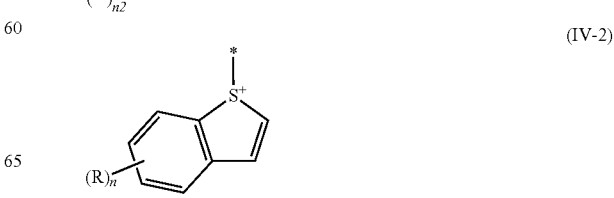

(IV-2)

-continued

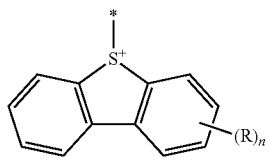
(IV-3)

Among the compounds of general formula (ZA-1-1B), as preferred cation structures, there can be mentioned the following cation structures (ZI-1) to (ZI-3).

The cation structure (ZI-1) refers to the structure of general formula (ZI-1) below.

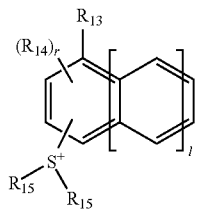
(ZI-1)

In general formula (ZI-1), $R_{13}$ represents a hydrogen atom, a fluorine atom, a hydroxyl group, an alkyl group, a cycloalkyl group, an alkoxy group, an alkoxycarbonyl group or a group with a mono- or polycycloalkyl skeleton.

$R_{14}$, or each of $R_{14}$s independently, represents an alkyl group, a cycloalkyl group, an alkoxy group, an alkylsulfonyl group, a cycloalkylsulfonyl group, a hydroxyl group or a group with a mono- or polycycloalkyl skeleton.

Each of $R_{15}$s independently represents an alkyl group, a cycloalkyl group or a naphthyl group, provided that two $R_{15}$s may be bonded to each other to thereby form a ring. A heteroatom may be introduced in the ring skeleton formed by the mutual bonding of two $R_{15}$s. The heteroatom introduced in the ring skeleton is preferably nitrogen, oxygen or sulfur, more preferably oxygen or sulfur, and most preferably oxygen.

In the formula, l is an integer of 0 to 2, and
r is an integer of 0 to 8.

Preferred particular examples of the cation structures of general formula (ZI-1) are shown below.

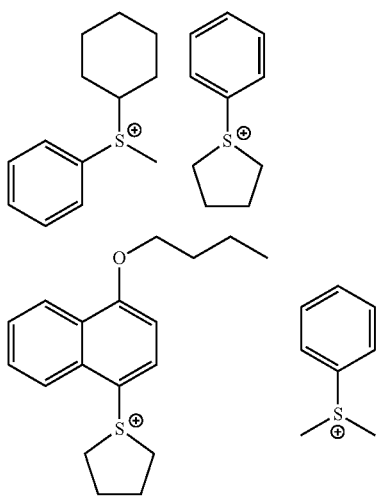

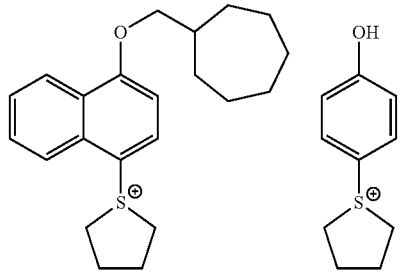

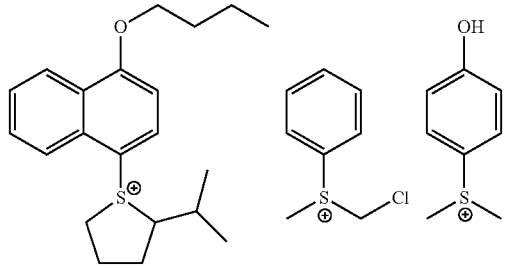

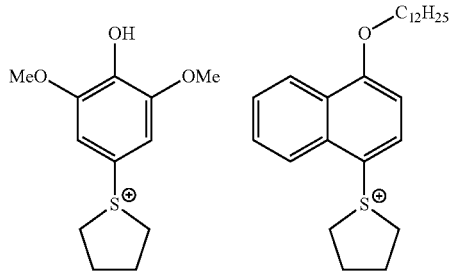

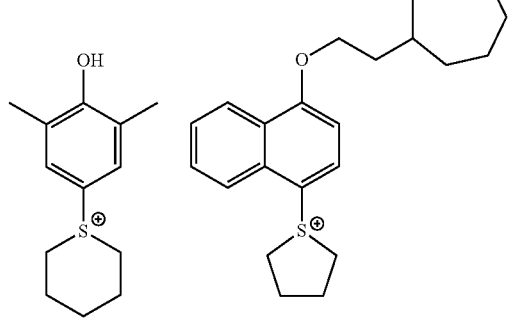

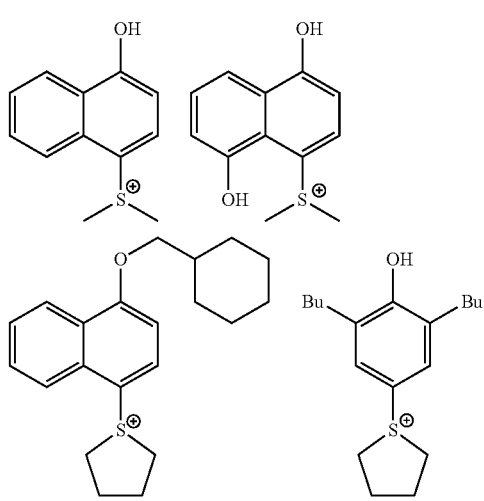

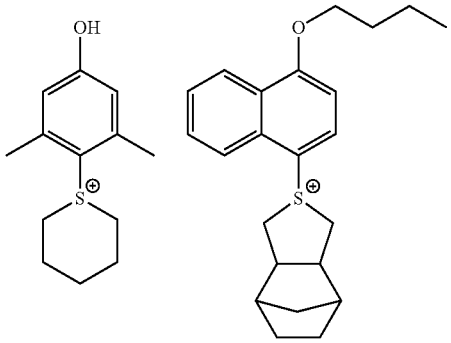
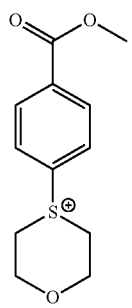
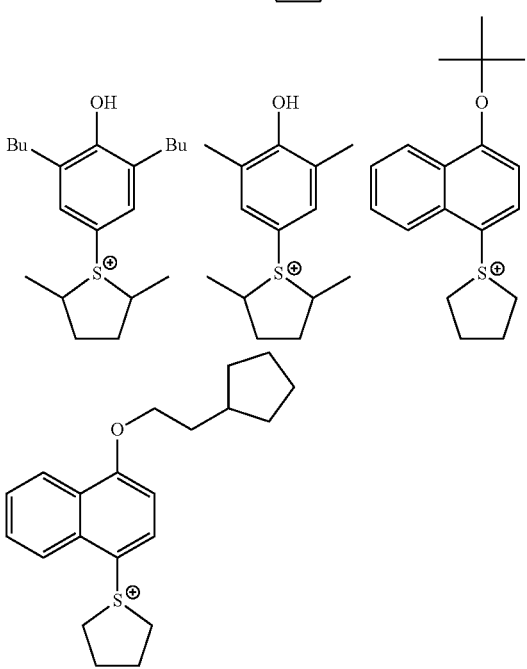
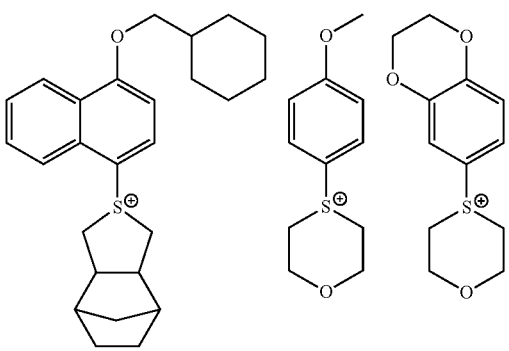
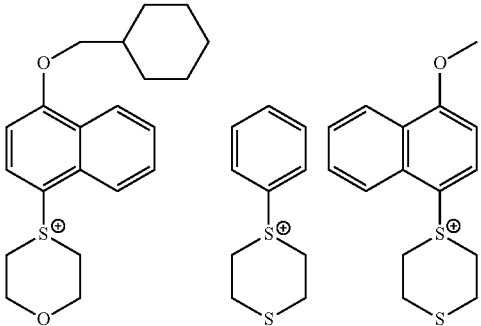

The cation structure (ZI-2) refers to the structure of general formula (ZI-2) below.

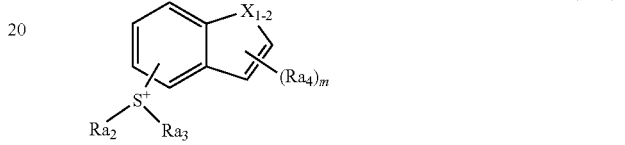

(ZI-2)

In general formula (ZI-2), $X_{I-2}$ represents an oxygen atom, a sulfur atom or any of the groups of the formula —$NRa_1$—, in which $Ra_1$ represents a hydrogen atom, an alkyl group, a cycloalkyl group, an aryl group or an acyl group.

Each of $Ra_2$ and $Ra_3$ independently represents an alkyl group, a cycloalkyl group, an alkenyl group or a naphthyl group, provided that $Ra_2$ and $Ra_3$ may be bonded to each other to thereby form a ring.

$Ra_4$, or each of $Ra_4$s independently, represents a monovalent group.

In the formula, m is an integer of 0 to 3.

Substitution with any of —$S^+(Ra_2)(Ra_3)$ groups and m $Ra_4$ groups may occur at any arbitrary one of the carbon atoms constructing the 6-membered ring and 5-membered ring containing $X_{I-2}$ in general formula (ZI-2).

Preferred particular examples of the cations in the compounds of general formula (ZI-2) are shown below.

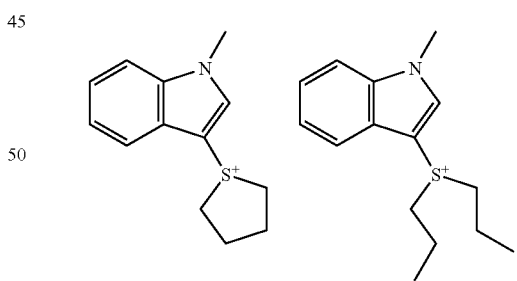
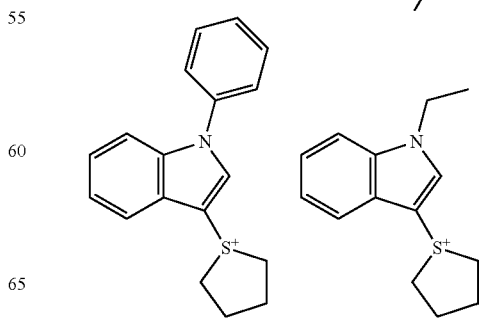

-continued

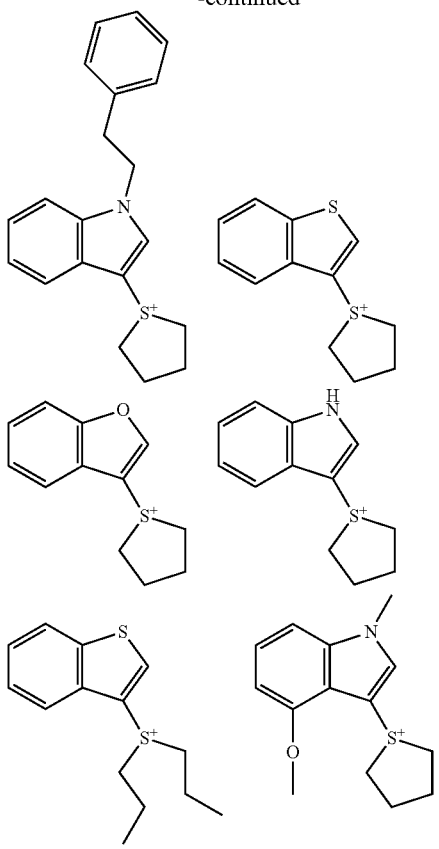

The cation structure (ZI-3) refers to the structure of general formula (ZI-3) below.

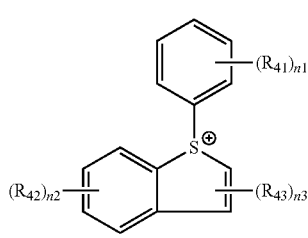
(ZI-3)

In general formula (ZI-3), each of $R_{41}$ to $R_{43}$ independently represents an alkyl group, an acetyl group, an alkoxy group, a carboxyl group, a halogen atom, a hydroxyl group or a hydroxyalkyl group.

As the alkyl groups and alkoxy groups represented by $R_{41}$ to $R_{43}$, there can be mentioned those set forth above in connection with $R_{13}$ to $R_{15}$ in general formula (ZI-1).

The hydroxyalkyl group is preferably a hydroxymethyl group, a hydroxyethyl group, a hydroxypropyl group or the like.

In the formula, n1 is an integer of 0 to 3, preferably 1 or 2 and more preferably 1;

n2 is an integer of 0 to 3, preferably 0 or 1 and more preferably 0; and n3 is an integer of 0 to 2, preferably 0 or 1 and more preferably 1.

Substituents may further be introduced in the groups represented by $R_{41}$ to $R_{43}$. As optionally introduced further substituents, there can be mentioned those set forth above as being optionally introduced in the groups represented by $R_{13}$ to $R_{15}$ in general formula (ZI-1).

Preferred particular examples of the cations in the compounds of general formula (ZI-3) are shown below.

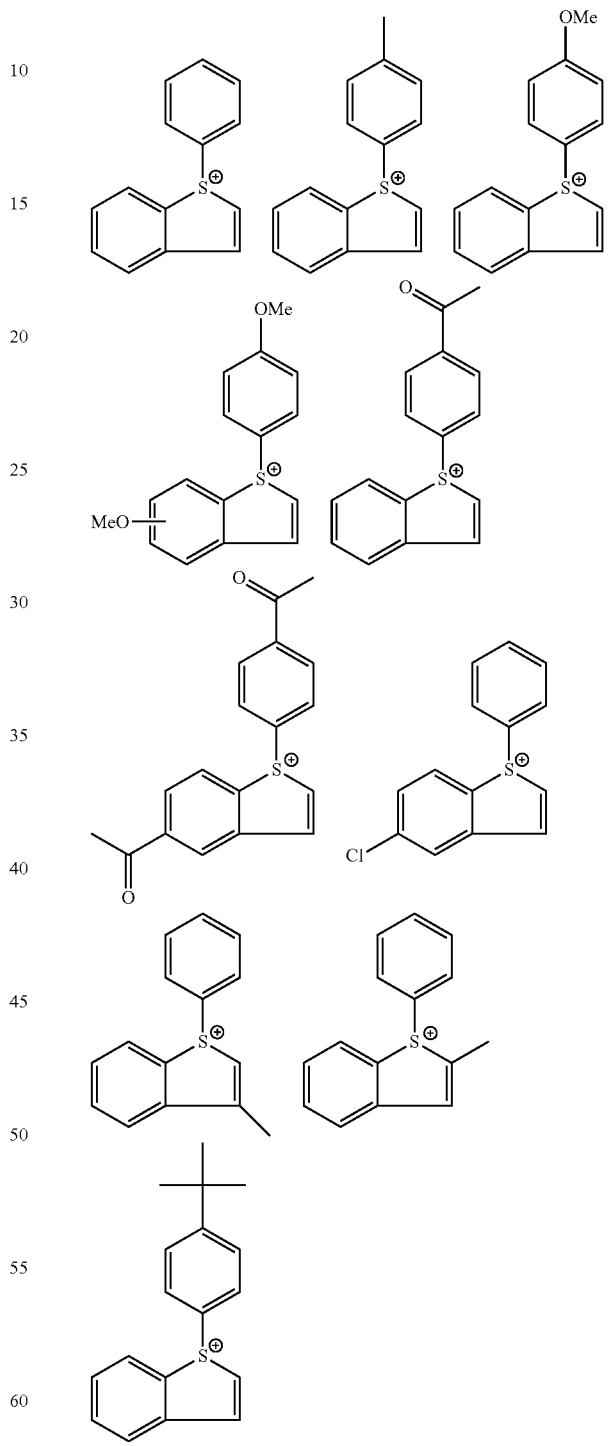

Among the cation structures of general formulae (ZI-1) to (ZI-3), the structures of general formulae (ZI-1) and (ZI-2) are preferred. The structure of general formula (ZI-1) is more preferred.

The groups (ZA-1-2) will be described below.

The groups (ZA-1-2) refer to the groups of general formula (ZA-1) wherein each of $R_{201}$ to $R_{203}$ independently represents an organic group containing no aromatic ring. Herein, the aromatic ring includes one containing a heteroatom.

Each of the organic groups containing no aromatic ring represented by $R_{201}$ to $R_{203}$ generally has 1 to 30 carbon atoms, preferably 1 to 20 carbon atoms.

The groups (ZA-1-3) will be described below.

The groups (ZA-1-3) refer to the groups of the following general formula, each having a phenacylsulfonium salt structure.

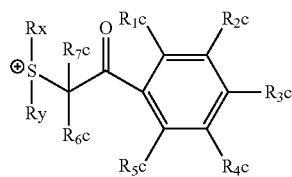

(ZA-1-3)

In general formula (ZA-1-3), each of $R_{1c}$ to $R_{5c}$ independently represents a hydrogen atom, an alkyl group, a cycloalkyl group, an alkoxy group, a phenylthio group or a halogen atom.

Each of $R_{6c}$ and $R_{7c}$ independently represents a hydrogen atom, an alkyl group or a cycloalkyl group.

Each of Rx and Ry independently represents an alkyl group, a cycloalkyl group, an allyl group or a vinyl group.

Any two or more of $R_{1c}$ to $R_{5c}$, and $R_{6c}$ and $R_{7c}$, and Rx and Ry may be bonded to each other to thereby form a ring structure. This ring structure may contain an oxygen atom, a sulfur atom, an ester bond or an amide bond. As the group formed by bonding of any two or more of $R_{1c}$ to $R_{5c}$, and $R_{6c}$ and $R_{7c}$, and Rx and Ry, there can be mentioned a butylene group, a pentylene group or the like.

Now, general formula (ZXI) will be described.

In general formula (ZXI), each of $R_{204}$ and $R_{205}$ independently represents an aryl group, an alkyl group or a cycloalkyl group.

Substituents may be introduced in these aryl, alkyl and cycloalkyl groups.

Preferred examples of the aryl groups represented by $R_{204}$ and $R_{205}$ are the same as set forth above in connection with $R_{201}$ to $R_{203}$ with respect to the compounds (ZI-1).

As preferred examples of the alkyl groups and cycloalkyl groups represented by $R_{204}$ and $R_{205}$, there can be mentioned the linear or branched chains and cycloalkyl groups set forth above in connection with $R_{201}$ to $R_{203}$ with respect to the compounds (ZI-2).

In an aspect of the present invention, the compounds (B) are expressed by general formula (II) below.

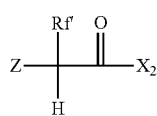

(II)

In formula (II),

Rf' represents a fluorine atom or a perfluoroalkyl group having 1 to 4 carbon atoms.

$X_2$ represents a monovalent organic group having at least one carbon atom.

Z represents a moiety that when exposed to actinic rays or radiation, is converted to a sulfonic acid group, an imidic acid group or a methide acid group.

General formula (II) will be described in detail below.

Z in general formula (II) has the same meaning as that of the above-mentioned Z in general formula (I).

As mentioned above, Rf' represents a fluorine atom or a perfluoroalkyl group having 1 to 4 carbon atoms. In an aspect of the present invention, a fluorine atom is preferred.

In an aspect of the present invention, the organic group represented by $X_2$ is the substituent represented by $X_{11}$ in general formula (Ia) above.

In a further aspect of the present invention, the organic group represented by $X_2$ is either *—$OR_3$ or *—$NR_4R_5$. In the formulae, * represents a position of bonding to the carbonyl group in general formula (II). $R_3$ represents an alkyl group, a mono- or polycycloalkyl group, an alkenyl group, an oxoalkyl group, an oxocycloalkyl group, an aryl group, an aralkyl group, a lactone group or a sultone group. Each of $R_4$ and $R_5$ independently represents a hydrogen atom, an alkyl group, a mono- or polycycloalkyl group, an alkenyl group, an oxoalkyl group, an oxocycloalkyl group, an aryl group, an aralkyl group, a lactone group or a sultone group, provided that $R_4$ and $R_5$ are not simultaneously hydrogen atoms. $R_4$ and $R_5$ may be bonded to each other to thereby form a ring structure in cooperation with the nitrogen atom to which $R_4$ and $R_5$ are bonded.

Particular examples and preferred forms of $R_3$, $R_4$ and $R_5$ are the same as set forth above in connection with $R_3$, $R_4$ and $R_5$ in general formula (I).

In an aspect of the present invention, the compounds (B) are expressed by general formula (IIa) below.

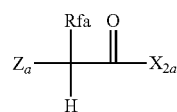

(IIa)

In the formula,

Rfa represents a fluorine atom or $CF_3$.

$X_{2a}$ represents an alkyl group, a cycloalkyl group, an alkoxy group, a cycloalkyloxy group, an aryloxy group, an adamantylmethyloxy group, an adamantylcarbonyl group, an oxocycloalkyl group, an oxocycloalkyloxy group or *—$NR_{4a}R_{5a}$ in which * represents a position of bonding to the carbonyl group in general formula (IIa) above, and each of $R_{4a}$ and $R_{5a}$ independently represents an alkyl group or a cycloalkyl group, provided that $R_{4a}$ and $R_{5a}$ may be bonded to each other to thereby form a ring structure in cooperation with the nitrogen atom to which $R_{4a}$ and $R_{5a}$ are bonded.

$Z_a$ represents a moiety that when exposed to actinic rays or radiation, is converted to a sulfonic acid group, an imidic acid group or a methide acid group.

Particular examples of the groups represented by $X_{2a}$ are the same as set forth above in connection with $R_3$, $R_4$ and $R_5$. Substituents may be introduced in the groups represented by $X_{2a}$. Introducible substituents are the same as set forth above in connection with $R_3$, $R_4$ and $R_5$.

Za has the same meaning as that of the above-mentioned Z in general formula (I).

Particular examples of the acid anions generated by the decomposition upon exposure to actinic rays or radiation of compounds (B) are shown below.

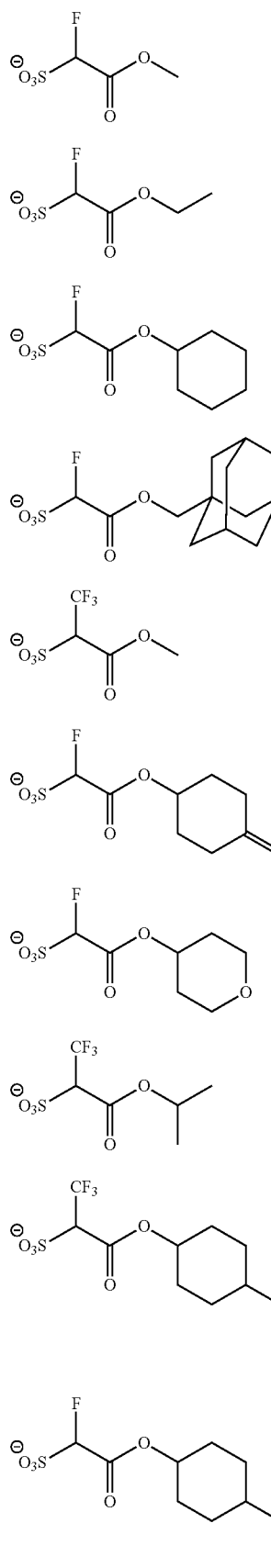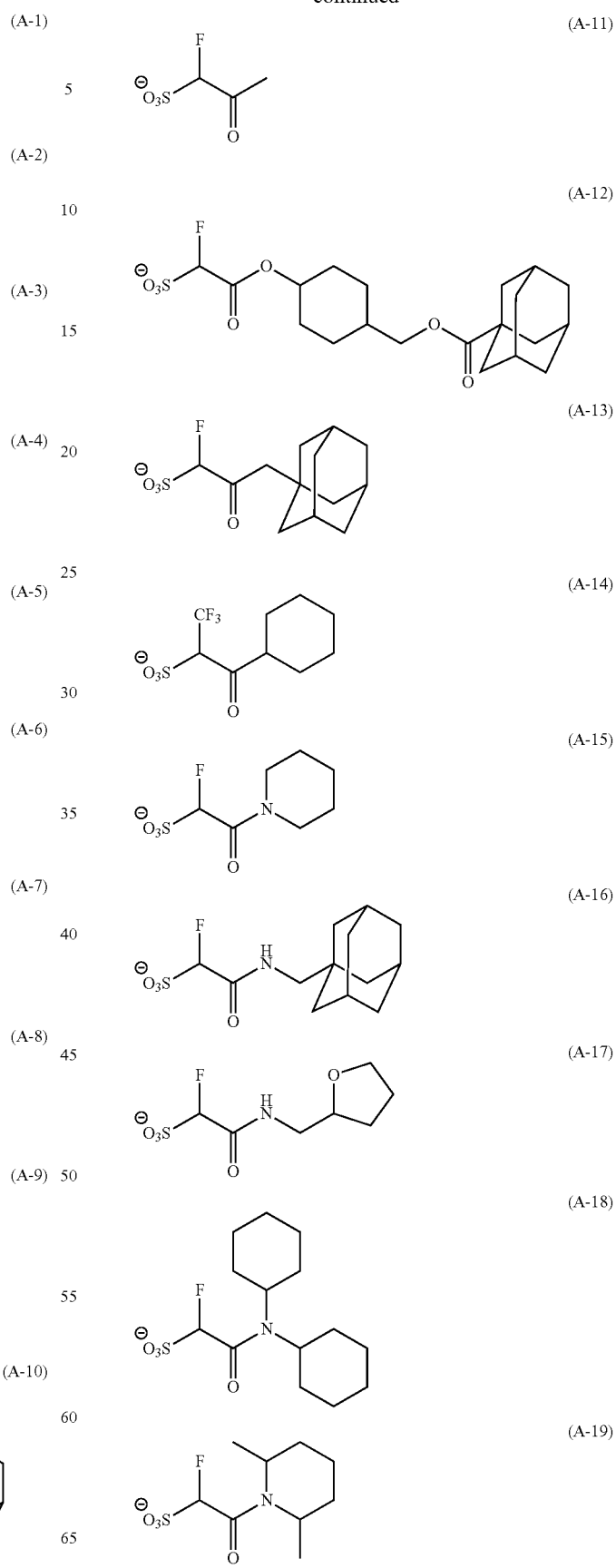

-continued
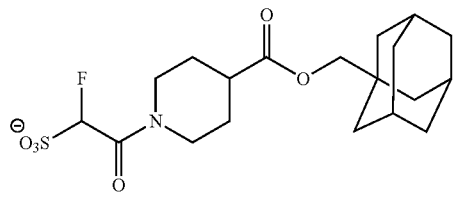
(A-20)
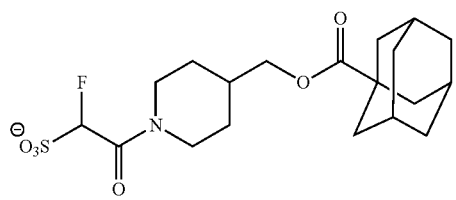
(A-21)
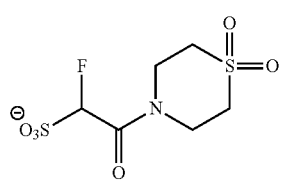
(A-22)
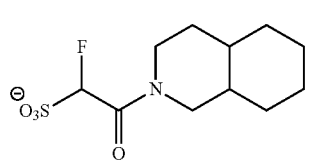
(A-23)
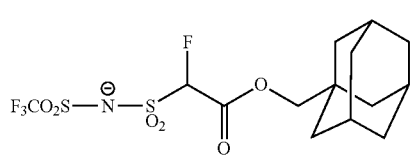
(A-24)
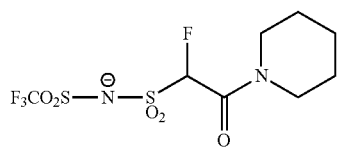
(A-25)
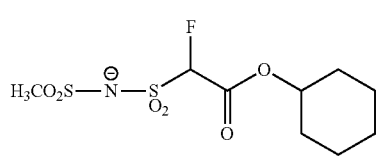
(A-26)
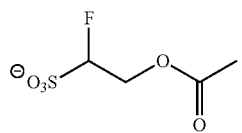
(A-27)
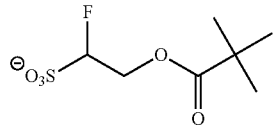
(A-28)
-continued
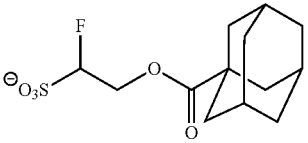
(A-29)
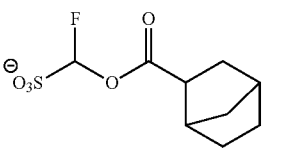
(A-30)
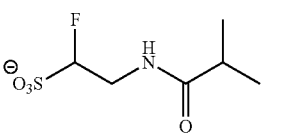
(A-31)
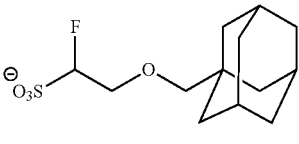
(A-32)
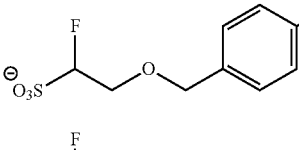
(A-33)
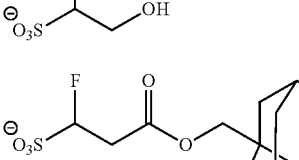
(A-34)
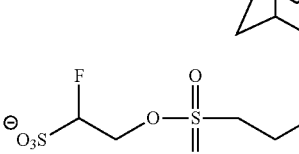
(A-35)
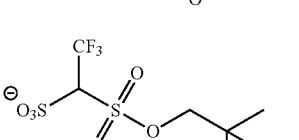
(A-36)
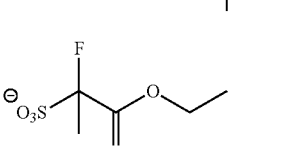
(A-37)
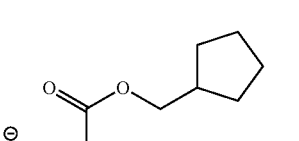
(A-38)
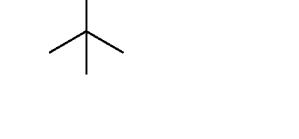
(A-39)

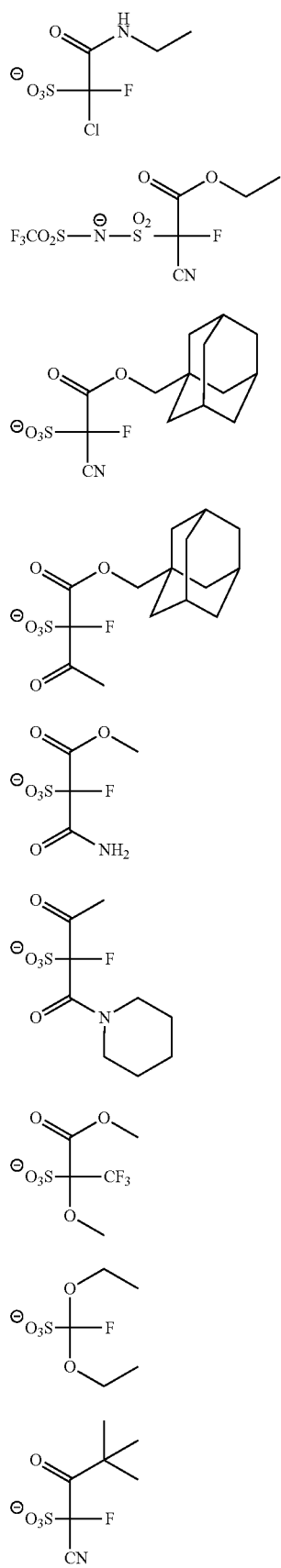
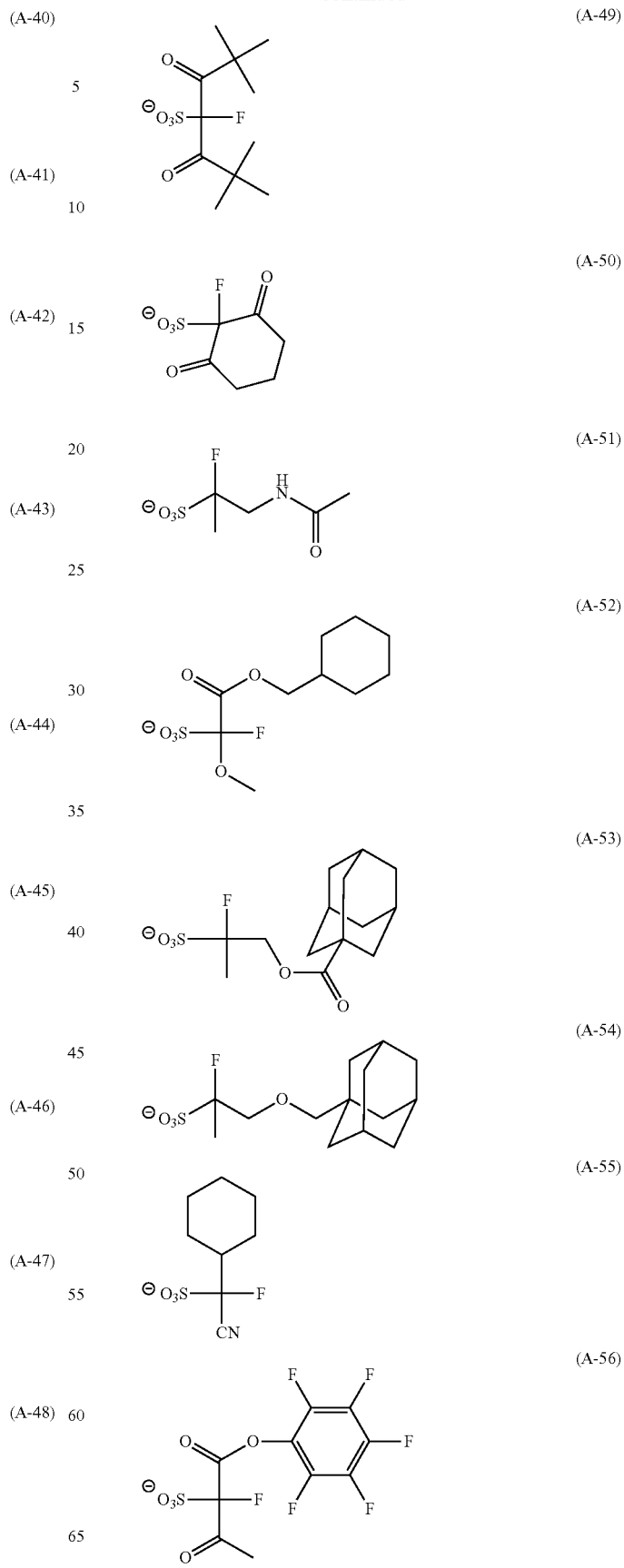

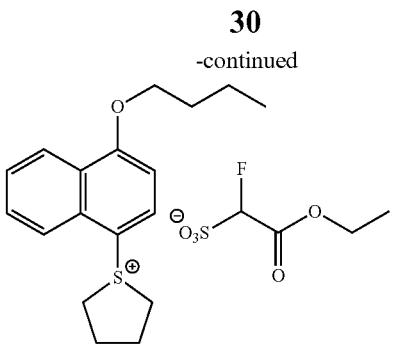
(A-57)
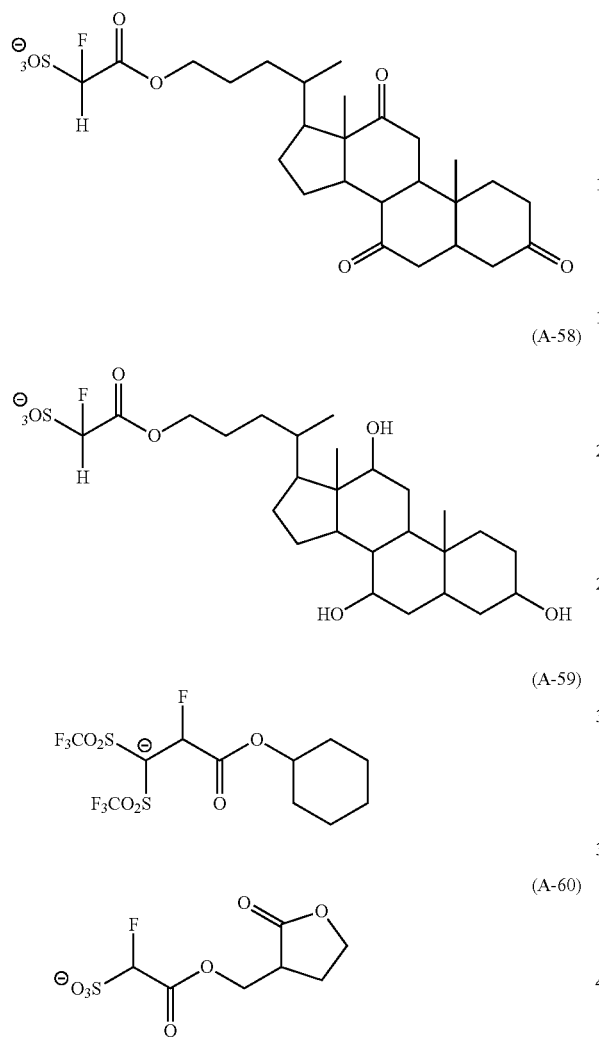
(A-58)
(A-59)
(A-60)
Particular examples of the compounds (B) are shown below.
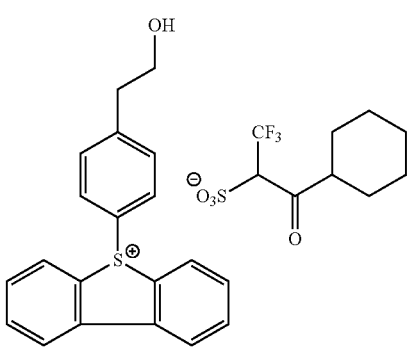
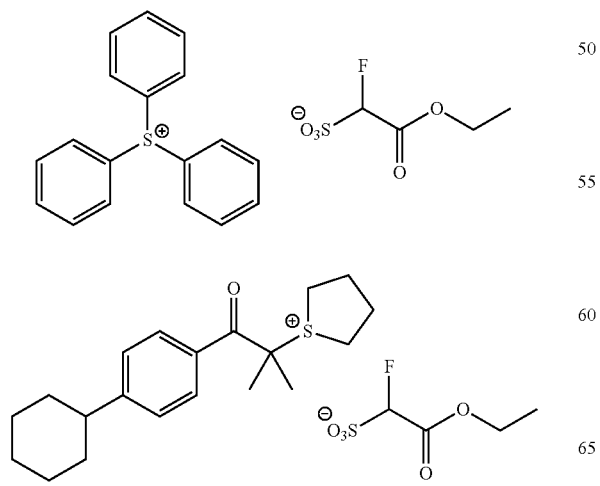
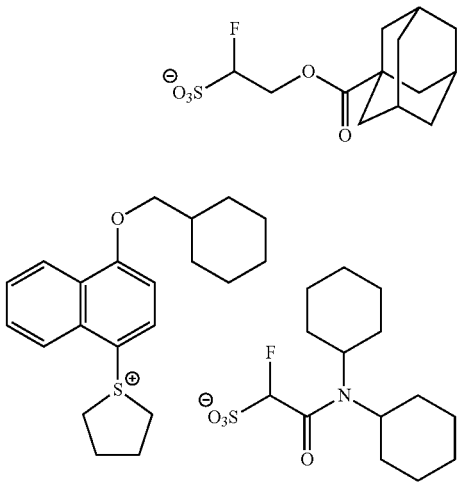

31
-continued
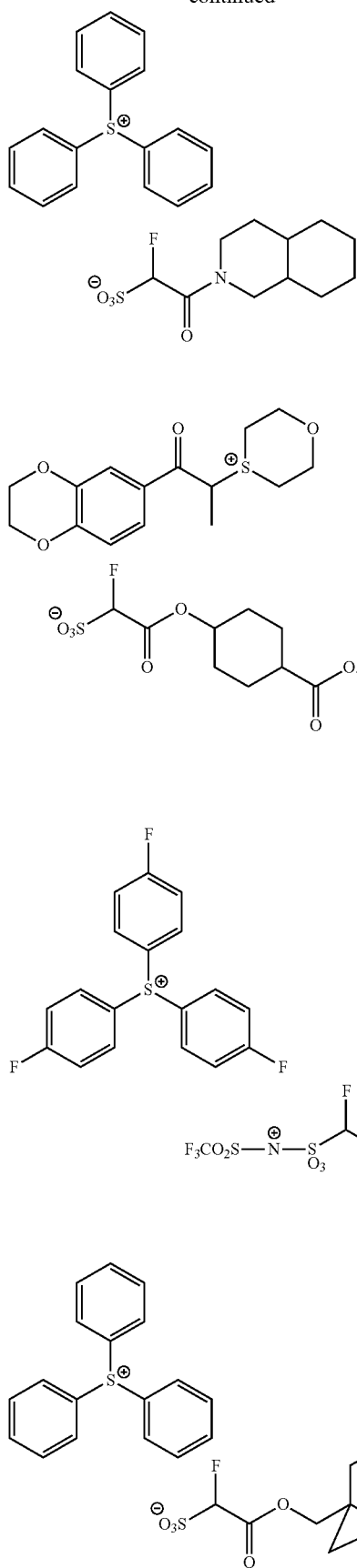
32
-continued
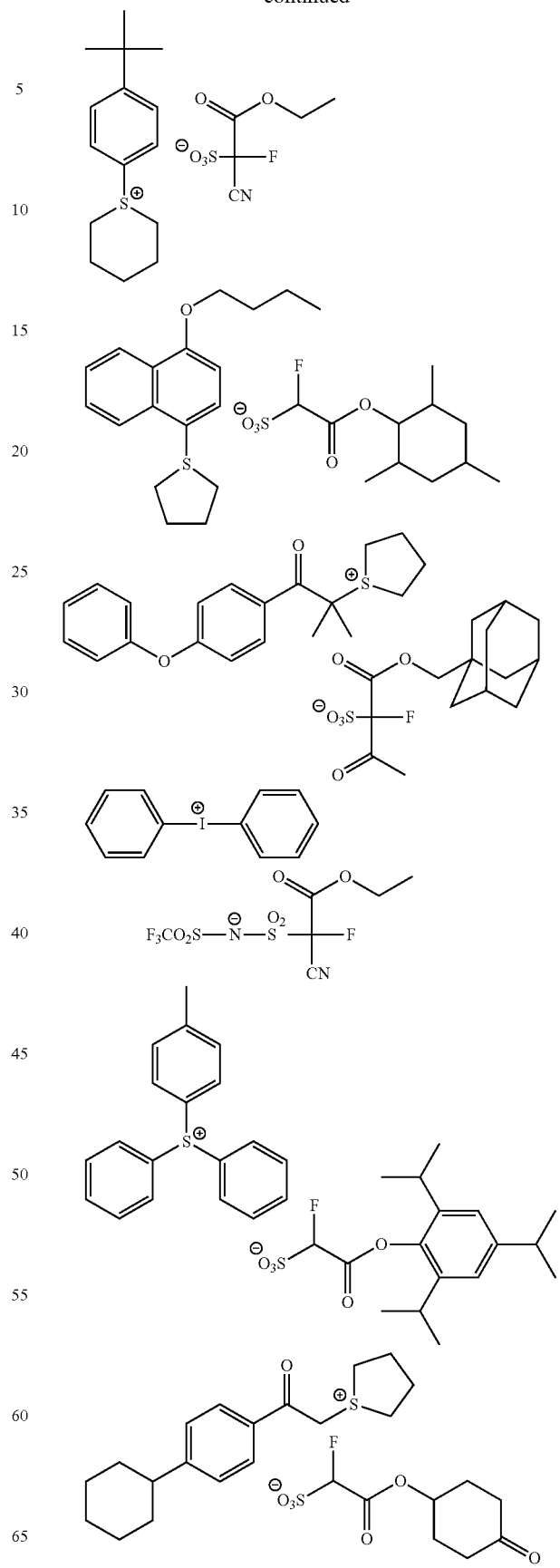

33
-continued
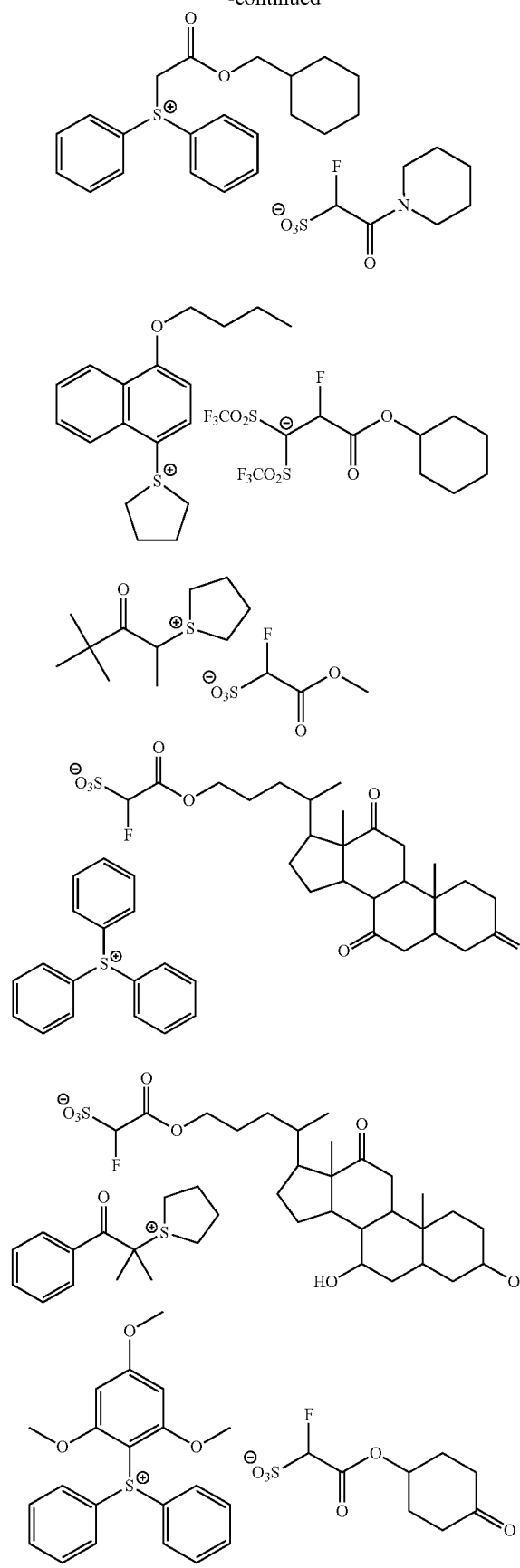
34
-continued
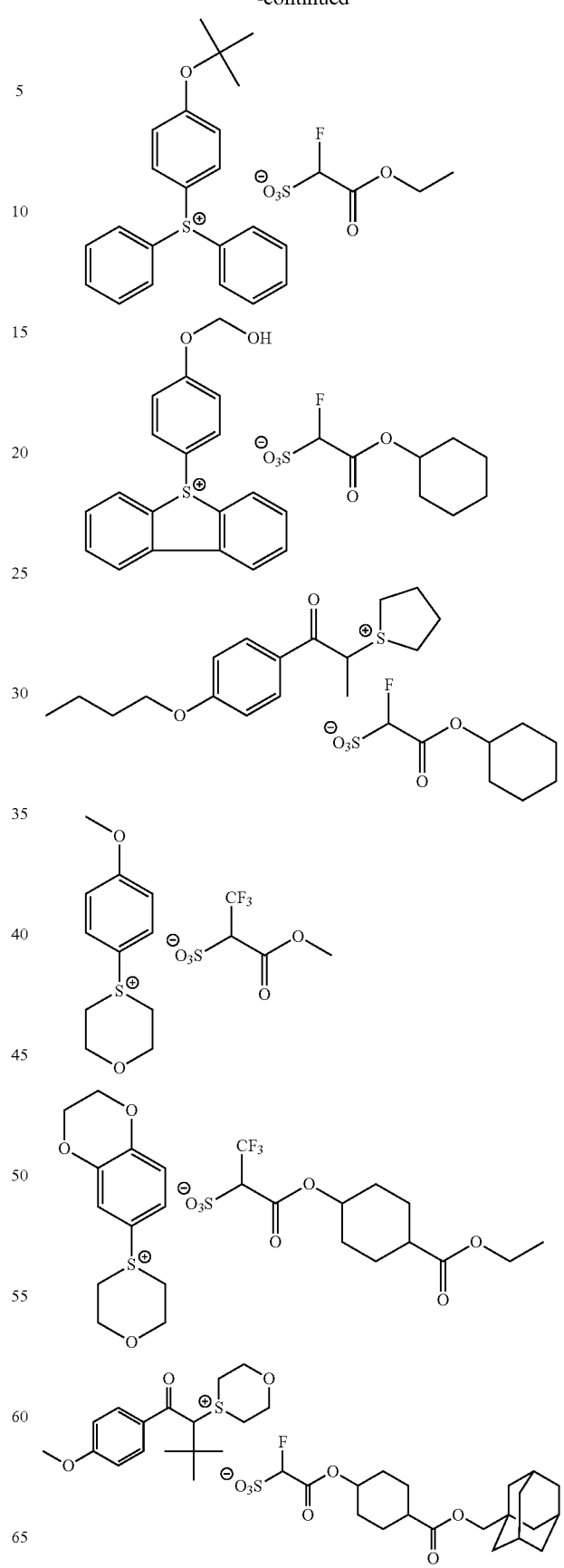

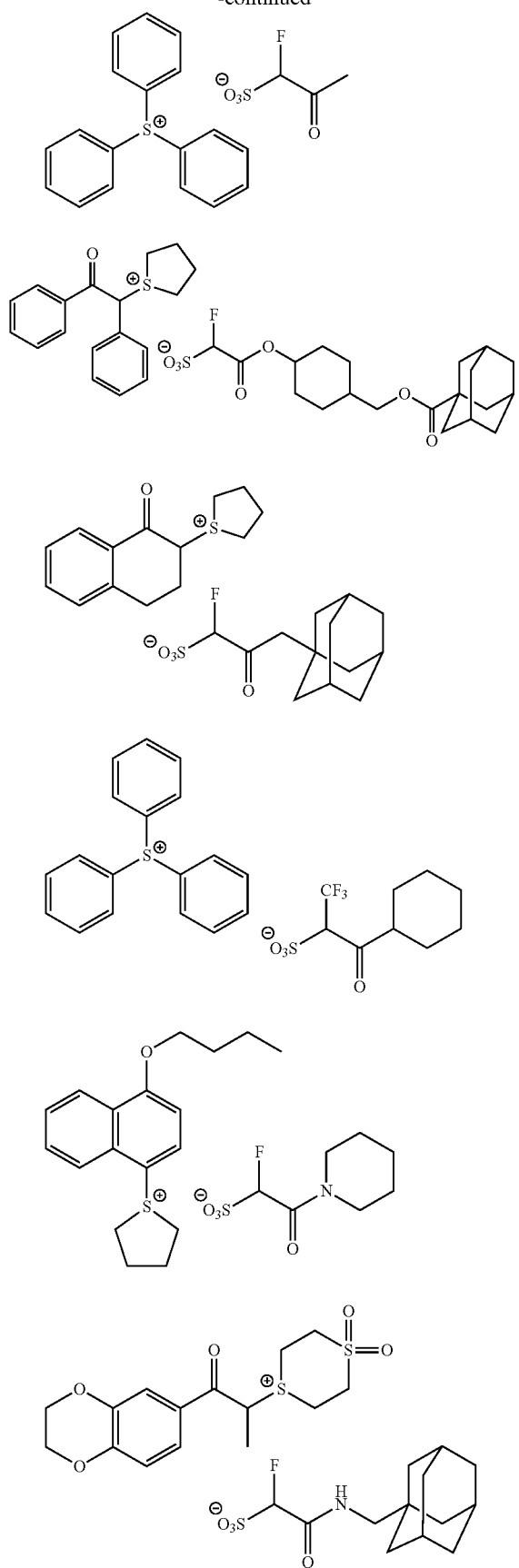
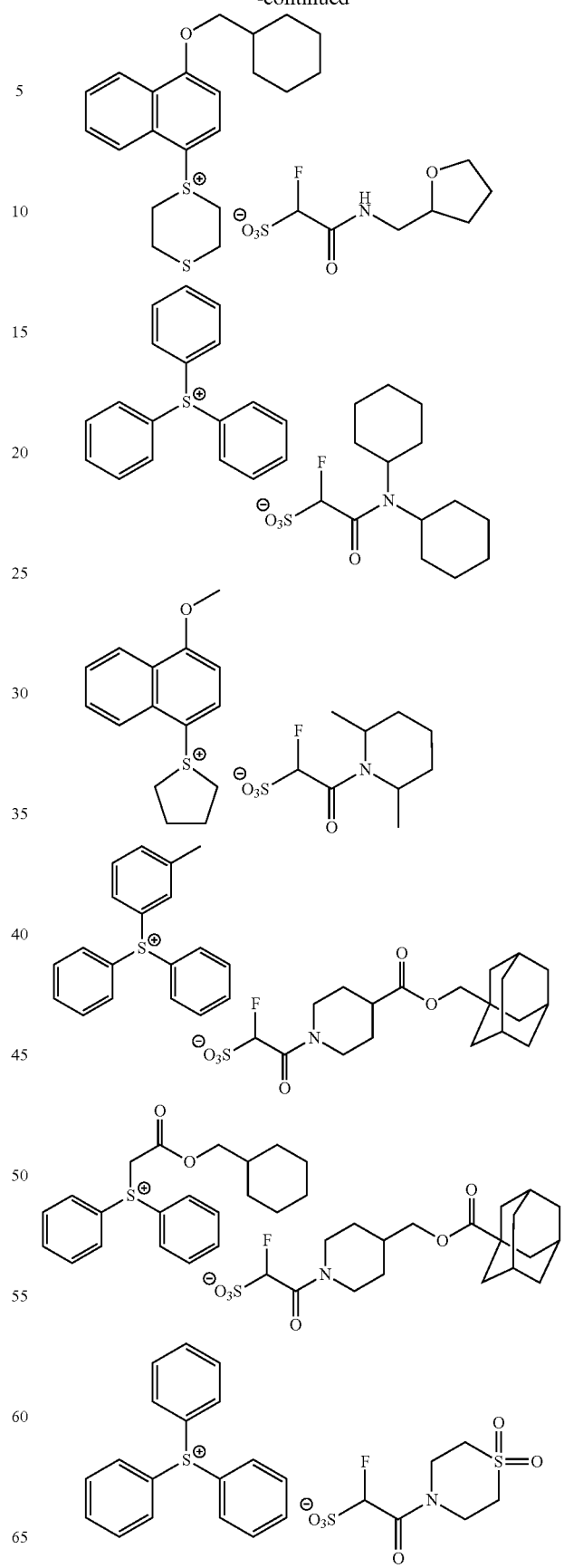

37
-continued
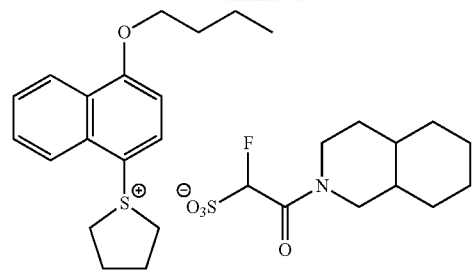
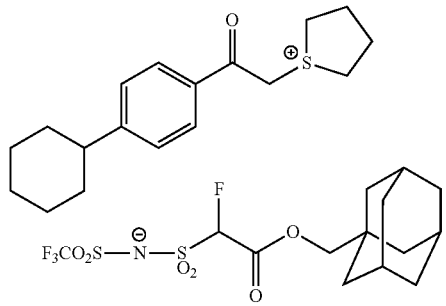
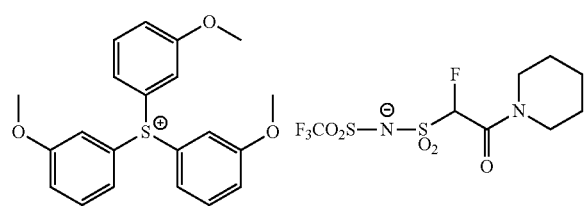
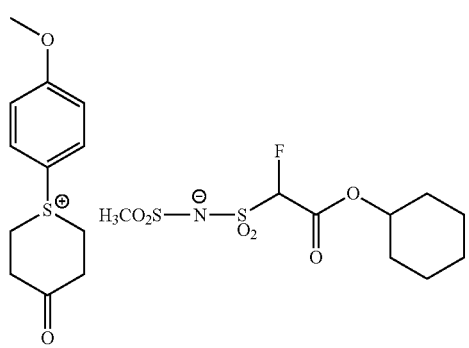
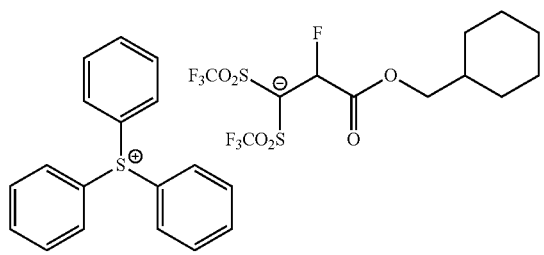
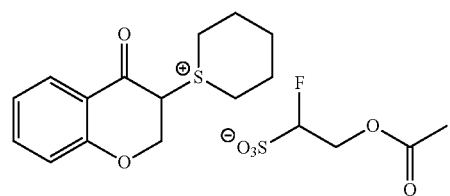
38
-continued
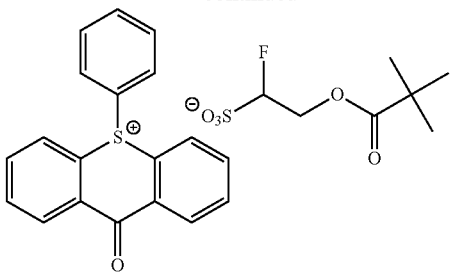
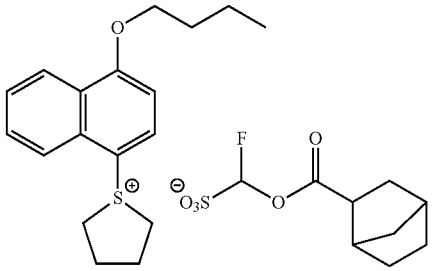
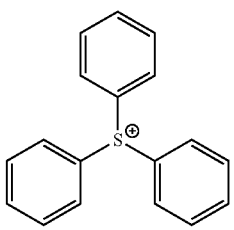
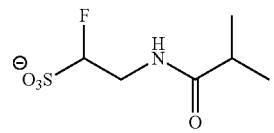
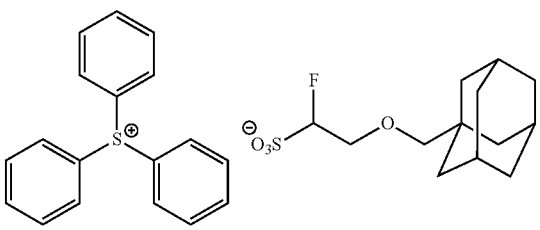
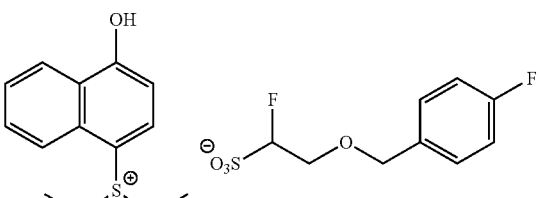
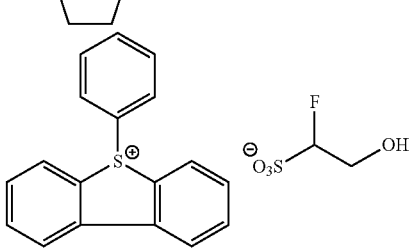

39
-continued
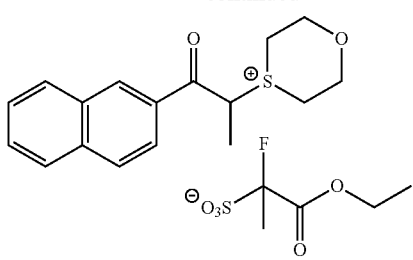
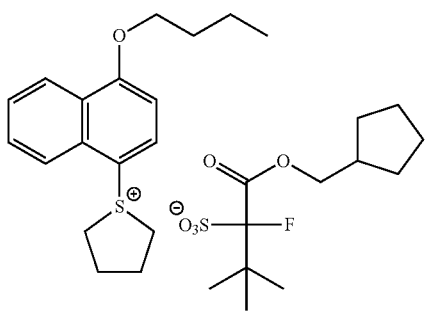
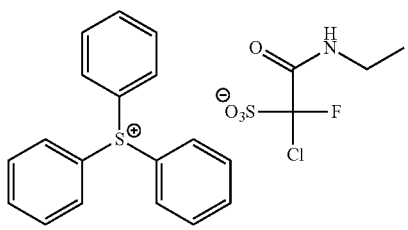
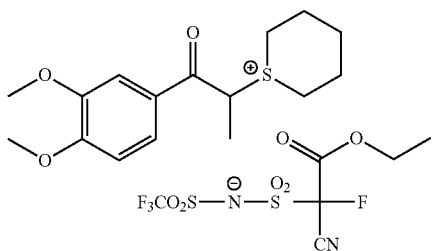
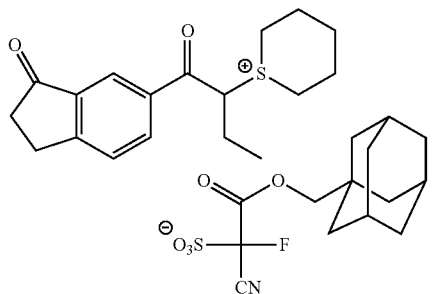
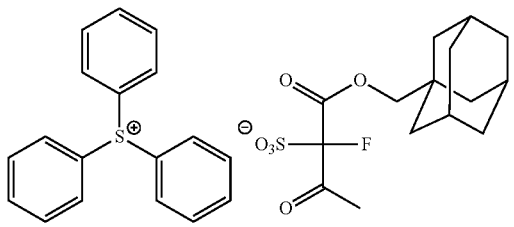
40
-continued
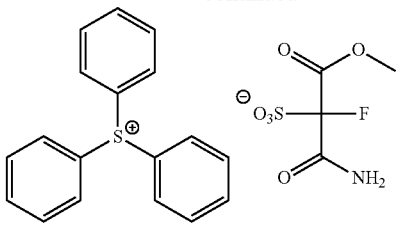
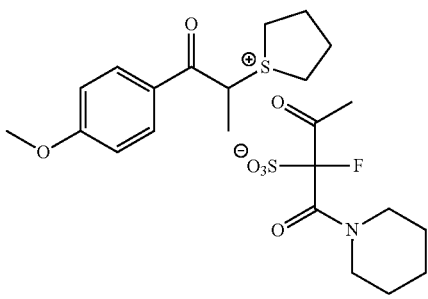
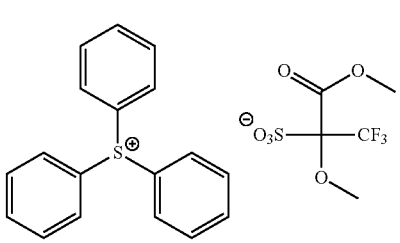
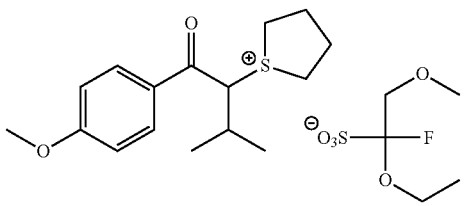
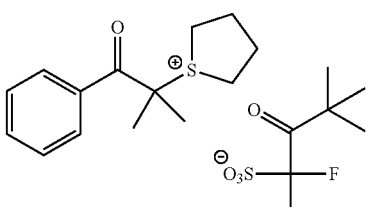
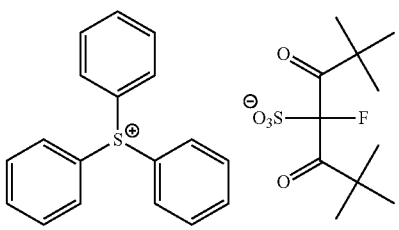

41
-continued
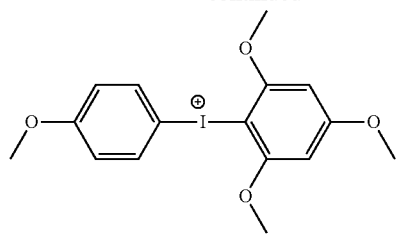
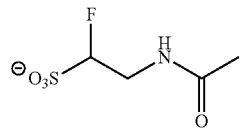
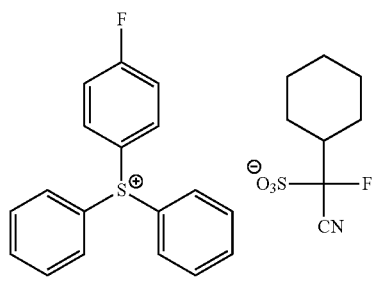
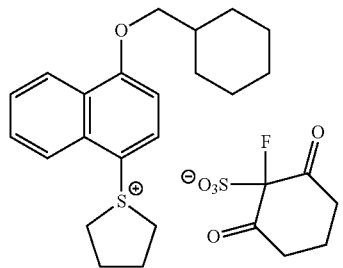
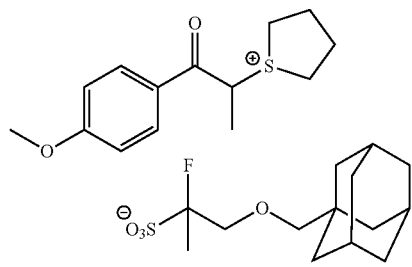
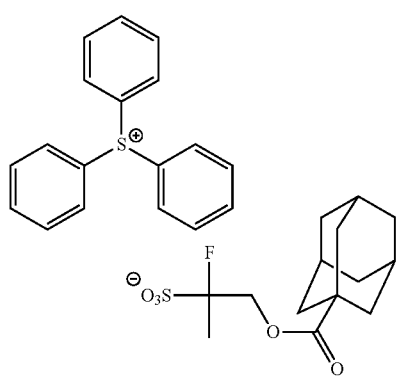
42
-continued
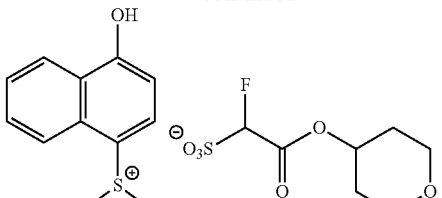
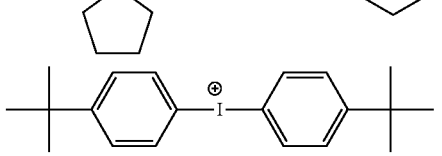
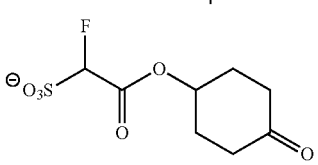
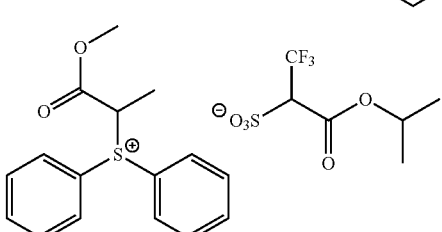
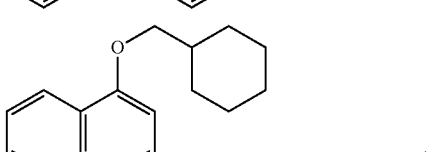
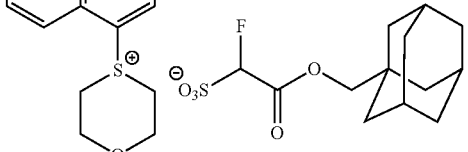
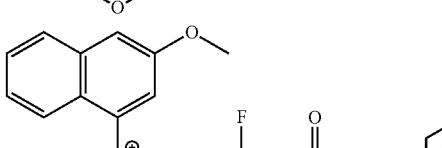
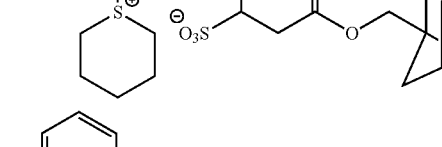
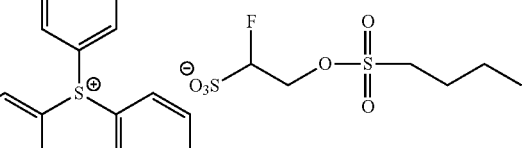
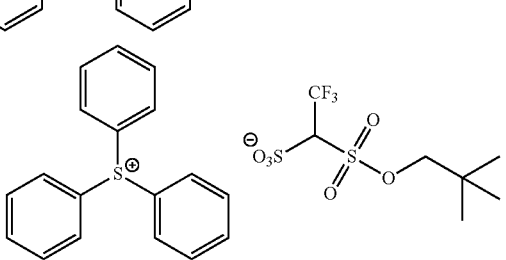

In an aspect of the present invention, the acid generated upon exposure to actinic rays or radiation by the compounds (B) of general formula (I) contains one fluorine atom.

Also, in an aspect of the present invention, the compounds (B) of general formula (I) each contains one fluorine atom.

In the composition of the present invention, one type of compound (B) above may be used alone, or two or more types thereof may be used in combination. The content of compound (B) in the composition of the present invention is preferably in the range of 1 to 99 mass %, more preferably 5 to 80 mass %, and further more preferably 8 to 50 mass %, based on the total solids of the composition.

[Acid Generator Other than Compound (B)]

In the present invention, the compound (B) may be used in combination with an acid generator (hereinafter also referred as "compound (B')" or acid generator (B')) other than the compound (B).

The compound (B') is not particularly limited. As preferred compounds (B'), there can be mentioned the compounds of general formulae (ZI'), (ZII') and (ZIII') below.

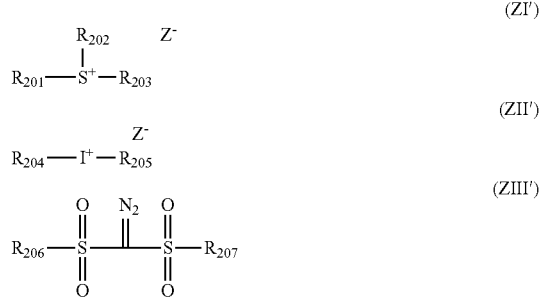

In general formula (ZI') above, each of $R_{201}$, $R_{202}$ and $R_{203}$ independently represents an organic group.

The number of carbon atoms of each of the organic groups represented by $R_{201}$, $R_{202}$ and $R_{203}$ is generally in the range of 1 to 30, preferably 1 to 20.

Two of $R_{201}$ to $R_{203}$ may be bonded to each other to thereby form a ring structure, and the ring within the same may contain an oxygen atom, a sulfur atom, an ester bond, an amide bond or a carbonyl group. As the group formed by the mutual bonding of two of $R_{201}$ to $R_{203}$, there can be mentioned an alkylene group (for example, a butylene group or a pentylene group).

As the organic groups represented by $R_{201}$, $R_{202}$ and $R_{203}$, there can be mentioned, for example, corresponding groups in the compounds (ZI'-1) to be described hereinafter.

Use can be made of a compound containing a plurality of structures of general formula (ZI'). For example, use can be made of a compound with a structure in which at least one of $R_{201}$ to $R_{203}$ of a compound expressed by general formula (ZI') is bonded through a single bond or a connecting group to at least one of $R_{201}$ to $R_{203}$ of another compound expressed by general formula (ZI')

Z⁻ represents a nonnucleophilic anion (anion whose capability of inducing a nucleophilic reaction is markedly low)

As Z⁻, there can be mentioned, for example, a sulfonate anion (an aliphatic sulfonate anion, an aromatic sulfonate anion, a camphor sulfonate anion or the like), a carboxylate anion (an aliphatic carboxylate anion, an aromatic carboxylate anion, an aralkyl carboxylate anion or the like), a sulfonylimide anion, a bis(alkylsulfonyl)imide anion, a tris(alkylsulfonyl)methide anion or the like.

The aliphatic moiety in the aliphatic sulfonate anion and aliphatic carboxylate anion may be an alkyl group or a cycloalkyl group, being preferably a linear or branched alkyl group having 1 to 30 carbon atoms or a cycloalkyl group having 3 to 30 carbon atoms.

As a preferred aromatic group in the aromatic sulfonate anion and aromatic carboxylate anion, there can be mentioned an aryl group having 6 to 14 carbon atoms, for example, a phenyl group, a tolyl group, a naphthyl group or the like.

Substituents may be introduced in the above-mentioned alkyl group, cycloalkyl group and aryl group. As particular examples of the substituents, there can be mentioned a nitro group, a halogen atom such as a fluorine atom, a carboxyl group, a hydroxyl group, an amino group, a cyano group, an alkoxy group (preferably having 1 to 15 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms), an alkylthio group (preferably having 1 to 15 carbon atoms), an alkylsulfonyl group (preferably having 1 to 15 carbon atoms), an alkyliminosulfonyl group (preferably having 2 to 15 carbon atoms), an aryloxysulfonyl group (preferably having 6 to 20 carbon atoms), an alkylaryloxysulfonyl group (preferably having 7 to 20 carbon atoms), a cycloalkylaryloxysulfonyl group (preferably having 10 to 20 carbon atoms), an alkyloxyalkyloxy group (preferably having 5 to 20 carbon atoms), a cycloalkylalkyloxyalkyloxy group (preferably having 8 to 20 carbon atoms) and the like. With respect to the aryl group or ring structure of each of these groups, as its substituent, there can further be mentioned an alkyl group (preferably having 1 to 15 carbon atoms).

As a preferred aralkyl group in the aralkyl carboxylate anion, there can be mentioned an aralkyl group having 7 to 12 carbon atoms, for example, a benzyl group, a phenethyl group, a naphthylmethyl group, a naphthylethyl group, a naphthylbutyl group or the like.

As the sulfonylimide anion, there can be mentioned, for example, a saccharin anion.

The alkyl group in the bis(alkylsulfonyl)imide anion and tris(alkylsulfonyl)methide anion is preferably an alkyl group having 1 to 5 carbon atoms.

In the bis(alkylsulfonyl)imide anion, two alkyl groups may be connected to each other to thereby form an alkylene group (preferably 2 to 4 carbon atoms), which may form a ring in cooperation with the imide group and two sulfonyl groups.

As substituents that can be introduced in the above alkyl groups and alkylene group formed by the mutual connection of two alkyl groups in the bis(alkylsulfonyl)imide anion, there can be mentioned a halogen atom, an alkyl group substituted with a halogen atom, an alkoxy group, an alkylthio group, an alkyloxysulfonyl group, an aryloxysulfonyl group, a cycloalkylaryloxysulfonyl group and the like.

From the viewpoint of acid strength, it is preferred for the pKa value of generated acid to be −1 or below. This contributes to an enhancement of sensitivity.

The compounds (ZI') can preferably be compounds (ZI'-1) to be described below.

The compounds (ZI'-1) are arylsulfonium compounds of general formula (ZI') above in which at least one of $R_{201}$ to $R_{203}$ is an aryl group, namely, compounds each comprising an arylsulfonium as a cation.

In the arylsulfonium compounds, all of $R_{201}$ to $R_{203}$ may be aryl groups. Alternatively, $R_{201}$ to $R_{203}$ may be an aryl group in part and an alkyl group or a cycloalkyl group in the remainder. All of $R_{201}$ to $R_{203}$ being aryl groups is preferred.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound. A triarylsulfonium compound is preferred.

The aryl group in the arylsulfonium compounds is preferably a phenyl group or a naphthyl group, more preferably a phenyl group. The aryl group may be one with a heterocyclic structure containing an oxygen atom, a nitrogen atom, a sulfur atom or the like. As the heterocyclic structure, there can be mentioned a pyrrole residue, a furan residue, a thiophene residue, an indole residue, a benzofuran residue, a benzothiophene residue or the like. When the arylsulfonium compound contains two or more aryl groups, the two or more aryl groups may be identical to or different from each other.

The alkyl group or cycloalkyl group contained in the arylsulfonium compounds according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

Each of the aryl groups, alkyl groups and cycloalkyl groups represented by $R_{201}$ to $R_{203}$ may contain as a substituent thereof an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. An alkyl group having 1 to 4 carbon atoms and an alkoxy group having 1 to 4 carbon atoms are more preferred. Each of the substituents may be introduced in any one of the three $R_{201}$ to $R_{203}$, or alternatively may be introduced in all of the three $R_{201}$ to $R_{203}$. When $R_{201}$ to $R_{203}$ represent aryl groups, each of the substituents is preferably introduced in the p-position of the aryl group.

General formulae (ZII') and (ZIII') will be described below.

In general formulae (ZII') and (ZIII'), each of $R_{204}$ to $R_{207}$ independently represents an aryl group, an alkyl group or a cycloalkyl group.

The aryl groups, alkyl groups and cycloalkyl groups represented by $R_{204}$ to $R_{207}$ are the same as set forth above in connection with $R_{201}$ to $R_{203}$ with respect to the compounds (ZI'-1).

Substituents may be introduced in the aryl groups, alkyl groups and cycloalkyl groups represented by $R_{204}$ to $R_{207}$. As the substituents, there can be mentioned those set forth above as being introducible in the aryl groups, alkyl groups and cycloalkyl groups represented by $R_{201}$ to $R_{203}$ with respect to the compounds (ZI'-1).

$Z^-$ represents a nonnucleophilic anion, which is the same as set forth above in connection with Z in general formula (ZI').

As further acid generators (B') that can be used in combination with the acid generator according to the present invention, there can be mentioned the compounds of general formulae (ZIV'), (ZV') and (ZVI') below.

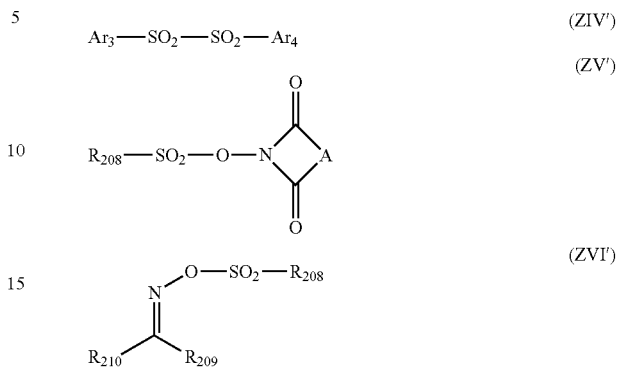

In general formulae (ZIV') to (ZVI'), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Particular examples of the aryl groups represented by $Ar_3$, $Ar_4$, $R_{208}$, $R_{209}$ and $R_{210}$ are the same as set forth above in connection with the aryl groups represented by $R_{201}$, $R_{202}$ and $R_{203}$ in general formula (ZI'-1).

Particular examples of the alkyl groups and cycloalkyl groups represented by $R_{208}$, $R_{209}$ and $R_{210}$ are the same as set forth above in connection with the alkyl groups and cycloalkyl groups represented by $R_{201}$, $R_{202}$ and $R_{203}$ in general formula (ZI'-1).

As the alkylene group represented by A, there can be mentioned an alkylene group having 1 to 12 carbon atoms (e.g., a methylene group, an ethylene group, a propylene group, an isopropylene group, a butylene group, an isobutylene group or the like). As the alkenylene group represented by A, there can be mentioned an alkenylene group having 2 to 12 carbon atoms (e.g., an ethenylene group, a propenylene group, a butenylene group or the like). As the arylene group represented by A, there can be mentioned an arylene group having 6 to 10 carbon atoms (e.g., a phenylene group, a tolylene group, a naphthylene group or the like).

Especially preferred examples of the acid generators (B') that can be used in combination with the acid generators (B) according to the present invention are shown below.

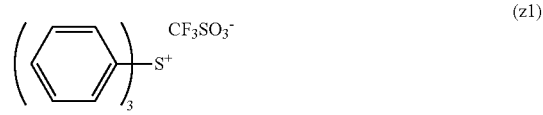

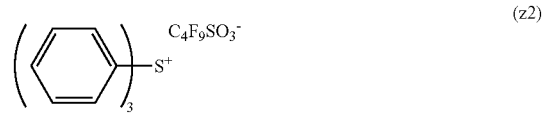

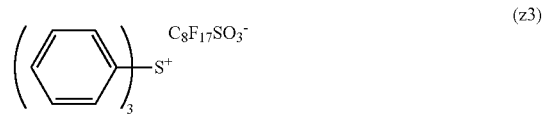

-continued
(z4) 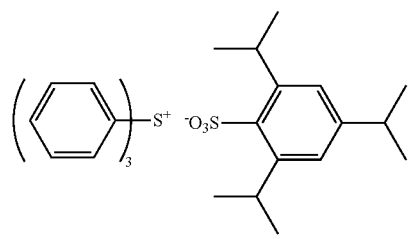
(z5) 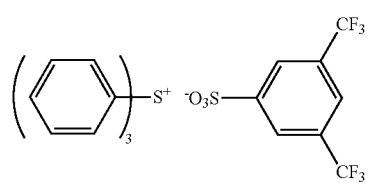
(z6) 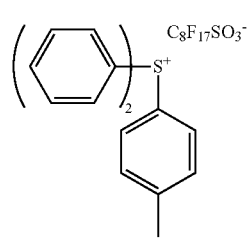
(z7) 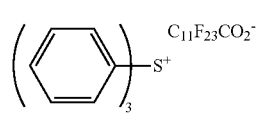
(z8) 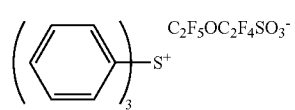
(z9) 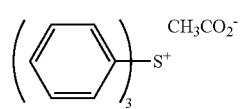
(z10) 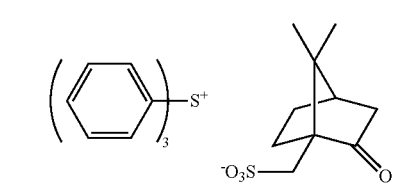
(z11) 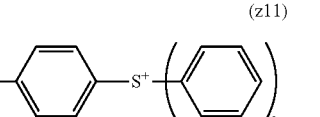
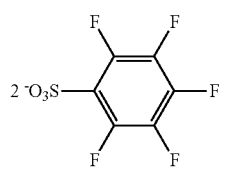
-continued
(z12) 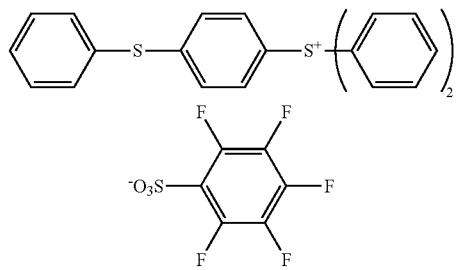
(z13) 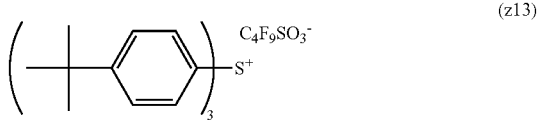
(z14) 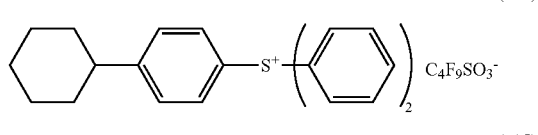
(z15) 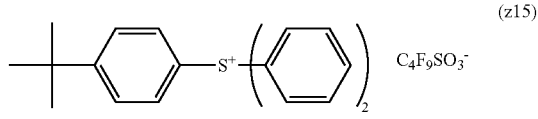
(z16) 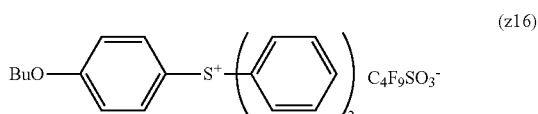
(z17) 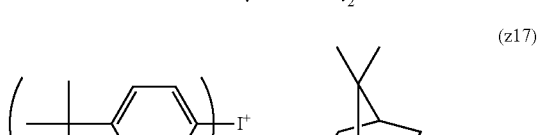
(z18) 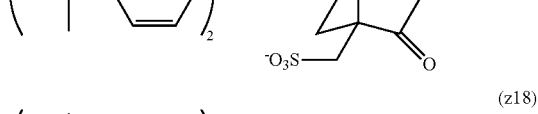
(z19) 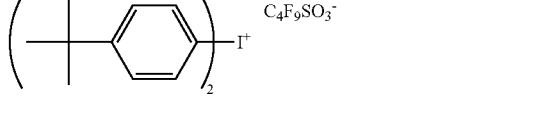
(z20) 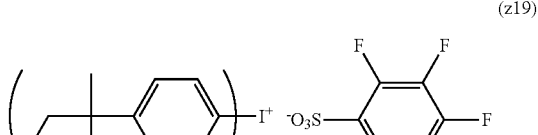
(z21) 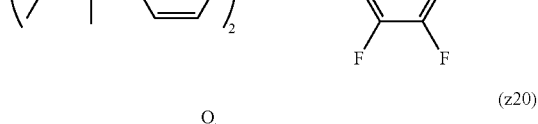

(z22) 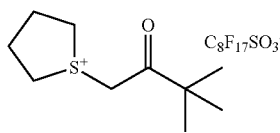
(z23) 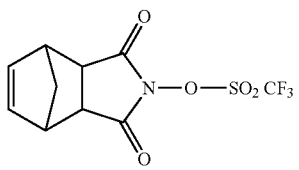
(z24) 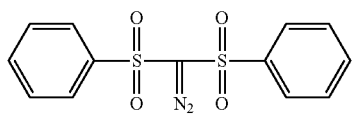
(z25) 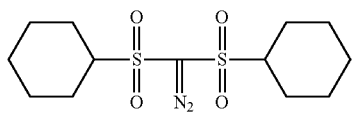
(z26) 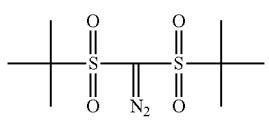
(z27) 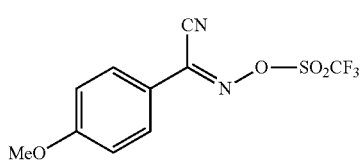
(z28) 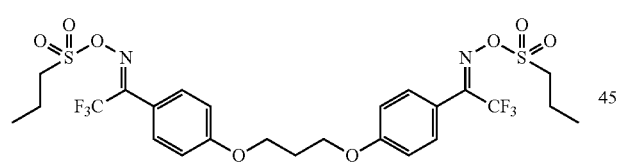
(z29) 
(z30) 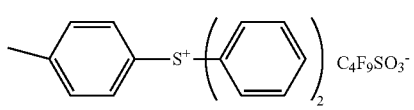
(z31) 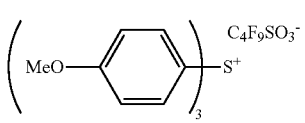
(z32) 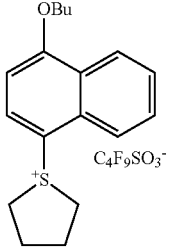
(z33) 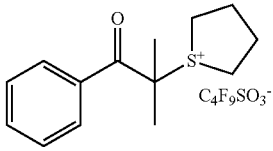
(z34) 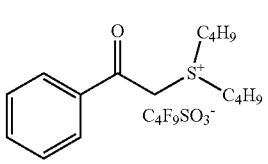
(z35) 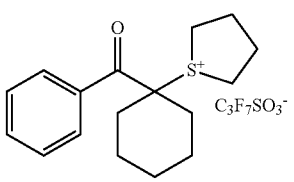
(z36) 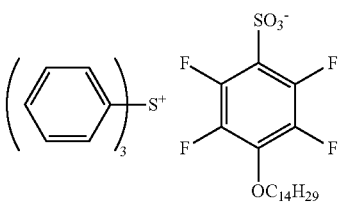
(z37) 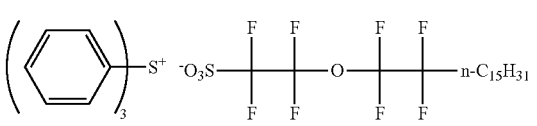
(z38) 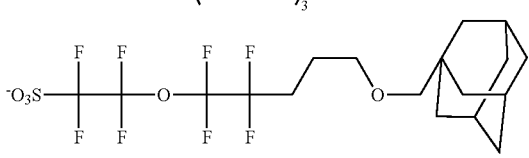
(z39) 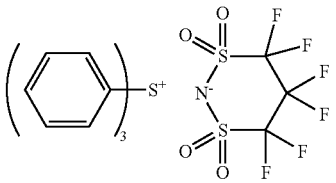

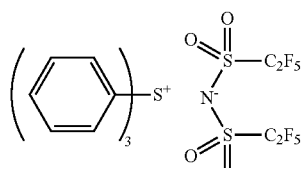 (z40)
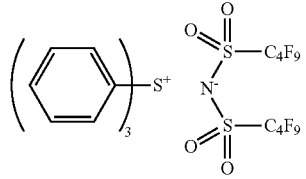 (z41)
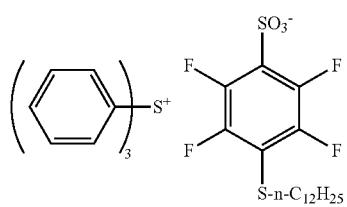 (z42)
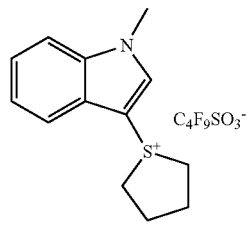 (z43)
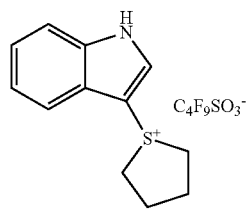 (z44)
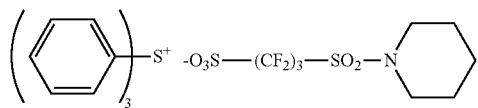 (z45)
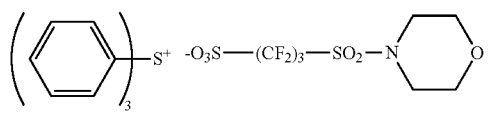 (z46)
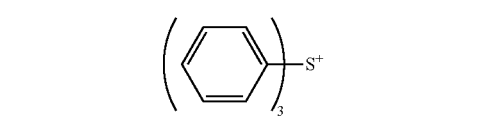 (z47)
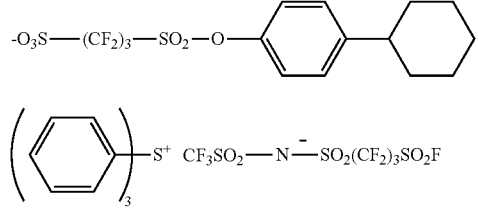 (z48)
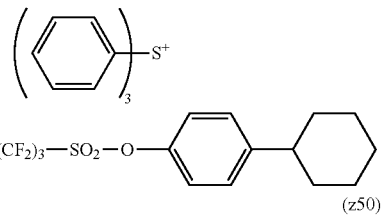 (z49)
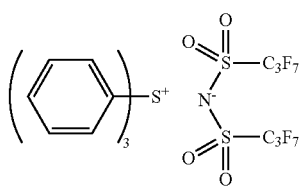 (z50)
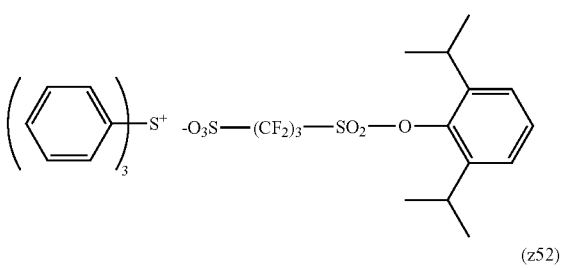 (z51)
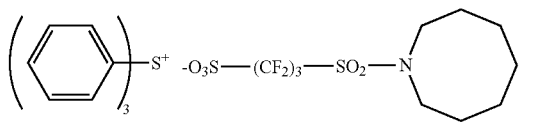 (z52)
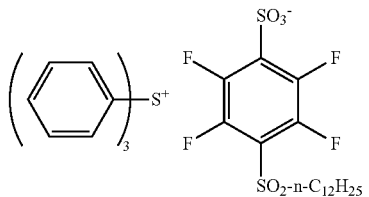 (z53)
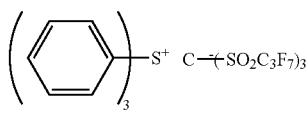 (z54)
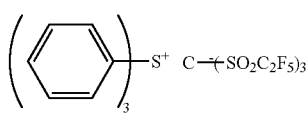 (z55)
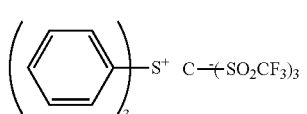 (z56)
 (z57)
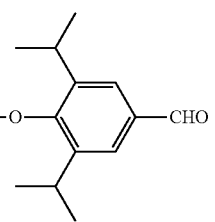

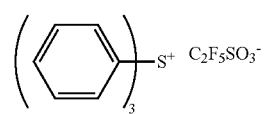
(z58)
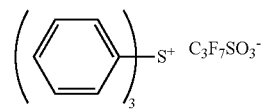
(z59)
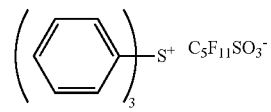
(z60)
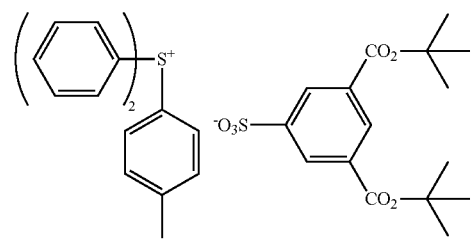
(z61)
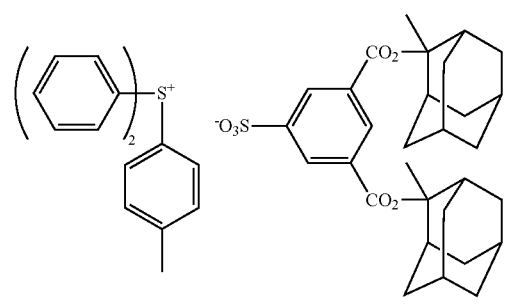
(z62)
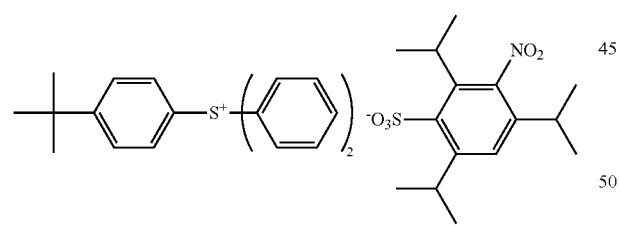
(z63)
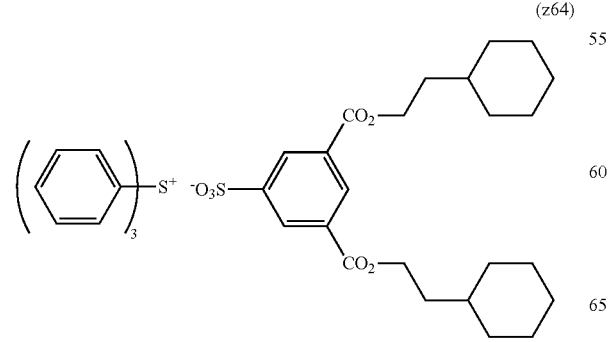
(z64)
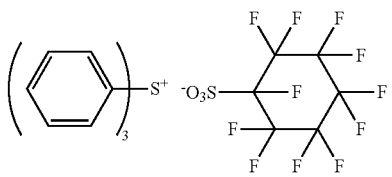
(z65)
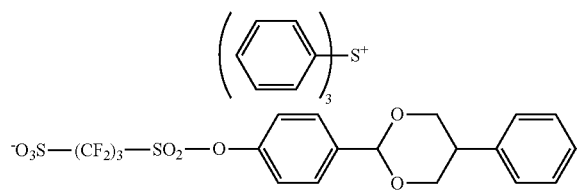
(z66)
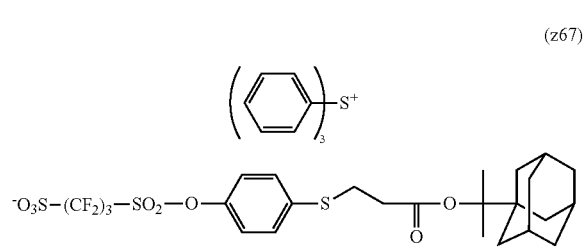
(z67)
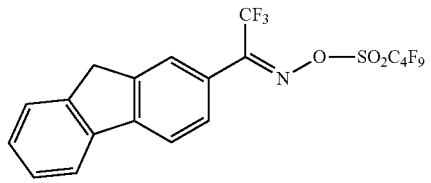
(z68)
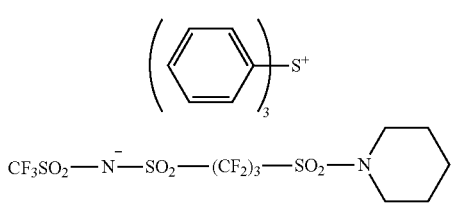
(z69)
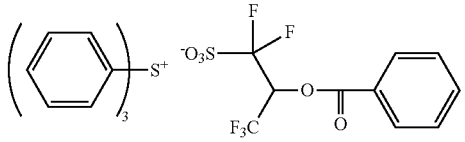
(z70)
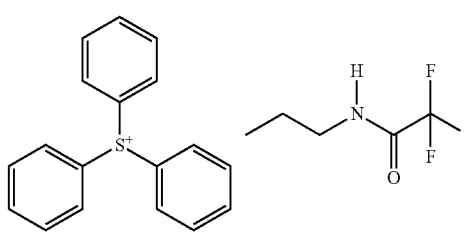
(z71)

(z72) 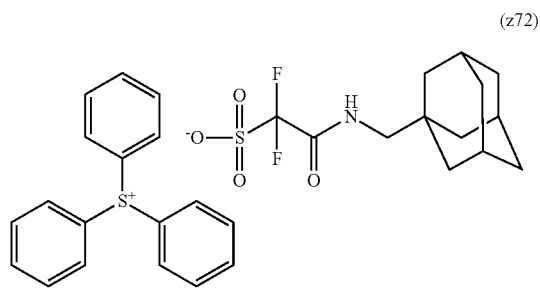
(z73) 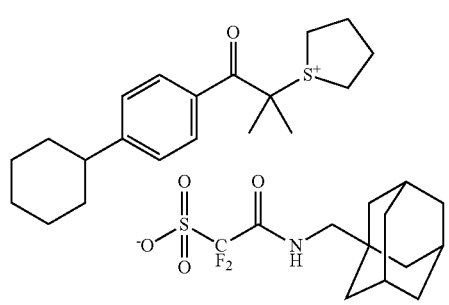
(z74) 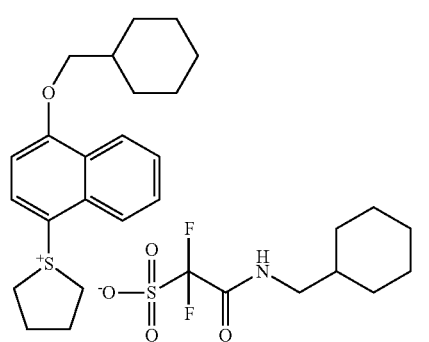
(z75) 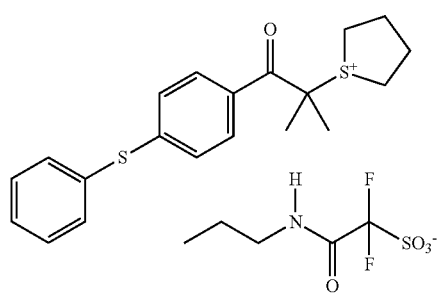
(z76) 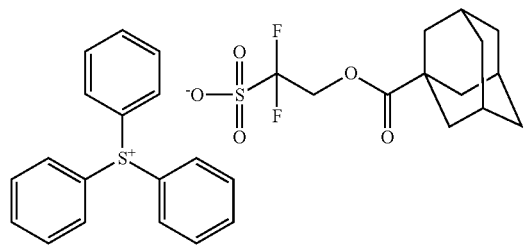
(z77) 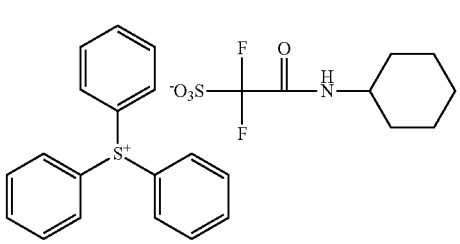
(z78) 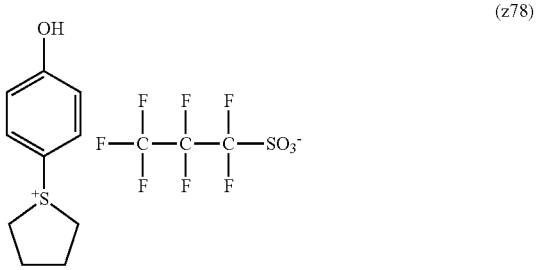
(z79) 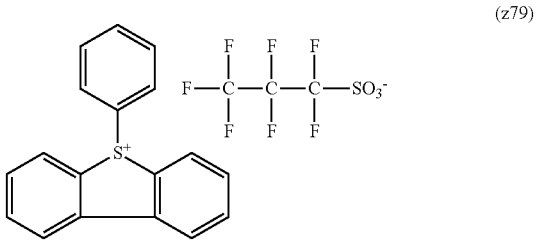
(z80) 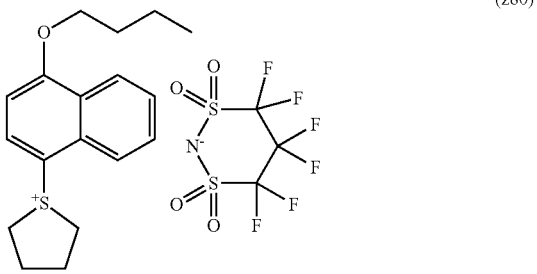
(z81) 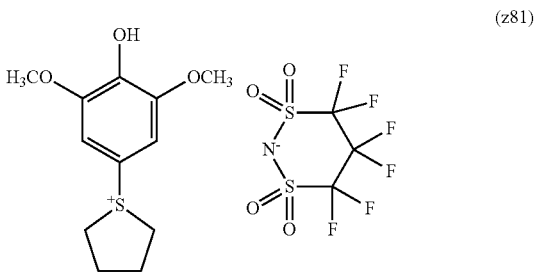
(z82) 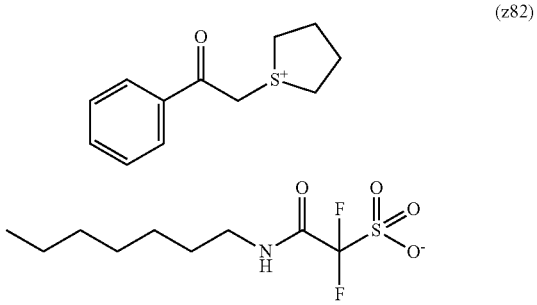

(z83) 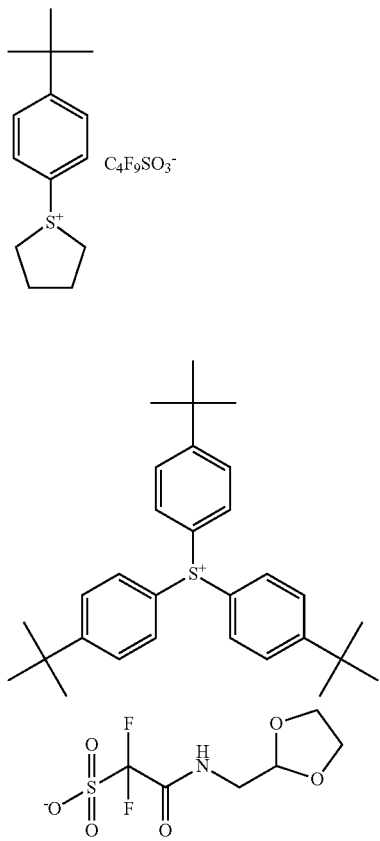
(z84)
(z85) 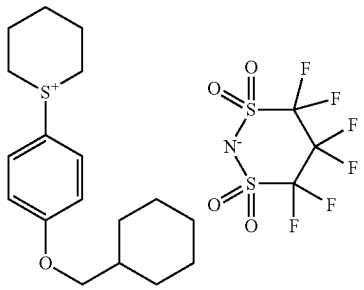
(z86) 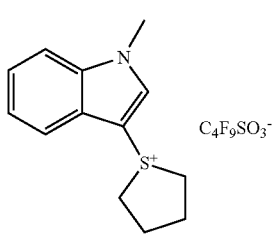
(z87) 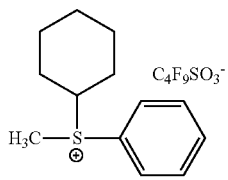
(z88) 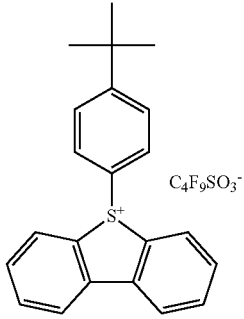
(z89) 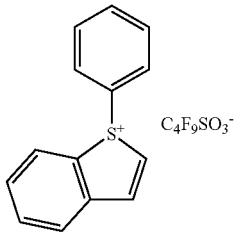
(z90) 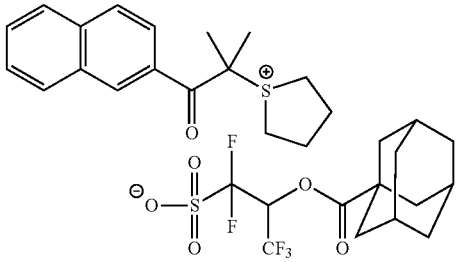
(z91) 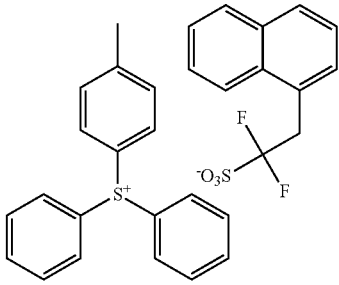
(z92) 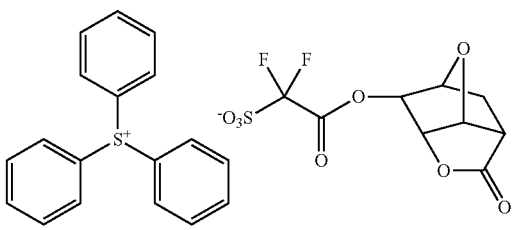
(z93) 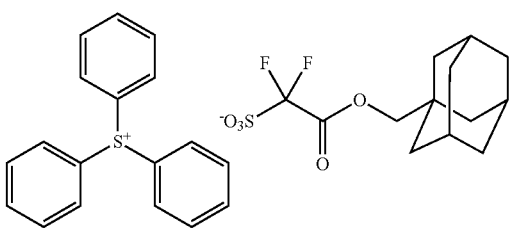

-continued (z94)
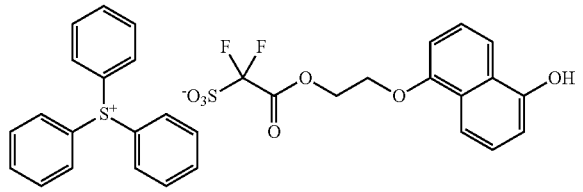

(z95)
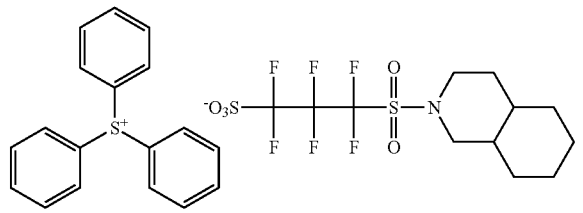

(z96)
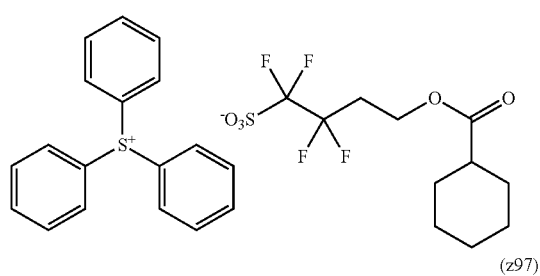

(z97)

(z98)
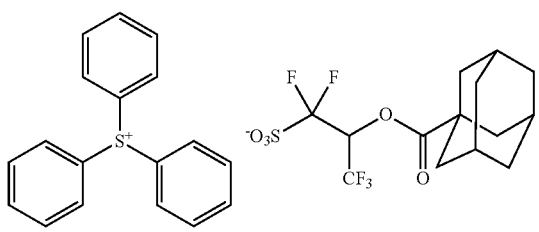

When the compound (B) is used in combination with the compound (B'), the mass ratio of used acid generator (compound (B)/compound (B')) is preferably in the range of 10/0 to 1/9, more preferably 10/0 to 13/7 and further more preferably 10/0 to 5/5.

<Resin (A)>

The resin (A) is a resin whose polarity is changed under the action of an acid. The composition of the present invention in its one form comprises a resin containing a group that when acted on by an acid, is decomposed (hereinafter also referred to as "resin (A1)") as the resin (A), and in its another form comprises a resin containing a phenolic hydroxyl group (hereinafter also referred to as "resin (A2)") as the resin (A).

[1] Resin (A1) containing a group that when acted on by an acid, is decomposed

The resin (A1) is a resin whose solubility in an alkali developer is increased under the action of an acid, or whose solubility in a developer comprising an organic solvent as its main component is decreased under the action of an acid. The resin (A1) contains a group (hereinafter also referred to as "acid-decomposable group") that when acted on by an acid, is decomposed to thereby produce an alkali-soluble group, which group is introduced in the principal chain or a side chain, or both the principal chain and a side chain, of the resin.

It is preferred for the resin (A1) to be insoluble or highly insoluble in an alkali developer.

It is preferred for the acid-decomposable group to have a structure in which an alkali-soluble group is protected by a group leaving by decomposition under the action of an acid. As the alkali-soluble group, there can be mentioned a phenolic hydroxyl group, a carboxyl group, a fluoroalcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

Preferred alkali-soluble groups include a carboxyl group, a fluoroalcohol group (preferably a hexafluoroisopropanol group) and a sulfonic acid group.

It is preferred for the acid-decomposable group to be a group resulting from the replacement of a hydrogen atom of such an alkali-soluble group with a group leaving under the action of an acid.

As the group leaving under the action of an acid, there can be mentioned, for example, $-C(R_{36})(R_{37})(R_{38})$, $-C(R_{36})(R_{37})(OR_{39})$, $-C(R_{01})(R_{02})(OR_{39})$ or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded to each other to thereby form a ring.

Each of $R_{01}$ and $R_{02}$ independently represents a hydrogen atom, an alkyl group, a cycloalkyl group, an aryl group, an aralkyl group or an alkenyl group.

It is preferred for the acid-decomposable group to be a cumyl ester group, an enol ester group, an acetal ester group, a tertiary alkyl ester group or the like. A tertiary alkyl ester group is more preferred.

The repeating unit containing an acid-decomposable group that can be introduced in the resin (A1) is preferably any of repeating units of general formula (AI) below.

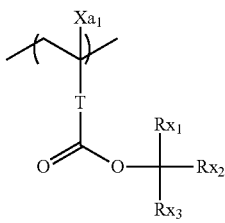

(AI)

In general formula (AI), $Xa_1$ represents a hydrogen atom or an optionally substituted alkyl group.

T represents a single bond or a bivalent connecting group.

Each of $Rx_1$ to $Rx_3$ independently represents an alkyl group (linear or branched) or a cycloalkyl group (mono- or polycycle).

Any two of $Rx_1$ to $Rx_3$ may be bonded to each other to thereby form a cycloalkyl group (mono- or polycycle).

As the optionally substituted alkyl group represented by $Xa_1$, there can be mentioned, for example, a methyl group or any of groups of the formula —$CH_2$—$R_{11}$. $R_{11}$ represents a halogen atom (e.g., a fluorine atom), a hydroxyl group or a monovalent organic group. $R_{11}$ is, for example, an alkyl group having up to 5 carbon atoms or an acyl group having up to 5 carbon atoms, preferably an alkyl group having up to 3 carbon atoms, and more preferably a methyl group. It is preferred for $Xa_1$ in its one form to be a hydrogen atom, a methyl group, a trifluoromethyl group, a hydroxymethyl group or the like.

As the bivalent connecting group represented by T, there can be mentioned an alkylene group, any of groups of the formula —COO-Rt-, any of groups of the formula —O-Rt- or the like. In the formulae, Rt represents an alkylene group or a cycloalkylene group.

T is preferably a single bond or any of groups of the formula —COO-Rt-. Rt is preferably an alkylene group having 1 to 5 carbon atoms, more preferably a —$CH_2$— group, a —$(CH_2)_2$— group or a —$(CH_2)_3$— group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a monocycloalkyl group, such as a cyclopentyl group or a cyclohexyl group, or a polycycloalkyl group, such as a norbornyl group, a tetracyclodecanyl group, a tetracyclododecanyl group or an adamantyl group.

The cycloalkyl group formed by the mutual bonding of two of $Rx_1$ to $Rx_3$ is preferably a monocycloalkyl group, such as a cyclopentyl group or a cyclohexyl group, or a polycycloalkyl group, such as a norbornyl group, a tetracyclodecanyl group, a tetracyclododecanyl group or an adamantyl group. A monocycloalkyl group having 5 or 6 carbon atoms is especially preferred.

In the cycloalkyl group formed by the mutual bonding of two of $Rx_1$ to $Rx_3$, for example, one of the methylene groups constructing the ring may be replaced by a heteroatom, such as an oxygen atom, or a group containing a heteroatom, such as a carbonyl group.

In a preferred form of the repeating units of general formula (AI), $Rx_1$ is a methyl group or an ethyl group, and $Rx_2$ and $Rx_3$ are bonded to each other to thereby form any of the above-mentioned cycloalkyl groups.

Substituents may be introduced in these groups. As the substituents, there can be mentioned, for example, an alkyl group (1 to 4 carbon atoms), a halogen atom, a hydroxyl group, an alkoxy group (1 to 4 carbon atoms), a carboxyl group, an alkoxycarbonyl group (2 to 6 carbon atoms) and the like. The number of carbon atoms of each of these substituents is preferably up to 8.

The content of repeating units containing acid-decomposable groups in total, based on all the repeating units of the resin (A1), is preferably in the range of 20 to 90 mol %, more preferably 25 to 85 mol % and further more preferably 30 to 80 mol %.

Particular examples of preferred repeating units containing acid-decomposable groups are shown below, which in no way limit the scope of the present invention.

In the particular examples, each of Rx and $Xa_1$ represents a hydrogen atom, $CH_3$, $CF_3$ or $CH_2OH$. Each of Rxa and Rxb represents an alkyl group having 1 to 4 carbon atoms. Z, or each of Z's independently, represents a substituent containing a polar group. In the formulae, p is 0 or a positive integer. As the substituent containing a polar group represented by Z, there can be mentioned, for example, a linear or branched alkyl group or cycloalkyl group each containing a hydroxyl group, a cyano group, an amino group, an alkylamido group or a sulfonamido group. An alkyl group containing a hydroxyl group is preferred. The branched alkyl group is most preferably an isopropyl group.

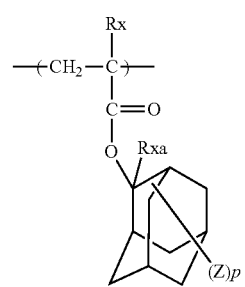

1

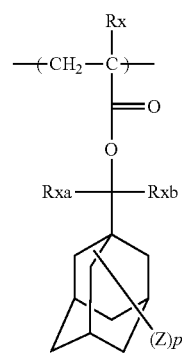

2

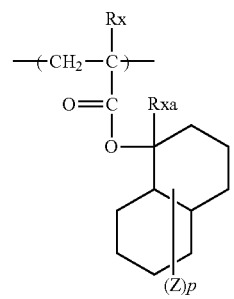

3

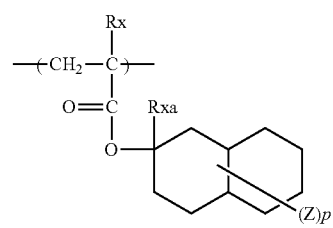

4

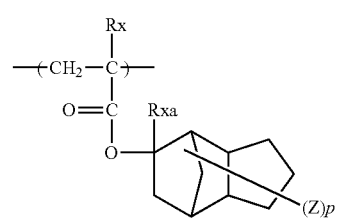

5

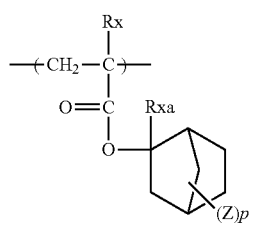
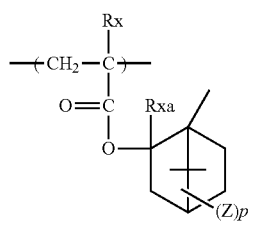
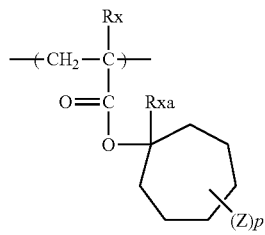
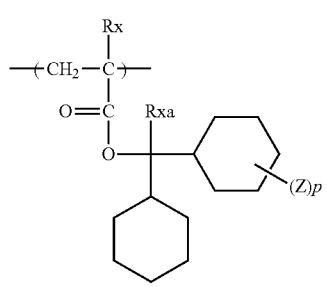
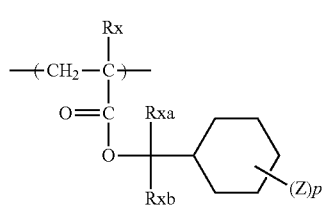
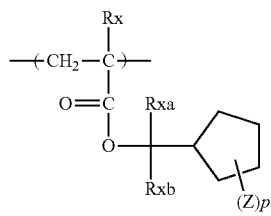
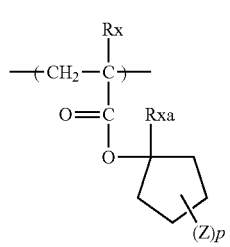
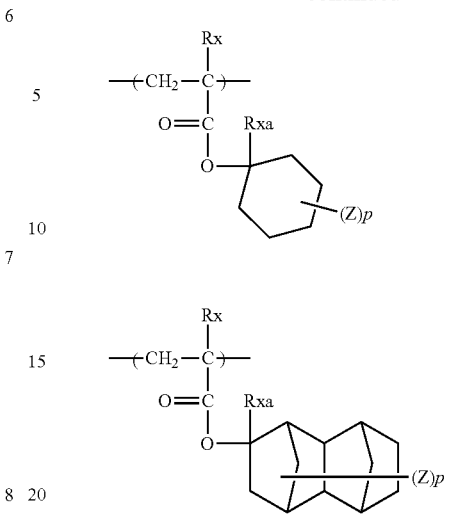
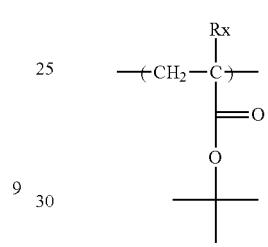
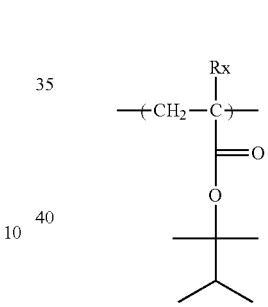
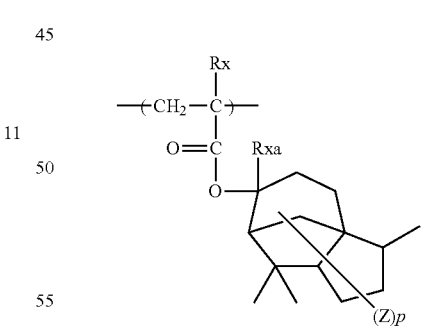
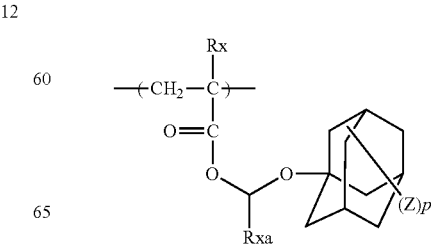

19

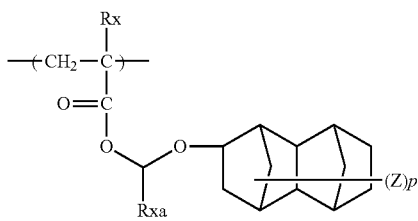

20

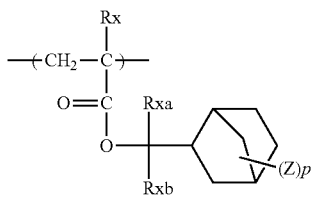

21

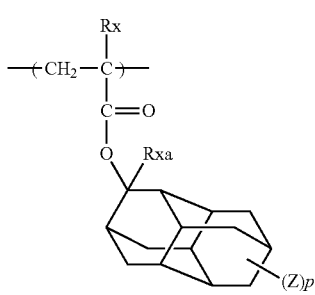

22

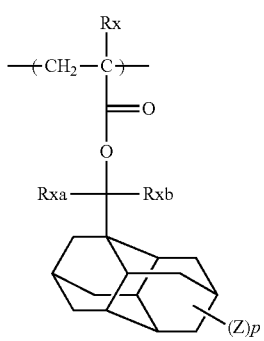

23

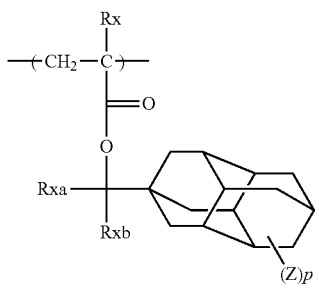

24

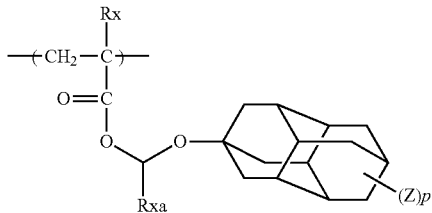

25

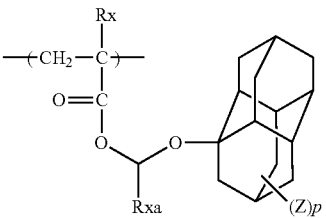

The resin (A1) preferably comprises, for example, any of repeating units of general formula (3) below as repeating units of general formula (AI).

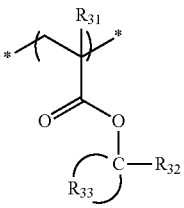

(3)

In general formula (3), $R_{31}$ represents a hydrogen atom or an alkyl group.

$R_{32}$ represents a methyl group, an ethyl group, an n-propyl group, an isopropyl group, an n-butyl group, an isobutyl group or a sec-butyl group.

$R_{33}$ represents an atomic group required for forming a monoalicyclic hydrocarbon structure in cooperation with the carbon atom to which $R_{32}$ is bonded. In the alicyclic hydrocarbon structure, the carbon atoms constructing the ring may partially be replaced by a heteroatom or a group containing a heteroatom.

A substituent may be introduced in the alkyl group represented by $R_{31}$. The substituent is, for example, a fluorine atom or a hydroxyl group.

$R_{31}$ is preferably a hydrogen atom, a methyl group, a trifluoromethyl group or a hydroxymethyl group.

$R_{32}$ is preferably a methyl group, an ethyl group, an n-propyl group or an isopropyl group. $R_{32}$ is more preferably a methyl group or an ethyl group.

The monoalicyclic hydrocarbon structure formed by $R_{33}$ in cooperation with the carbon atom is preferably a 3- to 8-membered ring, more preferably a 5- or 6-membered ring.

In the monoalicyclic hydrocarbon structure formed by $R_{33}$ in cooperation with the carbon atom, the heteroatom as a constituent of the ring is, for example, an oxygen atom or a sulfur atom. As the group containing a heteroatom, there can be mentioned a carbonyl group or the like. Preferably, the group containing a heteroatom is not an ester group (ester bond).

It is preferred for the monoalicyclic hydrocarbon structure formed by $R_{33}$ in cooperation with the carbon atom to be comprised only of a carbon atom and a hydrogen atom.

The repeating units of general formula (3) are preferably repeating units of general formula (3') below.

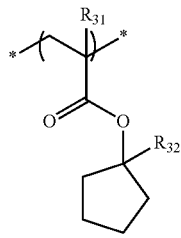
(3')
In general formula (3'), $R_{31}$ and $R_{32}$ are as defined above in connection with general formula (3).
Nonlimiting particular examples of the repeating units with the structure of general formula (3) are shown below.
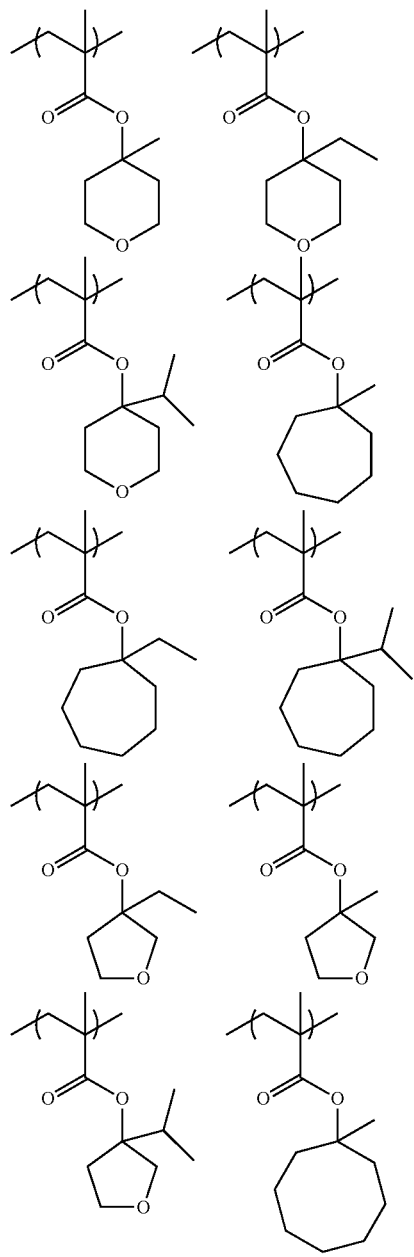
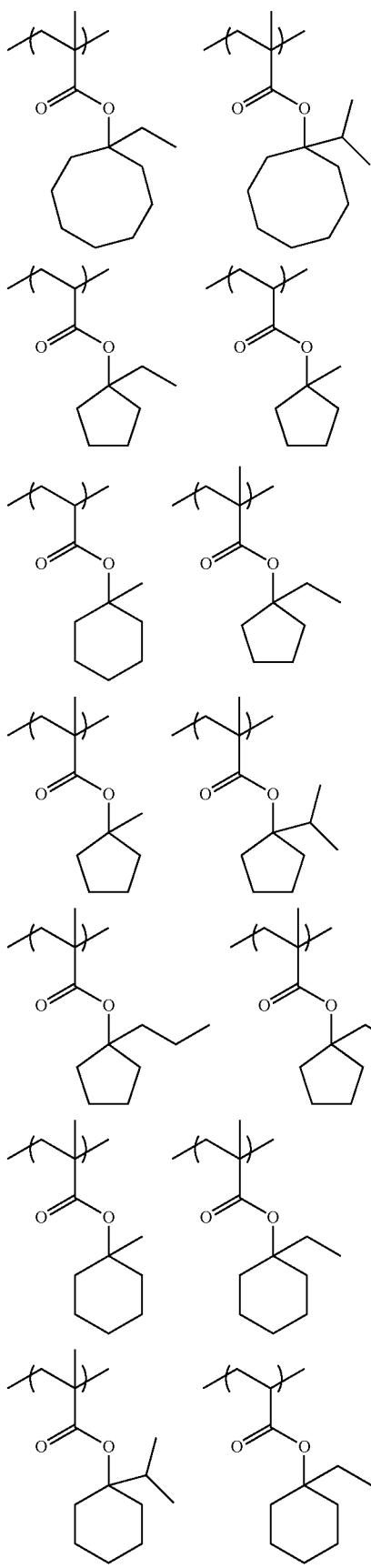

-continued

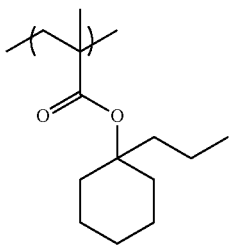

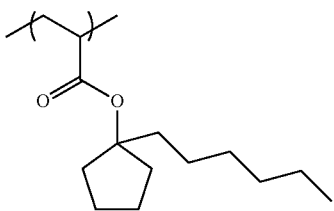

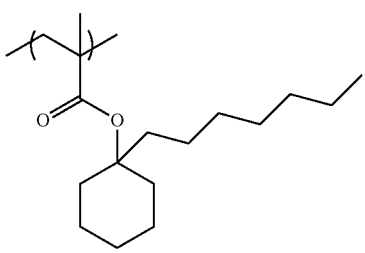

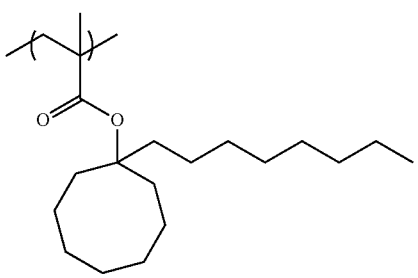

The content of repeating unit with the structure of general formula (3), based on all the repeating units of the resin (A1), is preferably in the range of 20 to 80 mol %, more preferably 25 to 75 mol % and further more preferably 30 to 70 mol %.

Further preferably, the resin (A1) is a resin comprising, as the repeating units of general formula (AI), for example, at least any of the repeating units of general formula (I) below and repeating units of general formula (II) below.

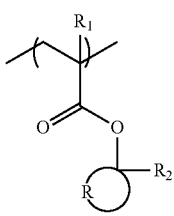

(I)

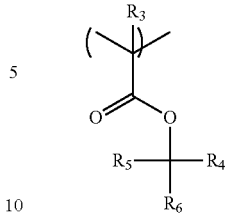

(II)

In general formulae (I) and (II),
each of $R_1$ and $R_3$ independently represents a hydrogen atom, an optionally substituted methyl group or any of groups of the formula —$CH_2$—$R_{11}$. $R_{11}$ represents a monovalent organic group.

Each of $R_2$, $R_4$, $R_5$ and $R_6$ independently represents an alkyl group or a cycloalkyl group.

R represents an atomic group required for forming an alicyclic structure in cooperation with the carbon atom to which $R_2$ is bonded.

Each of $R_1$ and $R_3$ is preferably a hydrogen atom, a methyl group, a trifluoromethyl group or a hydroxymethyl group.

Particular examples and preferred examples of the monovalent organic groups represented by $R_{11}$ are the same as set forth above in connection with $R_{11}$ in general formula (AI).

The alkyl group represented by $R_2$ may be linear or branched, and a substituent may be introduced therein.

The cycloalkyl group represented by $R_2$ may be monocyclic or polycyclic, and a substituent may be introduced therein.

$R_2$ is preferably an alkyl group, more preferably an alkyl group having 1 to 10 carbon atoms, further more preferably 1 to 5 carbon atoms. As examples thereof, there can be mentioned a methyl group, an ethyl group and the like.

R represents an atomic group required for forming an alicyclic structure in cooperation with the carbon atom. The alicyclic structure formed by R in cooperation with the carbon atom is preferably a monoalicyclic structure, which preferably has 3 to 7 carbon atoms, more preferably 5 or 6 carbon atoms.

$R_3$ is preferably a hydrogen atom or a methyl group, more preferably a methyl group.

Each of the alkyl groups represented by $R_4$, $R_5$ and $R_6$ may be linear or branched, and a substituent may be introduced therein. The alkyl groups are preferably those each having 1 to 4 carbon atoms, such as a methyl group, an ethyl group, an n-propyl group, an isopropyl group, an n-butyl group, an isobutyl group and a t-butyl group.

Each of the cycloalkyl groups represented by $R_4$, $R_5$ and $R_6$ may be monocyclic or polycyclic, and a substituent may be introduced therein. The cycloalkyl groups are preferably a monocycloalkyl group, such as a cyclopentyl group or a cyclohexyl group, and a polycycloalkyl group, such as a norbornyl group, a tetracyclodecanyl group, a tetracyclododecanyl group or an adamantyl group.

The substituents introducible in these groups are the same as set forth above in connection with the groups in general formula (AI).

It is preferred for the acid-decomposable resin to be a resin comprising any of repeating units of general formula (I) and any of repeating units of general formula (II) as the repeating units of general formula (AI).

The acid-decomposable resin in another form thereof is preferably a resin comprising at least two of repeating units of general formula (I) as the repeating units of general formula (AI). When the acid-decomposable resin comprises at least two of repeating units of general formula (I), it is preferred for the acid-decomposable resin to comprise both a repeating unit with an alicyclic structure wherein the alicyclic structure formed by R in cooperation with the carbon atom is monocyclic and a repeating unit with an alicyclic structure wherein the alicyclic structure formed by R in cooperation with the carbon atom is polycyclic. The monoalicyclic structure preferably has 5 to 8 carbon atoms, more preferably 5 or 6 carbon atoms and most preferably 5 carbon atoms. The polyalicyclic structure is preferably a norbornyl group, a tetracyclodecanyl group, a tetraclododecanyl group or an adamantyl group.

The resin (A1) may comprise one type of repeating unit containing an acid-decomposable group, or may comprise two or more types thereof in combination. When two or more types thereof are used in combination, the following combinations are preferred. In the formulae, each of R's independently represents a hydrogen atom or a methyl group.

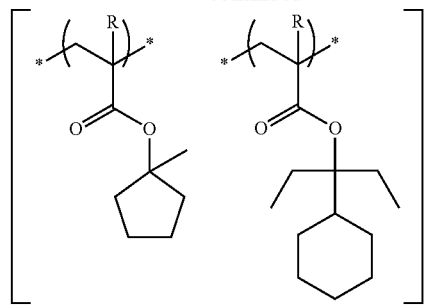

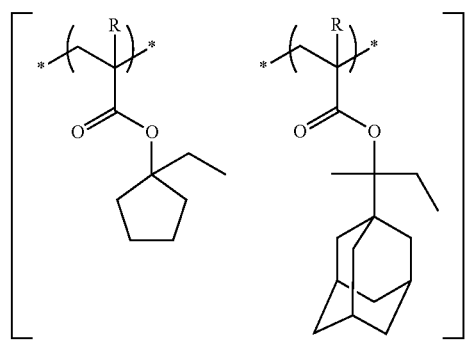

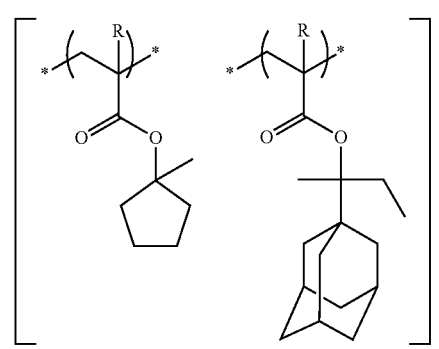

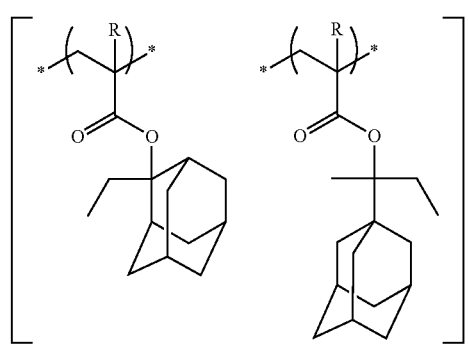

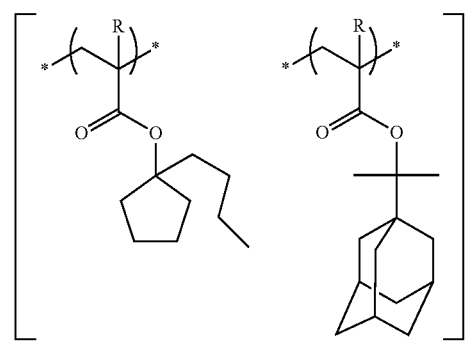

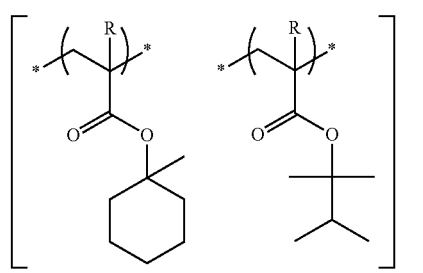

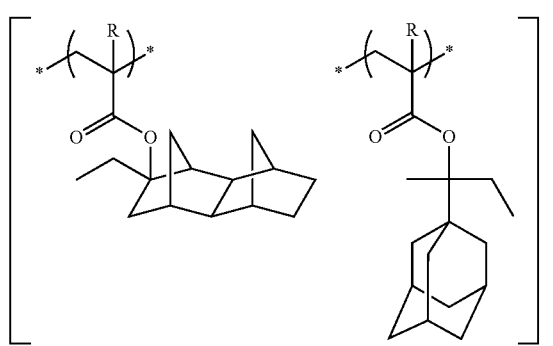

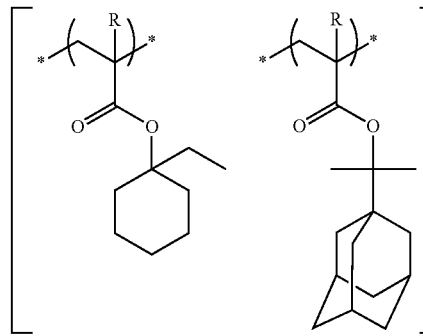

-continued
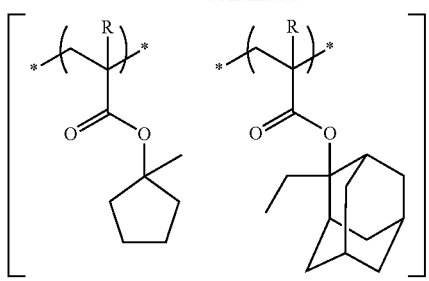
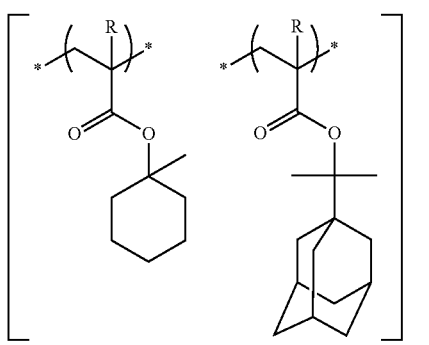
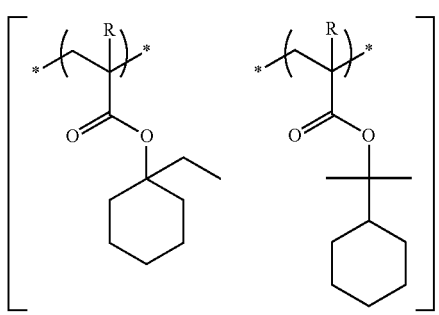
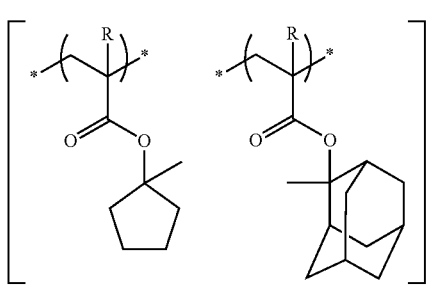
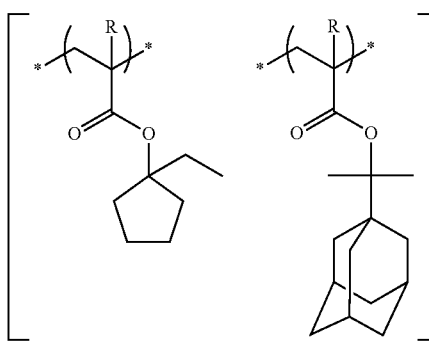
-continued
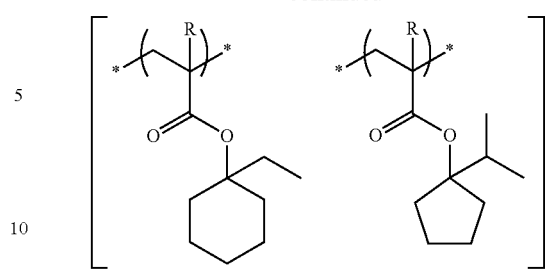
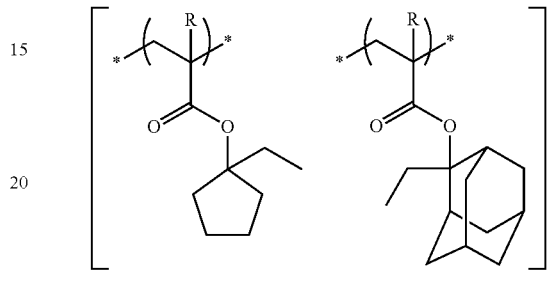
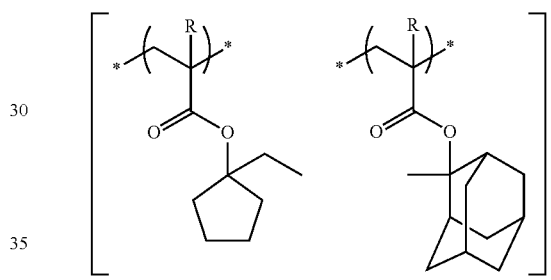
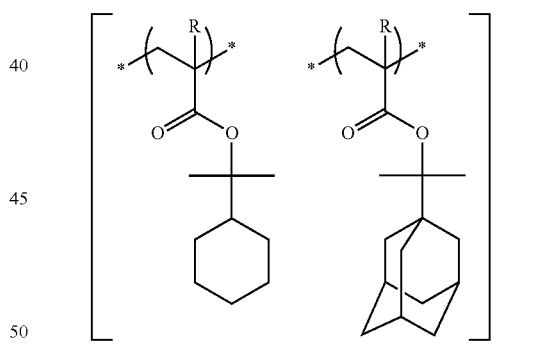
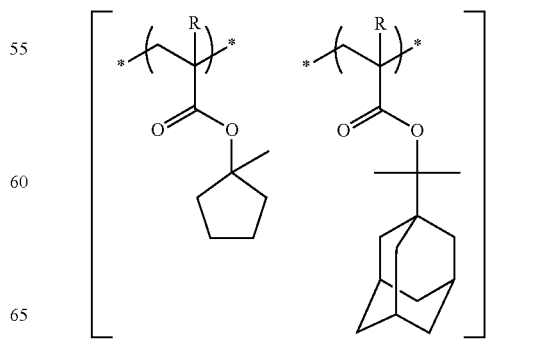

-continued

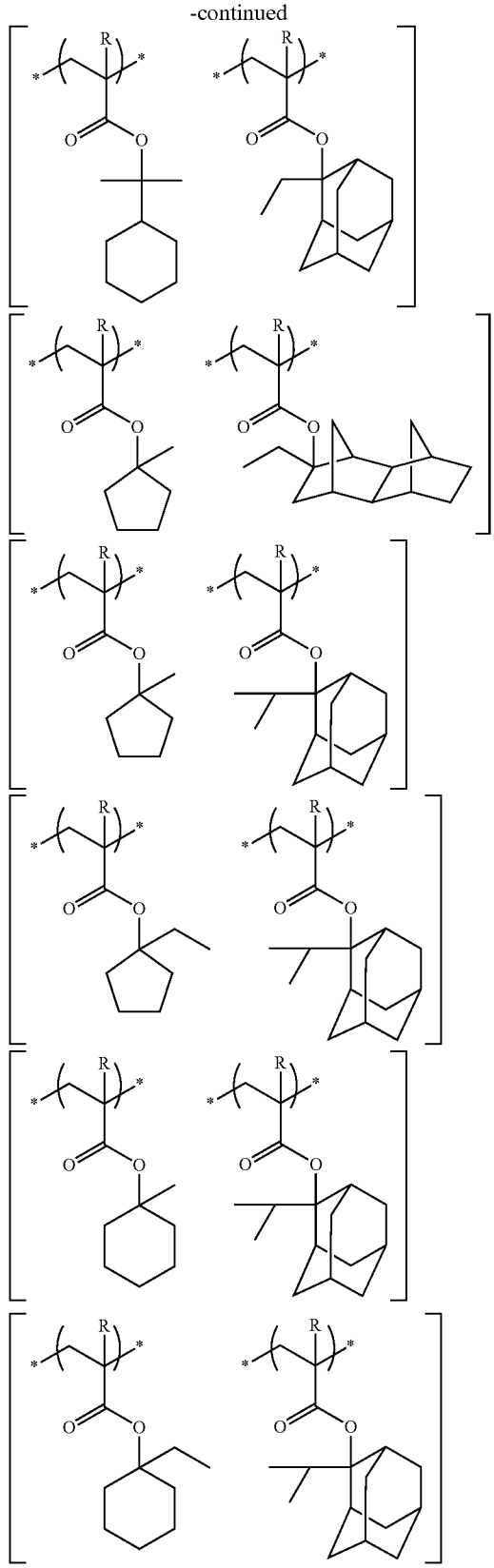

The resin (A1) in its one form preferably comprises a repeating unit with a cyclic carbonic ester structure. This cyclic carbonic ester structure is a structure with a ring containing the bond of the formula —O—C(=O)—O— as an atomic group constructing a ring. The ring containing the bond of the formula —O—C(=O)—O— as an atomic group constructing a ring is preferably a 5- to 7-membered ring, most preferably a 5-membered ring. This ring may be condensed with another ring to thereby form a condensed ring.

It is preferred for the resin (A1) to contain a repeating unit with a lactone structure or a sultone (cyclosulfonic ester) structure.

Lactone and sultone groups are not particularly limited as long as lactone and sultone structures are contained respectively. A 5- to 7-membered ring lactone or sultone structure is preferred, and one resulting from the condensation of a 5- to 7-membered ring lactone or sultone structure with another cyclic structure effected in a fashion to form a bicyclo structure or spiro structure is also preferred. More preferably, the resin comprises a repeating unit with any of the lactone and sultone structures of general formulae (LC1-1) to (LC1-17) and (SL1-1) and (SL1-2) below. The lactone or sultone structure may be directly bonded to the principal chain of the resin. Preferred lactone and sultone structures are those of formulae (LC1-1), (LC1-4), (LC1-5) and (LC1-8). Lactone structure (LC1-4) is more preferred. Using these specified lactone and sultone structures enhances LWR characteristic and reduces development defects.

LC1-1

LC1-2

LC1-3

LC1-4

LC1-5

LC1-6
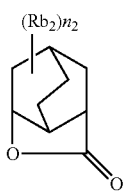

LC1-7
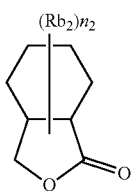

LC1-8
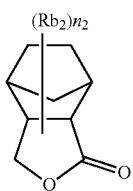

LC1-9
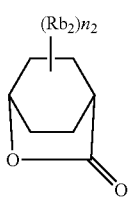

LC1-10
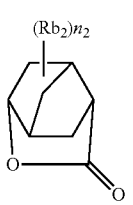

LC1-11
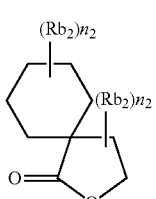

LC1-12
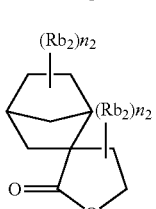

LC1-13
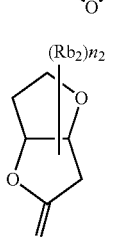

LC1-14
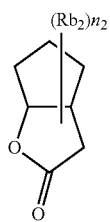

LC1-15
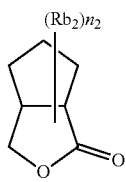

LC1-16
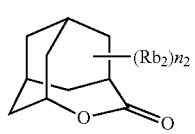

LC1-17
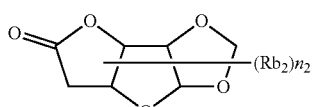

SL1-1
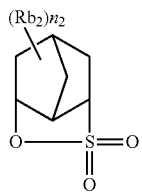

SL1-2

A substituent ($Rb_2$) is optionally introduced in the portion of the lactone or sultone structure. As preferred substituents ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, an acid-decomposable group and the like. An alkyl group having 1 to 4 carbon atoms, a cyano group and an acid-decomposable group are more preferred. In the formulae, $n_2$ is an integer of 0 to 4. When $n_2$ is 2 or greater, the plurality of introduced substituents ($Rb_2$) may be identical to or different from each other. Further, the plurality of introduced substituents ($Rb_2$) may be bonded to each other to thereby form a ring.

It is preferred for the resin (A1) to comprise a repeating unit with any of lactone and sultone structures of general formula (III) below.

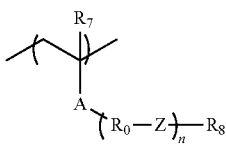

(III)

In formula (III),

A represents an ester bond (group expressed by —COO—) or an amide bond (group expressed by —CONH—).

$R_0$, or each of $R_0$s independently, represents an alkylene group, a cycloalkylene group or a combination thereof.

Z, or each of Z's independently, represents a single bond, an ether bond, an ester bond, an amide bond, any of urethane bonds of the formula:

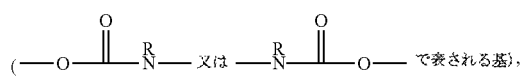

or any of urea bonds of the formula:

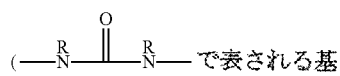

in which each of R's independently represents a hydrogen atom, an alkyl group, a cycloalkyl group or an aryl group.

$R_8$ represents a monovalent organic group with a lactone structure or sultone structure.

In the general formula, n is the number of repetitions of the structure —$R_0$—Z—, being an integer of 0 to 2.

$R_7$ represents a hydrogen atom, a halogen atom or an alkyl group.

Substituents may be introduced in the alkylene group and cycloalkylene group represented by $R_0$.

Z is preferably an ether bond or an ester bond, most preferably an ester bond.

The alkyl group represented by $R_7$ is preferably an alkyl group having 1 to 4 carbon atoms, more preferably a methyl group or an ethyl group and most preferably a methyl group. Substituents may be introduced in the alkylene group and cycloalkylene group represented by $R_0$ and alkyl group represented by $R_7$. As substituents, there can be mentioned, for example, a halogen atom, such as a fluorine atom, a chlorine atom or a bromine atom; a mercapto group; a hydroxyl group; an alkoxy group, such as a methoxy group, an ethoxy group, an isopropoxy group, a t-butoxy group or a benzyloxy group; an acetoxy group, such as an acetyloxy group or a propionyloxy group. $R_7$ is preferably a hydrogen atom, a methyl group, a trifluoromethyl group or a hydroxymethyl group.

The chain alkylene group represented by $R_0$ is preferably a chain alkylene having 1 to 10 carbon atoms, more preferably 1 to 5 carbon atoms, for example, a methylene group, an ethylene group, a propylene group or the like. The cycloalkylene group is preferably a cycloalkylene having 3 to 20 carbon atoms. As such, there can be mentioned, for example, a cyclohexylene group, a cyclopentylene group, a norbornylene group, an adamantylene group or the like. The chain alkylene groups are preferred from the viewpoint of the exertion of the effect of the present invention. A methylene group is most preferred.

The monovalent organic group with a lactone structure or sultone structure represented by $R_8$ is not limited as long as a lactone structure or sultone structure is contained. As particular examples thereof, there can be mentioned the lactone structures and sultone structures of general formulae (LC1-1) to (LC1-17) and (SL1-1) and (SL1-2) above. Of these, the structure of general formula (LC1-4) is most preferred. In the general formulae (LC1-1) to (LC1-17) and (SL1-1) and (SL1-2), $n_2$ is preferably 2 or less.

$R_8$ is preferably a monovalent organic group with an unsubstituted lactone structure or sultone structure, or a monovalent organic group with a lactone structure or sultone structure substituted with a methyl group, a cyano group or an alkoxycarbonyl group. More preferably, $R_8$ is a monovalent organic group with a lactone structure substituted with a cyano group (cyanolactone) or a sultone structure substituted with a cyano group (cyanosultone).

In general formula (III), n is preferably 1 or 2.

Specific examples of the repeating units containing the groups with a lactone structure or sultone structure of general formula (III) are shown below, which in no way limit the scope of the present invention.

In the following specific examples, R represents a hydrogen atom, an optionally substituted alkyl group or a halogen atom. Preferably, R is a hydrogen atom, a methyl group, a hydroxymethyl group or an acetoxymethyl group.

In the following formulae, Me represents a methyl group.

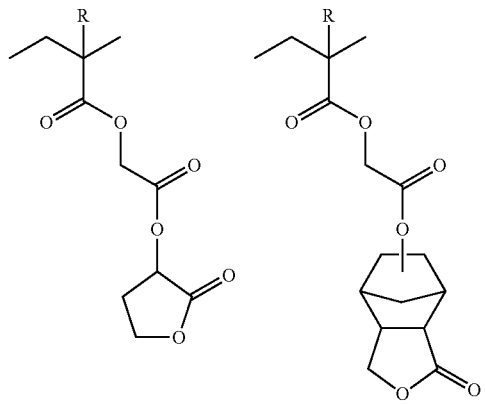

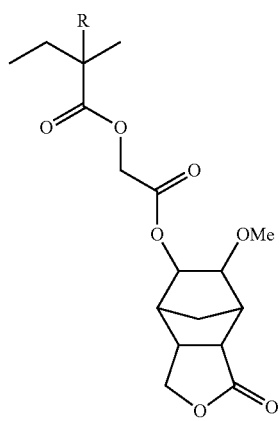

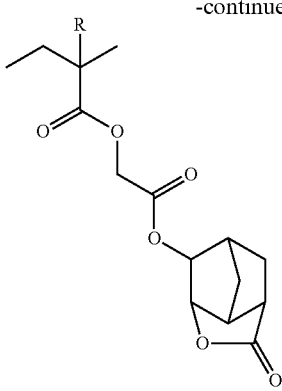

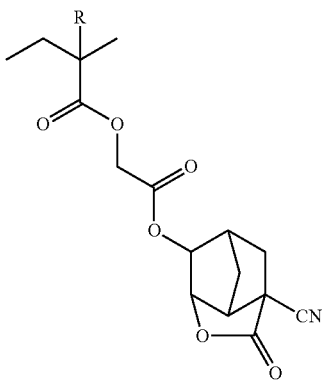

The repeating units with a lactone structure or sultone structure are preferably repeating units of general formulae (III-1) and (III-1') below.

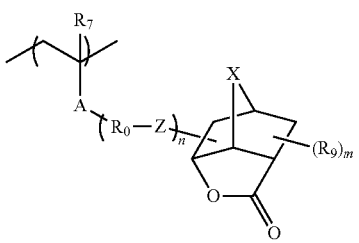

(III-1)

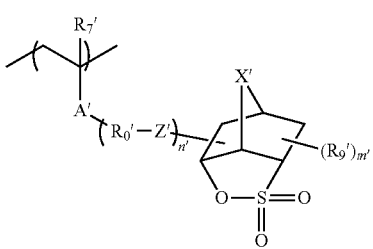

(III-1')

In general formulae (III-1) and (III-1'),

R$_7$, A, R$_0$, Z and n are as defined above in connection with general formula (III).

R$_7$', A', R$_0$', Z' and n' are respectively the same as R$_7$, A, R$_0$, Z and n in general formula (III) above.

R$_9$, or each of R$_9$s independently, represents an alkyl group, a cycloalkyl group, an alkoxycarbonyl group, a cyano group, a hydroxyl group or an alkoxy group, provided that any two of two or more R$_9$s may be bonded to each other to thereby form a ring.

R$_9$', or each of R$_9$'s independently, represents an alkyl group, a cycloalkyl group, an alkoxycarbonyl group, a cyano group, a hydroxyl group or an alkoxy group, provided that any two of two or more R$_9$'s may be bonded to each other to thereby form a ring.

Each of X and X' independently represents an alkylene group, an oxygen atom or a sulfur atom.

Each of m and m' means the number of substituents, being independently an integer of 0 to 5, preferably 0 or 1.

Each of the alkyl groups represented by R$_9$ and R$_9$' is preferably an alkyl group having 1 to 4 carbon atoms, more preferably a methyl group or an ethyl group and most preferably a methyl group. As the cycloalkyl group, there can be mentioned a cyclopropyl group, a cyclobutyl group, a cyclopentyl group or a cyclohexyl group. As the alkoxycarbonyl group, there can be mentioned a methoxycarbonyl group, an ethoxycarbonyl group, an n-butoxycarbonyl group, a t-butoxycarbonyl group or the like. As the alkoxy group, there can be mentioned a methoxy group, an ethoxy group, a propoxy group, an isopropoxy group, a butoxy group or the like. Substituents may be introduced in these groups. As such substituents, there can be mentioned a hydroxyl group; an alkoxy group, such as a methoxy group or an ethoxy group; a cyano group; and a halogen atom, such as a fluorine atom. Each of R$_9$ and R$_9$' is preferably a methyl group, a cyano group or an alkoxycarbonyl group, more preferably a cyano group.

As the alkylene groups represented by X and X', there can be mentioned a methylene group, an ethylene group and the like. Each of X and X' is preferably an oxygen atom or a methylene group, more preferably a methylene group.

When m or m' is 1 or greater, it is preferred for the substitution with at least one R$_9$ or R$_9$' to take place at the α- or β-position to the carbonyl group of the lactone or sulfonyl group of the sultone. The substitution at the α-position is especially preferred.

Particular examples of the repeating units with a lactone structure or sultone structure of general formulae (III-1) and (III-1') are shown below, which in no way limit the scope of the present invention. In the particular examples, R represents a hydrogen atom, an optionally substituted alkyl group or a halogen atom. Preferably, R is a hydrogen atom, a methyl group, a hydroxymethyl group or an acetoxymethyl group.

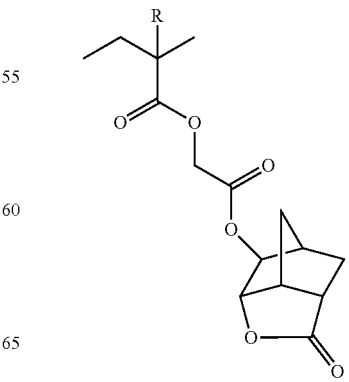

-continued
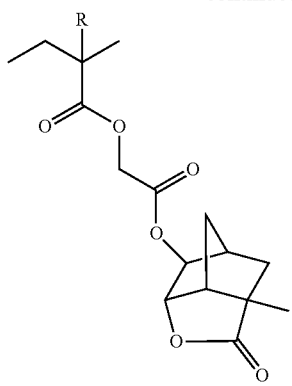
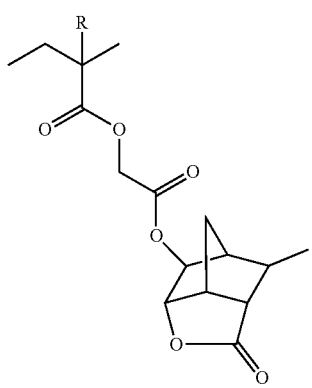
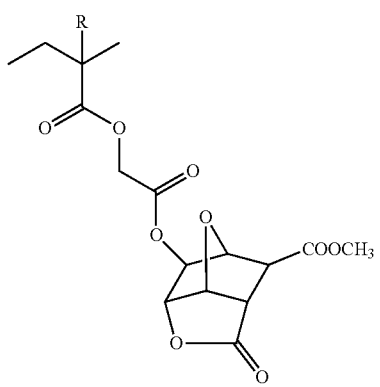
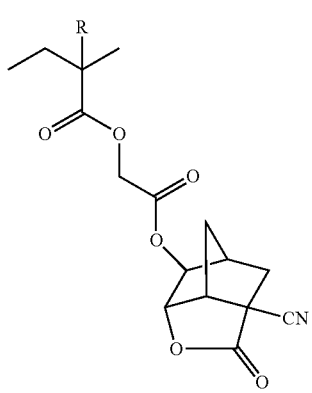
-continued
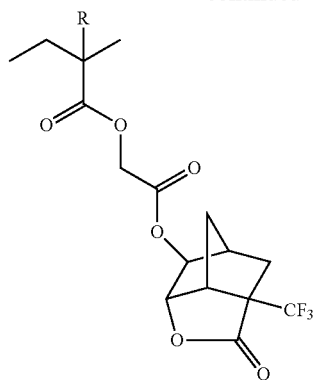
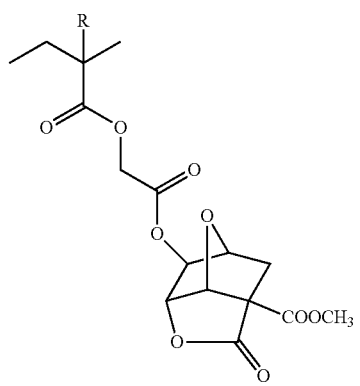
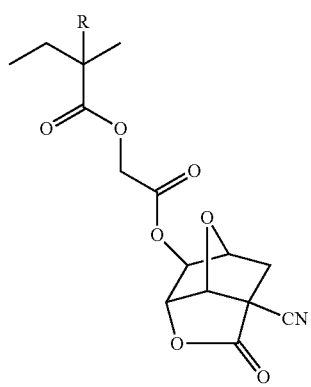
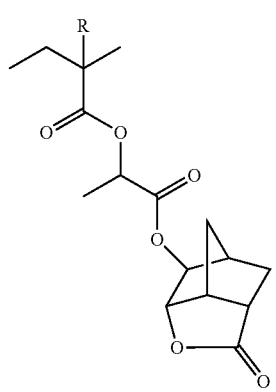

85
-continued
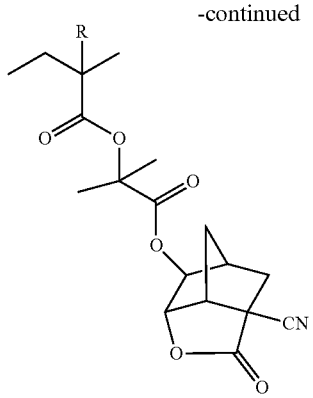
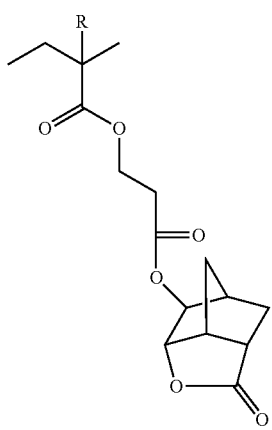
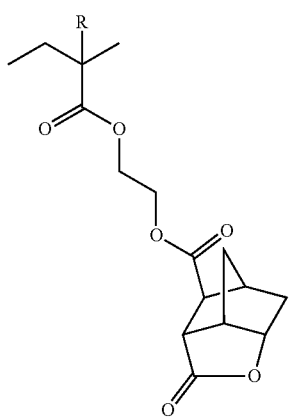
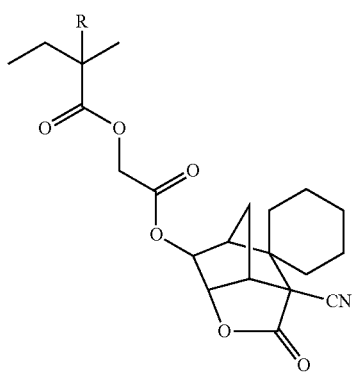
86
-continued
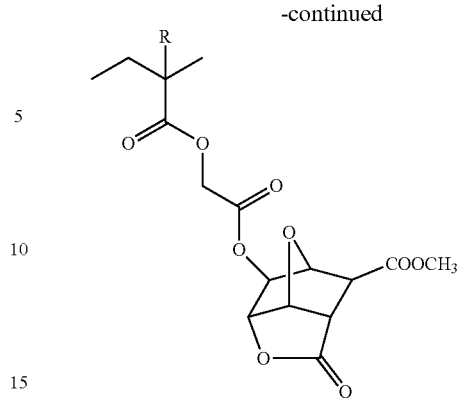
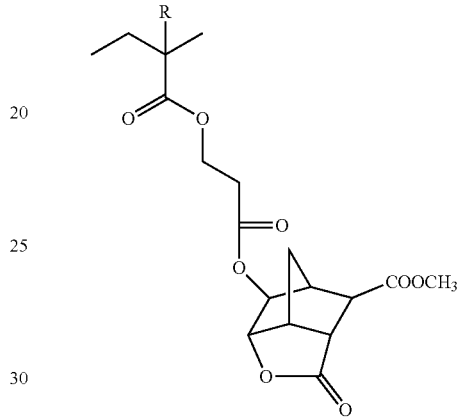
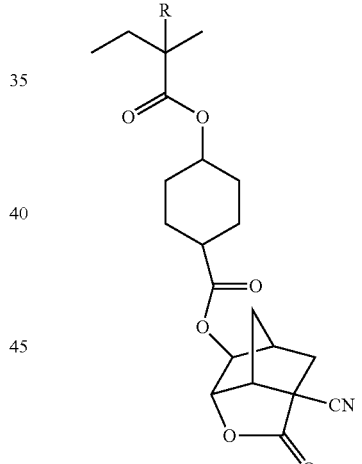
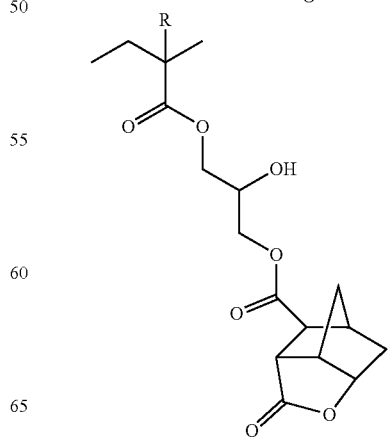

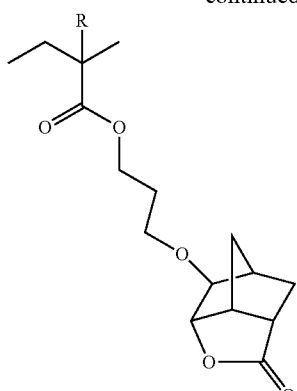

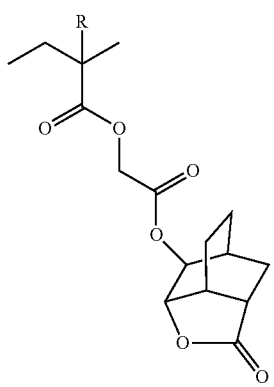

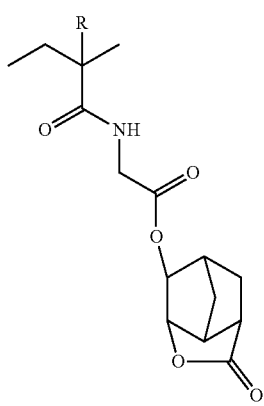

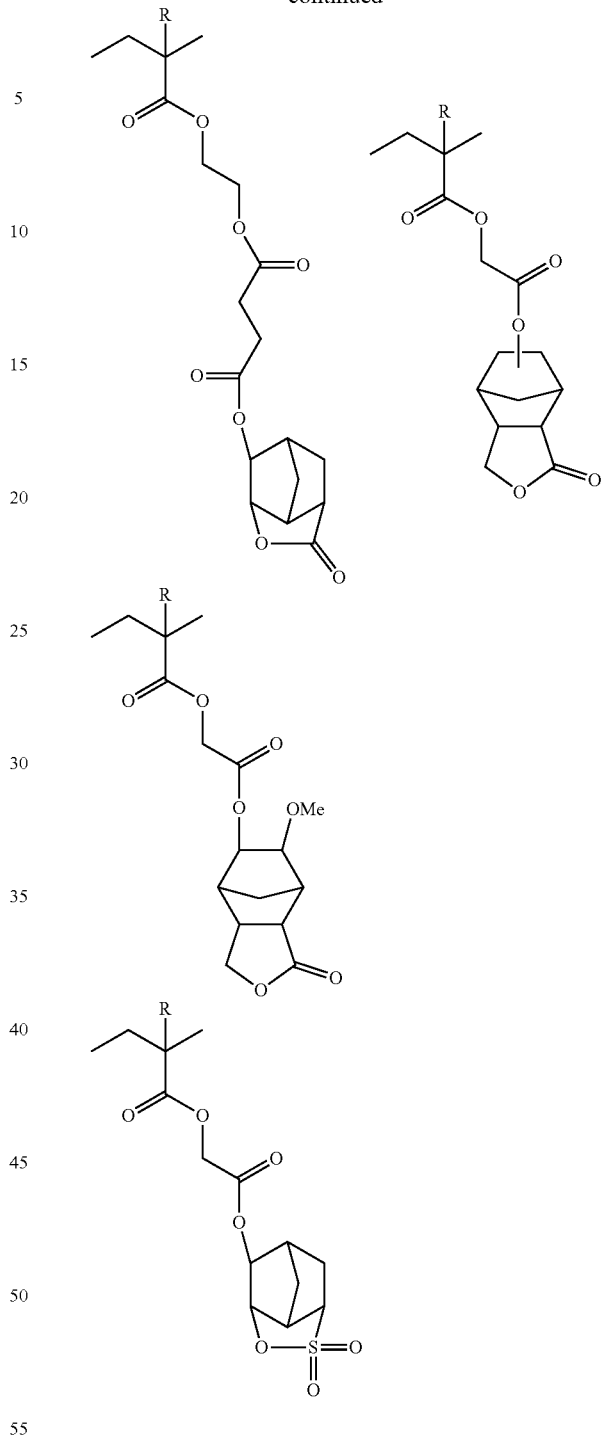

The content of repeating unit expressed by general formula (III) or repeating units expressed by general formula (III) in total, based on all the repeating units of the resin (A1), is preferably in the range of 15 to 60 mol %, more preferably 20 to 60 mol % and further more preferably 30 to 50 mol %.

The resin (A1) may comprise any of the above-mentioned repeating units with a lactone structure or sultone structure other than the repeating units of general formula (III).

Particular examples of repeating units containing a lactone group or sultone group, in addition to the above particular examples, are shown below, which in no way limit the scope of the present invention. In the particular examples, Rx represents H, CH₃, CH₂OH or CF₃.
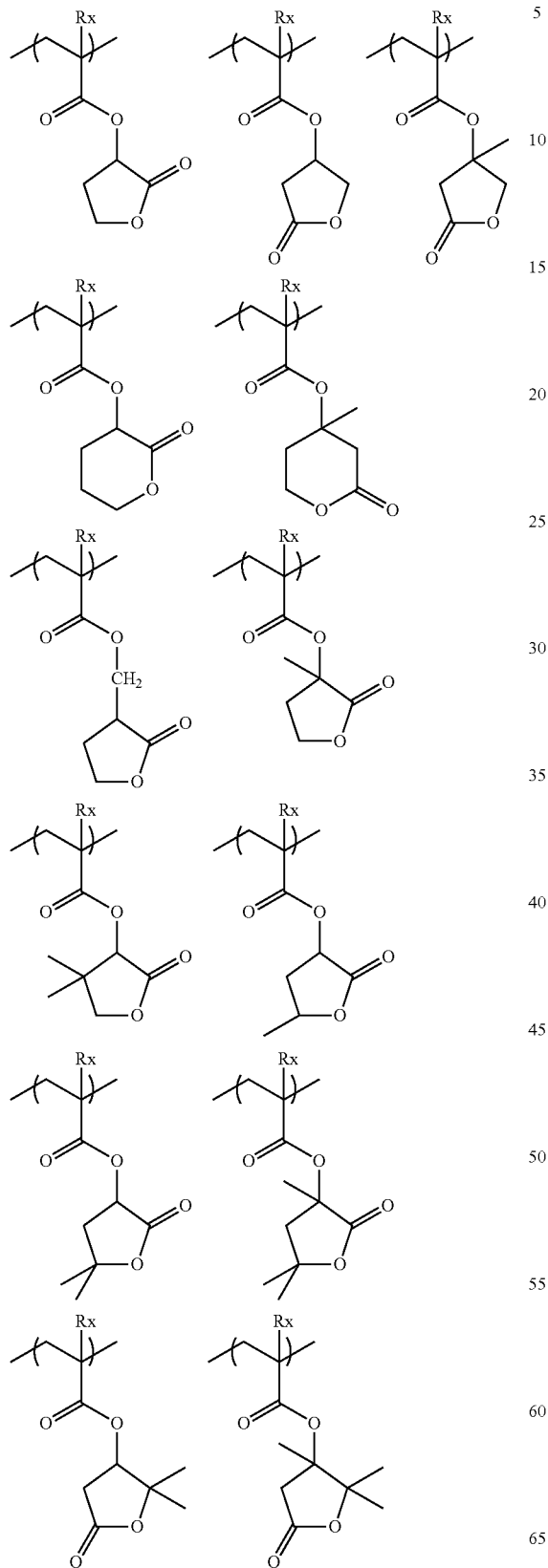
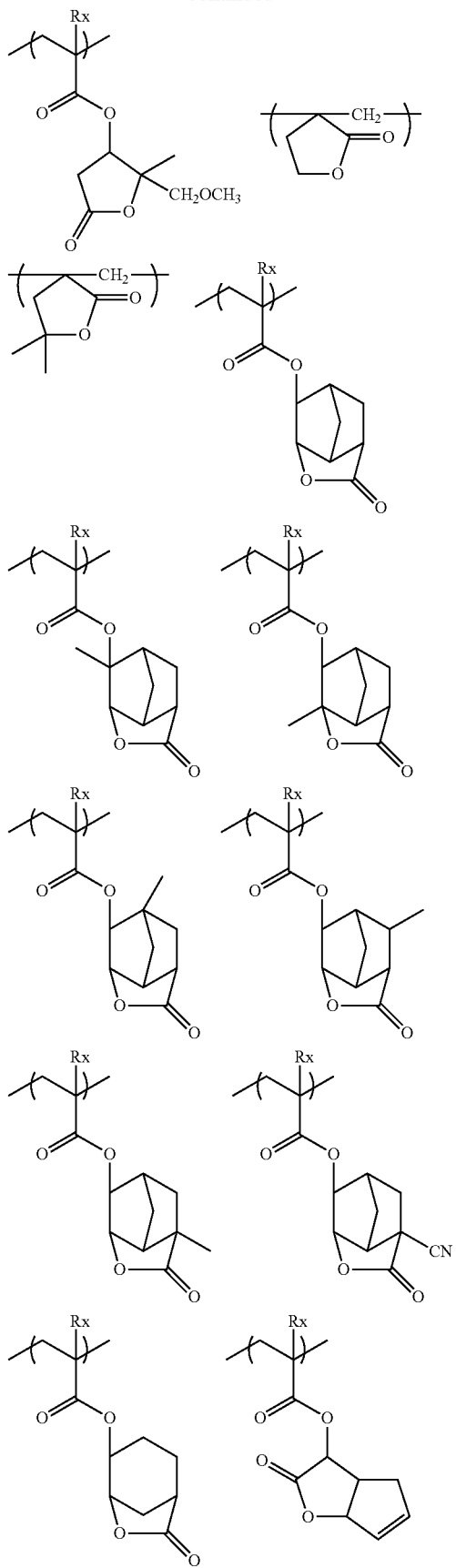

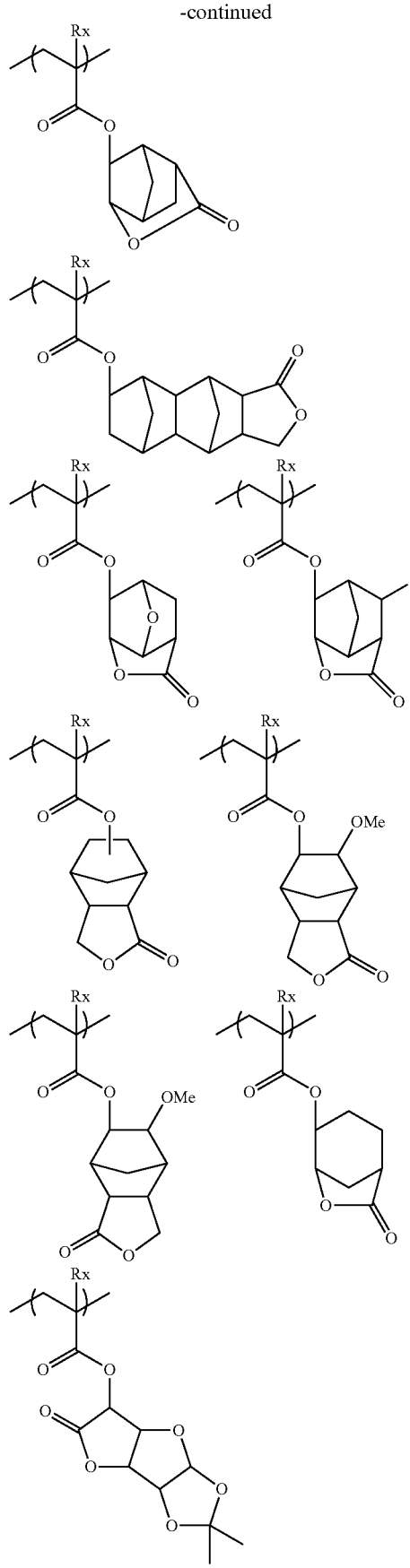
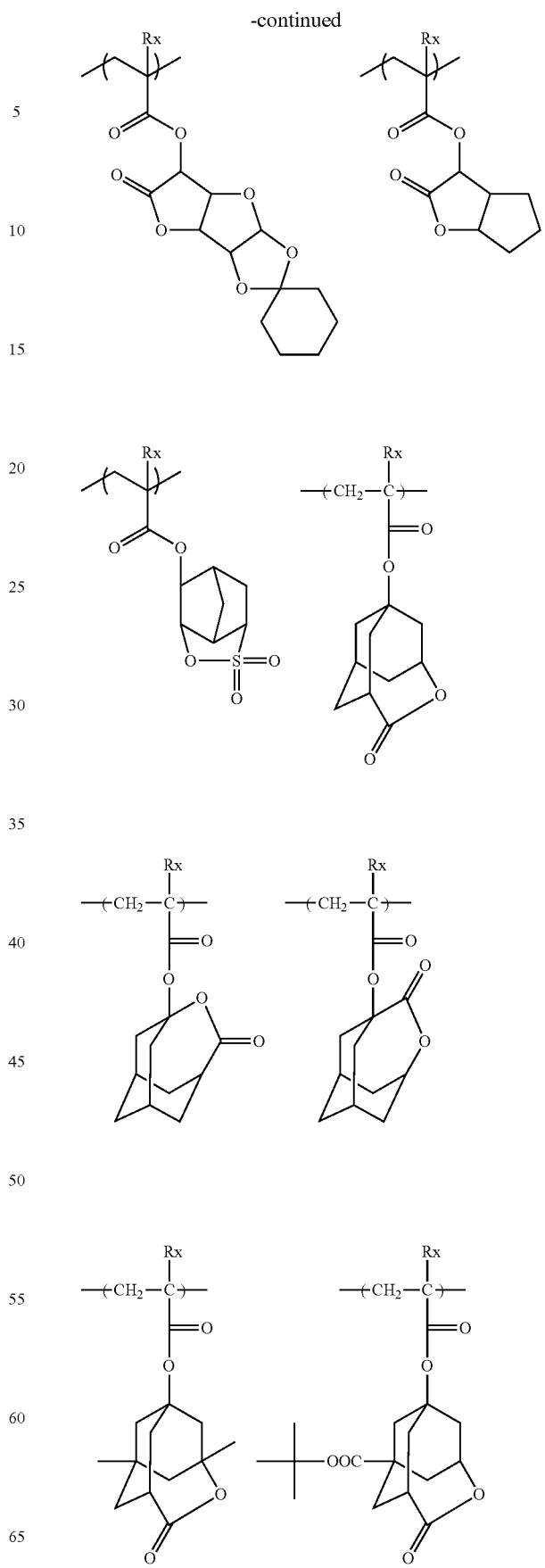

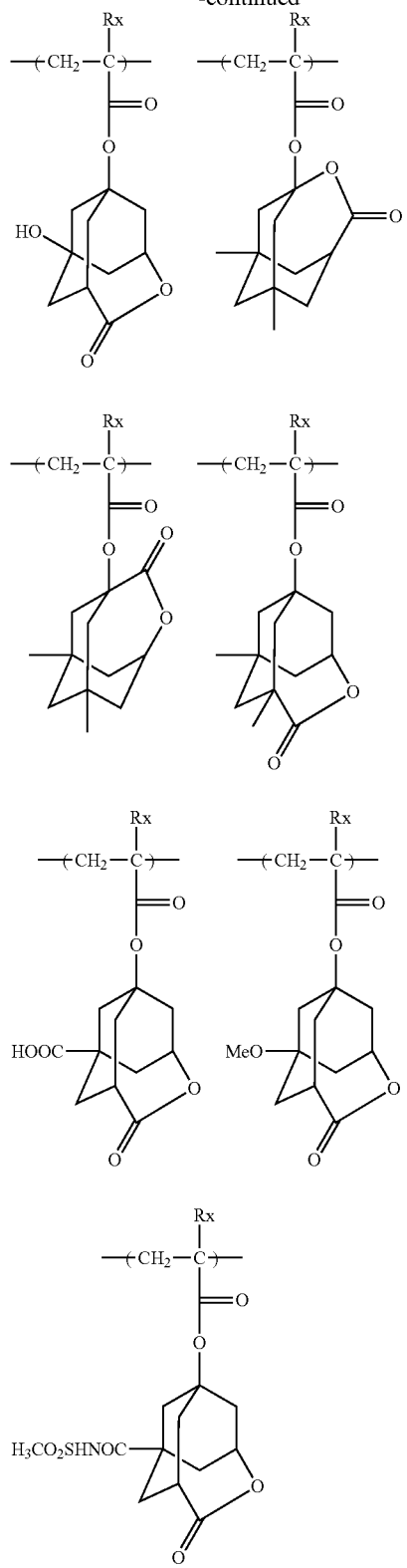

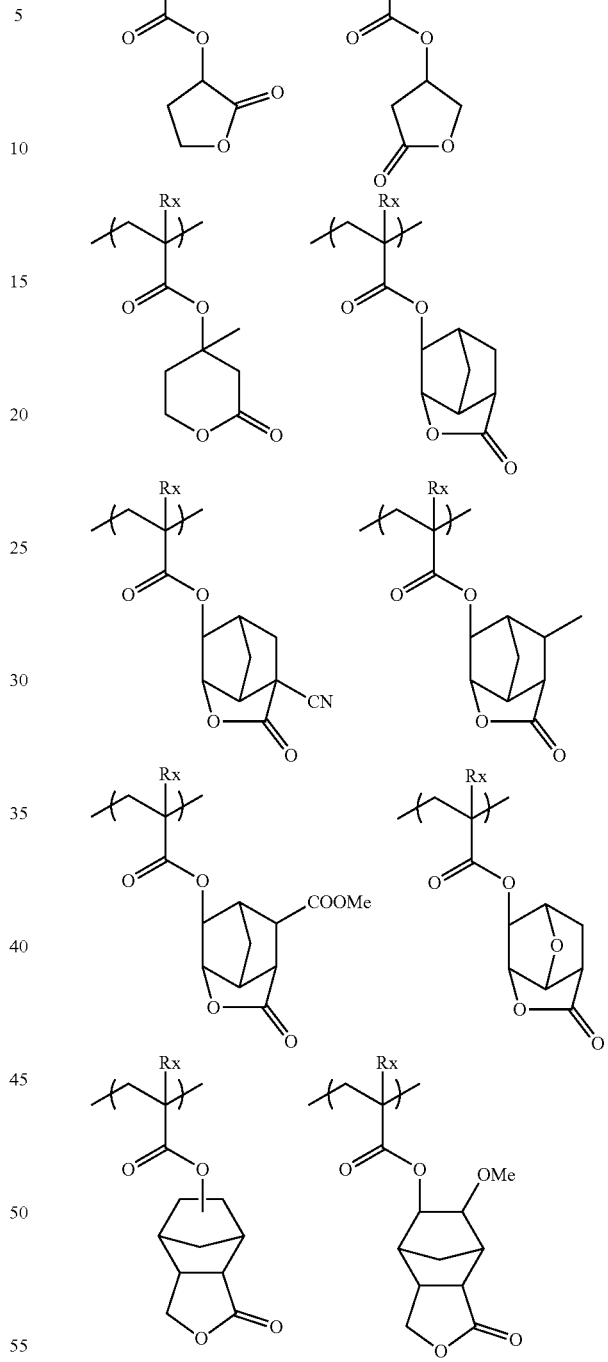

Especially preferred repeating units among the above particular examples are the following. Selection of the most appropriate lactone group or sultone group enhances the pattern profile and iso/dense bias. In the particular examples, Rx represents H, $CH_3$, $CH_2OH$ or $CF_3$.

The repeating unit containing a lactone group or sultone group is generally present in the form of optical isomers. Any of the optical isomers may be used. It is both appropriate to use one type of optical isomer alone and to use a plurality of optical isomers in the form of a mixture. When one type of optical isomer is mainly used, the optical purity (ee) thereof is preferably 90% or higher, more preferably 95% or higher.

The content of repeating unit with a lactone structure or sultone structure other than the repeating units of general formula (III) or repeating units each with a lactone structure or sultone structure other than the repeating units of general formula (III) in total, based on all the repeating units of the resin, is preferably in the range of 15 to 60 mol %, more preferably 20 to 50 mol % and further more preferably 30 to 50 mol %.

In order to enhance the effect of the present invention, two or more types of lactone or sultone repeating units selected from among those of general formula (III) can be used in combination. In such a combination use, it is preferred to select two or more types from among the lactone or sultone repeating units of general formula (III) in which n is 1 and use them in combination.

It is preferred for the resin (A1) to comprise a repeating unit containing a hydroxyl group or a cyano group other than the repeating units of general formulae (AI) and (III). This enhances the adhesion to substrate and developer affinity. The repeating unit containing a hydroxyl group or a cyano group is preferably a repeating unit having an alicyclic hydrocarbon structure substituted with a hydroxyl group or a cyano group, which repeating unit preferably contains no acid-decomposable group. In the alicyclic hydrocarbon structure substituted with a hydroxyl group or a cyano group, the alicyclic hydrocarbon structure is preferably an adamantyl group, a diamantyl group or a norbornane group. The alicyclic hydrocarbon structure substituted with a hydroxyl group or a cyano group is preferably any of the partial structures of general formulae (VIIa) to (VIId) below.

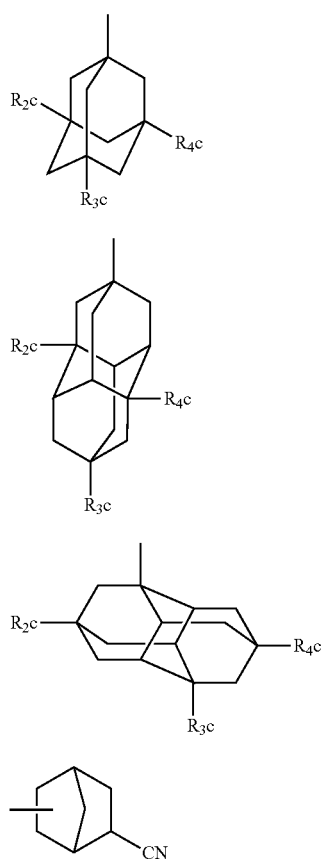

In general formulae (VIIa) to (VIIc),
each of $R_2c$ to $R_4c$ independently represents a hydrogen atom, a hydroxyl group or a cyano group, provided that at least one of $R_2c$ to $R_4c$ represents a hydroxyl group or a cyano group. Preferably, one or two of $R_2c$ to $R_4c$ are hydroxyl groups and the remainders are hydrogen atoms. In general formula (VIIa), more preferably, two of $R_2c$ to $R_4c$ are hydroxyl groups and the remainders are hydrogen atoms.

As the repeating units with any of the partial structures of general formulae (VIIa) to (VIId), there can be mentioned the repeating units of general formulae (AIIa) to (AIId) below.

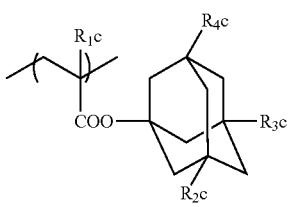

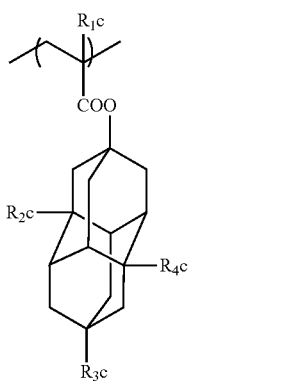

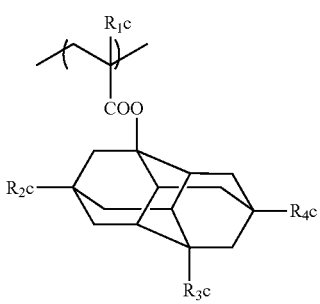

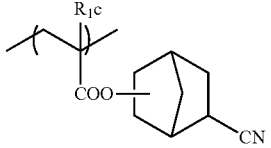

In general formulae (AIIa) to (AIId),
$R_1c$ represents a hydrogen atom, a methyl group, a trifluoromethyl group or a hydroxymethyl group.

$R_2c$ to $R_4c$ have the same meanings as those of $R_2c$ to $R_4c$ in general formulae (VIIa) to (VIIc).

The content of repeating unit containing a hydroxyl group or a cyano group, based on all the repeating units of the resin (A1), is preferably in the range of 5 to 40 mol %, more preferably 5 to 30 mol % and further more preferably 10 to 25 mol %.

Specific examples of the repeating units each containing a hydroxyl group or a cyano group are shown below, which in no way limit the scope of the present invention.

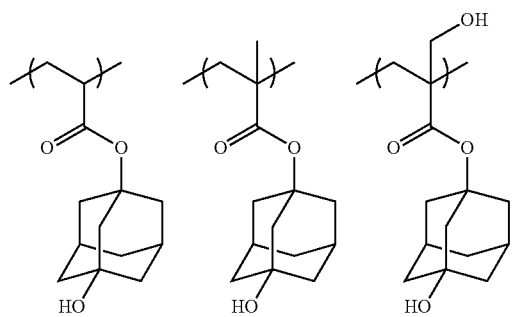

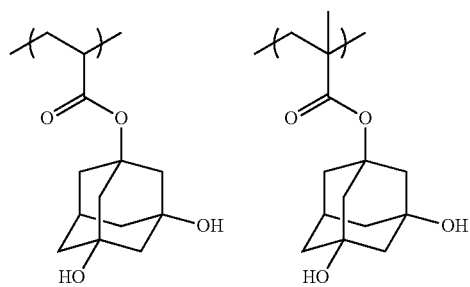

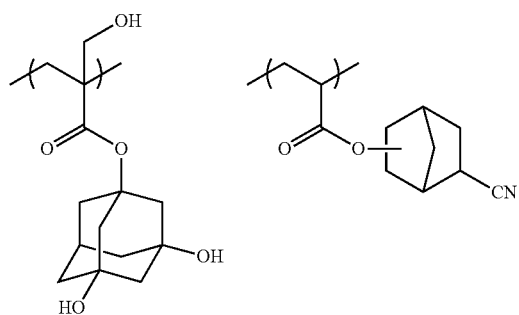

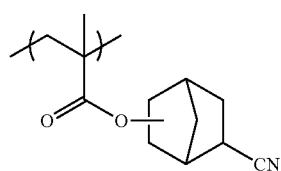

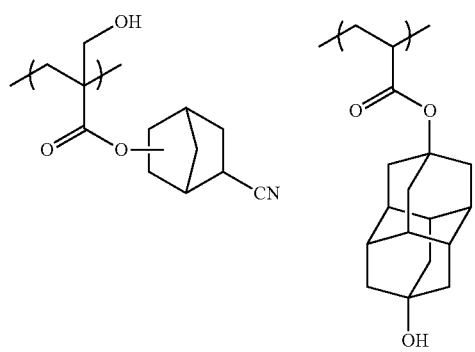

-continued

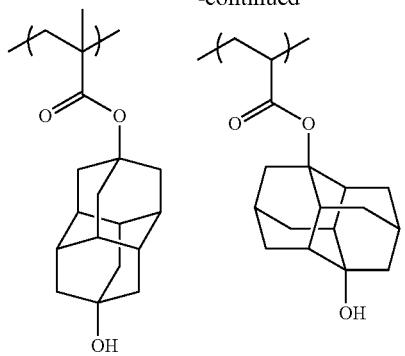

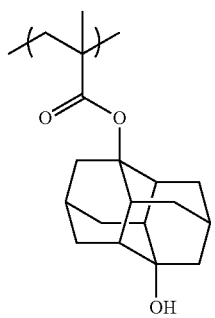

The resin (A1) for use in the actinic-ray- or radiation-sensitive resin composition of the present invention may comprise a repeating unit containing an alkali-soluble group. As the alkali-soluble group, there can be mentioned a carboxyl group, a sulfonamido group, a sulfonylimido group, a bissulfonylimido group or an aliphatic alcohol substituted at its α-position with an electron-withdrawing group (for example, a hexafluoroisopropanol group). It is preferred for the resin to comprise a repeating unit containing a carboxyl group. The incorporation of the repeating unit containing an alkali-soluble group increases the resolution in contact hole usage. The repeating unit containing an alkali-soluble group is preferably any of a repeating unit wherein the alkali-soluble group is directly bonded to the principal chain of a resin, such as a repeating unit of acrylic acid or methacrylic acid; a repeating unit wherein the alkali-soluble group is bonded via a connecting group to the principal chain of a resin; and a repeating unit wherein the alkali-soluble group is introduced in a terminal of a polymer chain by the use of a chain transfer agent or polymerization initiator containing the alkali-soluble group in the stage of polymerization. The connecting group may have a mono- or polycyclohydrocarbon structure. The repeating unit of acrylic acid or methacrylic acid is especially preferred.

The content of repeating unit containing an alkali-soluble group, based on all the repeating units of the resin (A1), is preferably in the range of 0 to 20 mol %, more preferably 3 to 15 mol % and further more preferably 5 to 10 mol %.

Specific examples of the repeating units each containing an alkali-soluble group are shown below, which in no way limit the scope of the present invention.

In the specific examples, Rx represents H, $CH_3$, $CH_2OH$ or $CF_3$.

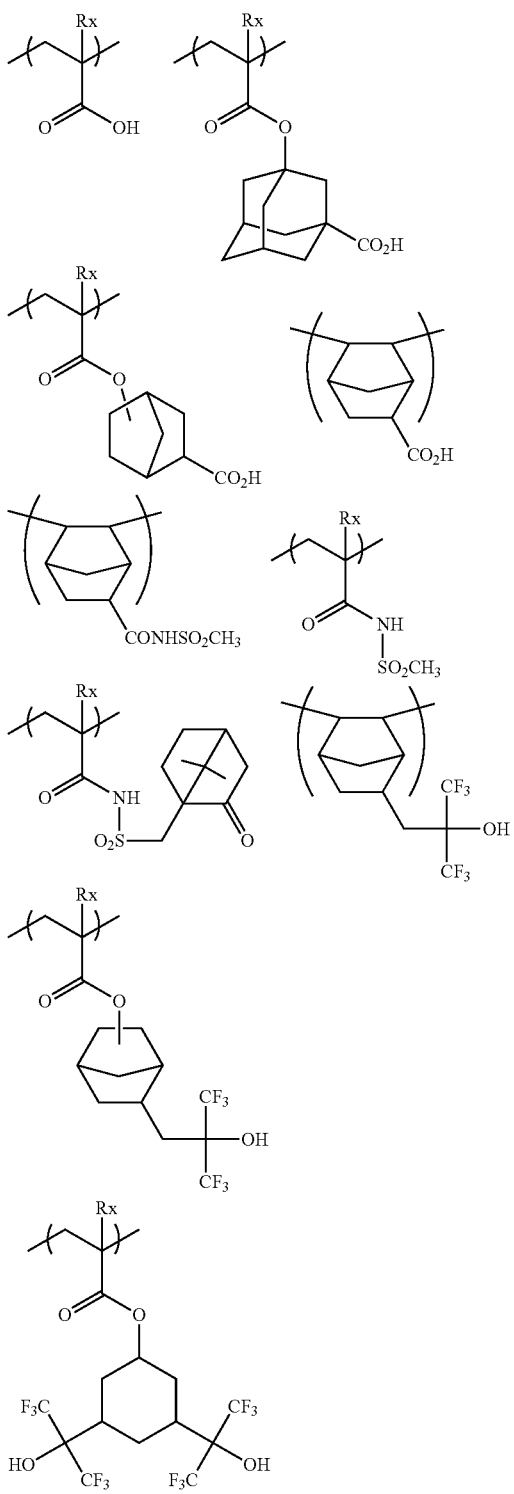

(IV)

In general formula (IV) above, $R_5$ represents a hydrocarbon group having at least one cyclic structure in which no polar group is introduced.

Ra represents a hydrogen atom, an alkyl group or a group of the formula —$CH_2$—O—$Ra_2$. In this formula, $Ra_2$ represents a hydrogen atom, an alkyl group or an acyl group. Ra is preferably a hydrogen atom, a methyl group, a hydroxymethyl group or a trifluoromethyl group, most preferably a hydrogen atom or a methyl group.

The cyclic structures introduced in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group and a perhydronaphthalenyl group. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1] octane ring); tricyclic hydrocarbon rings, such as homobledane, adamantane, tricyclo[5.2.1.0$^{2,6}$]decane and tricyclo [4.3.1.1$^{2,5}$]undecane rings; and tetracyclic hydrocarbon rings, such as tetracyclo[4.4.0.1$^{2,5}$.1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from the condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenalene rings.

As preferred crosslinked-ring hydrocarbon rings, there can be mentioned a norbornyl group, an adamantyl group, a bicyclooctanyl group and a tricyclo[5,2,1,0$^{2,6}$]decanyl group and the like. As more preferred crosslinked-ring hydrocarbon rings, there can be mentioned a norbornyl group and an adamantyl group.

Substituents may be introduced in these alicyclic hydrocarbon groups. As preferred substituents, there can be mentioned a halogen atom, an alkyl group, a hydroxyl group having its hydrogen atom replaced, an amino group having its hydrogen atom replaced and the like. The halogen atom is preferably a bromine, chlorine or fluorine atom, and the alkyl group is preferably a methyl, ethyl, butyl or t-butyl group. A substituent may further be introduced in the alkyl group. As the optional further substituent, there can be The resin (A1) according to the present invention can further comprise a repeating unit having an alicyclic hydrocarbon structure in which none of polar groups (for example, the above-described alkali-soluble group, a hydroxyl group, a cyano group and the like) is introduced and exhibiting no acid-decomposability. As such a repeating unit, there can be mentioned any of repeating units of general formula (IV) below.

mentioned a halogen atom, an alkyl group, a hydroxyl group having its hydrogen atom replaced or an amino group having its hydrogen atom replaced.

As a group replacing the hydrogen atom, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably 1-ethoxyethyl or 1-methyl-1-methoxyethyl. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

It is optional for the resin (A1) to comprise the repeating unit having an alicyclic hydrocarbon structure in which no polar group is introduced and exhibiting no acid-decomposability. When this repeating unit is contained, the content thereof based on all the repeating units of the resin (A1) is preferably in the range of 1 to 40 mol %, more preferably 2 to 20 mol %.

Particular examples of the repeating units having an alicyclic hydrocarbon structure in which no polar group is introduced and exhibiting no acid-decomposability are shown below, which in no way limit the scope of the present invention. In the formulae, Ra represents H, CH$_3$, CH$_2$OH or CF$_3$.

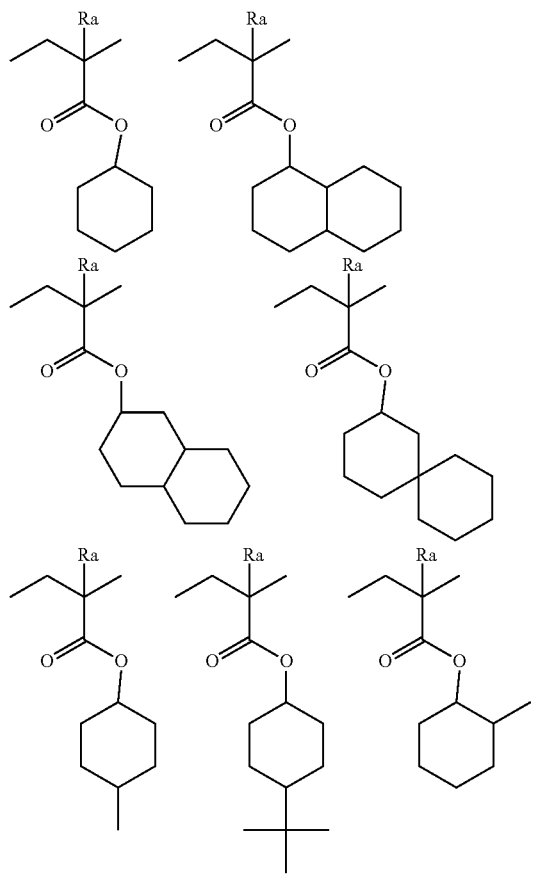

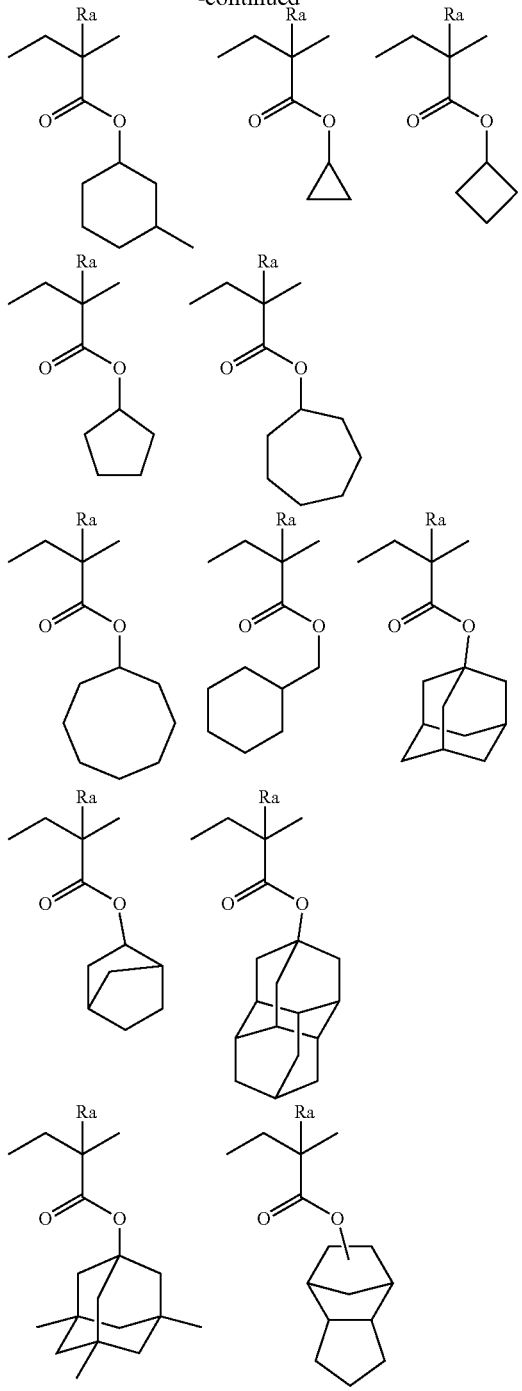

The resin (A1) for use in the composition of the present invention can comprise, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which are nonlimiting.

The incorporation of such repeating structural units would realize fine regulation of the required properties of the resin for use in the composition of the present invention, especially: (1) solubility in application solvents, (2) film forming easiness (glass transition point), (3) alkali developability, (4) film thinning (selections of hydrophilicity/hydrophobicity and alkali-soluble group), (5) adhesion of unexposed area to substrate, (6) dry etching resistance, etc.

As appropriate monomers, there can be mentioned, for example, compounds each having one unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

In the resin (A1) for use in the composition of the present invention, the molar ratios of individual repeating structural units contained are appropriately determined from the viewpoint of regulating the dry etching resistance, standard developer adaptability, substrate adhesion and resist profile of the resist and generally required properties of the resist such as resolving power, heat resistance and sensitivity.

When the composition of the present invention is one for ArF exposure, from the viewpoint of transparency to ArF light, it is preferred for the resin (A1) for use in the composition of the present invention to contain substantially no aromatic ring. In particular, the ratio of repeating unit containing an aromatic group, based on all the repeating units of the resin (A1), is preferably 5 mol % or less, more preferably 3 mol % or less, and ideally 0 mol %, namely, containing no repeating unit containing an aromatic group. It is preferred for the resin (A1) to have a mono- or polyalicyclic hydrocarbon structure.

When the composition of the present invention is exposed to KrF excimer laser light, electron beams, X-rays or high-energy light rays of 50 nm or less wavelength (for example, EUV), it is preferred for the resin (A1) to comprise hydroxystyrene repeating units. More preferably, the resin (A1) is a copolymer of hydroxystyrene and hydroxystyrene protected by a group leaving under the action of an acid, or a copolymer of hydroxystyrene and a (meth)acrylic acid tertiary alkyl ester.

In particular, as such a resin, there can be mentioned a resin comprising any of repeating units of general formula (A) below.

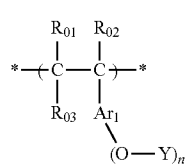

(A)

In the formula, each of $R_{01}$, $R_{02}$ and $R_{03}$ independently represents, for example, a hydrogen atom, an alkyl group, a cycloalkyl group, a halogen atom, a cyano group or an alkoxycarbonyl group; and $Ar_1$ represents, for example, an aromatic ring group, provided that $R_{03}$ and $Ar_1$ may be simultaneously alkylene groups and bonded to each other so as to form a 5-membered or 6-membered ring in cooperation with the —C—C— chain.

Each of n Y's independently represents a hydrogen atom or a group leaving under the action of an acid, provided that at least one of the Y's is a group leaving under the action of an acid.

In the formula, n is an integer of 1 to 4, preferably 1 or 2 and more preferably 1.

The alkyl groups represented by $R_{01}$ to $R_{03}$ are, for example, alkyl groups each having up to 20 carbon atoms. The alkyl groups are preferably a methyl group, an ethyl group, a propyl group, an isopropyl group, an n-butyl group, a sec-butyl group, a hexyl group, a 2-ethylhexyl group, an octyl group and a dodecyl group. Alkyl groups having up to 8 carbon atoms are more preferred. Substituents may be introduced in these alkyl groups.

The alkyl groups contained in the alkoxycarbonyl groups are preferably the same as the above-mentioned alkyl groups represented by $R_{01}$ to $R_{03}$.

The cycloalkyl groups may each be monocyclic or polycyclic. As preferred examples thereof, there can be mentioned monocycloalkyl groups each having 3 to 8 carbon atoms, such as a cyclopropyl group, a cyclopentyl group and a cyclohexyl group. Substituents may be introduced in these cycloalkyl groups.

As the halogen atom, there can be mentioned a fluorine atom, a chlorine atom, a bromine atom or an iodine atom. A fluorine atom is preferred.

When $R_{03}$ represents an alkylene group, this alkylene group is preferably one having 1 to 8 carbon atoms, such as a methylene group, an ethylene group, a propylene group, a butylene group, a hexylene group or an octylene group.

The aromatic ring group represented by $Ar_1$ is preferably one having 6 to 14 carbon atoms. For example, there can be mentioned a benzene ring, a toluene ring or a naphthalene ring. A substituent may be introduced in this aromatic ring group.

As the group leaving under the action of an acid, Y, there can be mentioned, for example, any of the groups of the formulae —C($R_{36}$)($R_{37}$)($R_{38}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$) and —CH($R_{36}$)(Ar).

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded to each other to thereby form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl groups represented by $R_{36}$ to $R_{39}$ and $R_{01}$ and $R_{02}$ are preferably alkyl groups each having 1 to 8 carbon atoms. For example, there can be mentioned a methyl group, an ethyl group, a propyl group, an n-butyl group, a sec-butyl group, a hexyl group and an octyl group.

The cycloalkyl groups represented by $R_{36}$ to $R_{39}$ and $R_{01}$ and $R_{02}$ may be monocyclic or polycyclic. The monocycloalkyl groups are preferably cycloalkyl groups having 3 to 8 carbon atoms. As such, there can be mentioned, for example, a cyclopropyl group, a cyclobutyl group, a cyclopentyl group, a cyclohexyl group and a cyclooctyl group. The polycycloalkyl groups are preferably cycloalkyl groups having 6 to 20 carbon atoms. As such, there can be mentioned, for example, an adamantyl group, a norbornyl group, an isobornyl group, a camphonyl group, a dicyclopentyl group, an α-pinanyl group, a tricyclodecanyl group, a tetracyclododecyl group and an androstanyl group. With respect to these, the carbon atoms of each of the cycloalkyl groups may be partially replaced with a heteroatom, such as an oxygen atom.

The aryl groups represented by $R_{36}$ to $R_{39}$, $R_{01}$, $R_{02}$ and Ar are preferably aryl groups each having 6 to 10 carbon atoms. For example, there can be mentioned a phenyl group, a naphthyl group and an anthryl group.

The aralkyl groups represented by $R_{36}$ to $R_{39}$, $R_{01}$ and $R_{02}$ are preferably aralkyl groups each having 7 to 12 carbon atoms. As preferred examples thereof, there can be mentioned a benzyl group, a phenethyl group and a naphthylmethyl group.

The alkenyl groups represented by $R_{36}$ to $R_{39}$, $R_{01}$ and $R_{02}$ are preferably alkenyl groups each having 2 to 8 carbon atoms. For example, there can be mentioned a vinyl group, an allyl group, a butenyl group and a cyclohexenyl group.

The ring formed by the mutual bonding of $R_{36}$ and $R_{37}$ may be monocyclic or polycyclic. The monocyclic ring is preferably a cycloalkane structure having 3 to 8 carbon atoms. As such, there can be mentioned, for example, a cyclopropane structure, a cyclobutane structure, a cyclopentane structure, a cyclohexane structure, a cycloheptane structure or a cyclooctane structure. The polycyclic ring is preferably a cycloalkane structure having 6 to 20 carbon atoms. As such, there can be mentioned, for example, an adamantane structure, a norbornane structure, a dicyclopentane structure, a tricyclodecane structure or a tetracyclododecane structure. With respect to these, the carbon atoms of each of the ring structures may be partially replaced with a heteroatom, such as an oxygen atom.

Substituents may be introduced in these groups. As the substituents, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group and a nitro group. Preferably, the number of carbon atoms of each of the substituents is up to 8.

The group leaving under the action of an acid, Y, preferably has any of structures of general formula (B) below.

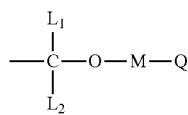

(B)

In the formula, each of $L_1$ and $L_2$ independently represents a hydrogen atom, an alkyl group, a cycloalkyl group, an aryl group or an aralkyl group.

M represents a single bond or a bivalent connecting group.

Q represents an alkyl group, a cycloalkyl group, a cycloaliphatic group, an aromatic ring group, an amino group, an ammonium group, a mercapto group, a cyano group or an aldehyde group. Heteroatoms may be introduced in the cycloaliphatic group and aromatic ring group.

At least two of Q, M and $L_1$ may be bonded to each other to thereby form a 5-membered or 6-membered ring.

The alkyl groups represented by $L_1$ and $L_2$ are, for example, alkyl groups each having 1 to 8 carbon atoms. As particular examples thereof, there can be mentioned a methyl group, an ethyl group, a propyl group, an n-butyl group, a sec-butyl group, a hexyl group and an octyl group.

The cycloalkyl groups represented by $L_1$ and $L_2$ are, for example, cycloalkyl groups each having 3 to 15 carbon atoms. As particular examples thereof, there can be mentioned a cyclopentyl group, a cyclohexyl group, a norbornyl group and an adamantyl group.

The aryl groups represented by $L_1$ and $L_2$ are, for example, aryl groups each having 6 to 15 carbon atoms. As particular examples thereof, there can be mentioned a phenyl group, a tolyl group, a naphthyl group and an anthryl group.

The aralkyl groups represented by $L_1$ and $L_2$ are, for example, aralkyl groups each having 6 to 20 carbon atoms. As particular examples thereof, there can be mentioned a benzyl group and a phenethyl group.

The bivalent connecting group represented by M is, for example, an alkylene group (e.g., a methylene group, an ethylene group, a propylene group, a butylene group, a hexylene group or an octylene group), a cycloalkylene group (e.g., a cyclopentylene group or a cyclohexylene group), an alkenylene group (e.g., an ethylene group, a propenylene group or a butenylene group), an arylene group (e.g., a phenylene group, a tolylene group or a naphthylene group), —S—, —O—, —CO—, —SO$_2$—, —N(R$_0$)— or a combination of two or more of these groups. $R_0$ represents a hydrogen atom or an alkyl group. The alkyl group represented by $R_0$ is, for example, an alkyl group having 1 to 8 carbon atoms. As particular examples thereof, there can be mentioned a methyl group, an ethyl group, a propyl group, an n-butyl group, a sec-butyl group, a hexyl group and an octyl group.

The alkyl group and cycloalkyl group represented by Q are the same as those mentioned above in connection with $L_1$ and $L_2$.

As the cycloaliphatic group and aromatic ring group represented by Q, there can be mentioned, for example, the cycloalkyl group and aryl group mentioned above as being represented by $L_1$ and $L_2$. Preferably, each of the cycloalkyl group and aryl group has 3 to 15 carbon atoms.

As the cycloaliphatic group and aromatic ring group containing a heteroatom represented by Q, there can be mentioned, for example, groups having a heterocyclic structure, such as thiirane, cyclothiorane, thiophene, furan, pyrrole, benzothiophene, benzofuran, benzopyrrole, triazine, imidazole, benzimidazole, triazole, thiadiazole, thiazole and pyrrolidone. However, the cycloaliphatic groups and aromatic ring groups are not limited to these as long as the ring is formed by carbon and a heteroatom or by heteroatoms only.

As the ring structure that may be formed by the mutual bonding of at least two of Q, M and $L_1$, there can be mentioned, for example, a 5-membered or 6-membered ring structure resulting from the formation of a propylene group or a butylene group thereby. The 5-membered or 6-membered ring structure contains the oxygen atom.

Substituents may be introduced in the groups represented by $L_1$, $L_2$, M and Q in general formula (B). As the substituents, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group and a nitro group. Preferably, the number of carbon atoms of each of the substituents is up to 8.

The groups of the formula -M-Q are preferably groups each having 1 to 20 carbon atoms, more preferably groups each having 1 to 10 carbon atoms and further more preferably groups each having 1 to 8 carbon atoms.

Specific examples of the resins (A1) comprising hydroxystyrene repeating units are shown below, which in no way limit the scope of the present invention.

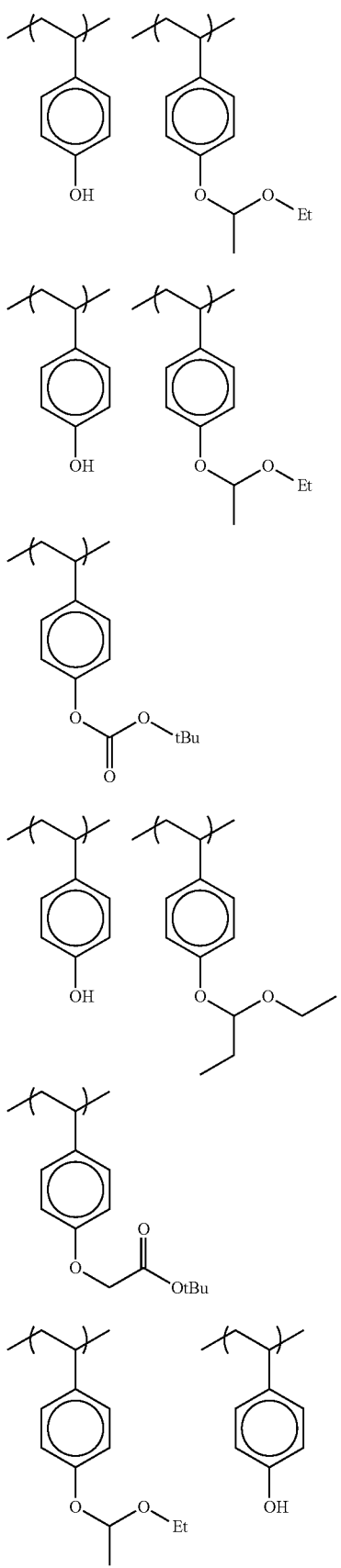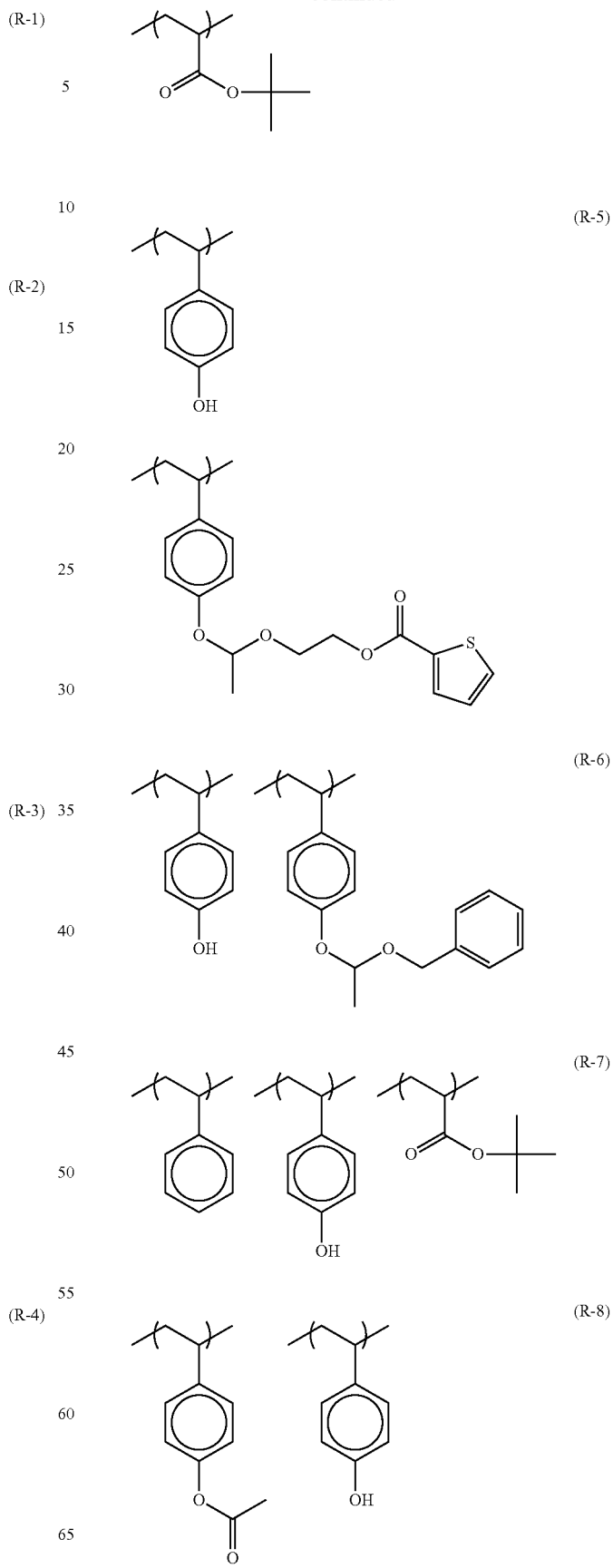

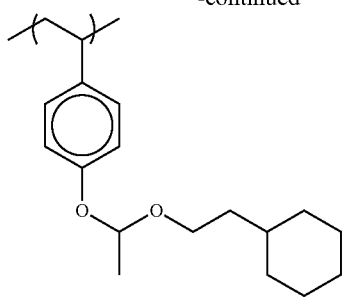
(R-9)
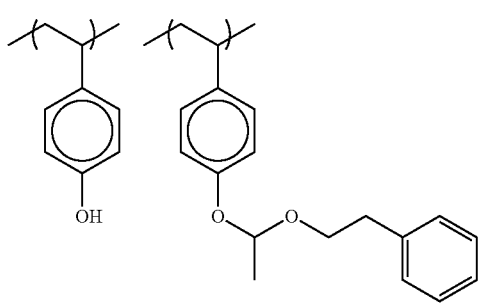
(R-10)
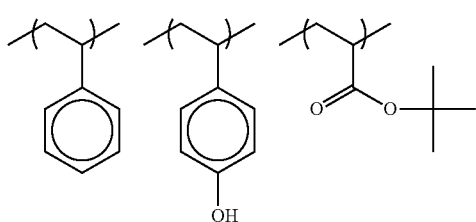
(R-11)
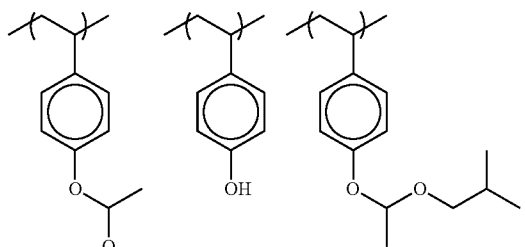
(R-12)
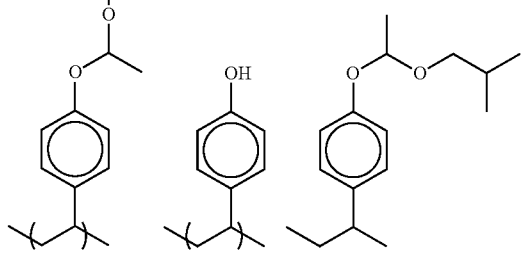
(R-13)
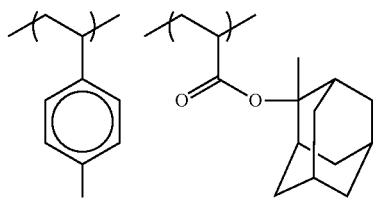
(R-14)
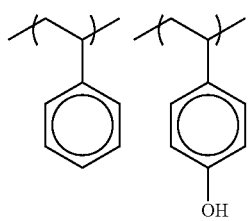
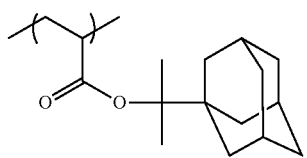

(R-15)
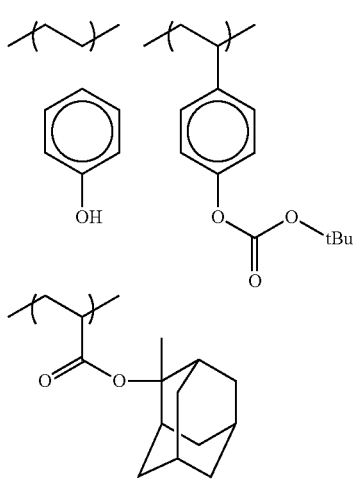
(R-16)
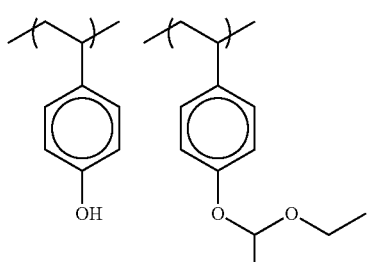
(R-17)
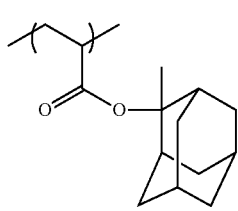
R-18
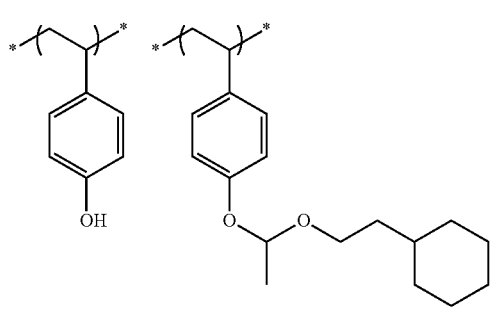
R-19
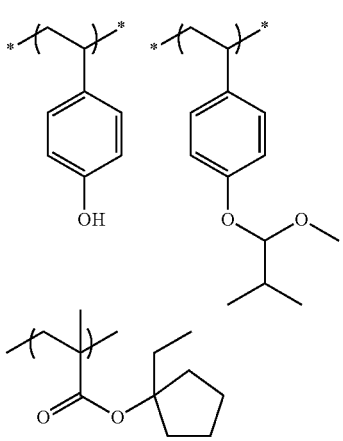
R-20
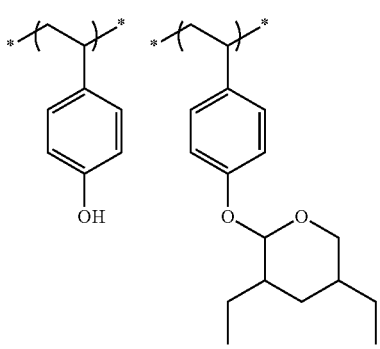
R-21
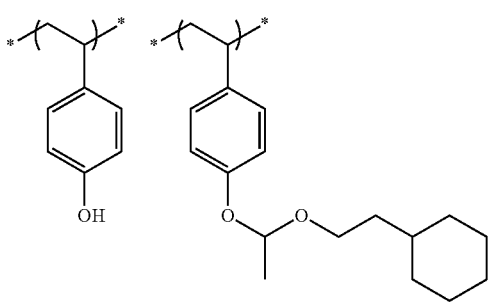
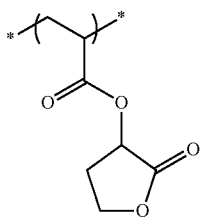
R-22
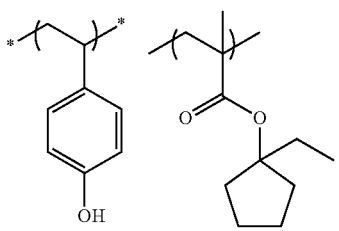

-continued
R-23
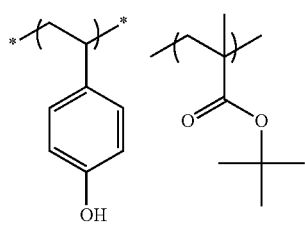
R-24
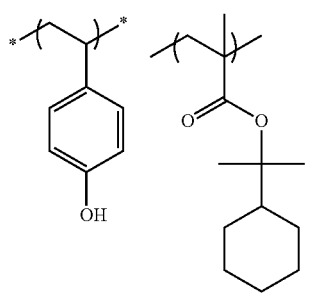
R-25
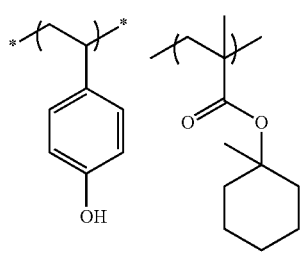
R-26
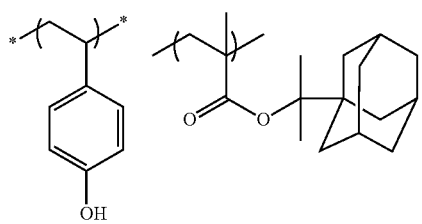
R-27
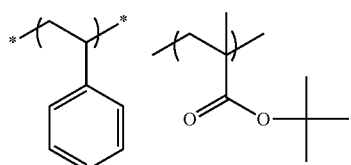
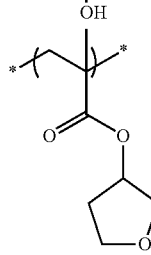
-continued
R-28
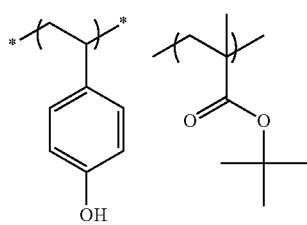
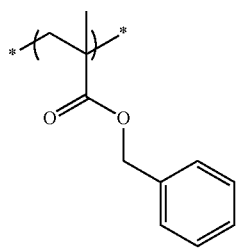
R-29
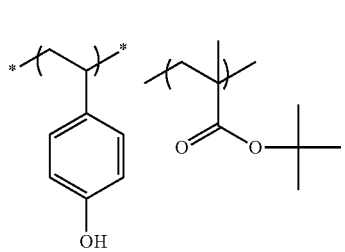
R-30
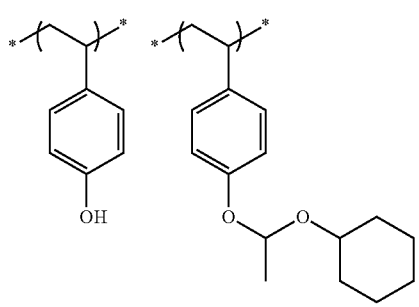
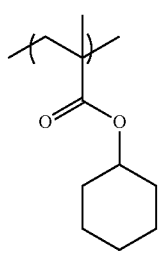

-continued

R-31
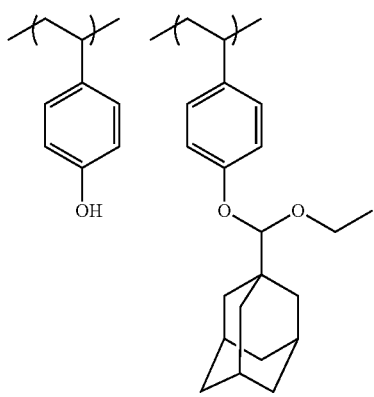

R-32
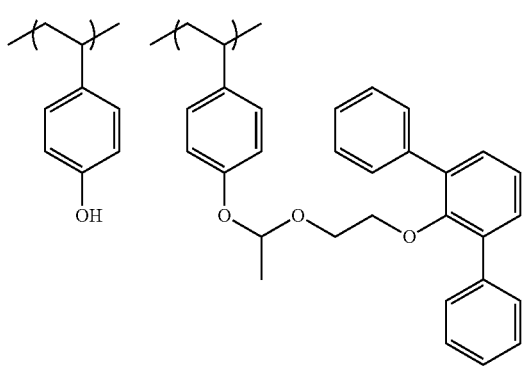

R-33
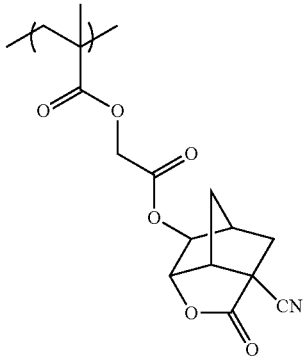

R-34
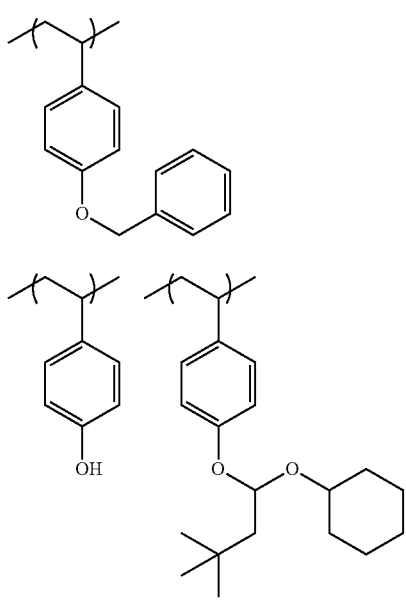

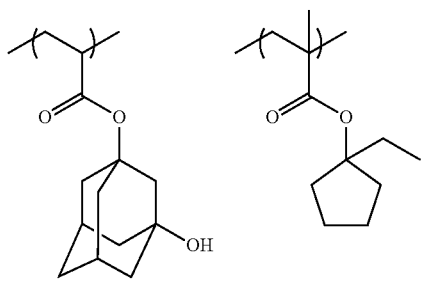

-continued

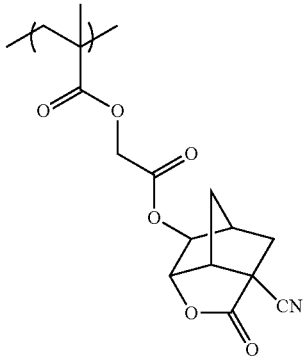

In the above particular examples, tBu represents a t-butyl group.

It is preferred for the resin (A1) to contain neither a fluorine atom nor a silicon atom from the viewpoint of the compatibility with the hydrophobic resin (HR) to be described hereinafter.

In the resin (A1) for use in the composition of the present invention, preferably, all the repeating units thereof are comprised of (meth)acrylate repeating units. In that instance, use can be made of any of a resin wherein all the repeating units are comprised of methacrylate repeating units, a resin wherein all the repeating units are comprised of acrylate repeating units and a resin wherein all the repeating units are comprised of methacrylate repeating units and acrylate repeating units. However, it is preferred for the acrylate repeating units to account for 50 mol % or less of all the repeating units. It is also preferred to employ a copolymer comprising 20 to 50 mol % of (meth)acrylate repeating units containing an acid-decomposable group, 20 to 50 mol % of (meth)acrylate repeating units containing a lactone group, 5 to 30 mol % of (meth)acrylate repeating units with an alicyclic hydrocarbon structure substituted with a hydroxyl group or a cyano group and 0 to 20 mol % of other (meth)acrylate repeating units.

The resins (A1) according to the present invention can be synthesized in accordance with routine methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a heated solvent over a period of 1 to 10 hours, and the like. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or any of solvents capable of dissolving the composition of the present invention, such as propylene glycol monomethyl ether acetate, propylene glycol monomethyl ether and cyclohexanone, to be described hereinafter. Preferably, the polymerization is carried out with the use of the same solvent as that to be used in the actinic-ray- or radiation-sensitive resin composition of the present invention. This inhibits any particle generation during storage.

The polymerization reaction is preferably carried out in an atmosphere comprised of an inert gas, such as nitrogen or argon. The polymerization is initiated by use of a commercially available radical initiator (azo initiator, peroxide, etc.)

as a polymerization initiator. Among the radical initiators, an azo initiator is preferred, and azo initiators containing an ester group, a cyano group and a carboxyl group are especially preferred. As specific preferred initiators, there can be mentioned azobisisobutyronitrile, azobisdimethylvaleronitrile, dimethyl 2,2'-azobis(2-methylpropionate) and the like. If desirable, the initiator may be supplemented, or may be added in fractional amounts. After the completion of the reaction, the reaction liquid is poured into a solvent, and the intended polymer is recovered by a method of powder or solid recovery or the like. The reaction concentration is in the range of 5 to 50 mass %, preferably 10 to 30 mass %. The reaction temperature is generally in the range of 10 to 150° C., preferably 30 to 120° C. and more preferably 60 to 100° C.

The weight average molecular weight of the resin (A1) according to the present invention, in terms of polystyrene-equivalent value measured by GPC, is preferably in the range of 1000 to 200,000. It is more preferably in the range of 2000 to 20,000, further more preferably 3000 to 15,000 and most preferably 3000 to 11,000. By regulating the weight average molecular weight so as to fall within the range of 1000 to 200,000, not only can any deteriorations of heat resistance and dry etching resistance be prevented but also any deterioration of developability and any increase of viscosity leading to poor film forming property can be prevented.

The polydispersity index (molecular weight distribution) of the resin is generally in the range of 1.0 to 3.0, preferably 1.0 to 2.6, more preferably 1.0 to 2.0 and most preferably 1.1 to 2.0. When the molecular weight distribution is small to these ranges, excellent resolution and resist shape can be attained, and the side wall of the resist pattern is smooth to thereby ensure excellent roughness characteristics.

In the present invention, the content of resin (A1) in the whole composition is preferably in the range of 30 to 99 mass %, more preferably 50 to 95 mass %, based on the total solids of the composition.

In the present invention, one type of rein (A1) may be used alone, or two or more types thereof may be used in combination.

[2] Resin (A2) Containing Phenolic Hydroxyl Group

The composition of the present invention in its one form comprises a resin (A2) containing a phenolic hydroxyl group.

The term "phenolic hydroxyl group" used in the present invention refers to a group resulting from the replacement of a hydrogen atom of an aromatic ring group by a hydroxyl group. The aromatic ring in the aromatic ring group is a mono- or polycyclic aromatic ring. As the aromatic ring, there can be mentioned a benzene ring, a naphthalene ring or the like.

In the composition of the present invention comprising the resin (A2), at exposed areas, a crosslinking reaction between the resin (A2) containing a phenolic hydroxyl group and an acid crosslinking agent (C) to be described hereinafter progresses under the action of an acid generated from the compound (B) upon exposure to actinic rays or radiation, thereby forming a negative pattern.

The resin (A2) containing a phenolic hydroxyl group according to the present invention preferably comprises a repeating unit containing at least one phenolic hydroxyl group. The repeating unit containing a phenolic hydroxyl group is not particularly limited, which is however preferably any of repeating units of general formula (1) below.

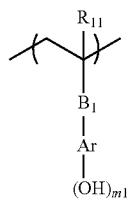

(1)

In general formula (1), $R_{11}$ represents a hydrogen atom, an optionally substituted methyl group or a halogen atom.

$B_1$ represents a single bond or a bivalent connecting group.

Ar represents an aromatic ring; and m1 is an integer of 1 or greater.

As the optionally substituted methyl group represented by $R_{11}$, there can be mentioned a trifluoromethyl group, a hydroxymethyl group or the like.

$R_{11}$ is preferably a hydrogen atom or a methyl group. A hydrogen atom is more preferred from the viewpoint of developability.

The bivalent connecting group represented by $B_1$ is preferably a carbonyl group, an alkylene group (preferably having 1 to 10 carbon atoms, more preferably 1 to 5 carbon atoms), a sulfonyl group ($-S(=O)_2-$), $-O-$, $-NH-$, or a bivalent connecting group comprised of a combination of these.

$B_1$ is preferably a single bond, a carbonyloxy group ($-C(=O)-O-$) or $-C(=O)-NH-$, more preferably a single bond or a carbonyloxy group ($-C(=O)-O-$). A single bond is especially preferred from the viewpoint of dry etching resistance.

The aromatic ring represented by Ar is a monocyclic or polycyclic aromatic ring. As such, there can be mentioned an optionally substituted aromatic hydrocarbon ring having 6 to 18 carbon atoms, such as a benzene ring, a naphthalene ring, an anthracene ring, a fluorene ring or a phenanthrene ring, or an aromatic ring heterocycle containing a heteroring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring or a thiazole ring. Of these, a benzene ring and a naphthalene ring are preferred from the viewpoint of resolution. A benzene ring is most preferred from the viewpoint of sensitivity.

In the formula, m1 is preferably an integer of 1 to 5, most preferably 1. When m1 is 1 and Ar is a benzene ring, the position of —OH substitution may be any of the para-, meta- and ortho-positions to the site of bonding to $B_1$ (when $B_1$ is a single bond, the principal chain of the polymer) in the benzene ring. However, from the viewpoint of crosslinking reactivity, the para- and meta-positions are preferred, and the para-position is more preferred.

A substituent other than the above —OH group may be introduced in the aromatic ring represented by Ar. As such a substituent, there can be mentioned, for example, an alkyl group, a cycloalkyl group, a halogen atom, a hydroxyl group, an alkoxy group, a carboxyl group, an alkoxycarbonyl group, an alkylcarbonyl group, an alkylcarbonyloxy group, an alkylsulfonyloxy group or an arylcarbonyl group.

From the viewpoint of crosslinking reactivity, developability and dry etching resistance, it is preferred for the repeating unit containing a phenolic hydroxyl group to be any of repeating units of general formula (2) below.

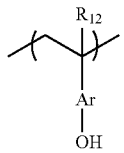

(2)

In general formula (2), $R_{12}$ represents a hydrogen atom or a methyl group.

Ar represents an aromatic ring.

As $R_{12}$, a hydrogen atom is preferred to a methyl group from the viewpoint of developability.

Ar in general formula (2) has the same meaning as that of Ar in general formula (1). Preferred ranges are also the same. From the viewpoint of sensitivity, it is preferred for the repeating units of general formula (2) to be repeating units derived from hydroxystyrene (namely, repeating units of general formula (2) in which $R_{12}$ is a hydrogen atom and Ar is a benzene ring).

The resin (A2) may be comprised only of the above repeating unit containing a phenolic hydroxyl group. The resin (A2) may comprise repeating units to be described below other than the above repeating units containing a phenolic hydroxyl group. In that instance, the content of repeating unit containing a phenolic hydroxyl group, based on all the repeating units of the resin (A2), is preferably in the range of 10 to 98 mol %, more preferably 30 to 97 mol % and further more preferably 40 to 95 mol %. This highly reliably lowers, especially when the resist film is thin (for example, when the thickness of the resist film is in the range of 10 to 150 nm), the rate of dissolution, in alkali developers, of exposed areas of the resist film according to the present invention formed using the resin (A2) (namely, the rate of dissolution of the resist film formed using the resin (A2) can be highly reliably controlled to the most appropriate rate). As a result, the sensitivity can be highly reliably enhanced.

Nonlimiting examples of repeating units each containing a phenolic hydroxyl group are shown below.

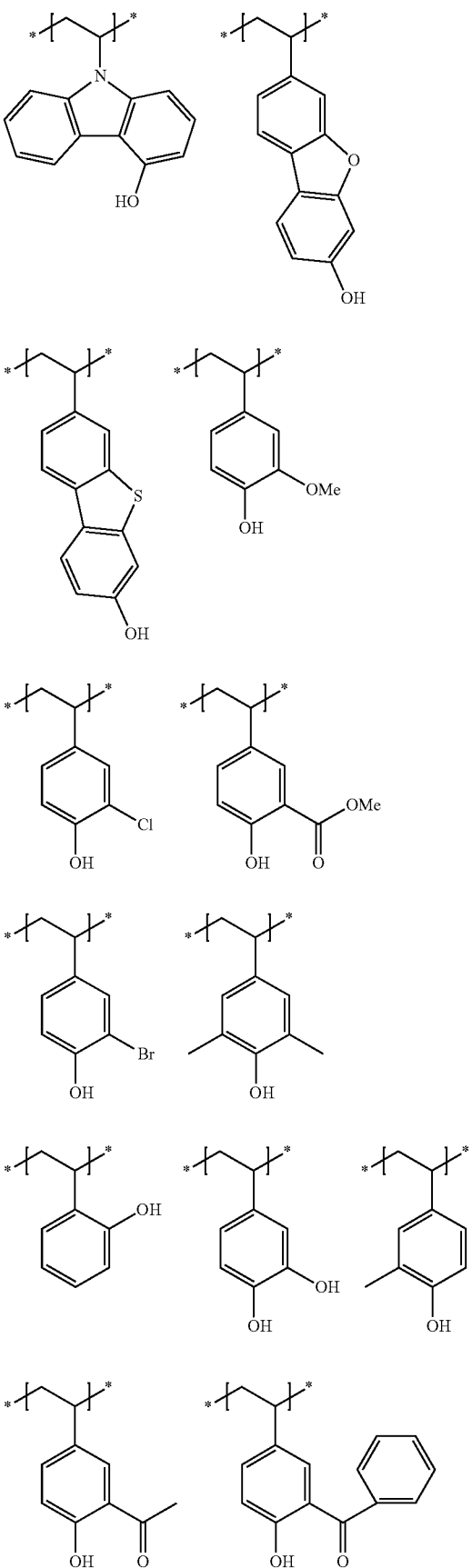

-continued
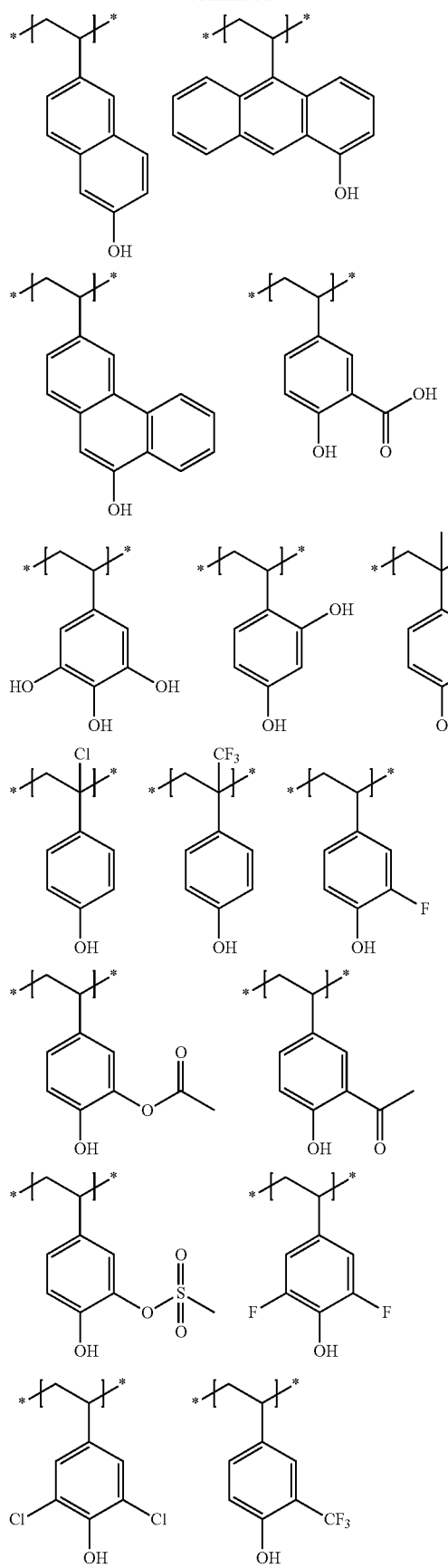
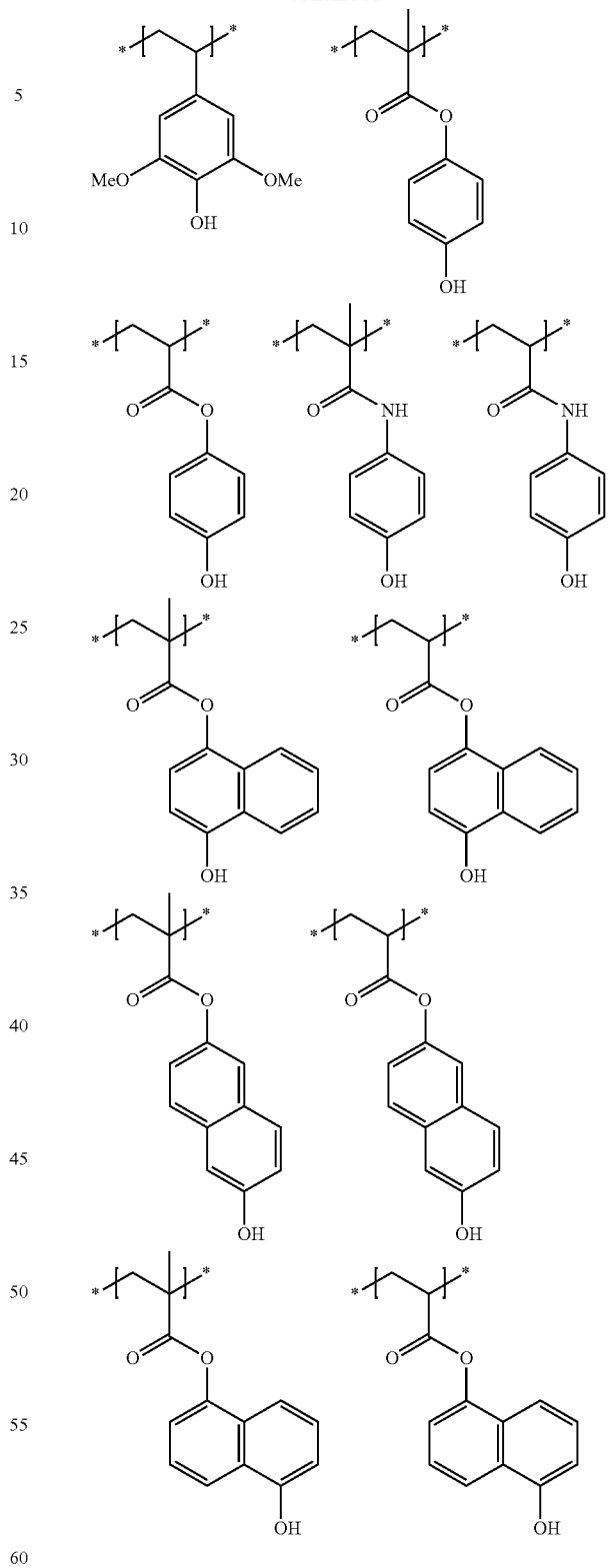
It is preferred for the resin (A2) to have a structure in which the hydrogen atom of the phenolic hydroxyl group is replaced by a group with a non-acid-decomposable polyalicyclic hydrocarbon structure from the viewpoint that high glass transition temperature (Tg) can be realized and dry etching resistance can be enhanced.

When the resin (A2) has the above specified structure, the glass transition temperature (Tg) of the resin (A2) is increased, so that a very hard resist film can be formed, thereby permitting the control of acid diffusion and dry etching resistance. Accordingly, the diffusion of acids in areas exposed to actinic rays or radiation, such as electron beams or extreme violet, can be highly inhibited, thereby enhancing the resolving power, pattern shape and LER with respect to micropatterns. It can also be presumed that the introduction of the non-acid-decomposable polyalicyclic hydrocarbon structure in the resin (A2) contributes toward enhancement of dry etching resistance. Furthermore, although the detail is not apparent, the polyalicyclic hydrocarbon structure exhibits a high hydrogen radical donating capability, thereby providing a hydrogen source at the decomposition of the above-mentioned acid generator (B) as a photoacid generator. Thus, it is presumed that the efficiency of decomposition of the photoacid generator is enhanced, thereby realizing an enhanced acid generating efficiency. It is assumed that this contributes toward an enhanced sensitivity.

In the above specified structure that may be introduced in the resin (A2) according to the present invention, the aromatic ring, such as a benzene ring, and the group with a non-acid-decomposable polyalicyclic hydrocarbon structure are connected to each other via the oxygen atom from the phenolic hydroxyl group. As mentioned above, this structure not only contributes toward high dry etching resistance but also can enhance the glass transition temperature (Tg) of the resin (A2). It is presumed that high resolving power is provided by the effect of a combination of these.

The term "non-acid-decomposable" used in the present invention means the property that no decomposition reaction is induced by acids generated by the above-described acid generators (B).

In particular, it is preferred for the group with a non-acid-decomposable polyalicyclic hydrocarbon structure to be a group that is stable in an acid and an alkali. The group that is stable in an acid and an alkali refers to a group exhibiting neither acid decomposability not alkali decomposability. The acid decomposability refers to the property that a decomposition reaction is induced by the action of acids generated by the above-described acid generators (B). As the group exhibiting acid decomposability, there can be mentioned any of the acid-decomposable groups set forth above in connection with the resin (A1).

The alkali decomposability refers to the property that a decomposition reaction is induced by the action of an alkali developer. As the group exhibiting alkali decomposability, there can be mentioned any of the heretofore known groups (for example, groups with lactone structures, etc.) that when acted on by an alkali developer, are decomposed to thereby increase the rate of dissolution in the alkali developer, which groups are contained in the resins appropriately used in positive chemically amplified resist compositions.

The group with a polyalicyclic hydrocarbon structure is not particularly limited as long as it is a monovalent group with a polyalicyclic hydrocarbon structure. The sum of carbon atoms thereof is preferably in the range of 5 to 40, more preferably 7 to 30. The polyalicyclic hydrocarbon structure within rings thereof may contain an unsaturated bond.

The polyalicyclic hydrocarbon structure in the group with a polyalicyclic hydrocarbon structure refers to a structure containing a plurality of monoalicyclic hydrocarbon groups, or a polycycle-containing alicyclic hydrocarbon structure, and may be a bridged one. The monoalicyclic hydrocarbon groups are preferably cycloalkyl groups each having 3 to 8 carbon atoms. As such, there can be mentioned, for example, a cyclopropyl group, a cyclopentyl group, a cyclohexyl group, a cyclobutyl group, a cyclooctyl group and the like. The structure containing a plurality of monoalicyclic hydrocarbon groups contains a plurality of these groups. The structure containing a plurality of monoalicyclic hydrocarbon groups preferably contains 2 to 4, most preferably 2, monoalicyclic hydrocarbon groups.

As the polycycle-containing alicyclic hydrocarbon structure, there can be mentioned, for example, a bicyclo, tricyclo or tetracyclo structure having 5 or more carbon atoms. A polycyclo structure having 6 to 30 carbon atoms is preferred. As such, there can be mentioned, for example, an adamantane structure, a decalin structure, a norbornane structure, a norbornene structure, a cedrol structure, an isobornane structure, a bornane structure, a dicyclopentane structure, an α-pinane structure, a tricyclodecane structure, a tetracyclododecane structure or an androstane structure. The carbon atoms of each of the mono- or polycycloalkyl groups may be partially replaced with a heteroatom, such as an oxygen atom.

As preferred polyalicyclic hydrocarbon structures, there can be mentioned an adamantane structure, a decalin structure, a norbornane structure, a norbornene structure, a cedrol structure, a structure containing a plurality of cyclohexyl groups, a structure containing a plurality of cycloheptyl groups, a structure containing a plurality of cyclooctyl groups, a structure containing a plurality of cyclodecanyl groups, a structure containing a plurality of cyclododecanyl groups and a tricyclodecane structure. An adamantane structure is most preferred from the viewpoint of dry etching resistance (namely, it is most preferred for the above-mentioned group with a non-acid-decomposable polyalicyclic hydrocarbon structure to be a group with a non-acid-decomposable adamantane structure).

Chemical formulae of these polyalicyclic hydrocarbon structures (with respect to the structure containing a plurality of monoalicyclic hydrocarbon groups, monoalicyclic hydrocarbon structures (in particular, the structures of formulae (47) to (50) below) corresponding to monoalicyclic hydrocarbon groups) are shown below.

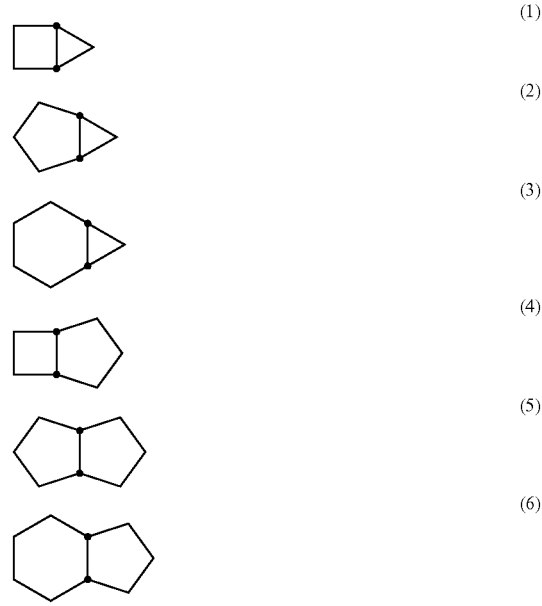

125
-continued
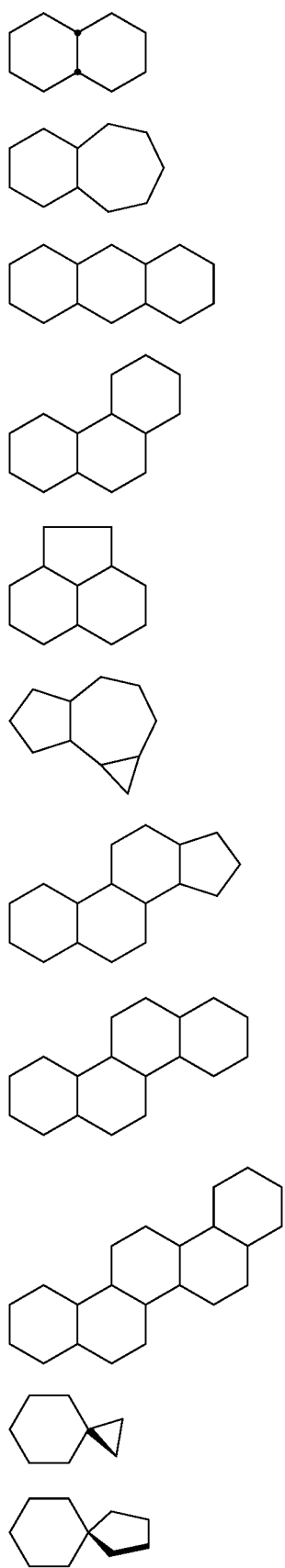
126
-continued
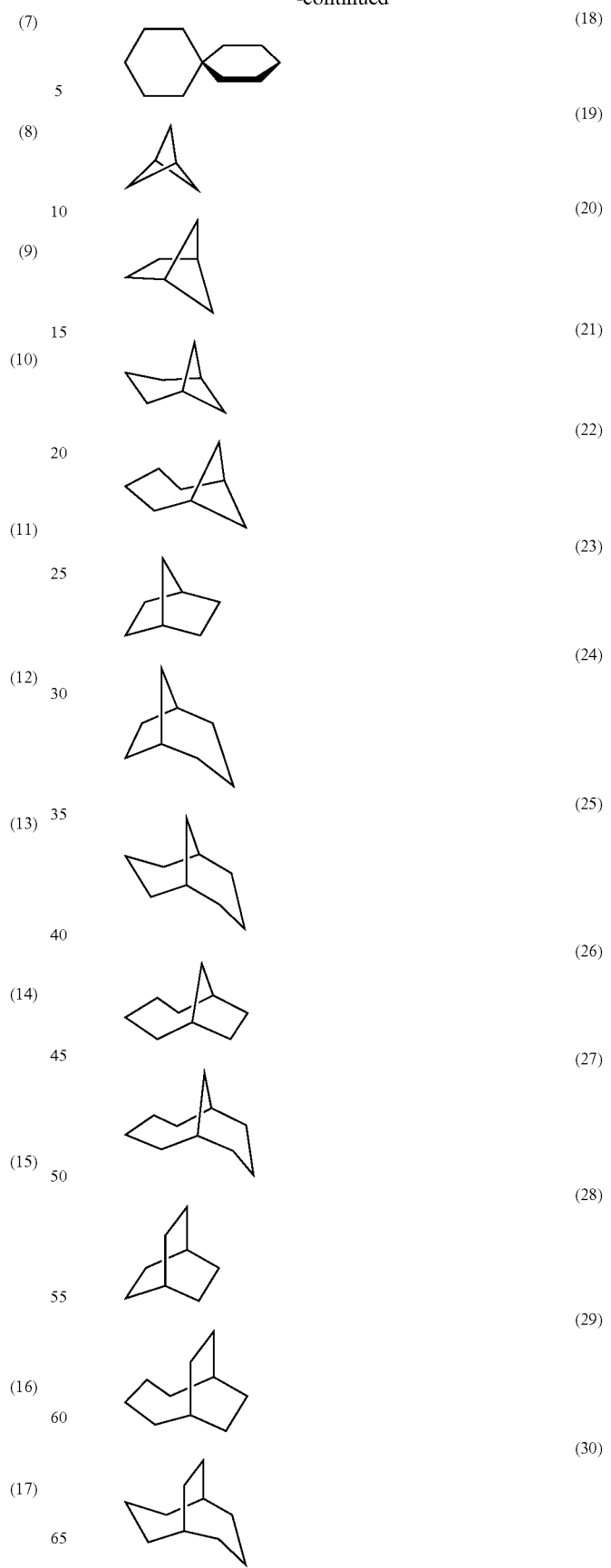

(31) 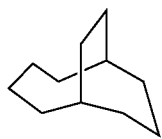

(32) 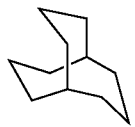

(33) 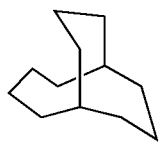

(34) 

(35) 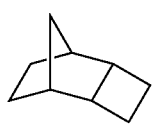

(36) 

(37) 

(38) 

(39) 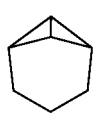

(40) 

(41) 

(42) 

(43) 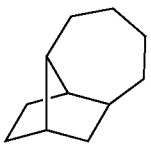

(44) 

(45) 

(46) 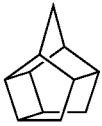

(47) 

(48)

(49) 

(50) 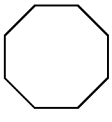

(51) 

Substituents may be introduced in these polyalicyclic hydrocarbon structures. As the substituents, there can be mentioned, for example, an alkyl group (preferably 1 to 6 carbon atoms), a cycloalkyl group (preferably 3 to 10 carbon atoms), an aryl group (preferably 6 to 15 carbon atoms), a halogen atom, a hydroxyl group, an alkoxy group (preferably 1 to 6 carbon atoms), a carboxyl group, a carbonyl group, a thiocarbonyl group, an alkoxycarbonyl group (preferably 2 to 7 carbon atoms), an aminoacyl group (preferably 2 to 20 carbon atoms) and groups each comprised of a combination of these (preferably 1 to 30 carbon atoms in total, more preferably 1 to 15 carbon atoms in total).

Among these polyalicyclic hydrocarbon structures, the structures of formulae (7), (23), (40), (41) and (51) above and the structure containing two monovalent groups each corresponding to the structure of formula (48) above in which a bonding hand is created at an arbitrary hydrogen atom are preferred. The structures of formulae (23), (40) and (51) above and the structure containing two monovalent groups each corresponding to the structure of formula (48) above in which a bonding hand is created at an arbitrary hydrogen atom are more preferred. The structure of formula (40) above is most preferred.

It is preferred for the group with a polyalicyclic hydrocarbon structure to be a monovalent group corresponding to any of these polyalicyclic hydrocarbon structures in which a bonding hand is created at an arbitrary hydrogen atom.

It is preferred for the structure in which the hydrogen atom of phenolic hydroxyl group is replaced by the above group with a non-acid-decomposable polyalicyclic hydrocarbon structure to be contained in the resin (A2) as a repeating unit with the structure in which the hydrogen atom of phenolic hydroxyl group is replaced by the above group with a non-acid-decomposable polyalicyclic hydrocarbon structure. More preferably, the structure is contained in the resin (A2) as any of repeating units of general formula (3) below.

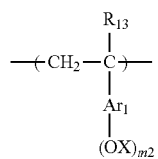

(3)

In general formula (3), $R_{13}$ represents a hydrogen atom or a methyl group.

X represents a group with a non-acid-decomposable polyalicyclic hydrocarbon structure.

$Ar_1$ represents an aromatic ring; and m2 is an integer of 1 or greater.

$R_{13}$ in general formula (3) is a hydrogen atom or a methyl group, preferably a hydrogen atom.

As the aromatic ring represented by $Ar_1$ in general formula (3), there can be mentioned, for example, an optionally substituted aromatic hydrocarbon ring having 6 to 18 carbon atoms, such as a benzene ring, a naphthalene ring, an anthracene ring, a fluorene ring or a phenanthrene ring, or an aromatic ring heterocycle containing a heteroring, such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring or a thiazole ring. Of these, a benzene ring and a naphthalene ring are preferred from the viewpoint of resolution. A benzene ring is most preferred.

A substituent other than the above —OX groups may be introduced in the aromatic ring represented by $Ar_1$. As the substituent, there can be mentioned, for example, an alkyl group (preferably 1 to 6 carbon atoms), a cycloalkyl group (preferably 3 to 10 carbon atoms), an aryl group (preferably 6 to 15 carbon atoms), a halogen atom, a hydroxyl group, an alkoxy group (preferably 1 to 6 carbon atoms), a carboxyl group or an alkoxycarbonyl group (preferably 2 to 7 carbon atoms). The substituent is preferably an alkyl group, an alkoxy group or an alkoxycarbonyl group, more preferably an alkoxy group.

X represents a group with a non-acid-decomposable polyalicyclic hydrocarbon structure. Particular examples and preferred ranges of the groups each with a non-acid-decomposable polyalicyclic hydrocarbon structure represented by X are the same as mentioned above. It is preferred for X to be any of groups of the formula —Y—$X_2$ in general formula (4) to be described hereinafter.

In the general formula, m2 is preferably an integer of 1 to 5, most preferably 1. When m2 is 1 and $Ar_1$ is a benzene ring, the position of —OX substitution may be any of the para-, meta- and ortho-positions to the site of bonding to the principal chain of the polymer in the benzene ring. The para- and meta-positions are preferred, and the para-position is more preferred.

In the present invention, it is preferred for the repeating units of general formula (3) above to be the repeating units of general formula (4) below.

When use is made of the resin (A2) comprising any of repeating units of general formula (4), the Tg value of the resin (A2) is high, so that a very hard resist film is formed. Accordingly, the acid diffusion and dry etching resistance can be controlled highly reliably.

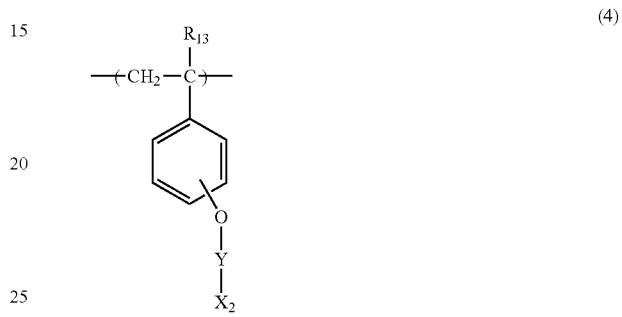

(4)

In general formula (4), $R_{13}$ represents a hydrogen atom or a methyl group.

Y represents a single bond or a bivalent connecting group.

$X_2$ represents a non-acid-decomposable polyalicyclic hydrocarbon group.

Among the repeating units of general formula (4) above, examples preferably employed in the present invention will be described below.

$R_{13}$ in general formula (4) is a hydrogen atom or a methyl group, preferably a hydrogen atom.

In general formula (4), Y is preferably a bivalent connecting group. The bivalent connecting group represented by Y is preferably a carbonyl group, a thiocarbonyl group, an alkylene group (preferably 1 to 10 carbon atoms, more preferably 1 to 5 carbon atoms), a sulfonyl group, —COCH$_2$—, —NH—, or a bivalent connecting group comprised of a combination of these (preferably, in total, 1 to 20 carbon atoms, more preferably 1 to 10 carbon atoms). The bivalent connecting group is more preferably a carbonyl group, —COCH$_2$—, a sulfonyl group, —CONH— or —CSNH—, further more preferably a carbonyl group or —COCH$_2$—, and most preferably a carbonyl group.

$X_2$ represents a polyalicyclic hydrocarbon group, being non-acid-decomposable. The sum of carbon atoms of the polyalicyclic hydrocarbon group is preferably in the range of 5 to 40, more preferably 7 to 30. The polyalicyclic hydrocarbon group within its rings may contain an unsaturated bond.

This polyalicyclic hydrocarbon group refers to a group containing a plurality of monoalicyclic hydrocarbon groups, or a polycycle-containing alicyclic hydrocarbon group, and may be a bridged one. The monoalicyclic hydrocarbon groups are preferably cycloalkyl groups each having 3 to 8 carbon atoms. As such, there can be mentioned, for example, a cyclopropyl group, a cyclopentyl group, a cyclohexyl group, a cyclobutyl group, a cyclooctyl group and the like. The group containing a plurality of monoalicyclic hydrocarbon groups contains a plurality of these groups. The group containing a plurality of monoalicyclic hydrocarbon groups preferably contains 2 to 4, most preferably 2, monoalicyclic hydrocarbon groups.

As the polycycle-containing alicyclic hydrocarbon group, there can be mentioned a group with, for example, a bicyclo, tricyclo or tetracyclo structure having 5 or more carbon atoms. A group with a polycyclo structure having 6 to 30 carbon atoms is preferred. As such, there can be mentioned, for example, an adamantyl group, a norbornyl group, a norbornenyl group, an isobornyl group, a camphonyl group, a dicyclopentyl group, an α-pinanyl group, a tricyclodecanyl group, a tetracyclododecyl group or an androstanyl group. The carbon atoms of each of the mono- or polycycloalkyl groups may be partially replaced with a heteroatom, such as an oxygen atom.

As preferred polyalicyclic hydrocarbon groups represented by $X_2$, there can be mentioned an adamantyl group, a decalin group, a norbornyl group, a norbornenyl group, a cedrol group, a group containing a plurality of cyclohexyl groups, a group containing a plurality of cycloheptyl groups, a group containing a plurality of cyclooctyl groups, a group containing a plurality of cyclodecanyl groups, a group containing a plurality of cyclododecanyl groups and a tricyclodecanyl group. An adamantyl group is most preferred from the viewpoint of dry etching resistance. Chemical formulae of the polyalicyclic hydrocarbon structures in the polyalicyclic hydrocarbon groups represented by $X_2$ are the same as the above chemical formulae of the polyalicyclic hydrocarbon structures in the groups each with a polyalicyclic hydrocarbon structure. Preferred ranges are also the same. As the polyalicyclic hydrocarbon group represented by $X_2$, there can be mentioned a monovalent group corresponding to any of the above-mentioned polyalicyclic hydrocarbon structures in which a bonding hand is created at an arbitrary hydrogen atom.

Substituents may be introduced in these alicyclic hydrocarbon groups. As such substituents, there can be mentioned those set forth above as being introducible in the polyalicyclic hydrocarbon structures.

In general formula (4), the position of —O—Y—$X_2$ substitution may be any of the para-, meta- and ortho-positions to the site of bonding to the principal chain of the polymer in the benzene ring. The para-position is preferred.

In the present invention, it is most preferred for the repeating units of general formula (3) above to be repeating units of general formula (4') below.

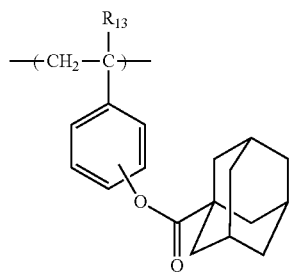

(4')

In general formula (4'), $R_{13}$ represents a hydrogen atom or a methyl group.

$R_{13}$ in general formula (4') is a hydrogen atom or a methyl group, preferably a hydrogen atom.

In general formula (4'), the position of substitution with the adamantyl ester group may be any of the para-, meta- and ortho-positions to the site of bonding to the principal chain of the polymer in the benzene ring. The para-position is preferred.

Specific examples of the repeating units of general formula (3) are shown below.

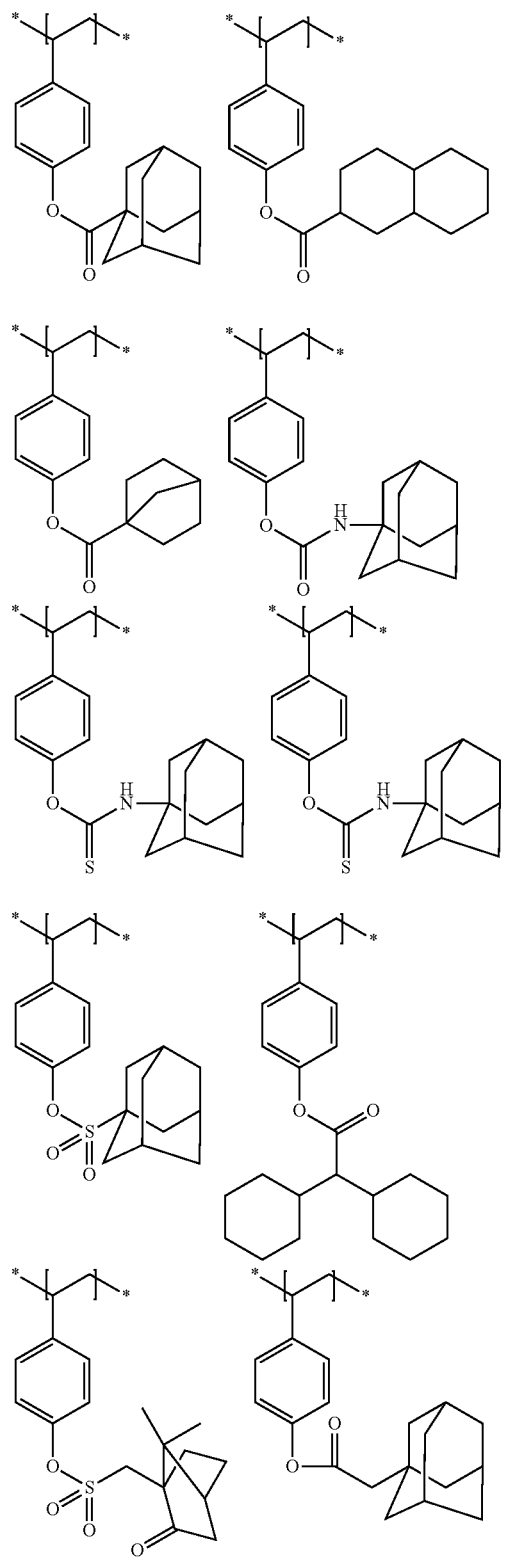

-continued
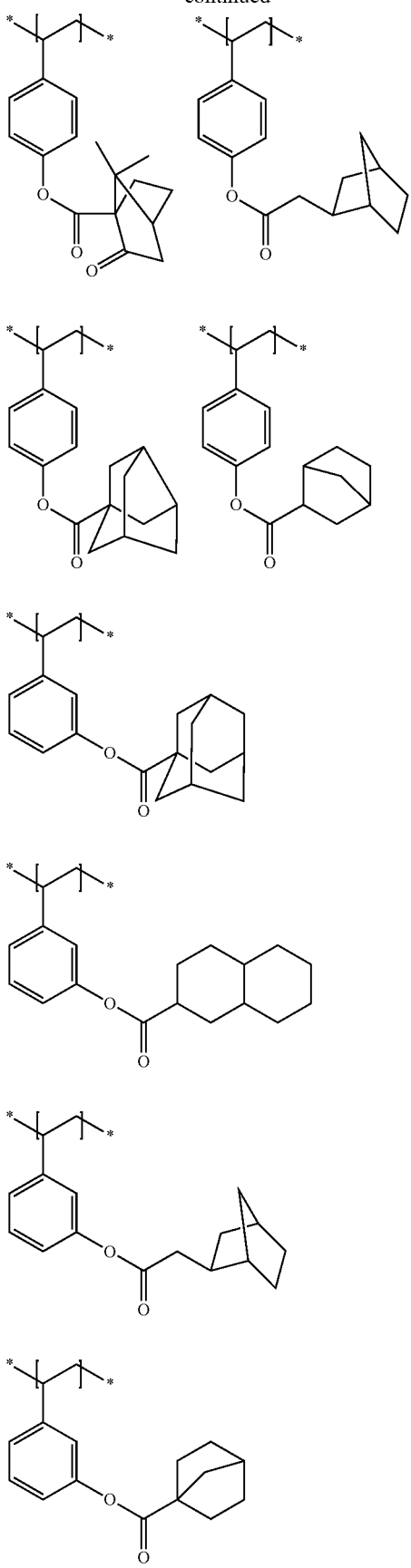
-continued
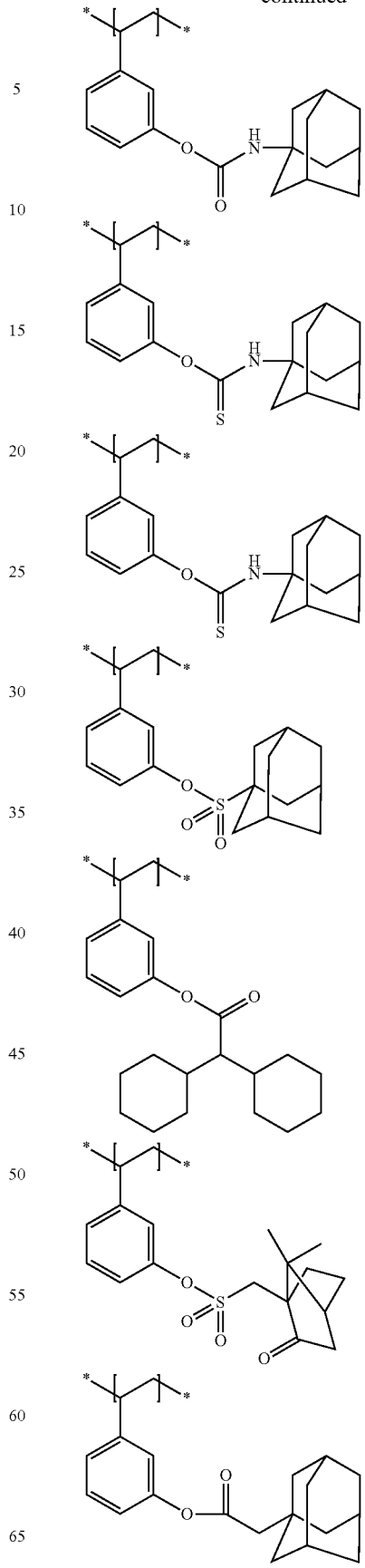

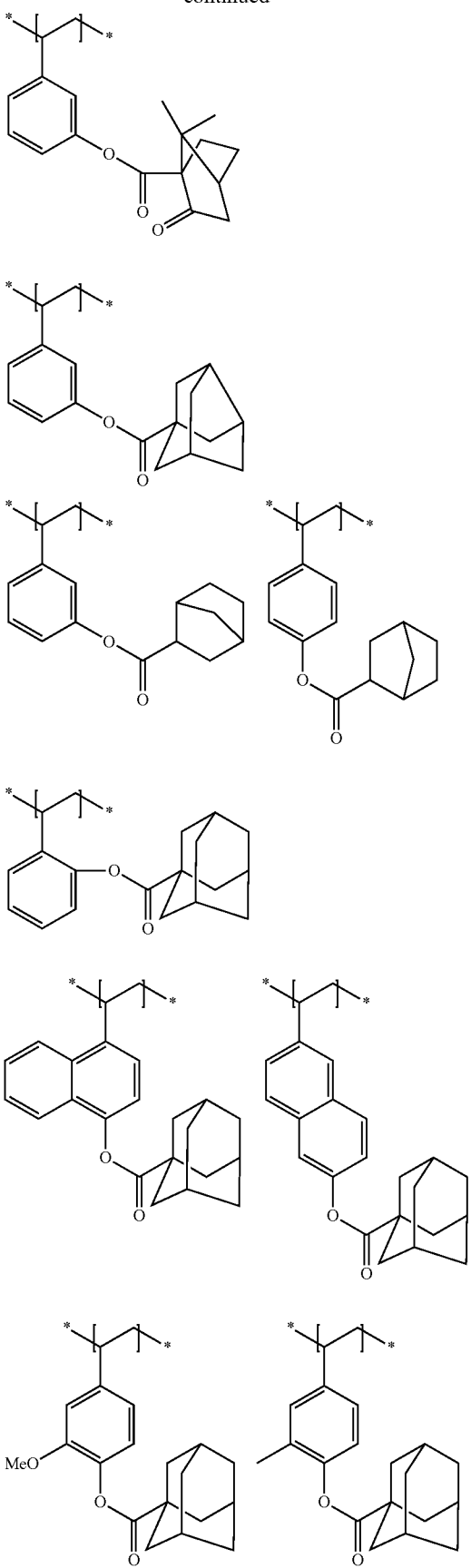

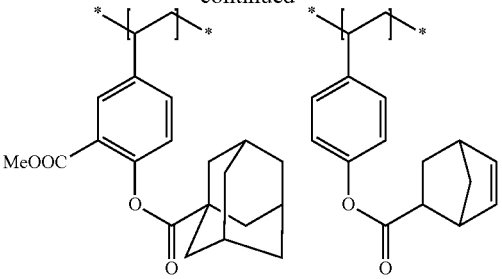

When the resin (A2) comprises a repeating unit with the structure in which the hydrogen atom of phenolic hydroxyl group is replaced by the above group with a non-acid-decomposable polyalicyclic hydrocarbon structure, the content of this repeating unit is preferably in the range of 1 to 40 mol %, more preferably 2 to 30 mol %, based on all the repeating units of the resin (A2) as a polymeric compound.

It is also preferred for the resin (A2) for use in the present invention to further comprise the following repeating units (hereinafter also referred to as "other repeating units") as repeating units other than the foregoing repeating units.

As examples of polymerizable monomers for the formation of such other repeating units, there can be mentioned styrene, an alkyl-substituted styrene, an alkoxy-substituted styrene, a halogenated styrene, an O-alkylated styrene, an O-acylated styrene, a hydrogenated hydroxystyrene, maleic anhydride, an acrylic acid derivative (acrylic acid, an acrylic ester or the like), a methacrylic acid derivative (methacrylic acid, a methacrylic ester or the like), an N-substituted maleimide, acrylonitrile, methacrylonitrile, vinylnaphthalene, vinylanthracene, an optionally substituted indene and the like.

It is optional for the resin (A2) to contain these other repeating units. When these other repeating units are contained, the content thereof in the resin (A2), based on all the repeating units constituting the resin (A2), is generally in the range of 1 to 30 mol %, preferably 1 to 20 mol %, and more preferably 2 to 10 mol %.

The resin (A2) can be synthesized in accordance with the heretofore known radical polymerization method, anion polymerization method or living radical polymerization method (iniferter method or the like). For example, in the anion polymerization method, a vinyl monomer is dissolved in an appropriate organic solvent, and reacted generally in cooled condition by use of a metal compound (butyllithium, etc.) as an initiator, thereby obtaining a polymer.

As the resin (A2), use can also be made of a polyphenol compound (for example, JP-A-2008-145539) produced by a condensation reaction between an aromatic ketone or aromatic aldehyde and a compound containing 1 to 3 phenolic hydroxyl groups; a calixarene derivative (for example, JP-A-2004-18421); a Noria derivative (for example, JP-A-2009-222920); or a polyphenol derivative (for example, JP-A-2008-94782). The resins may be synthesized through modification by a polymer reaction.

Preferably, the resin (A2) is prepared by synthesizing a polymer in accordance with the radical polymerization method or anion polymerization method and modifying the polymer through a polymer reaction.

The weight average molecular weight of the resin (A2) is preferably in the range of 1000 to 200,000, more preferably 2000 to 50,000 and further more preferably 2000 to 15,000.

The polydispersity index (molecular weight distribution, Mw/Mn) of the resin (A2) is preferably 2.0 or below. From the viewpoint of sensitivity and resolution enhancements, the polydispersity index is preferably in the range of 1.0 to 1.80, more preferably 1.0 to 1.60 and most preferably 1.0 to 1.20. The use of living polymerization, such as living anion polymerization, preferably uniformizes the polydispersity index (molecular weight distribution) of obtained polymeric compound. The weight average molecular weight and polydispersity index of the resin (A2) are defined as polystyrene-equivalent values determined by GPC measurement.

The amount of resin (A2) added to the composition of the present invention, based on the total solids of the composition, is preferably in the range of 30 to 95 mass %, more preferably 40 to 90 mass % and most preferably 50 to 85 mass %.

Specific examples of the resins (A2) are shown below, which in no way limit the scope of the present invention.

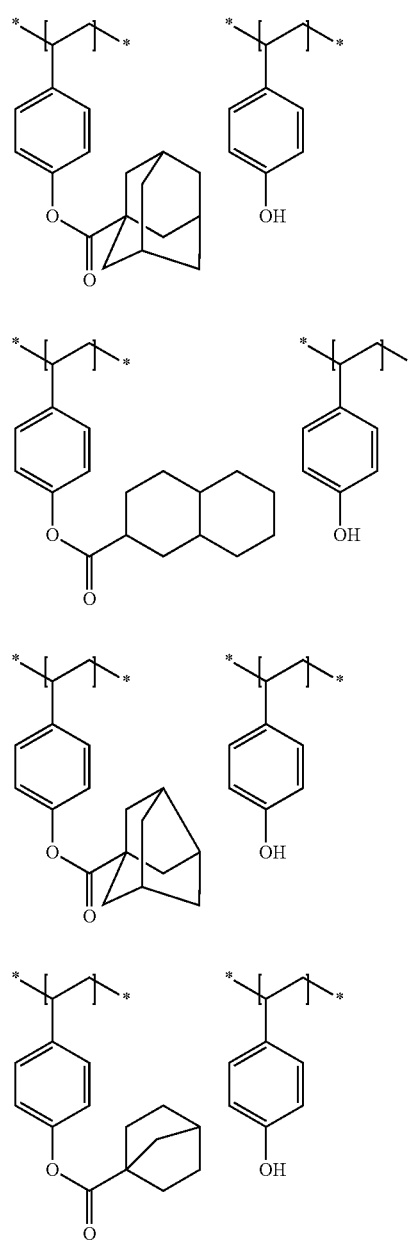

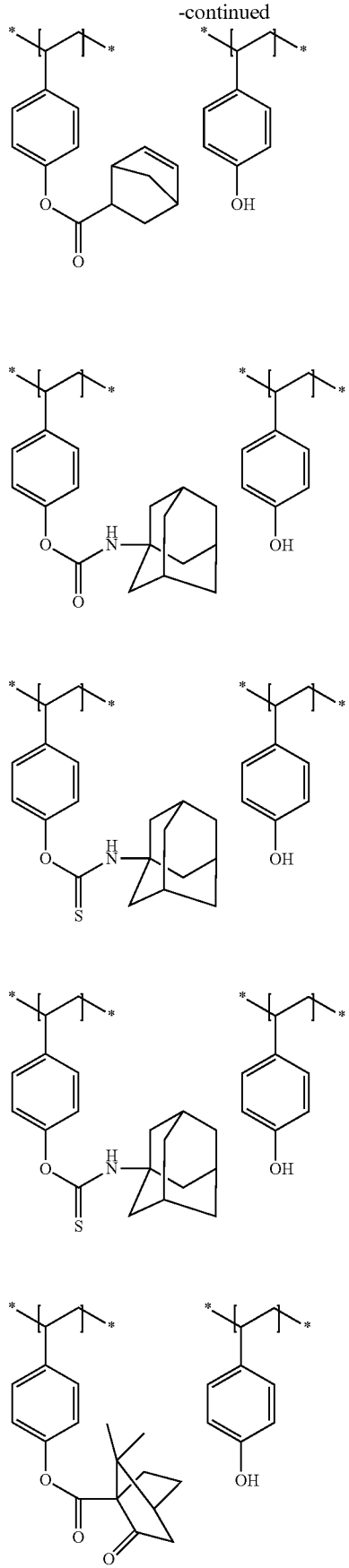

139
-continued
140
-continued
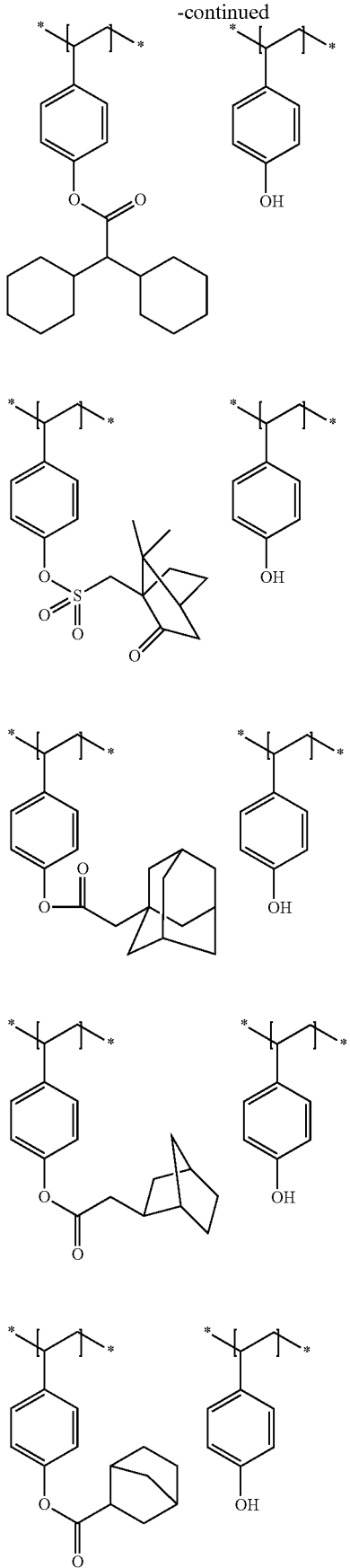
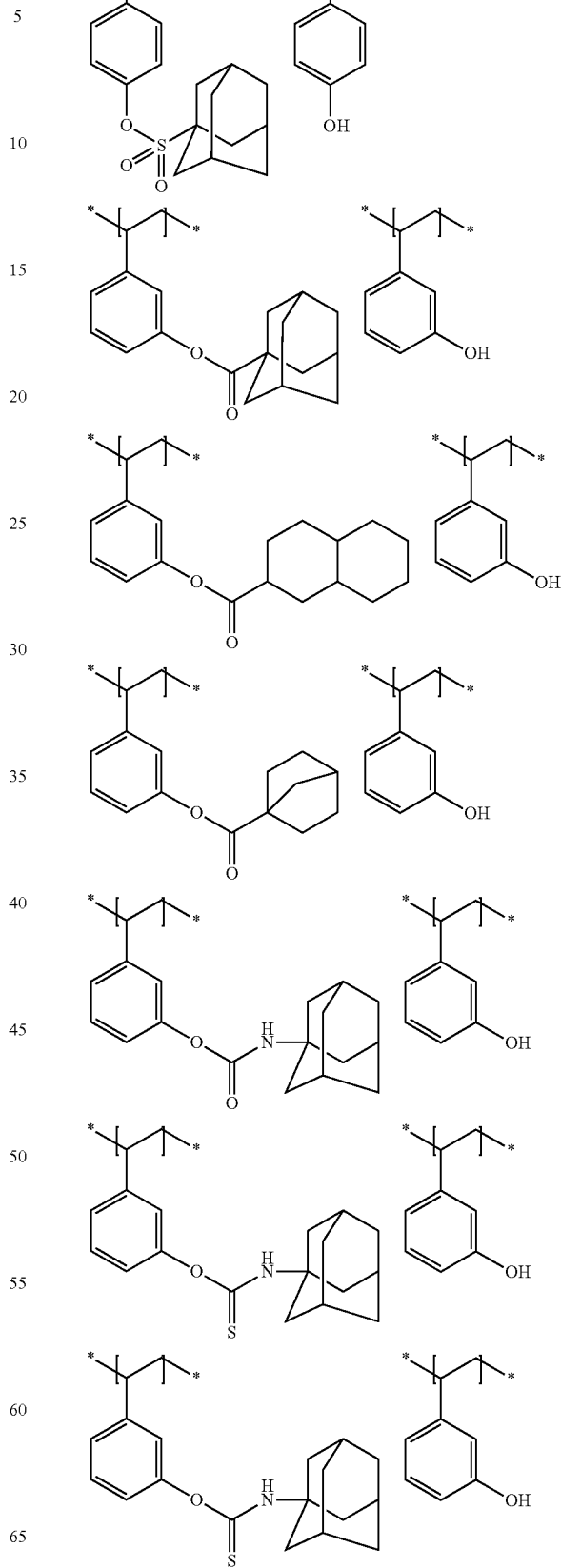

-continued
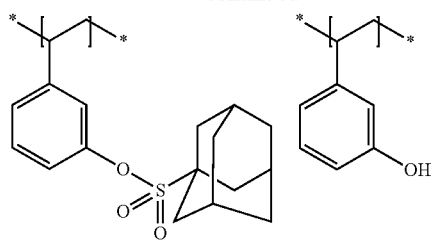
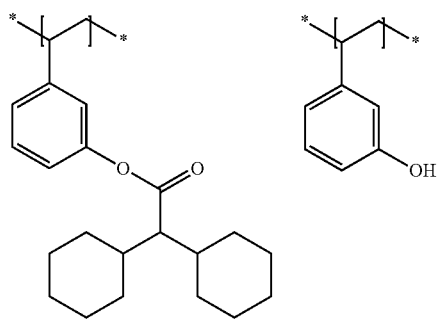
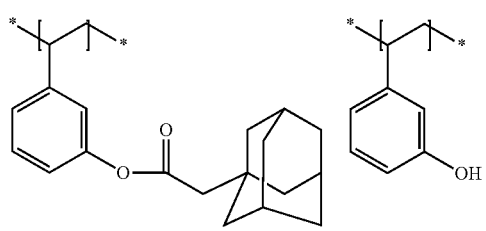
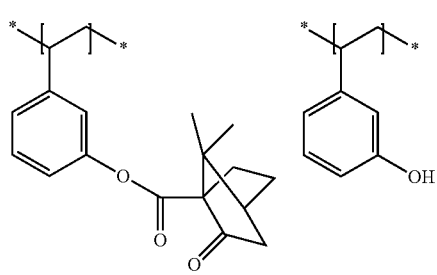
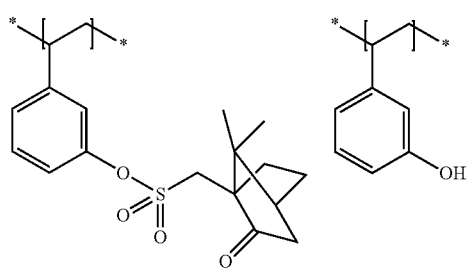
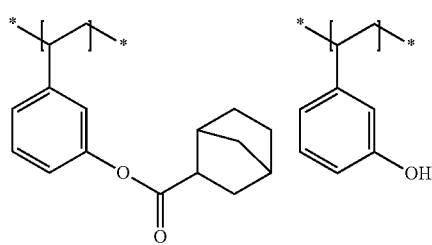
-continued
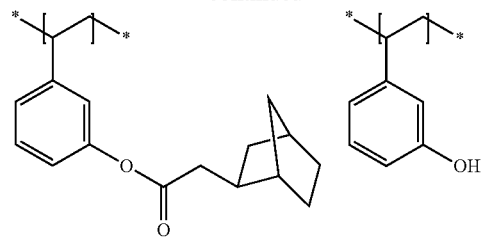
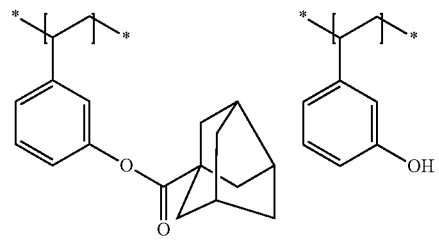
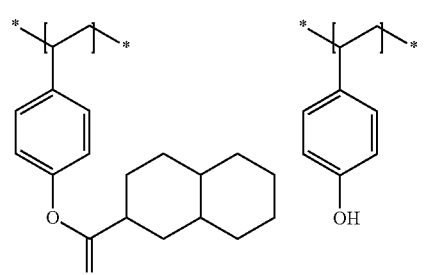
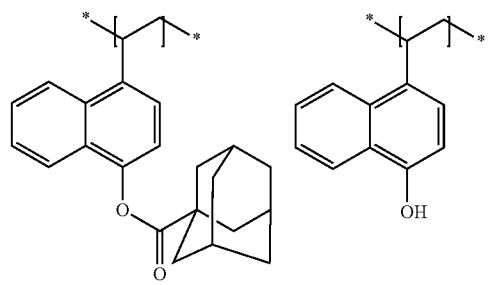
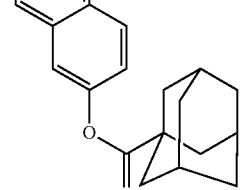
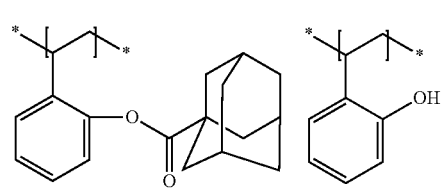

-continued
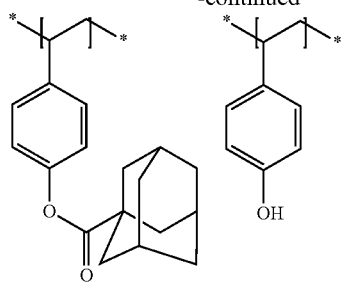
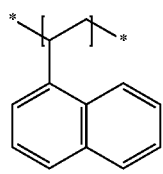
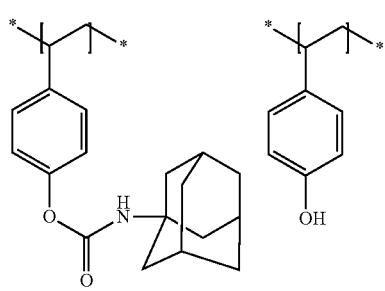
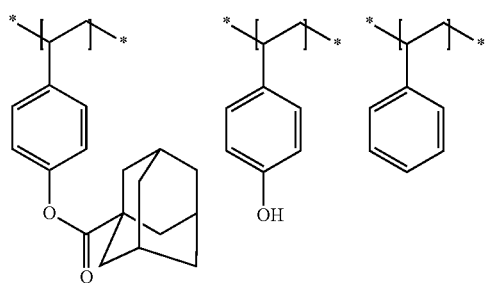
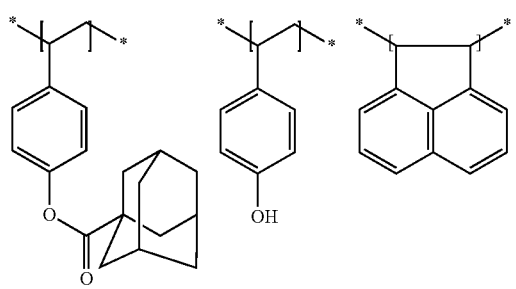
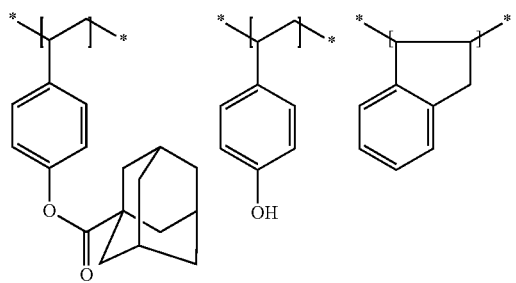
-continued
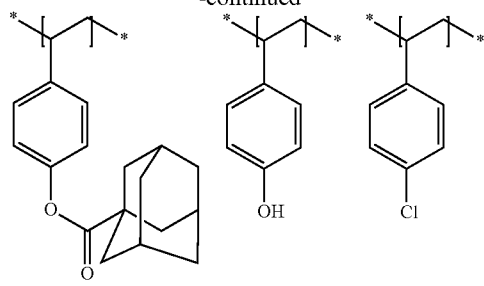
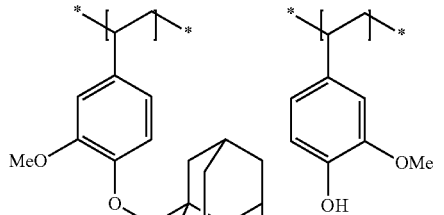
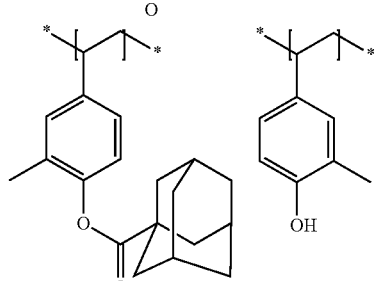
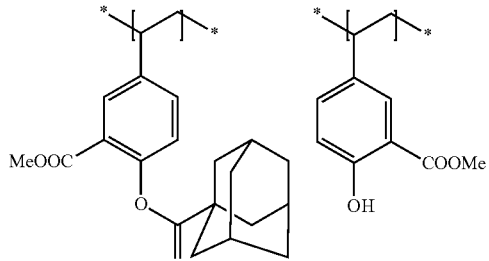
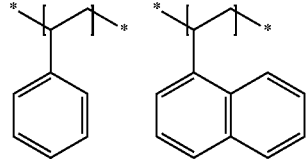
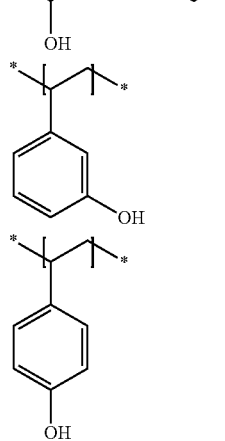

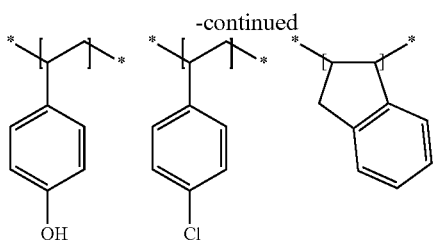
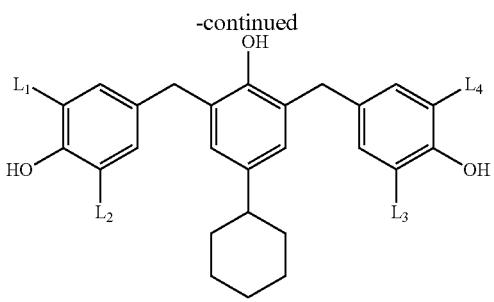

<Crosslinking Agent (C)>

When the resin (A2) containing a phenolic hydroxyl group is used as the resin (A) and when the composition of the present invention is used in the formation of a negative pattern, it is preferred for the composition of the present invention to contain a compound (hereinafter referred to as "compound (C)" or "crosslinking agent") containing two or more methylol groups in its molecule as a crosslinking agent. The methylol groups mentioned herein are the groups of general formula (M) above.

As preferred crosslinking agents, there can be mentioned a hydroxymethylated or alkoxymethylated phenol compound, an alkoxymethylated melamine compound, an alkoxymethylglycoluril compound and an alkoxymethylated urea compound. Arbitrary substituents may be introduced in these. The compound (C) most preferred as a crosslinking agent is an alkoxymethylglycoluril derivative or phenol derivative of 1200 or less molecular weight containing 3 to 5 benzene rings in each molecule and further containing two or more hydroxymethyl or alkoxymethyl groups in total.

It is preferred for the alkoxymethyl group to be a methoxymethyl group or an ethoxymethyl group.

Among these crosslinking agents, a phenol derivative containing a hydroxymethyl group can be obtained by reacting a corresponding phenol compound containing no hydroxymethyl group with formaldehyde in the presence of a base catalyst. Further, a phenol derivative containing an alkoxymethyl group can be obtained by reacting a corresponding phenol derivative containing a hydroxymethyl group with an alcohol in the presence of an acid catalyst.

As other preferred examples of crosslinking agents, there can be mentioned compounds each containing an N-hydroxymethyl group or an N-alkoxymethyl group, such as an alkoxymethylated melamine compound, an alkoxymethylglycoluril compound and an alkoxymethylated urea compound.

These compounds include hexamethoxymethylmelamine, hexaethoxymethylmelamine, tetramethoxymethylglycoluril, 1,3-bismethoxymethyl-4,5-bismethoxyethyleneurea, bismethoxymethylurea and the like. These are disclosed in EP 0133216 A, West German Patent Nos. 3634671 and 3711264 and EP 0212482 A.

Among these crosslinking agents, those particularly preferred are shown below.

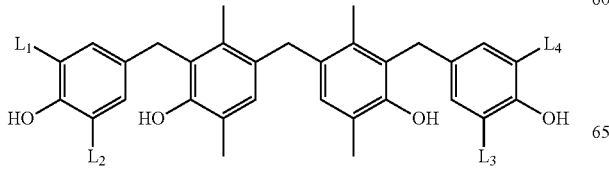
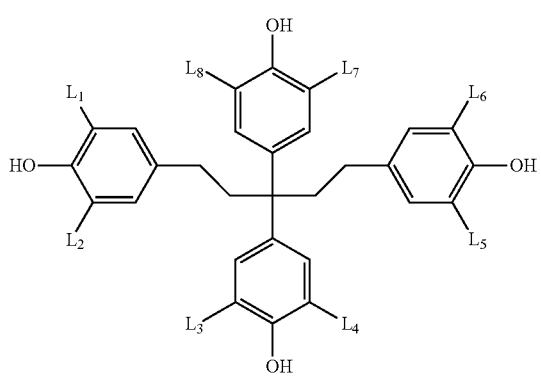
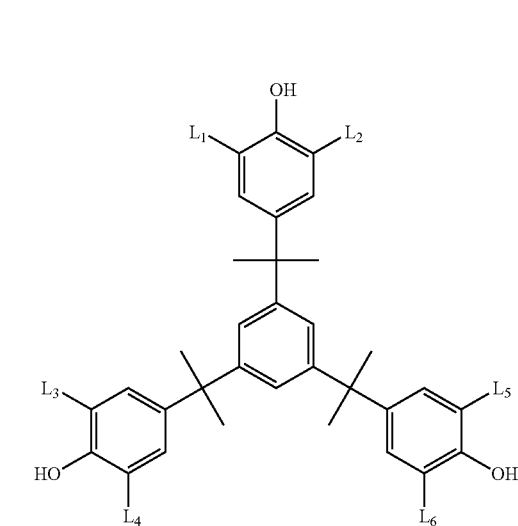
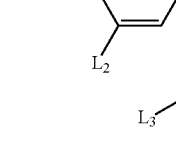
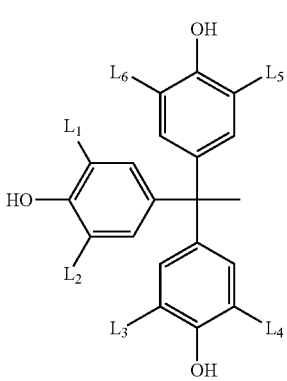

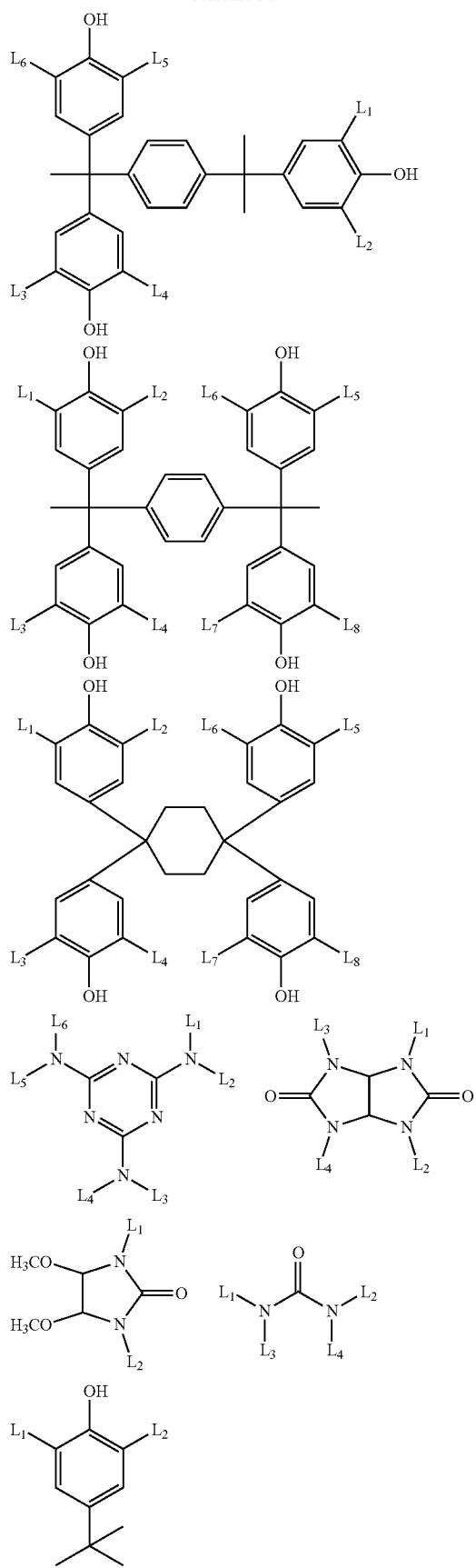

In the formulae, each of $L_1$ to $L_8$ independently represents a hydrogen atom, a hydroxymethyl group, a methoxymethyl group, an ethoxymethyl group or an alkyl group having 1 to 6 carbon atoms.

In the present invention, the content of crosslinking agent, based on the total solids of the composition of the present invention comprising the resin (A2) containing a phenolic hydroxyl group, is preferably in the range of 3 to 65 mass %, more preferably 5 to 50 mass %. When the content of crosslinking agent falls within the range of 3 to 65 mass %, not only can any deteriorations of remaining film ratio and resolving power be prevented but also the storage stability of the composition of the present invention can be favorably maintained.

In the present invention, one type of crosslinking agent (C) may be used alone, or two or more types thereof may be used in combination. Using two or more types thereof in combination is preferred from the viewpoint of favorable pattern shape.

For example, when any of the above phenol derivatives is used in combination with another crosslinking agent, e.g., the above compound containing an N-alkoxymethyl group, the ratio of phenol derivative/other crosslinking agent in terms of molar ratio is generally in the range of 90/10 to 20/80, preferably 85/15 to 40/60 and more preferably 80/20 to 50/50.

<Basic Compound>

From the viewpoint of diminishing any performance change over time from exposure to baking, it is preferred for the actinic-ray- or radiation-sensitive resin composition of the present invention to contain a basic compound.

As preferred basic compounds, there can be mentioned the compounds with the structures of the following formulae (A) to (E).

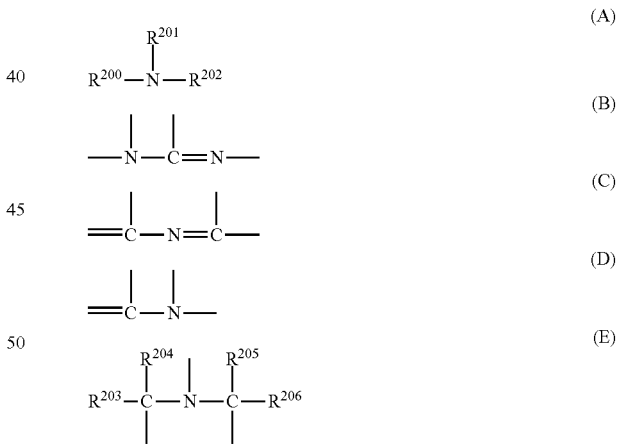

In general formulae (A) and (E), $R^{200}$, $R^{201}$ and $R^{202}$ may be identical to or different from each other, and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded to each other to thereby form a ring.

$R^{203}$, $R^{204}$, $R^{205}$ and $R^{206}$ may be identical to or different from each other, and each represent an alkyl group having 1 to 20 carbon atoms.

With respect to the above alkyl group, as a preferred substituted alkyl group, there can be mentioned an amino-alkyl group having 1 to 20 carbon atoms, a hydroxyalkyl group having 1 to 20 carbon atoms or a cyanoalkyl group having 1 to 20 carbon atoms.

In general formulae (A) and (E), it is preferred for the alkyl groups to be unsubstituted.

As preferred basic compounds, there can be mentioned guanidine, aminopyrrolidine, pyrazole, pyrazoline, piperazine, aminomorpholine, aminoalkylmorpholines, piperidine and the like. As further preferred compounds, there can be mentioned compounds with an imidazole structure, a diazabicyclo structure, an onium hydroxide structure, an onium carboxylate structure, a trialkylamine structure, an aniline structure or a pyridine structure; alkylamine derivatives containing a hydroxyl group and/or an ether bond; aniline derivatives containing a hydroxyl group and/or an ether bond; and the like.

As the compounds with an imidazole structure, there can be mentioned imidazole, 2,4,5-triphenylimidazole, benzimidazole, 2-phenylbenzimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, a triarylsulfonium hydroxide, phenacylsulfonium hydroxide, and sulfonium hydroxides containing a 2-oxoalkyl group, such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. The compounds with an onium carboxylate structure correspond to the compounds with an onium hydroxide structure wherein the anion moiety is a carboxylate, and as such, there can be mentioned, for example, an acetate, adamantane-1-carboxylate, a perfluoroalkyl carboxylate and the like. As the compounds with a trialkylamine structure, there can be mentioned tri(n-butyl)amine, tri(n-octyl)amine and the like. As the aniline compounds, there can be mentioned 2,6-diisopropylaniline, N,N-dimethylaniline, N,N-dibutylaniline, N,N-dihexylaniline and the like. As the alkylamine derivatives containing a hydroxyl group and/or an ether bond, there can be mentioned ethanolamine, diethanolamine, triethanolamine, N-phenyldiethanolamine, tris(methoxyethoxyethyl)amine and the like. As the aniline derivatives containing a hydroxyl group and/or an ether bond, there can be mentioned N,N-bis(hydroxyethyl)aniline and the like.

As preferred basic compounds, there can be further mentioned an amine compound containing a phenoxy group, an ammonium salt compound containing a phenoxy group, an amine compound containing a sulfonic ester group and an ammonium salt compound containing a sulfonic ester group.

As the amine compound, use can be made of primary, secondary and tertiary amine compounds. An amine compound having its at least one alkyl group bonded to the nitrogen atom thereof is preferred. Among the amine compounds, a tertiary amine compound is preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the amine compounds, it is preferred for the alkyl chain to contain an oxygen atom so as to form an oxyalkylene group. The number of oxyalkylene groups in each molecule is one or more, preferably 3 to 9 and more preferably 4 to 6. The oxyalkylene group is preferably an oxyethylene group ($-CH_2CH_2O-$) or an oxypropylene group ($-CH(CH_3)CH_2O-$ or $-CH_2CH_2CH_2O-$), more preferably an oxyethylene group.

As the ammonium salt compound, use can be made of primary, secondary, tertiary and quaternary ammonium salt compounds. An ammonium salt compound having its at least one alkyl group bonded to the nitrogen atom thereof is preferred. In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. In the ammonium salt compounds, it is preferred for the alkyl chain to contain an oxygen atom so as to form an oxyalkylene group. The number of oxyalkylene groups in each molecule is one or more, preferably 3 to 9 and more preferably 4 to 6. The oxyalkylene group is preferably an oxyethylene group ($-CH_2CH_2O-$) or an oxypropylene group ($-CH(CH_3)CH_2O-$ or $-CH_2CH_2CH_2O-$), more preferably an oxyethylene group.

As the anions of the ammonium salt compounds, there can be mentioned a halogen atom, a sulfonate, a borate, a phosphate and the like. Of these, a halogen atom and a sulfonate are preferred. Among halogen atoms, chloride, bromide and iodide are especially preferred. Among sulfonates, an organic sulfonate having 1 to 20 carbon atoms is especially preferred. As the organic sulfonate, there can be mentioned an alkyl sulfonate having 1 to 20 carbon atoms or an aryl sulfonate. A substituent may be introduced in the alkyl group in the alkyl sulfonate. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group in the aryl sulfonate, there can be mentioned a benzene ring, a naphthalene ring or an anthracene ring. A substituent may be introduced in the benzene ring, naphthalene ring or anthracene ring. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound containing a phenoxy group and ammonium salt compound containing a phenoxy group are those containing a phenoxy group at the end of the alkyl group of the amine compound or ammonium salt compound opposed to the nitrogen atom. A substituent may be introduced in the phenoxy group. As the substituent introducible in the phenoxy group, there can be mentioned, for example, an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The substitution position of the substituent may be any of 2- to 6-positions. The number of substituents is optional within the range of 1 to 5.

It is preferred for at least one oxyalkylene group to be present between the phenoxy group and the nitrogen atom. The number of oxyalkylene groups in each molecule is one or more, preferably 3 to 9 and more preferably 4 to 6. The oxyalkylene group is preferably an oxyethylene group ($-CH_2CH_2O-$) or an oxypropylene group ($-CH(CH_3)CH_2O-$ or $-CH_2CH_2CH_2O-$), more preferably an oxyethylene group.

The sulfonic ester group in the amine compound containing a sulfonic ester group or ammonium salt compound containing a sulfonic ester group may be any of an alkyl sulfonate, a cycloalkyl sulfonate and an aryl sulfonate. In the alkyl sulfonate, the alkyl group preferably has 1 to 20 carbon atoms. In the cycloalkyl sulfonate, the cycloalkyl group preferably has 3 to 20 carbon atoms. In the aryl sulfonate, the aryl group preferably has 6 to 12 carbon atoms. Substituents may be introduced in the alkyl sulfonate, cycloalkyl sulfonate and aryl sulfonate. As preferred substituents, there can be mentioned a halogen atom, a cyano group, a nitro group, a carboxyl group, a carboxylic ester group and a sulfonic ester group.

It is preferred for at least one oxyalkylene group to be present between the sulfonic ester group and the nitrogen atom. The number of oxyalkylene groups in each molecule is one or more, preferably 3 to 9 and more preferably 4 to 6. The oxyalkylene group is preferably an oxyethylene group (—CH$_2$CH$_2$O—) or an oxypropylene group (—CH(CH$_3$)CH$_2$O— or —CH$_2$CH$_2$CH$_2$O—), more preferably an oxyethylene group.

The following compounds are also preferred basic compounds.

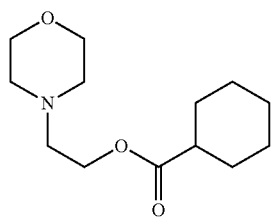
(MO-1)

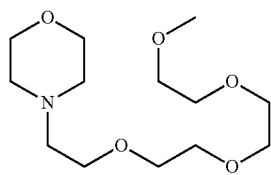
(MO-2)

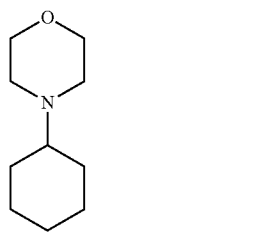
(MO-3)

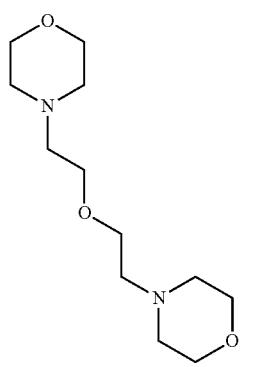
(MO-4)

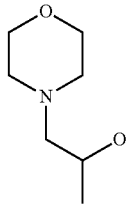
(MO-5)

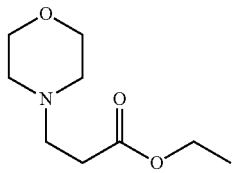
(MO-6)

Besides the foregoing compounds, as basic compounds, use can be made of the compounds described in sections [0180] to [0225] of JP-A-2011-22560, sections [0218] to [0219] of JP-A-2012-137735 and sections [0416] to [0438] of International Publication pamphlet WO2011/158687 A1, etc. The basic compound may be a basic compound or ammonium salt compound whose basicity is lowered upon exposure to actinic rays or radiation.

One type of basic compound may be used alone, or two or more types thereof may be used in combination.

It is optional for the composition of the present invention to contain a basic compound. When a basic compound is contained, the content thereof is generally in the range of 0.001 to 10 mass %, preferably 0.01 to 5 mass %, based on the total solids of the actinic-ray- or radiation-sensitive resin composition.

With respect to the ratio of the acid generator (including acid generator (B')) to basic compound used in the composition, it is preferred for the acid generator/basic compound (molar ratio) to fall within the range of 2.5 to 300. The reason is as follows. It is preferred for the molar ratio to be 2.5 or higher from the viewpoint of sensitivity and resolving power. It is preferred for the molar ratio to be 300 or below from the viewpoint of inhibiting any resolution deterioration due to thickening of resist pattern over time from exposure to baking treatment. The acid generator/basic compound (molar ratio) is more preferably in the range of 5.0 to 200, further more preferably 7.0 to 150.

These basic compounds are preferably used together with a low-molecular compound (D) to be described below in a molar ratio [low-molecular compound (D)/basic compound] of 100/0 to 10/90, more preferably 100/0 to 30/70 and most preferably 100/0 to 50/50.

The term "basic compound" used herein does not include the following low-molecular compound (D) containing a nitrogen atom and containing a group leaving under the action of an acid.

<Low-Molecular Compound Containing a Nitrogen Atom and Containing a Group Leaving Under the Action of an Acid>

The composition of the present invention may contain a low-molecular compound (hereinafter also referred to as "compound (D)") containing a nitrogen atom and containing a group leaving under the action of an acid.

The group leaving under the action of an acid is not particularly limited. However, the group is preferably an acetal group, a carbonate group, a carbamate group, a tertiary ester group, a tertiary hydroxyl group or a hemiaminal ether group, most preferably a carbamate group or a hemiaminal ether group.

The molecular weight of the compound (D) containing a group leaving under the action of an acid is preferably in the range of 100 to 1000, more preferably 100 to 700 and most preferably 100 to 500.

It is preferred for the compound (D) to be an amine derivative in which the group leaving under the action of an acid is contained on its nitrogen atom.

The compound (D) may contain a carbamate group in which a protective group is provided on its nitrogen atom. The protective group as a constituent of the carbamate group can be expressed by general formula (d-1) below.

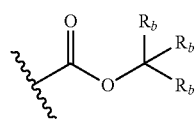
(d-1)

In general formula (d-1), each of Rb's independently represents a hydrogen atom, an alkyl group (preferably 1 to 10 carbon atoms), a cycloalkyl group (preferably 3 to 30 carbon atoms), an aryl group (preferably 3 to 30 carbon atoms), an aralkyl group (preferably 1 to 10 carbon atoms) or an alkoxyalkyl group (preferably 1 to 10 carbon atoms). Rb's may be connected to each other to thereby form a ring.

Each of the alkyl groups, cycloalkyl groups, aryl groups and aralkyl groups represented by Rb's may be substituted with a functional group, such as a hydroxyl group, a cyano group, an amino group, a pyrrolidino group, a piperidino group, a morpholino group or an oxo group, as well as an alkoxy group or a halogen atom. With respect to the alkoxyalkyl groups represented by Rb's, the same substitution can be performed.

As the alkyl groups, cycloalkyl groups, aryl groups and aralkyl groups represented by Rb's (these alkyl groups, cycloalkyl groups, aryl groups and aralkyl groups may be substituted with the above functional group, alkoxy group or halogen atom), there can be mentioned, for example, a group derived from a linear or branched alkane, such as methane, ethane, propane, butane, pentane, hexane, heptane, octane, nonane, decane, undecane or dodecane; a group as obtained by substituting the above alkane-derived group with at least one or at least one type of cycloalkyl group, such as a cyclobutyl group, a cyclopentyl group or a cyclohexyl group; a group derived from a cycloalkane, such as cyclobutane, cyclopentane, cyclohexane, cycloheptane, cyclooctane, norbornane, adamantane or noradamantane; a group as obtained by substituting the above cycloalkane-derived group with at least one or at least one type of linear or branched alkyl group, such as a methyl group, an ethyl group, an n-propyl group, an i-propyl group, an n-butyl group, a 2-methylpropyl group, a 1-methylpropyl group or a t-butyl group; a group derived from an aromatic compound, such as benzene, naphthalene or anthracene; a group as obtained by substituting the above aromatic-compound-derived group with at least one or at least one type of linear or branched alkyl group, such as a methyl group, an ethyl group, an n-propyl group, an i-propyl group, an n-butyl group, a 2-methylpropyl group, a 1-methylpropyl group or a t-butyl group; a group derived from a heterocyclic compound, such as pyrrolidine, piperidine, morpholine, tetrahydrofuran, tetrahydropyran, indole, indoline, quinoline, perhydroquinoline, indazole or benzimidazole; a group as obtained by substituting the above heterocyclic-compound-derived group with at least one or at least one type of linear or branched alkyl group or aromatic-compound-derived group; a group as obtained by substituting the above linear or branched-alkane-derived group or cycloalkane-derived group with at least one or at least one type of aromatic-compound-derived group, such as a phenyl group, a naphthyl group or an anthracenyl group; any of groups as obtained by substituting these substituents with a functional group, such as a hydroxyl group, a cyano group, an amino group, a pyrrolidino group, a piperidino group, a morpholino group or an oxo group; and the like.

Each of Rb's is preferably a linear or branched alkyl group, a cycloalkyl group or an aryl group, more preferably a linear or branched alkyl group or a cycloalkyl group.

As the ring formed by the mutual connection of two Rb's, there can be mentioned an alicyclic hydrocarbon group, an aromatic hydrocarbon group, a heterocyclic hydrocarbon group, any of derivatives from these, or the like.

Particular structures of the groups of general formula (d-1) are shown below.

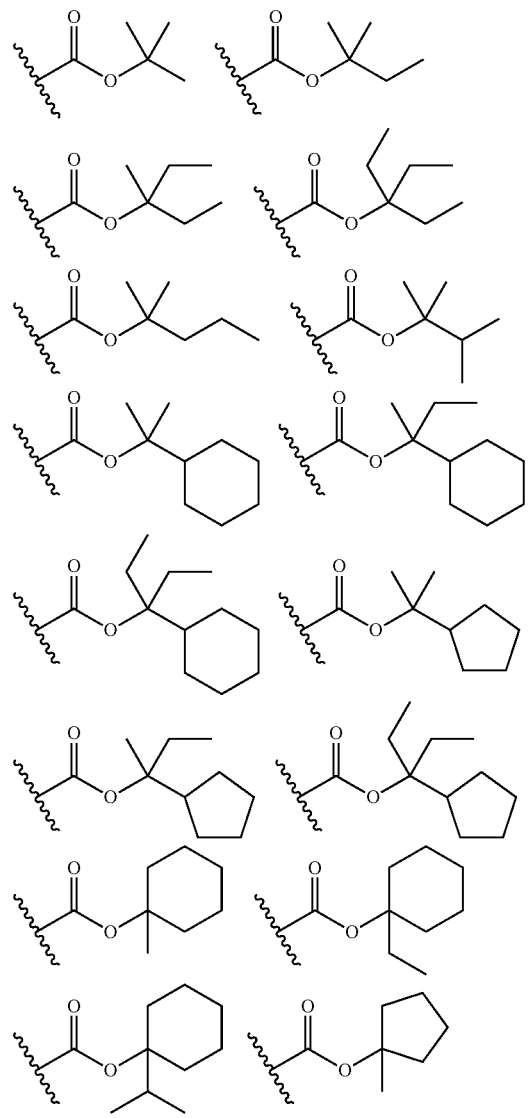

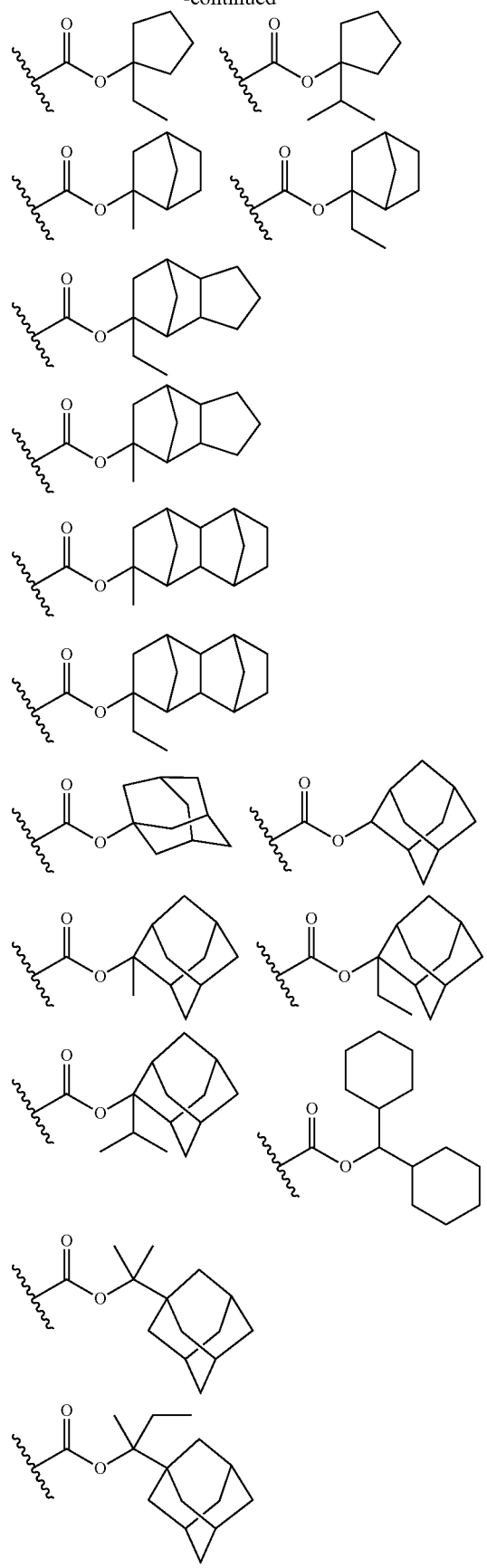
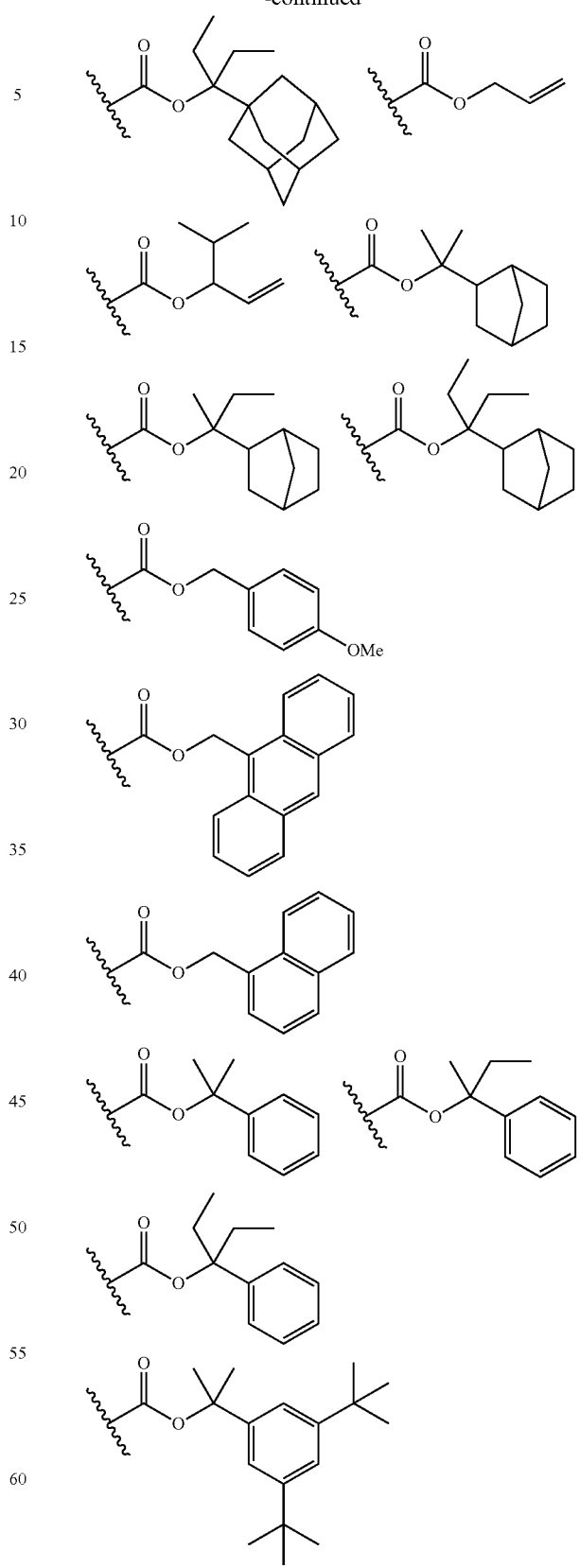
It is especially preferred for the compound (D) to have any of structures of general formula (6) below.

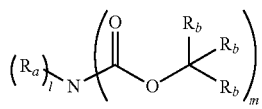
(6)

In general formula (6), Ra represents a hydrogen atom, an alkyl group, a cycloalkyl group, an aryl group or an aralkyl group. When l is 2, two Ra's may be identical to or different from each other. Two Ra's may be connected to each other to thereby form a heterocycle in cooperation with the nitrogen atom in the formula. The heterocycle may contain a heteroatom other than the nitrogen atom in the formula.

Rb's are as defined above in connection with general formula (d-1). Preferred examples are also the same.

In the formula, l is an integer of 0 to 2, and m is an integer of 1 to 3; and l and m satisfy the equality l+m=3.

In general formula (6), the alkyl group, cycloalkyl group, aryl group and aralkyl group represented by Ra may be substituted with the groups set forth above as being introducible in the alkyl group, cycloalkyl group, aryl group and aralkyl group represented by Rb.

Particular examples of the alkyl groups, cycloalkyl groups, aryl groups and aralkyl groups represented by Ra (these alkyl groups, cycloalkyl groups, aryl groups and aralkyl groups may be substituted with the above-mentioned groups) can be the same as set forth above in connection with Rb.

As the heterocycle formed by the mutual connection of Ra's, preferably having up to 20 carbon atoms, there can be mentioned, for example, a group derived from a heterocyclic compound, such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline or 1,5,9-triazacyclododecane; a group as obtained by substituting the above heterocyclic-compound-derived group with at least one or at least one type of linear or branched-alkane-derived group, cycloalkane-derived group, aromatic-compound-derived group, heterocyclic-compound-derived group or functional group, such as a hydroxyl group, a cyano group, an amino group, a pyrrolidino group, a piperidino group, a morpholino group or an oxo group; or the like.

Particular examples of compounds (D) especially preferred in the present invention are shown below, which in no way limit the scope of the present invention.

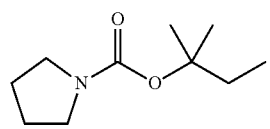
(D-1)

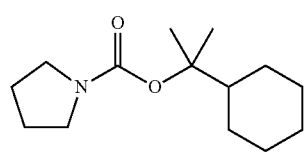
(D-2)

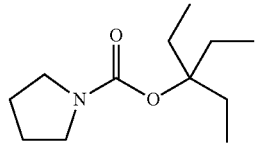
(D-3)

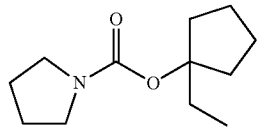
(D-4)

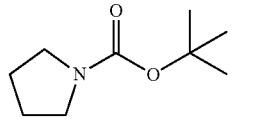
(D-5)

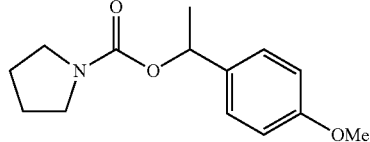
(D-6)

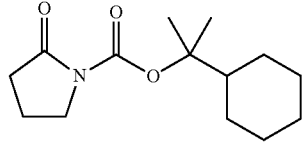
(D-7)

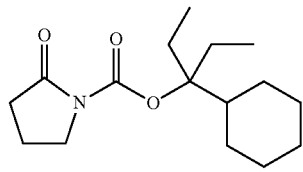
(D-8)

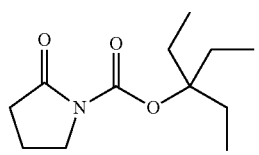
(D-9)

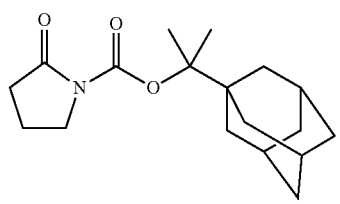
(D-10)

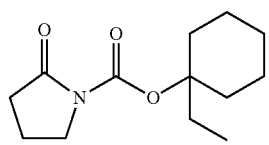
(D-11)

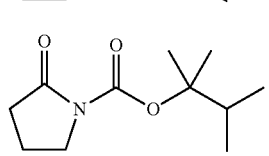
(D-12)

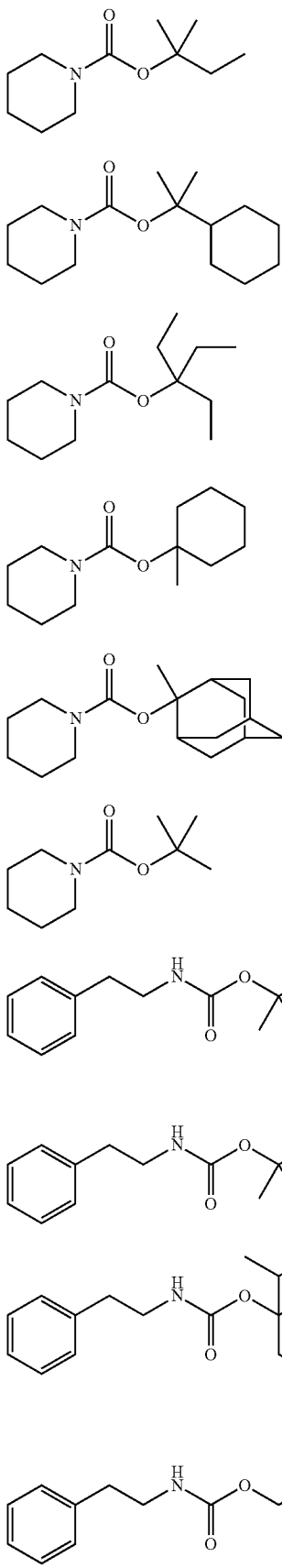
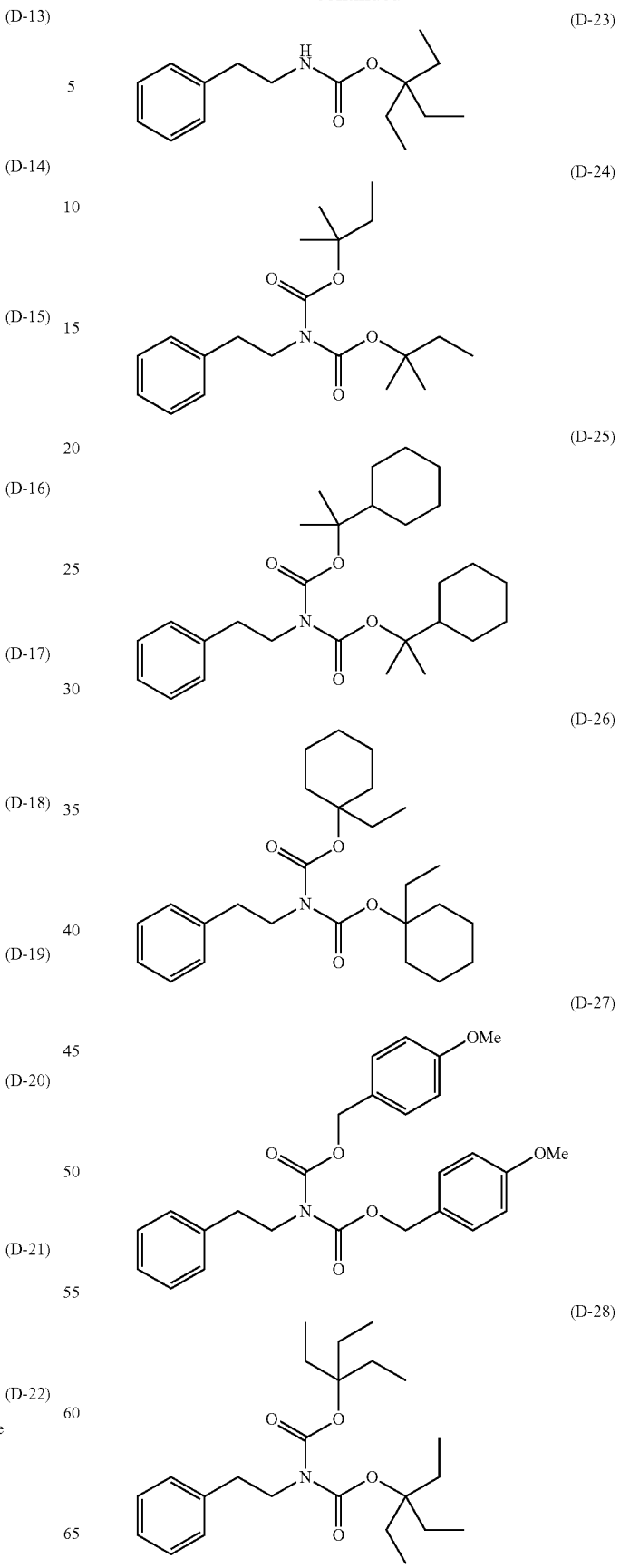

(D-29)
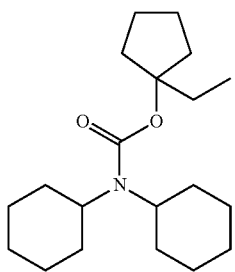
(D-30)
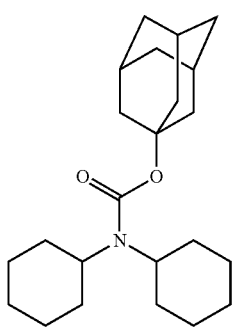
(D-31)
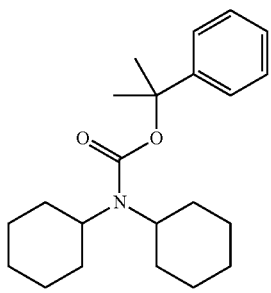
(D-32)
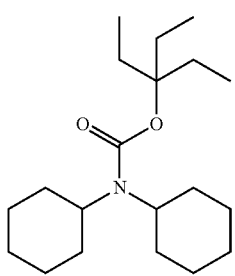
(D-33)
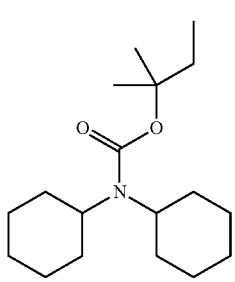
(D-34)
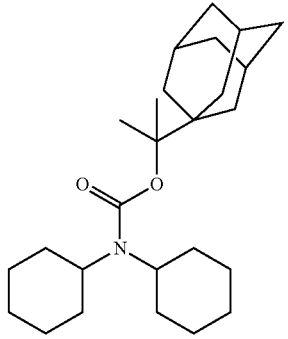
(D-35)
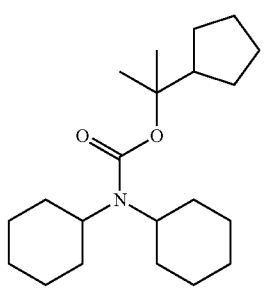
(D-36)
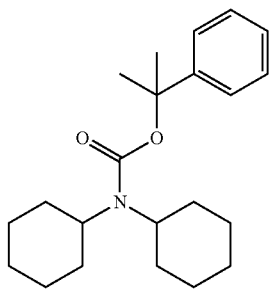
(D-37)
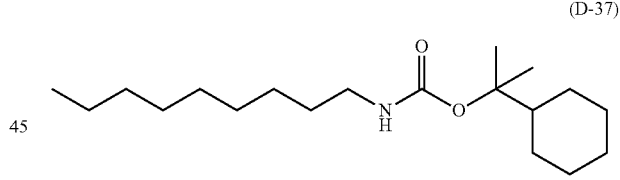
(D-38)
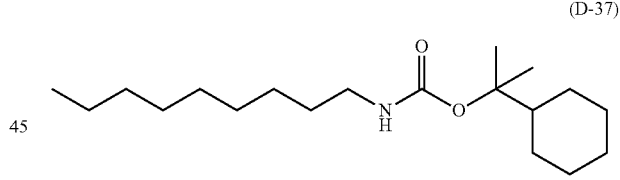
(D-39)
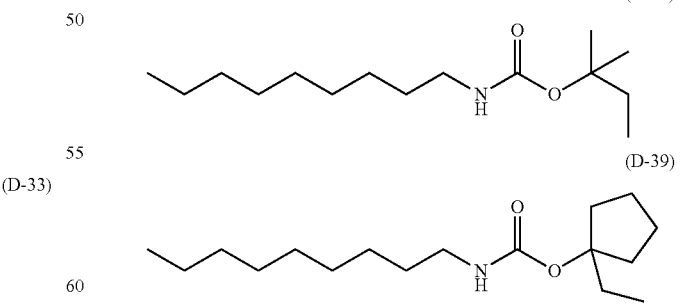
(D-40)
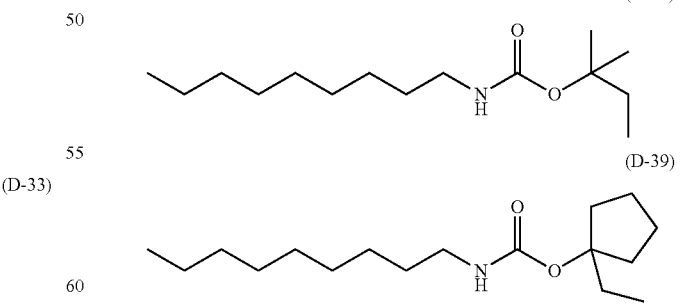

(D-41)
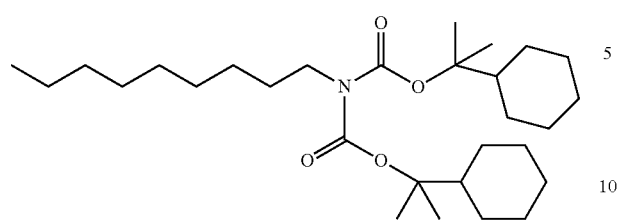
(D-42)
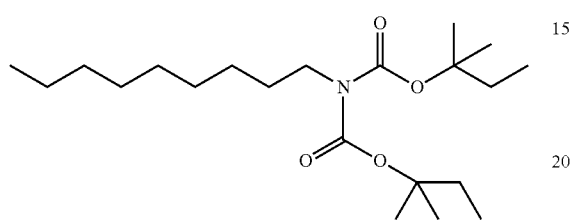
(D-43)
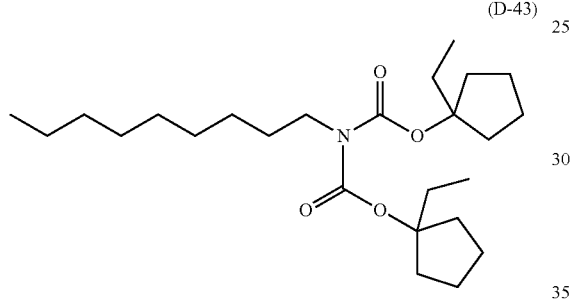
(D-44)
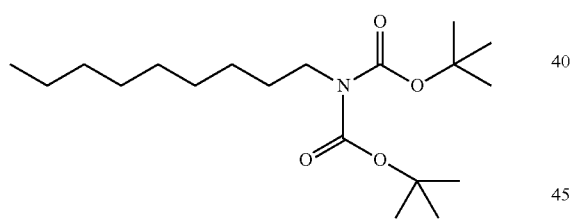
(D-45)
(D-46)
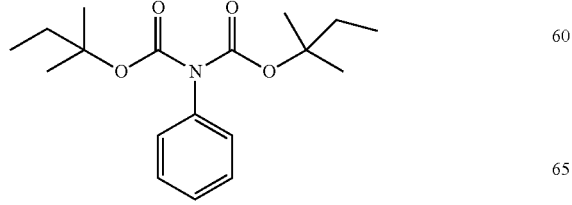
(D-47)
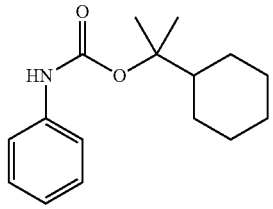
(D-48)
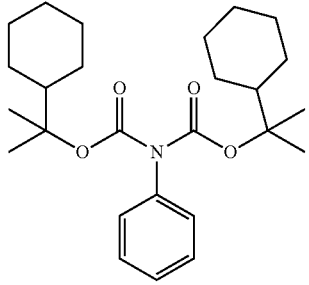
(D-49)
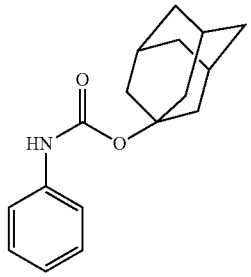
(D-50)
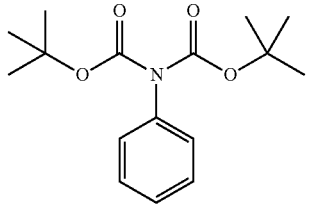
(D-51)
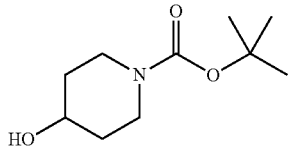
(D-52)
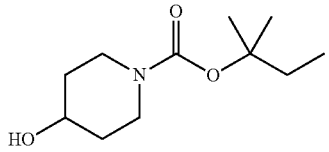
(D-53)
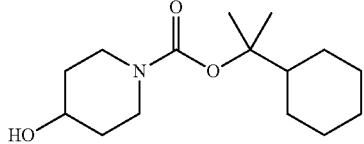

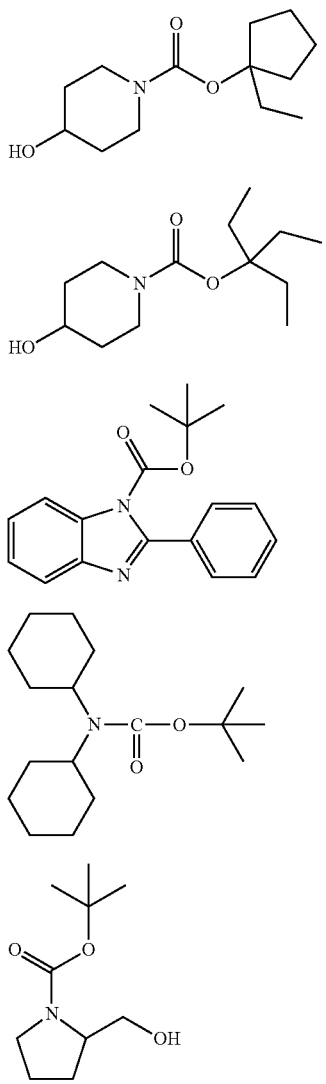

(D-54)

(D-55)

(D-56)

(D-57)

(D-58)

The compounds of general formula (6) can be synthesized in accordance with the processes described in JP-A's 2007-298569 and 2009-199021, etc.

In the present invention, one type of low-molecular compound (D) in which a group leaving under the action of an acid is contained on a nitrogen atom may be used alone, or two or more types thereof may be used in combination.

The content of compound (D) in the actinic-ray- or radiation-sensitive resin composition of the present invention is preferably in the range of 0.001 to 20 mass %, more preferably 0.001 to 10 mass % and further more preferably 0.01 to 5 mass %, based on the total solids of the composition.

<Basic Compound (E) Whose Basicity is Lowered or Lost Upon Exposure to Actinic Rays or Radiation>

The composition of the present invention may comprise a basic compound (E) whose basicity is lowered or lost upon exposure to actinic rays or radiation. As an example of the basic compound (E) whose basicity is lowered or lost upon exposure to actinic rays or radiation, there can be mentioned compounds described on pages 171 to 188 of WO 2011/083872 A1. Further, as an example of the basic compound (E) whose basicity is lowered or lost upon exposure to actinic rays or radiation, there can be mentioned any of sulfonium salt compounds of formula (a1) below and any of iodonium salt compounds of formula (a2) below.

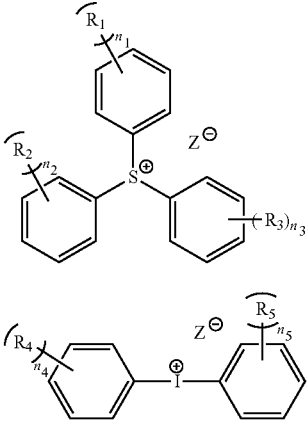

(a1)

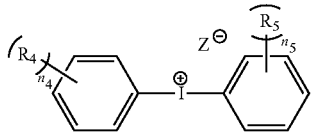

(a2)

In formulae (a1) and (a2) above, each of $R_1$ to $R_5$ independently represents a hydrogen atom, an alkyl group, a cycloalkyl group, an alkoxy group, a hydroxyl group or a halogen atom. $Z^-$ represents a counter anion, being, for example, $OH^-$, $R-COO^-$, $R-SO_3^-$ or any of anions of formula (a3) below, in which R represents a monovalent organic group.

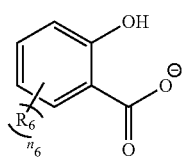

(a3)

In formula (a3) above, $R_6$ represents a substituent, and $n_6$ is an integer of 0 to 4.

As examples of the compounds (E) of formulae (a1) and (a2), there can be mentioned the compounds of the following structural formulae.

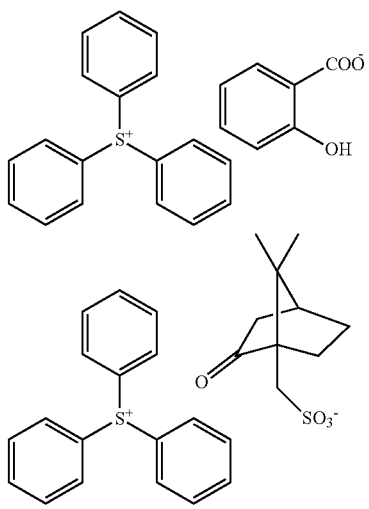

-continued

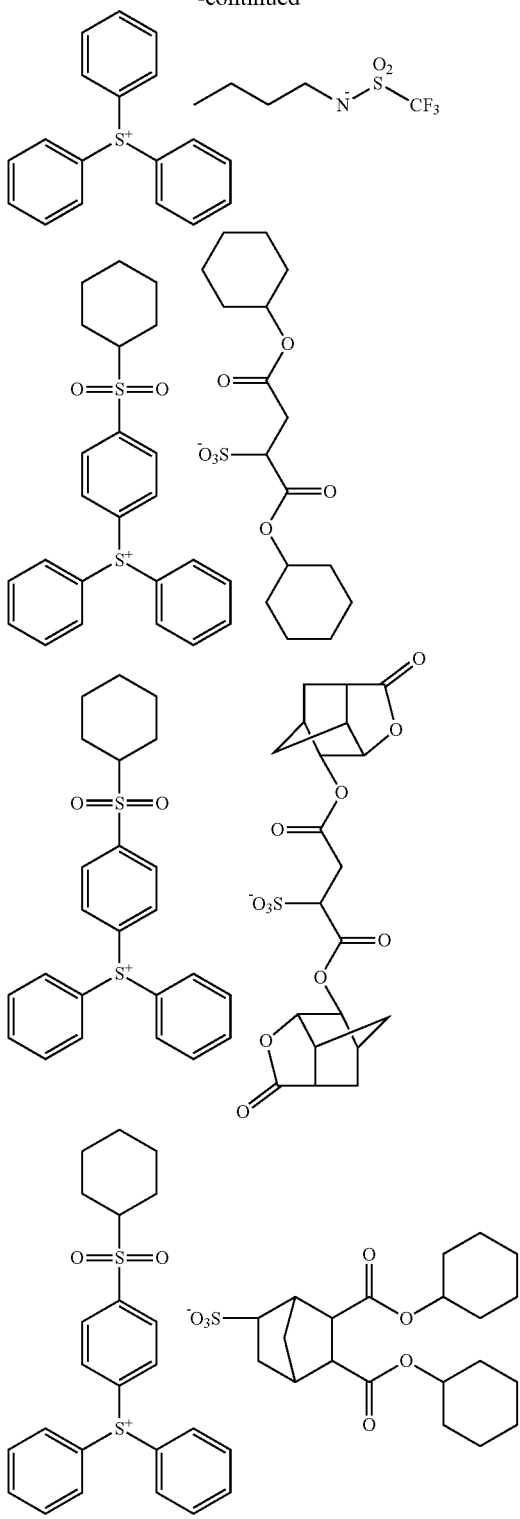

<Hydrophobic Resin (HR)>

The actinic-ray- or radiation-sensitive resin composition of the present invention may further comprise a hydrophobic resin (hereinafter also referred to as "hydrophobic resin (HR)" or simply "resin (HR)") especially when a liquid immersion exposure is applied thereto. It is preferred for the hydrophobic resin (HR) to be different from the above-described resins (A).

This localizes the hydrophobic resin (HR) in the surface layer of the film. Accordingly, when the immersion medium is water, the static/dynamic contact angle of the surface of the resist film with respect to water can be increased, thereby enhancing the immersion liquid tracking property.

Although the hydrophobic resin (HR) is preferably designed so as to be localized in the interface as mentioned above, as different from surfactants, the hydrophobic resin does not necessarily have to contain a hydrophilic group in its molecule and does not need to contribute toward uniform mixing of polar/nonpolar substances.

From the viewpoint of localization in the surface layer of the film, it is preferred for the hydrophobic resin (HR) to contain at least one member selected from among a "fluorine atom," a "silicon atom" and a "$CH_3$ partial structure introduced in a side chain portion of the resin." More preferably, two or more members are contained.

When the hydrophobic resin (HR) contains a fluorine atom and/or a silicon atom, in the hydrophobic resin (HR), the fluorine atom and/or silicon atom may be introduced in the principal chain of the resin, or a side chain thereof.

When the hydrophobic resin (HR) contains a fluorine atom, it is preferred for the resin to comprise, as a partial structure containing a fluorine atom, an alkyl group containing a fluorine atom, a cycloalkyl group containing a fluorine atom or an aryl group containing a fluorine atom.

The alkyl group containing a fluorine atom (preferably having 1 to 10 carbon atoms, more preferably 1 to 4 carbon atoms) is a linear or branched alkyl group having at least one hydrogen atom thereof replaced by a fluorine atom. Further, non-fluorine-atom substituents may be introduced therein.

The cycloalkyl group containing a fluorine atom is a mono- or polycycloalkyl group having at least one hydrogen atom thereof replaced by a fluorine atom. Further, non-fluorine-atom substituents may be introduced therein.

As the aryl group containing a fluorine atom, there can be mentioned an aryl group, such as a phenyl or naphthyl group, having at least one hydrogen atom thereof replaced by a fluorine atom. Further, non-fluorine-atom substituents may be introduced therein.

As preferred alkyl groups containing a fluorine atom, cycloalkyl groups containing a fluorine atom and aryl groups containing a fluorine atom, there can be mentioned groups of general formulae (F2) to (F4) below, which however in no way limit the scope of the present invention.

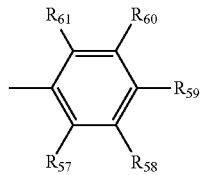 (F2)

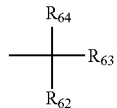 (F3)

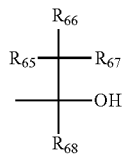 (F4)

In general formulae (F2) to (F4), each of $R_{57}$ to $R_{68}$ independently represents a hydrogen atom, a fluorine atom or an alkyl group (linear or branched), provided that each of at least one of $R_{57}$-$R_{61}$, at least one of $R_{62}$-$R_{64}$ and at least one of $R_{65}$-$R_{68}$ independently represents a fluorine atom or an alkyl group (preferably having 1 to 4 carbon atoms) having at least one hydrogen atom thereof replaced by a fluorine atom.

It is preferred for all of $R_{57}$-$R_{61}$ and $R_{65}$-$R_{67}$ to represent fluorine atoms. Each of $R_{62}$, $R_{63}$ and $R_{68}$ preferably represents an alkyl group (especially having 1 to 4 carbon atoms) having at least one hydrogen atom thereof replaced by a fluorine atom, more preferably a perfluoroalkyl group having 1 to 4 carbon atoms. $R_{62}$ and $R_{63}$ may be connected to each other to thereby form a ring.

Specific examples of the groups of general formula (F2) include a p-fluorophenyl group, a pentafluorophenyl group, a 3,5-di(trifluoromethyl)phenyl group and the like.

Specific examples of the groups of general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro (2-methyl) isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl) isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of general formula (F4) include —C(CF$_3$)$_2$OH, —C(C$_2$F5)$_2$OH, —C(CF$_3$)(CH$_3$)OH, —CH(CF$_3$)OH and the like. —C(CF$_3$)$_2$OH is preferred.

Each of the partial structures containing a fluorine atom may be directly bonded to the principal chain, or may be bonded to the principal chain via a group selected from the group consisting of an alkylene group, a phenylene group, an ether bond, a thioether bond, a carbonyl group, an ester bond, an amide bond, a urethane bond and a ureylene bond, or via a group composed of a combination of two or more of these.

Particular examples of the repeating units containing a fluorine atom are shown below, which in no way limit the scope of the present invention.

In the particular examples, $X_1$ represents a hydrogen atom, —CH$_3$, —F or —CF$_3$. $X_2$ represents —F or —CF$_3$.

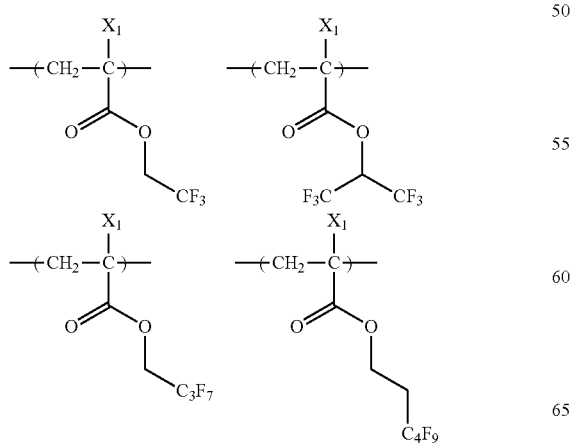

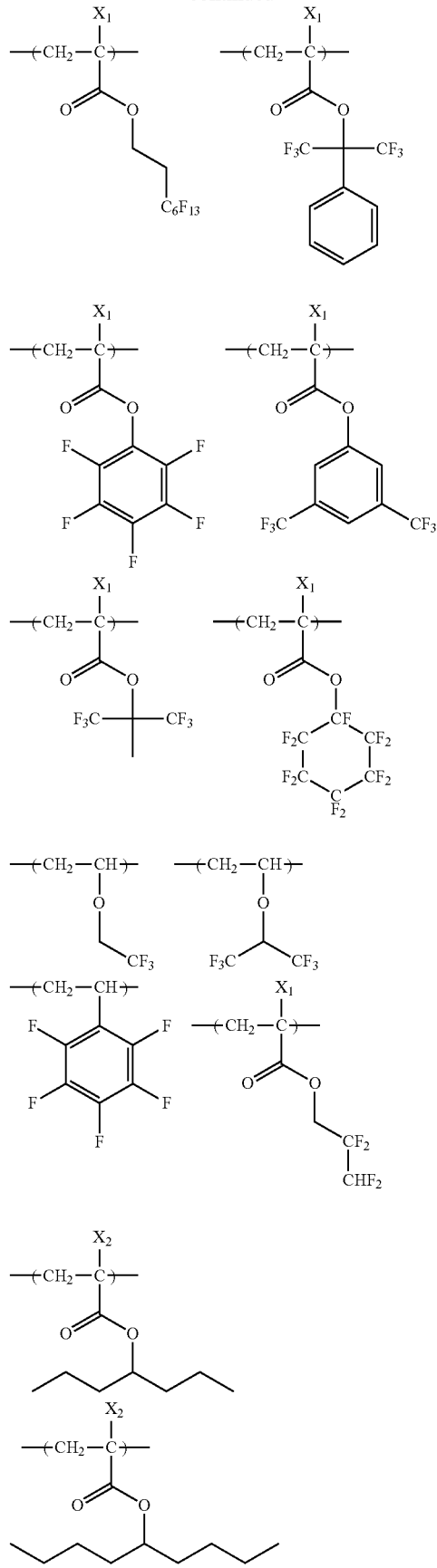

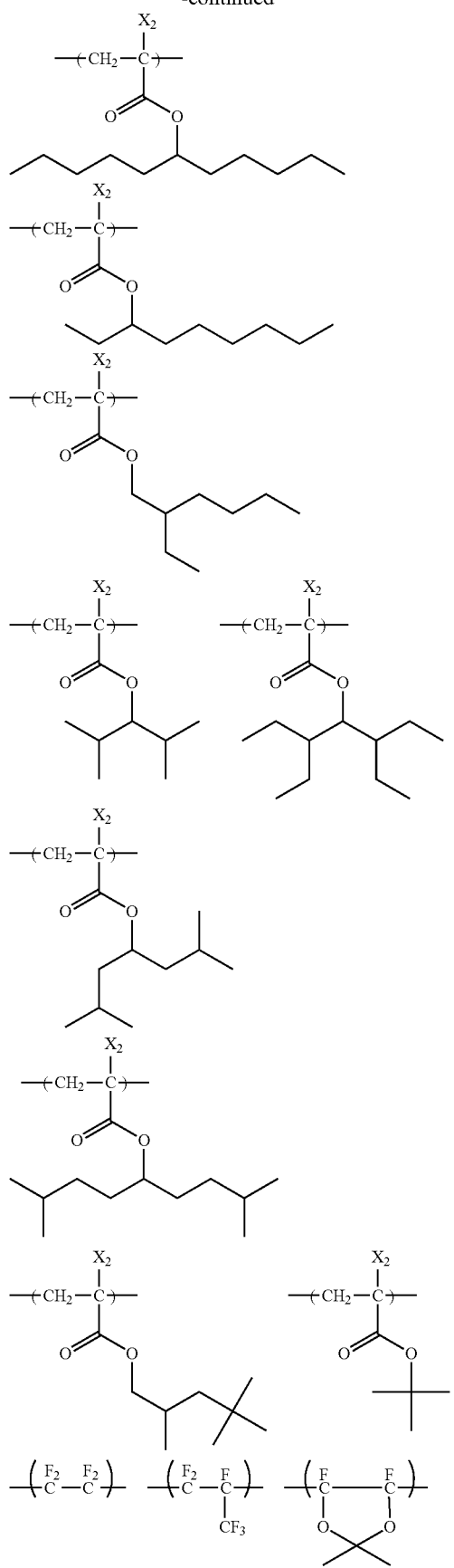

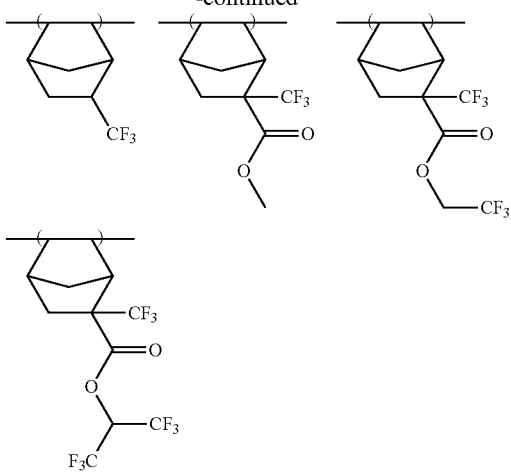

The hydrophobic resin (HR) may contain a silicon atom. It is preferred for the hydrophobic resin (HR) to be a resin with an alkylsilyl structure (preferably a trialkylsilyl group) or a cyclosiloxane structure as a partial structure containing a silicon atom.

As the alkylsilyl structure or cyclosiloxane structure, there can be mentioned, for example, any of the groups of general formulae (CS-1) to (CS-3) below or the like.

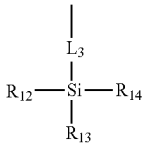

(CS-1)

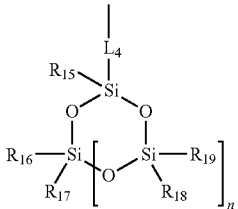

(CS-2)

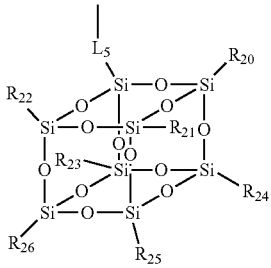

(CS-3)

In general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one, or a combination (preferably up to 12 carbon atoms in total) of two or more members, selected from the group consisting of an alkylene group, a phenylene group, an ether bond, a thioether bond, a carbonyl group, an ester bond, an amide bond, a urethane bond and a urea bond.

In the formulae, n is an integer of 1 to 5, preferably an integer of 2 to 4.

As mentioned above, it is also preferred for the hydrophobic resin (HR) to contain a $CH_3$ partial structure in its side chain portion.

Herein, the $CH_3$ partial structure (hereinafter also simply referred to as "side-chain $CH_3$ partial structure") contained in a side chain portion of the resin (HR) includes a $CH_3$ partial structure contained in an ethyl group, a propyl group or the like.

In contrast, a methyl group (for example, an α-methyl group in the repeating unit with a methacrylic acid structure) directly bonded to the principal chain of the resin (HR) is not included in the $CH_3$ partial structure according to the present invention, since the contribution thereof to the surface localization of the resin (HR) is slight due to the influence of the principal chain.

In particular, when the resin (HR) comprises, for example, a repeating unit derived from a monomer containing a polymerizable moiety having a carbon-carbon double bond, such as any of repeating units of general formula (M) below, and when each of $R_{11}$ to $R_{14}$ is $CH_3$ "per se," the $CH_3$ is not included in the $CH_3$ partial structure contained in a side chain portion according to the present invention.

In contrast, a $CH_3$ partial structure arranged via some atom apart from the C—C principal chain corresponds to the side-chain $CH_3$ partial structure according to the present invention. For example, when $R_{11}$ is an ethyl group ($CH_2CH_3$), it is deemed that "one" $CH_3$ partial structure according to the present invention is contained.

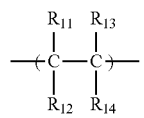

(M)

In general formula (M) above, each of $R_{11}$ to $R_{14}$ independently represents a side-chain portion.

As the side chain portion $R_{11}$ to $R_{14}$, there can be mentioned a hydrogen atom, a monovalent organic group and the like.

As the monovalent organic group represented by each of $R_{11}$ to $R_{14}$, there can be mentioned an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, an arylaminocarbonyl group or the like. Substituents may further be introduced in these groups.

It is preferred for the hydrophobic resin (HR) to be a resin comprising a repeating unit containing a $CH_3$ partial structure in its side chain portion. More preferably, the hydrophobic resin (HR) comprises, as such a repeating unit, at least one repeating unit (x) selected from among the repeating units of general formula (II) below and repeating units of general formula (III) below.

The repeating units of general formula (II) will be described in detail below.

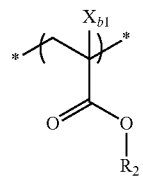

(II)

In general formula (II) above, $X_{b1}$ represents a hydrogen atom, an alkyl group, a cyano group or a halogen atom. $R_2$ represents an organic group having at least one $CH_3$ partial structure and being stable against acids. Herein, in particular, it is preferred for the organic group stable against acids to be an organic group not containing "any group that when acted on by an acid, is decomposed to thereby produce a polar group" described above in connection with the resin (A).

The alkyl group represented by $X_{b1}$ is preferably one having 1 to 4 carbon atoms, such as a methyl group, an ethyl group, a propyl group, a hydroxymethyl group or a trifluoromethyl group. A methyl group is preferred.

Preferably, $X_{b1}$ is a hydrogen atom or a methyl group.

As $R_2$, there can be mentioned an alkyl group, a cycloalkyl group, an alkenyl group, a cycloalkenyl group, an aryl group and an aralkyl group each containing at least one $CH_3$ partial structure. An alkyl group as a substituent may further be introduced in each of the above cycloalkyl group, alkenyl group, cycloalkenyl group, aryl group and aralkyl group.

$R_2$ is preferably an alkyl group or alkyl-substituted cycloalkyl group containing at least one $CH_3$ partial structure.

The organic group stable against acids containing at least one $CH_3$ partial structure represented by $R_2$ preferably contains 2 to 10 $CH_3$ partial structures, more preferably 2 to 8 $CH_3$ partial structures.

The alkyl group containing at least one $CH_3$ partial structure represented by $R_2$ is preferably a branched alkyl group having 3 to 20 carbon atoms. As preferred alkyl groups, there can be mentioned, for example, an isopropyl group, an isobutyl group, a t-butyl group, a 3-pentyl group, a 2-methyl-3-butyl group, a 3-hexyl group, a 2-methyl-3-pentyl group, a 3-methyl-4-hexyl group, a 3,5-dimethyl-4-pentyl group, an isooctyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group and the like. An isobutyl group, a t-butyl group, a 2-methyl-3-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group and a 2,3,5,7-tetramethyl-4-heptyl group are more preferred.

The cycloalkyl group containing at least one $CH_3$ partial structure represented by $R_2$ may be monocyclic or polycyclic. In particular, there can be mentioned groups with, for example, monocyclo, bicyclo, tricyclo and tetracyclo structures each having 5 or more carbon atoms. The cycloalkyl group preferably has 6 to 30 carbon atoms, most preferably 7 to 25 carbon atoms. As preferred cycloalkyl groups, there can be mentioned an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. As more preferred cycloalkyl groups, there can be mentioned an adamantyl group, a norbornyl group, a cyclohexyl group, a cyclopentyl group, a tetracyclododecanyl group and a tricyclodecanyl group. A norbornyl group, a cyclopentyl group and a cyclohexyl group are more preferred.

The alkenyl group containing at least one $CH_3$ partial structure represented by $R_2$ is preferably a linear or branched alkenyl group having 1 to 20 carbon atoms. A branched alkenyl group is more preferred.

The aryl group containing at least one $CH_3$ partial structure represented by $R_2$ is preferably an aryl group having 6 to 20 carbon atoms, such as a phenyl group or a naphthyl group. A phenyl group is more preferred.

The aralkyl group containing at least one $CH_3$ partial structure represented by $R_2$ is preferably one having 7 to 12 carbon atoms. For example, there can be mentioned a benzyl group, a phenethyl group, a naphthylmethyl group or the like.

Examples of hydrocarbon groups each containing two or more $CH_3$ partial structures represented by $R_2$ include an isopropyl group, an isobutyl group, a t-butyl group, a 3-pentyl group, a 2-methyl-3-butyl group, a 3-hexyl group, a 2,3-dimethyl-2-butyl group, a 2-methyl-3-pentyl group, a 3-methyl-4-hexyl group, a 3,5-dimethyl-4-pentyl group, an isooctyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group, a 3,5-dimethylcyclohexyl group, a 3,5-di-tert-butylcyclohexyl group, a 4-isopropylcyclohexyl group, a 4-t-butylcyclohexyl group, an isobornyl group and the like. An isobutyl group, a t-butyl group, a 2-methyl-3-butyl group, a 2,3-dimethyl-2-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group, a 3,5-dimethylcyclohexyl group, a 3,5-di-tert-butylcyclohexyl group, a 4-isopropylcyclohexyl group, a 4-t-butylcyclohexyl group and an isobornyl group are more preferred.

Preferred particular examples of the repeating units of general formula (II) are shown below, which in no way limit the scope of the present invention.

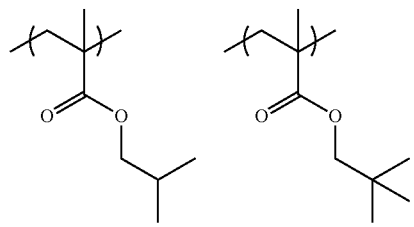

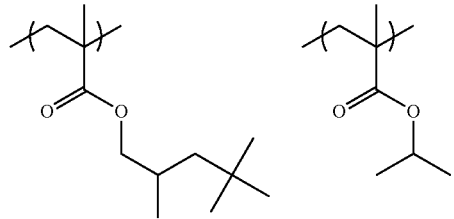

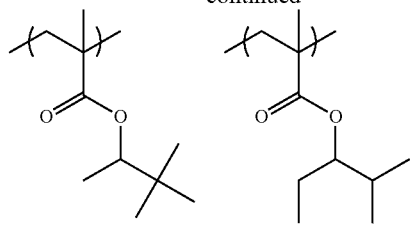

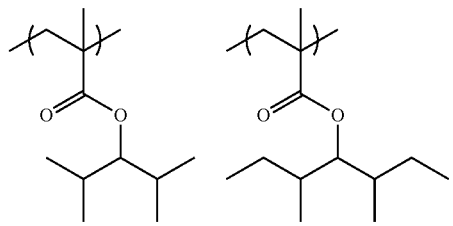

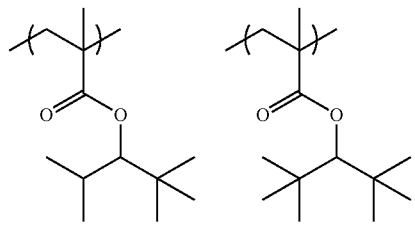

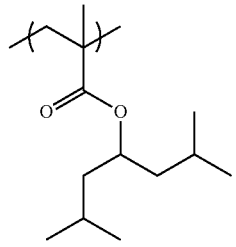

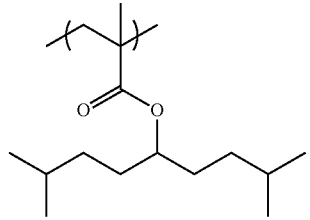

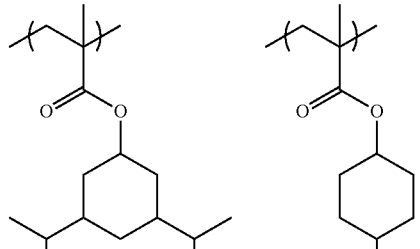

-continued

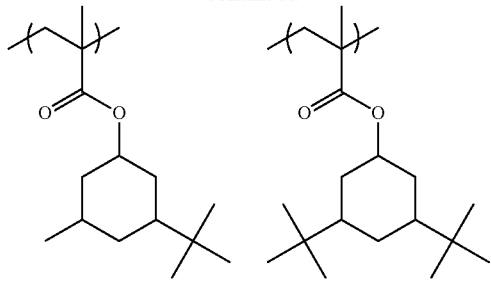
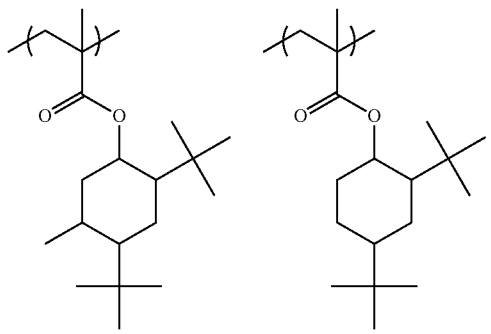
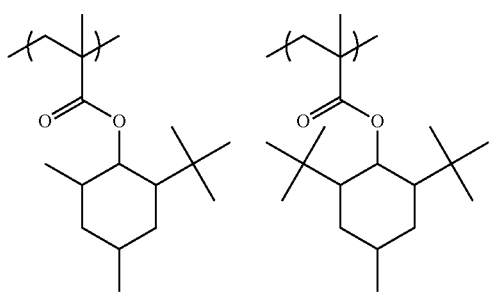
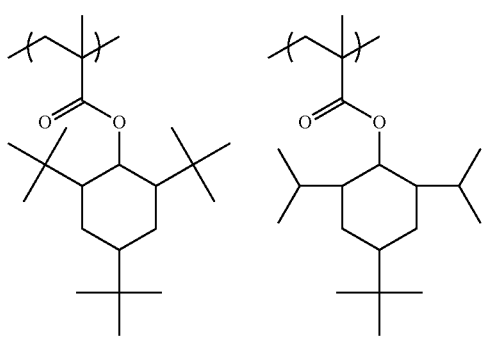
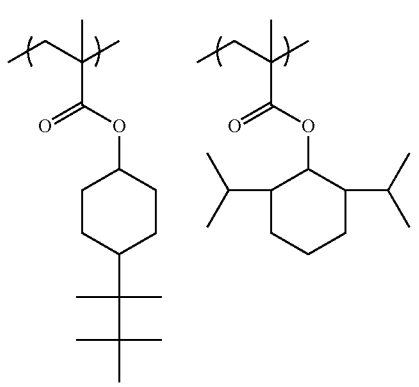

-continued

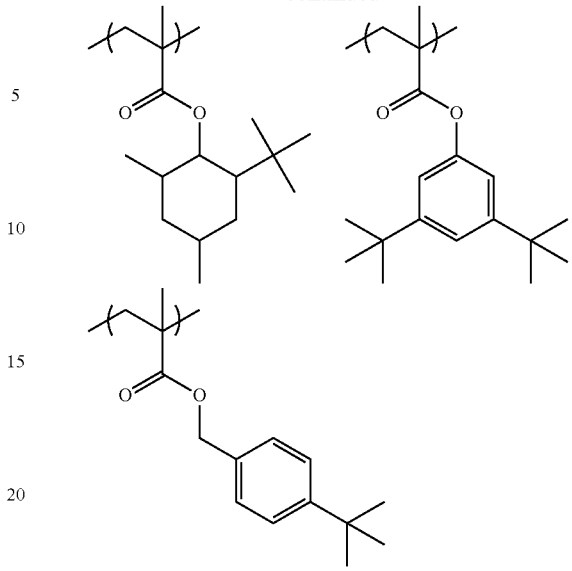

It is preferred for the repeating units of general formula (II) to be those stable against acids (non-acid-decomposable), in particular, repeating units containing none of groups that are decomposed under the action of an acid to thereby produce polar groups.

The repeating units of general formula (III) will be described in detail below.

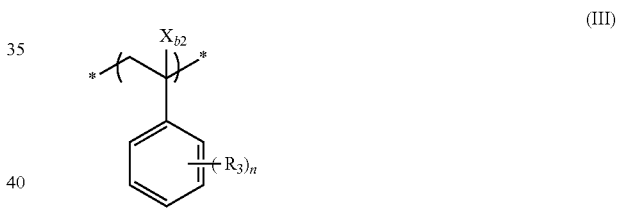

(III)

In general formula (III) above, $X_b2$ represents a hydrogen atom, an alkyl group, a cyano group or a halogen atom. $R_3$ represents an organic group having at least one $CH_3$ partial structure and being stable against acids; and n is an integer of 1 to 5.

The alkyl group represented by $X_b2$ is preferably one having 1 to 4 carbon atoms, such as a methyl group, an ethyl group, a propyl group, a hydroxymethyl group or a trifluoromethyl group. A methyl group is more preferred.

Preferably, $X_b2$ is a hydrogen atom.

$R_3$ is an organic group stable against acids. In particular, $R_3$ is preferably an organic group not containing "any group that when acted on by an acid, is decomposed to thereby produce a polar group" described above in connection with the resin (A).

As $R_3$, there can be mentioned an alkyl group containing at least one $CH_3$ partial structure.

The organic group stable against acids containing at least one $CH_3$ partial structure represented by $R_3$ preferably contains 1 to 10 $CH_3$ partial structures, more preferably 1 to 8 $CH_3$ partial structures and further more preferably 1 to 4 $CH_3$ partial structures.

The alkyl group containing at least one $CH_3$ partial structure represented by $R_3$ is preferably a branched alkyl group having 3 to 20 carbon atoms. As preferred alkyl groups, there can be mentioned, for example, an isopropyl group, an isobutyl group, a t-butyl group, a 3-pentyl group, a 2-methyl-3-butyl group, a 3-hexyl group, a 2-methyl-3-pentyl group, a 3-methyl-4-hexyl group, a 3,5-dimethyl-4-pentyl group, an isooctyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group and the like. An isobutyl group, a t-butyl group, a 2-methyl-3-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group and a 2,3,5,7-tetramethyl-4-heptyl group are more preferred.

Examples of alkyl groups each containing two or more $CH_3$ partial structures represented by $R_3$ include an isopropyl group, an isobutyl group, a t-butyl group, a 3-pentyl group, a 2,3-dimethylbutyl group, a 2-methyl-3-butyl group, a 3-hexyl group, a 2-methyl-3-pentyl group, a 3-methyl-4-hexyl group, a 3,5-dimethyl-4-pentyl group, an isooctyl group, a 2,4,4-trimethylpentyl group, a 2-ethylhexyl group, a 2,6-dimethylheptyl group, a 1,5-dimethyl-3-heptyl group, a 2,3,5,7-tetramethyl-4-heptyl group and the like. Alkyl groups having 5 to 20 carbon atoms are preferred, including an isopropyl group, a t-butyl group, a 2-methyl-3-butyl group, a 2-methyl-3-pentyl group, a 3-methyl-4-hexyl group, a 3,5-dimethyl-4-pentyl group, a 2,4,4-trimethylpentyl group, a 2-ethylhexyl group, a 2,6-dimethylheptyl group, a 1,5-dimethyl-3-heptyl group and a 2,3,5,7-tetramethyl-4-heptyl group are more preferred.

In the formula, n is an integer of 1 to 5, preferably 1 to 3, and more preferably 1 or 2.

Preferred particular examples of the repeating units of general formula (III) are shown below, which in no way limit the scope of the present invention.

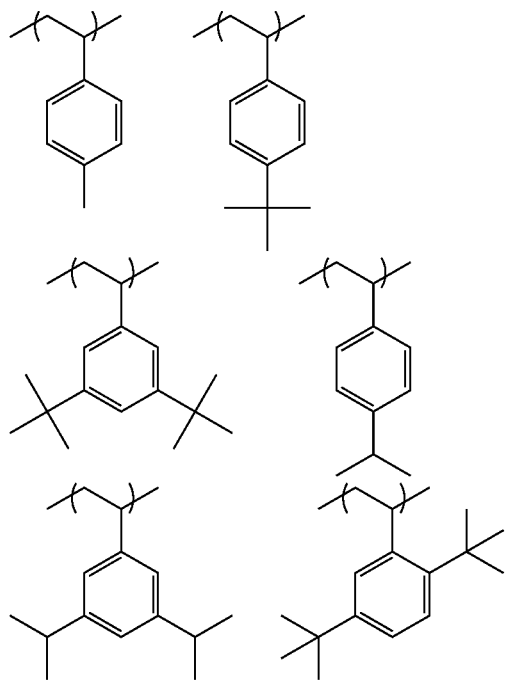

It is preferred for the repeating units of general formula (III) to be those stable against acids (non-acid-decomposable), in particular, repeating units not containing any groups that are decomposed under the action of an acid to thereby produce polar groups.

When the resin (HR) contains a $CH_3$ partial structure in its side chain portion and contains neither a fluorine atom nor a silicon atom, the content of at least one repeating unit (x) selected from among the repeating units of general formula (II) and repeating units of general formula (III) based on all the repeating units of the resin (HR) is preferably 90 mol % or more, more preferably 95 mol % or more. The above content based on all the repeating units of the resin (HR) is generally up to 100 mol %.

When the resin (HR) contains at least one repeating unit (x) selected from among the repeating units of general formula (II) and repeating units of general formula (III) in an amount of 90 mol % or more based on all the repeating units of the resin (HR), the surface free energy of the resin (HR) is increased. As a result, the localization of the resin (HR) in the surface of the resist film is promoted, so that the static/dynamic contact angle of the resist film with respect to water can be securely increased, thereby enhancing the immersion liquid tracking property.

In the instance of containing a fluorine atom and/or a silicon atom (i) and also in the instance of containing a $CH_3$ partial structure in its side chain (ii), the hydrophobic resin (HR) may contain at least one group selected from among the following groups (x) to (z).

Namely, (x) an acid group, (y) a group with a lactone structure, an acid anhydride group or an acid imido group, and (z) a group decomposed under the action of an acid.

As the acid group (x), there can be mentioned a phenolic hydroxyl group, a carboxylic acid group, a fluoroalcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred acid groups, there can be mentioned a fluoroalcohol group (preferably hexafluoroisopropanol), a sulfonimido group and a bis(alkylcarbonyl)methylene group.

The repeating unit containing an acid group (x) is, for example, a repeating unit wherein the acid group is directly bonded to the principal chain of a resin, such as a repeating unit derived from acrylic acid or methacrylic acid. Alternatively, this repeating unit may be a repeating unit wherein the acid group is bonded via a connecting group to the principal chain of a resin. Still alternatively, this repeating unit may be a repeating unit wherein the acid group is introduced in a terminal of polymer chain by using a chain transfer agent or polymerization initiator containing the acid group in the stage of polymerization. Any of these repeating units are preferred. The repeating unit containing an acid group (x) may contain at least either a fluorine atom or a silicon atom.

The content of repeating unit containing an acid group (x) based on all the repeating units of the hydrophobic resin (HR) is preferably in the range of 1 to 50 mol %, more preferably 3 to 35 mol % and further more preferably 5 to 20 mol %.

Particular examples of the repeating units each containing an acid group (x) are shown below, which in no way limit the scope of the present invention. In the formulae, Rx represents a hydrogen atom, $CH_3$, $CF_3$ or $CH_2OH$.

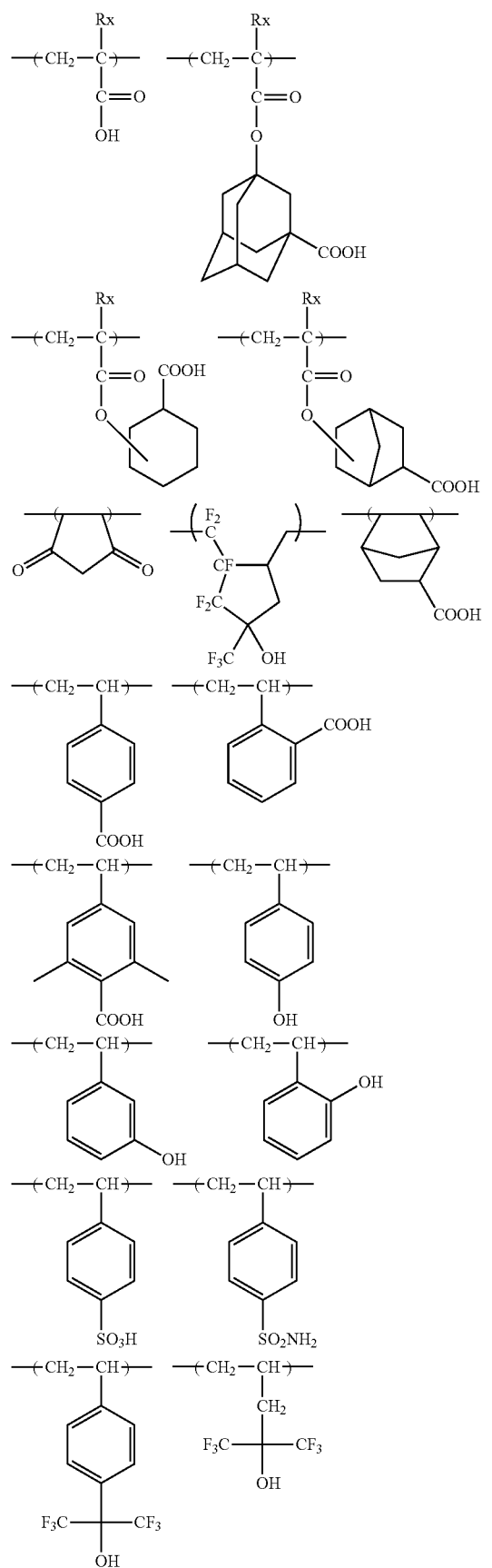
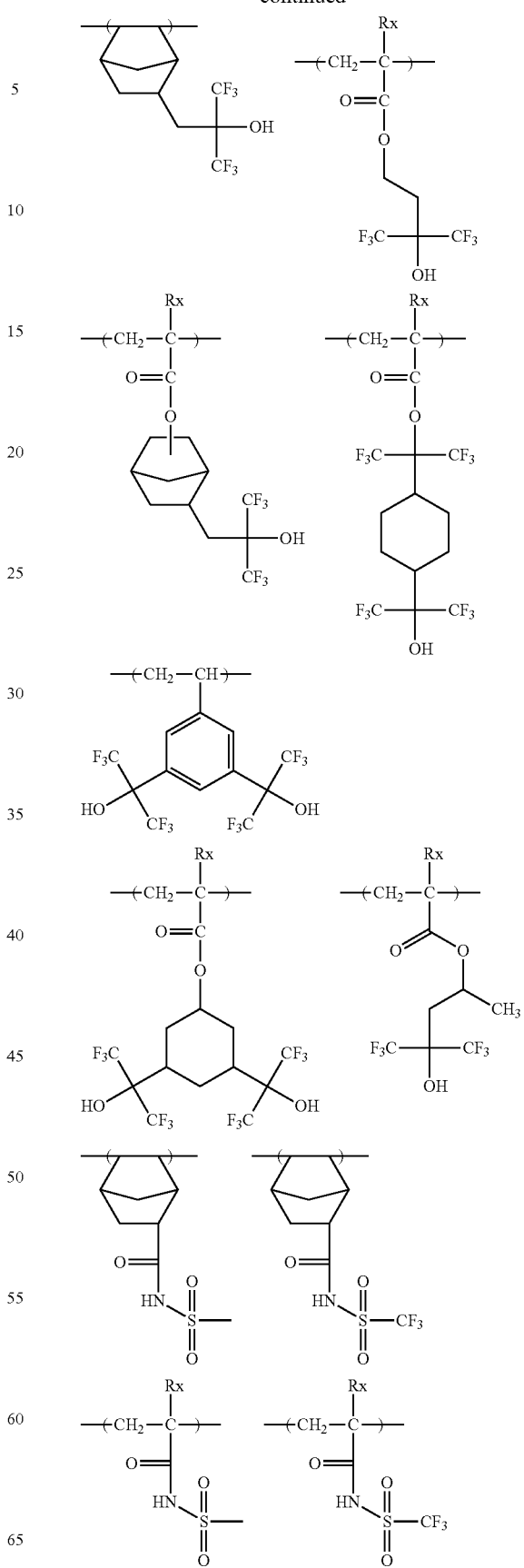

-continued

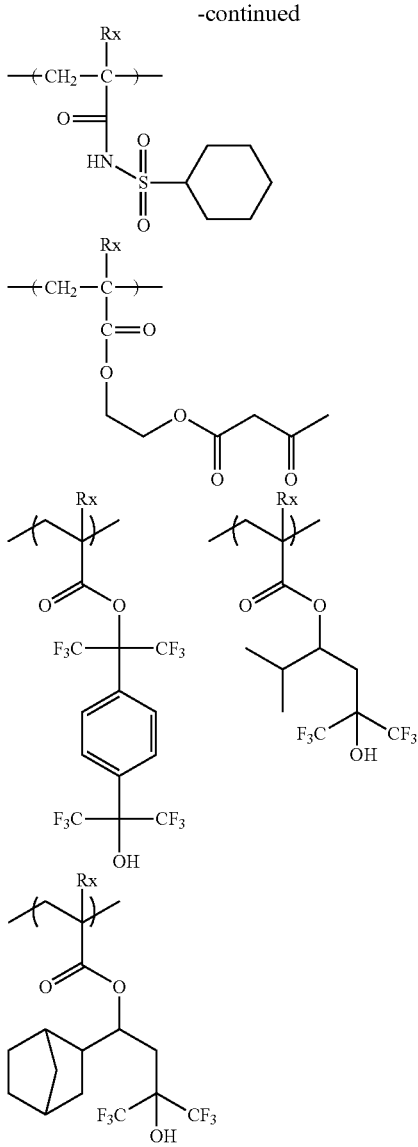

Among the group with a lactone structure, acid anhydride group and acid imido group (y), the group with a lactone structure is most preferred.

The repeating unit containing any of these groups is, for example, a repeating unit wherein the group is directly bonded to the principal chain of a resin, such as a repeating unit derived from an acrylic ester or a methacrylic ester. Alternatively, this repeating unit may be a repeating unit wherein the group is bonded via a connecting group to the principal chain of a resin. Still alternatively, this repeating unit may be a repeating unit wherein the group is introduced in a terminal of the resin by using a chain transfer agent or polymerization initiator containing the group in the stage of polymerization.

The repeating units each containing a group with a lactone structure can be, for example, the same as the repeating units each with a lactone structure described above in the section of the acid-decomposable resin (A1).

The content of repeating unit containing a group with a lactone structure, an acid anhydride group or an acid imido group, based on all the repeating units of the hydrophobic resin (HR), is preferably in the range of 1 to 100 mol %, more preferably 3 to 98 mol % and further more preferably 5 to 95 mol %.

The repeating unit containing the group (z) decomposable under the action of an acid in the hydrophobic resin (HR) can be the same as any of the repeating units each containing an acid-decomposable group set forth above in connection with the resin (A1). The repeating unit containing the group (z) decomposable under the action of an acid may contain at least either a fluorine atom or a silicon atom. The content of repeating unit containing the group (z) decomposable under the action of an acid in the hydrophobic resin (HR), based on all the repeating units of the resin (HR), is preferably in the range of 1 to 80 mol %, more preferably 10 to 80 mol % and further more preferably 20 to 60 mol %.

The hydrophobic resin (HR) may further comprise any of the repeating units of general formula (III) below.

In general formula (III), $R_{c31}$ represents a hydrogen atom, an alkyl group (optionally substituted with a fluorine atom or the like), a cyano group or any of groups of the formula —$CH_2$—O—$Rac_2$ in which $Rac_2$ represents a hydrogen atom, an alkyl group or an acyl group. $R_{c31}$ is preferably a hydrogen atom, a methyl group, a hydroxymethyl group or a trifluoromethyl group, most preferably a hydrogen atom or a methyl group.

$R_{c32}$ represents a group containing an alkyl group, cycloalkyl group, alkenyl group, cycloalkenyl group or aryl group. This group may be substituted with a group containing a fluorine atom or silicon atom.

$L_{c3}$ represents a single bond or a bivalent connecting group.

In general formula (III), the alkyl group in $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

The aryl group is preferably an aryl group having 6 to 20 carbon atoms. A phenyl group and a naphthyl group are more preferred. Substituents may be introduced therein.

Preferably, $R_{c32}$ is an unsubstituted alkyl group or an alkyl group substituted with a fluorine atom.

The bivalent connecting group represented by $L_{c3}$ is preferably an alkylene group (preferably having 1 to 5 carbon atoms), an ether bond, a phenylene group or an ester bond (group of the formula —COO—).

The content of repeating unit expressed by general formula (III), based on all the repeating units of the hydrophobic resin, is preferably in the range of 1 to 100 mol %, more preferably 10 to 90 mol % and further more preferably 30 to 70 mol %.

Preferably, the hydrophobic resin (HR) further comprises any of the repeating units of general formula (CII-AB) below.

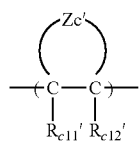

(CII-AB)

In general formula (CII-AB), each of $R_{c11'}$ and $R_{c12'}$ independently represents a hydrogen atom, a cyano group, a halogen atom or an alkyl group.

Zc' represents an atomic group for forming an alicyclic structure containing two mutually bonded carbon atoms (C—C).

The content of repeating unit expressed by general formula (CII-AB), based on all the repeating units of the hydrophobic resin, is preferably in the range of 1 to 100 mol %, more preferably 10 to 90 mol % and further more preferably 30 to 70 mol %.

Particular examples of the repeating units of general formula (III) and general formula (CII-AB) are shown below, which in no way limit the scope of the present invention. In the formulae, Ra represents H, $CH_3$, $CH_2OH$, $CF_3$ or CN.

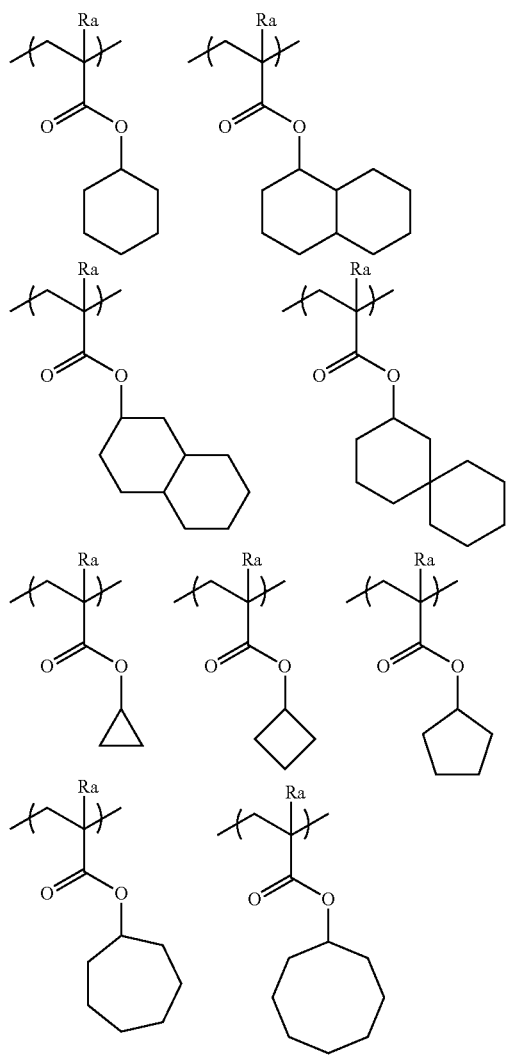

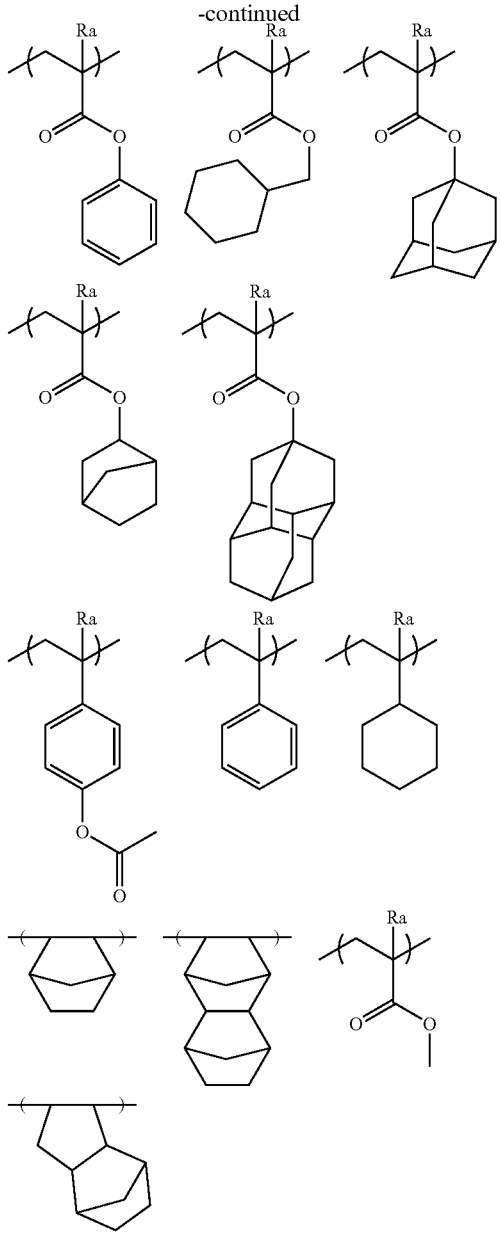

When the hydrophobic resin (HR) contains a fluorine atom, the content of fluorine atom is preferably in the range of 5 to 80 mass %, more preferably 10 to 80 mass %, based on the weight-average molecular weight of the hydrophobic resin (HR). The repeating unit containing a fluorine atom preferably accounts for 10 to 100 mol %, more preferably 30 to 100 mol %, in all the repeating units contained in the hydrophobic resin (HR).

When the hydrophobic resin (HR) contains a silicon atom, the content of silicon atom is preferably in the range of 2 to 50 mass %, more preferably 2 to 30 mass %, based on the weight-average molecular weight of the hydrophobic resin (HR). The repeating unit containing a silicon atom preferably accounts for 10 to 100 mol %, more preferably 20 to 100 mol %, in all the repeating units contained in the hydrophobic resin (HR).

In contrast, especially when the resin (HR) contains a $CH_3$ partial structure in its side-chain portion, a form of the resin (HR) in which substantially neither a fluorine atom nor a silicon atom is contained is also preferred. In that instance, in particular, the content of repeating unit containing a fluorine atom or a silicon atom, based on all the repeating units of the resin (HR), is preferably 5 mol % or less, more preferably 3 mol % or less, further more preferably 1 mol % or less, and ideally 0 mol %, namely, containing neither a fluorine atom nor a silicon atom. It is preferred for the resin (HR) to be comprised substantially only of a repeating unit comprised only of atoms selected from among a carbon atom, an oxygen atom, a hydrogen atom, a nitrogen atom and a sulfur atom. In particular, the content of repeating unit comprised only of atoms selected from among a carbon atom, an oxygen atom, a hydrogen atom, a nitrogen atom and a sulfur atom, based on all the repeating units of the resin (HR), is preferably 95 mol % or greater, more preferably 97 mol % or greater, further more preferably 99 mol % or less, and ideally 100 mol %.

The standard-polystyrene-equivalent weight average molecular weight of the hydrophobic resin (HR) is preferably in the range of 1000 to 100,000, more preferably 1000 to 50,000 and further more preferably 2000 to 15,000.

One type of hydrophobic resin (HR) may be used alone, or two or more thereof may be used in combination.

The content of hydrophobic resin (HR) in the composition, based on the total solids of the composition of the present invention, is preferably in the range of 0.01 to 10 mass %, more preferably 0.05 to 8 mass % and further more preferably 0.1 to 7 mass %.

Impurities, such as metals, should naturally be in low quantities in the hydrophobic resin (HR), as in the resin (A). The content of residual monomers and oligomer components is preferably 0.01 to 5 mass %, more preferably 0.01 to 3 mass % and further more preferably 0.05 to 1 mass %. Accordingly, there can be obtained an actinic-ray- or radiation-sensitive resin composition that is free from any change over time of in-liquid foreign matter, sensitivity, etc. From the viewpoint of resolution, resist shape, side wall of resist pattern, roughness, etc., the molecular weight distribution (Mw/Mn, also referred to as polydispersity index) thereof is preferably in the range of 1 to 5, more preferably 1 to 3 and further more preferably 1 to 2.

A variety of commercially available products can be used as the hydrophobic resin (HR). Alternatively, the hydrophobic resin (HR) can be synthesized in accordance with routine methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a heated solvent over a period of 1 to 10 hours, etc. The dropping polymerization method is preferred.

The reaction solvent, polymerization initiator, reaction conditions (temperature, concentration, etc.) and purification method after reaction are the same as described above in connection with the resin (A). In the synthesis of the hydrophobic resin (HR), it is preferred for the concentration at reaction to range from 30 to 50 mass %.

Specific examples of the hydrophobic resins (HR) are shown below. The following Tables will indicate the molar ratios of individual repeating units (corresponding to individual repeating units in the order from the left), weight average molecular weight and polydispersity index with respect to each of the resins.

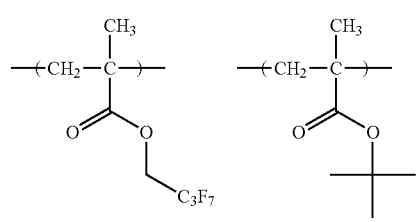 (HR-1)

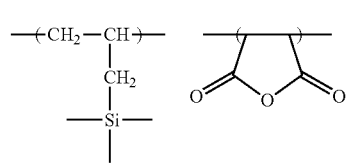 (HR-2)

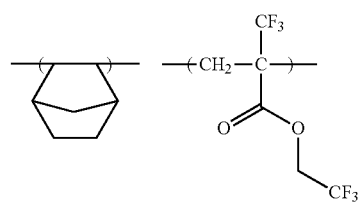 (HR-3)

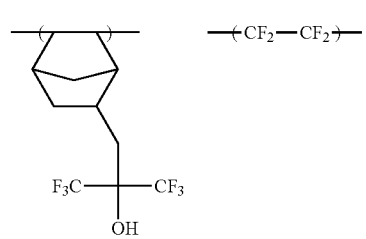 (HR-4)

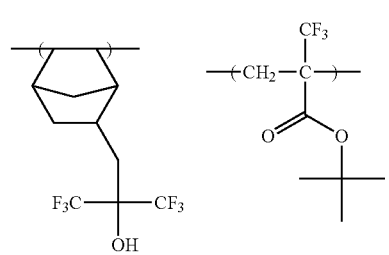 (HR-5)

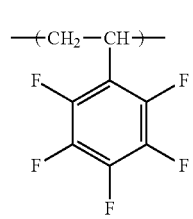 (HR-6)

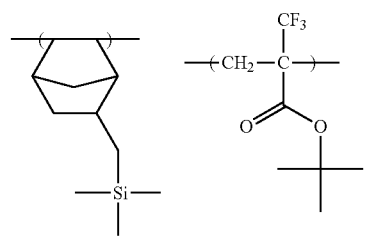 (HR-7)

(HR-8)
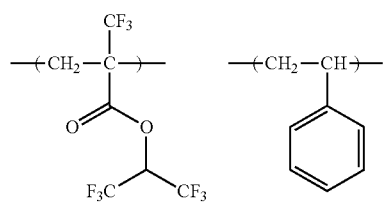
(HR-9)
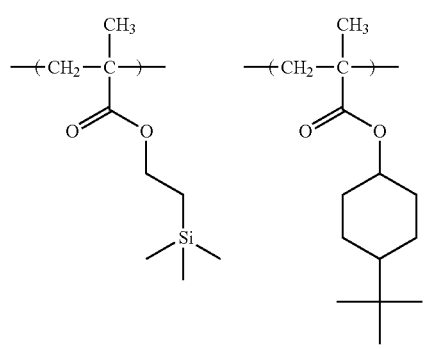
(HR-10)
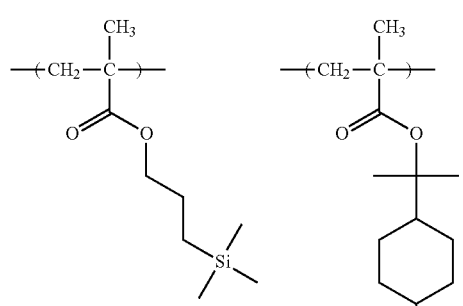
(HR-11)
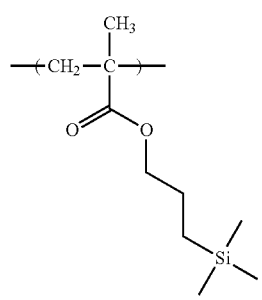
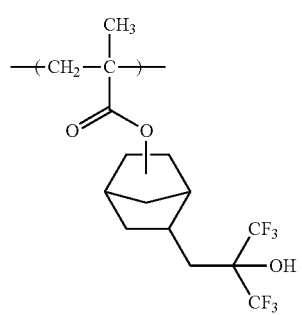
(HR-12)
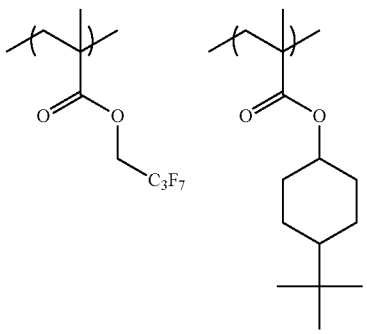
(HR-13)
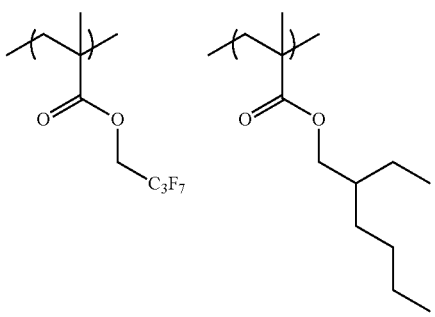
(HR-14)
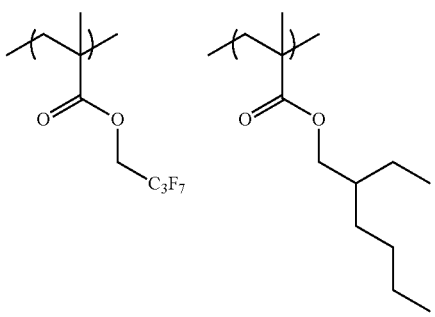
(HR-15)
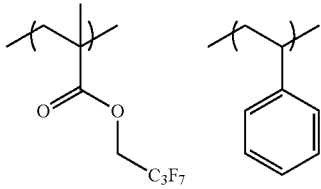
(HR-16)
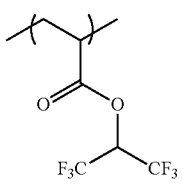
(HR-17)
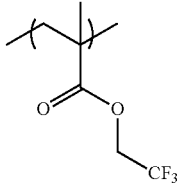

(HR-18) 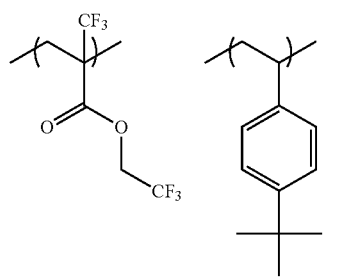
(HR-19) 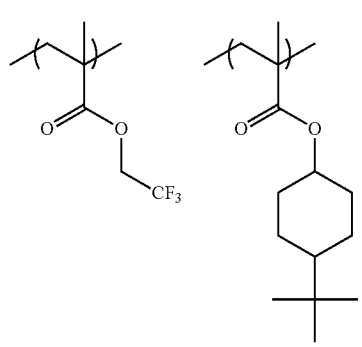
(HR-20) 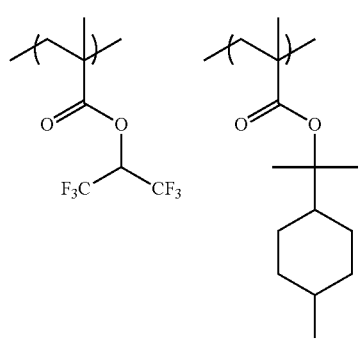
(HR-21) 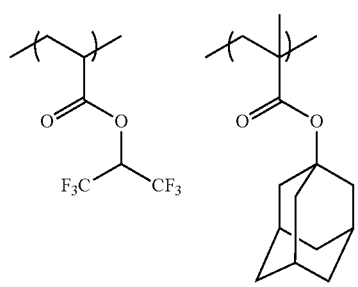
(HR-22) 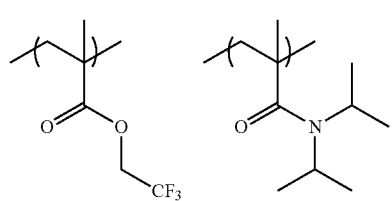
(HR-23) 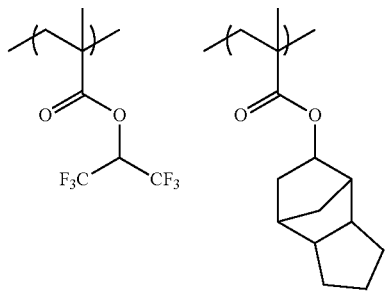
(HR-24) 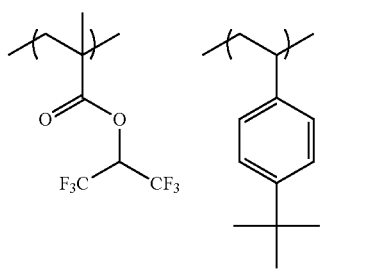
(HR-25) 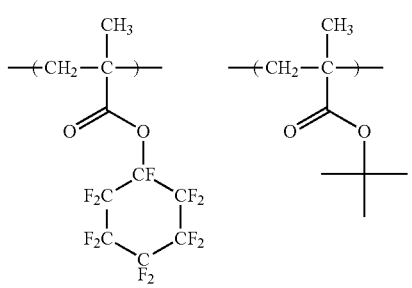
(HR-26) 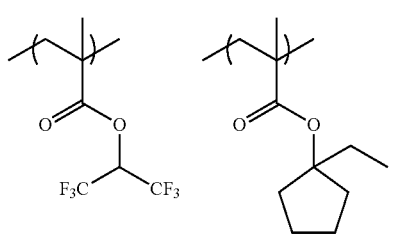
(HR-27) 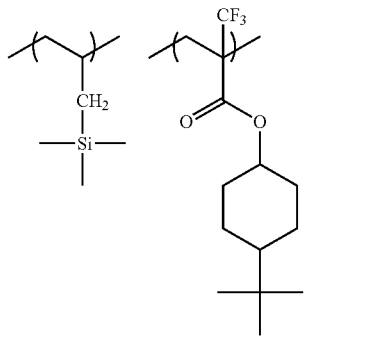
(HR-28) 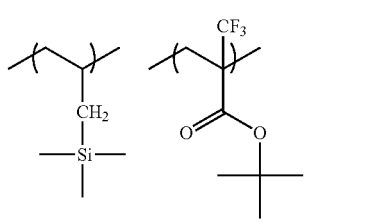

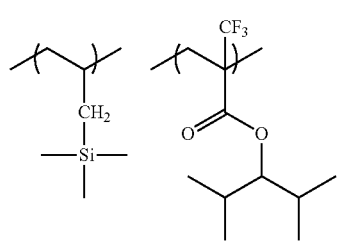
(HR-29)
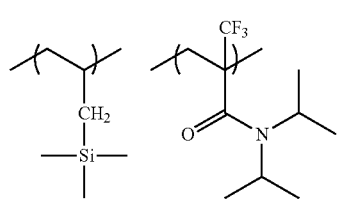
(HR-30)
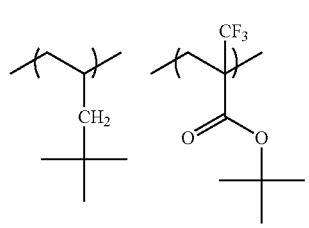
(HR-31)
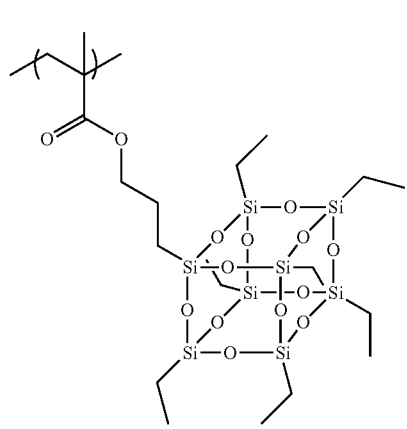
(HR-32)
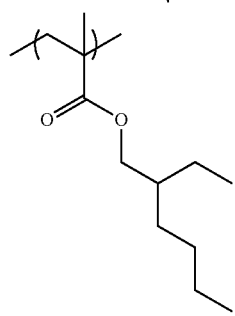
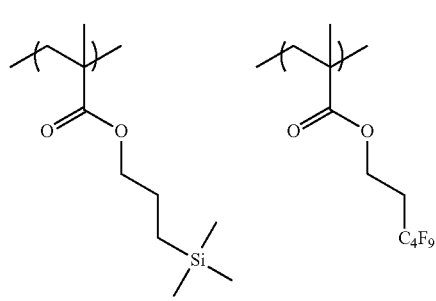
(HR-33)
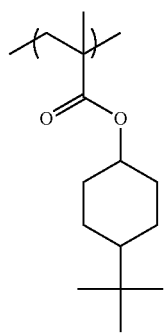
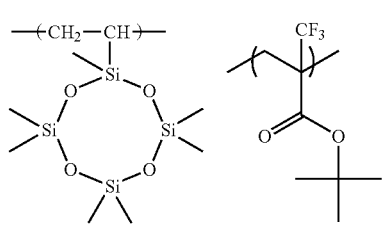
(HR-34)
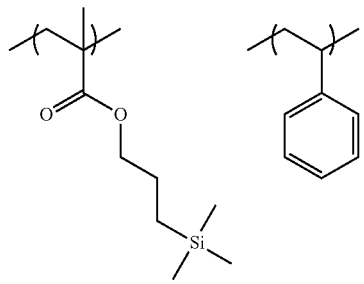
(HR-35)
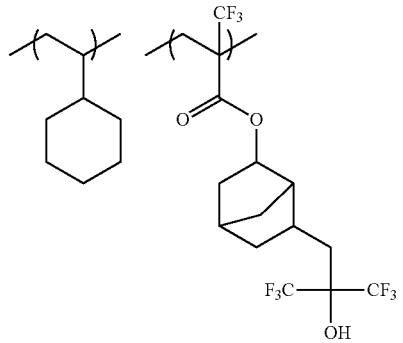
(HR-36)
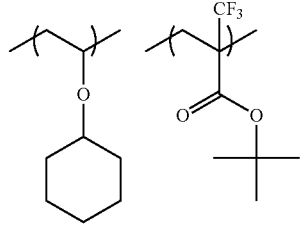
(HR-37)

(HR-38)
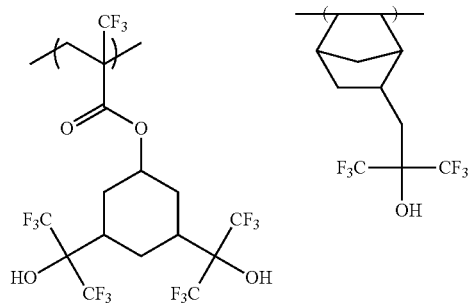
(HR-39)
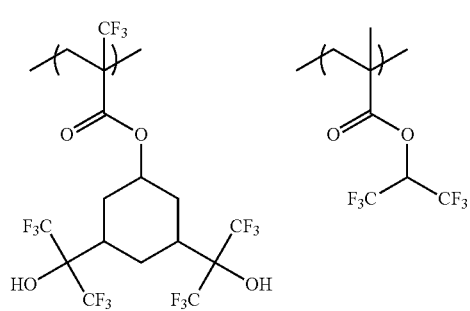
(HR-40)
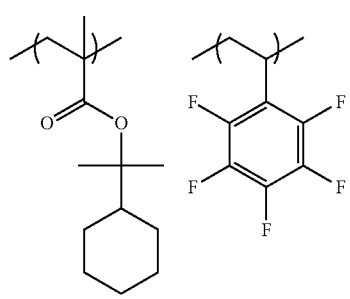
(HR-41)
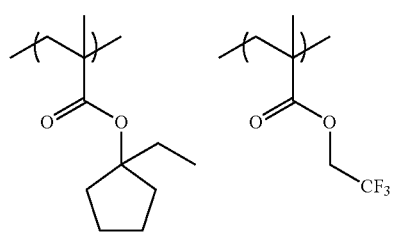
(HR-42)
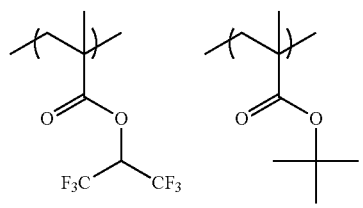
(HR-43)
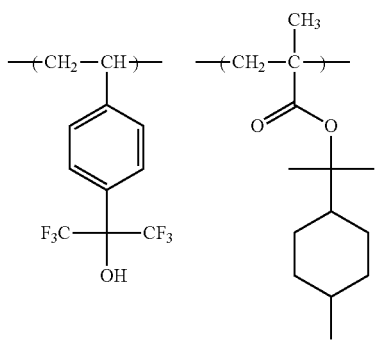
(HR-44)
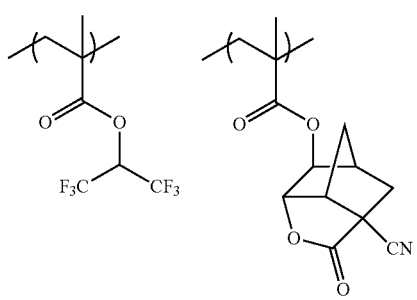
(HR-45)
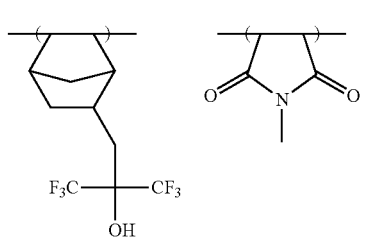
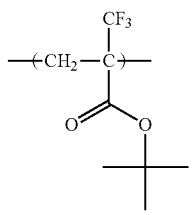
(HR-46)
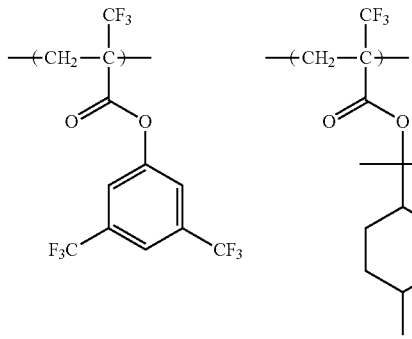

(HR-47) 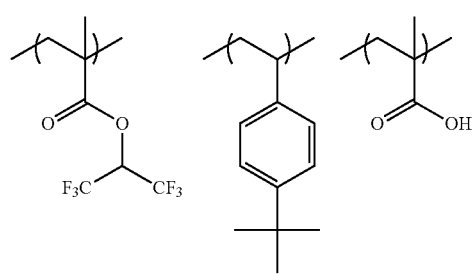
(HR-48) 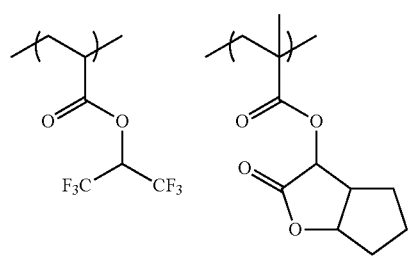
(HR-49) 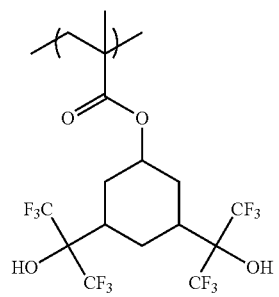
(HR-50) 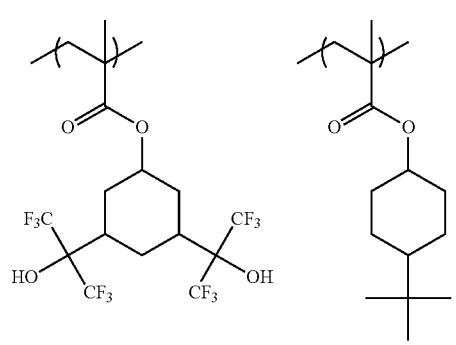
(HR-51) 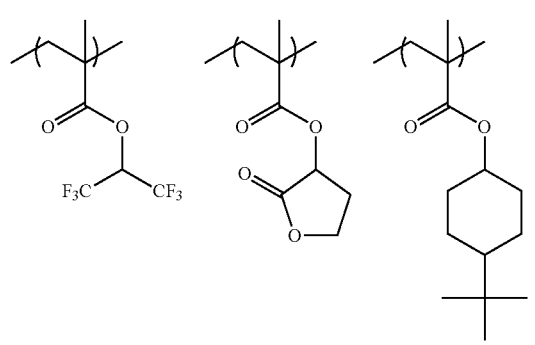
(HR-52) 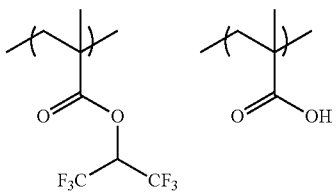
(HR-53) 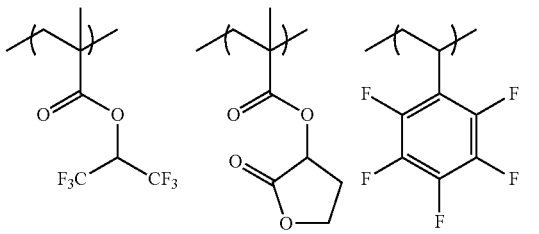
(HR-54) 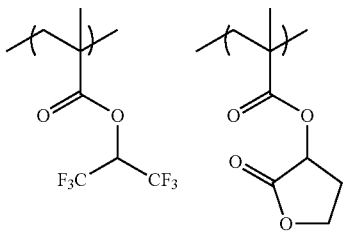
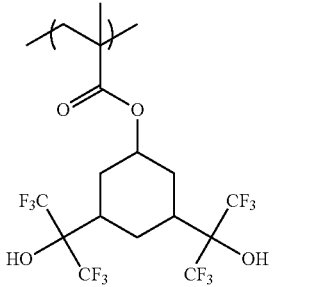
(HR-55) 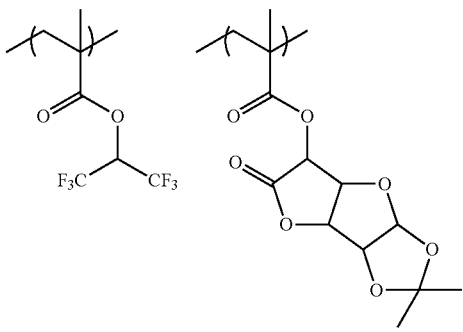

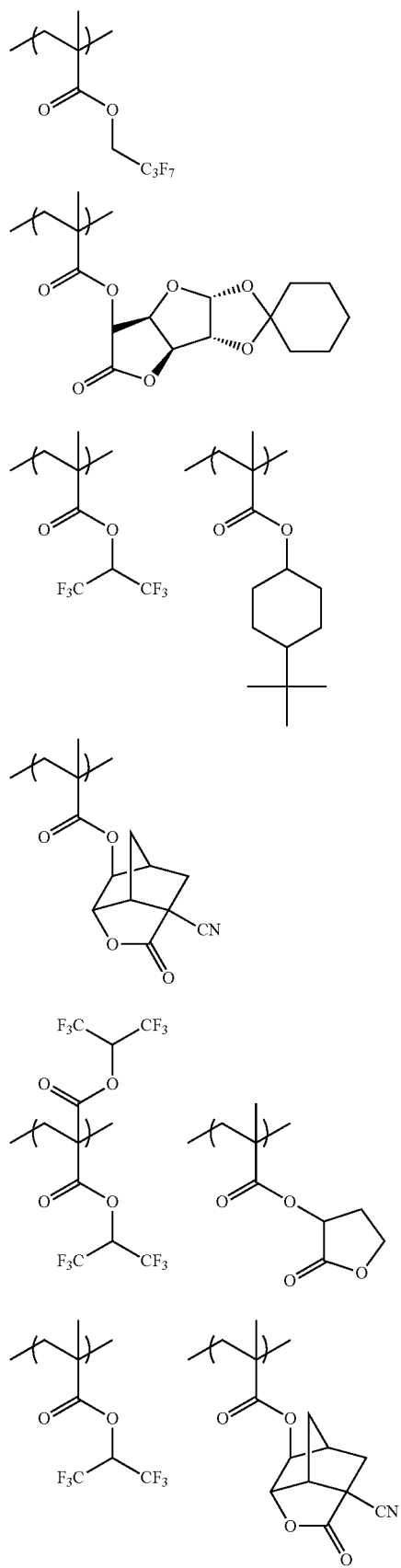
(HR-56)
(HR-57)
(HR-58)
(HR-59)
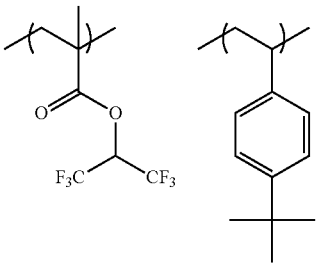
(HR-60)
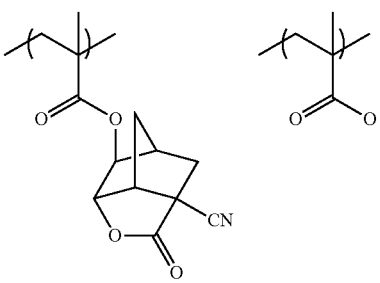
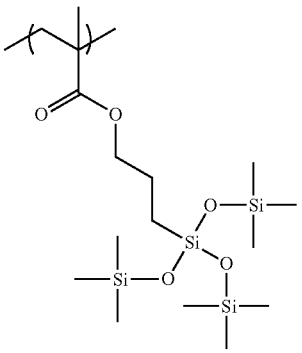
(HR-61)
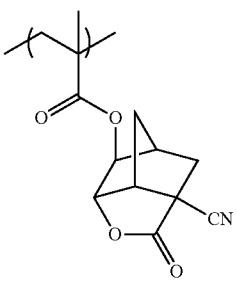
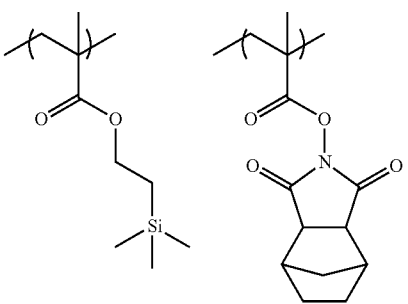
(HR-62)

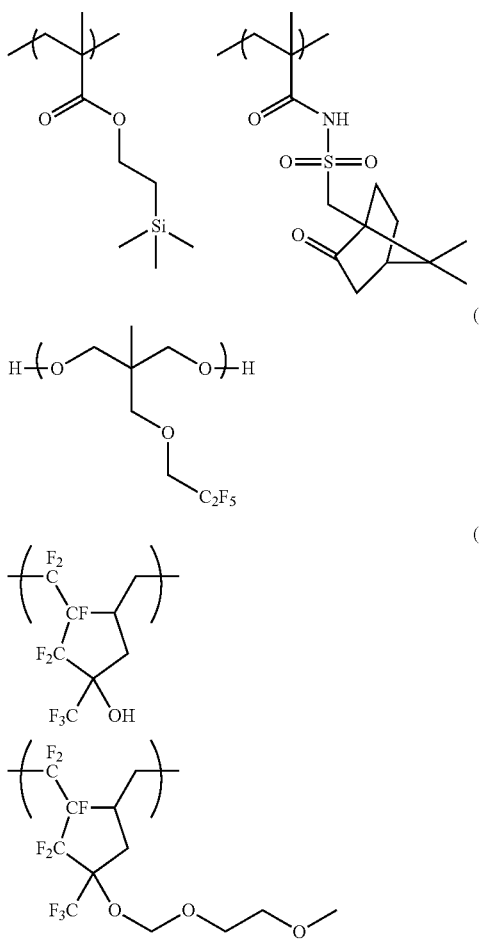
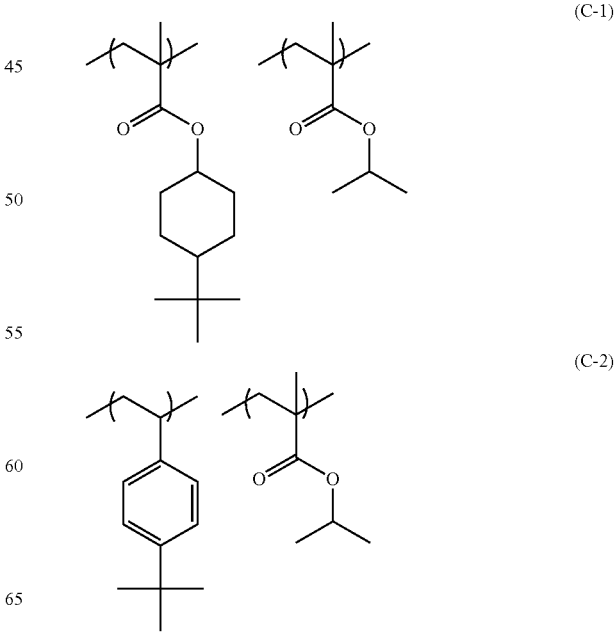
TABLE 1
| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

(C-3) 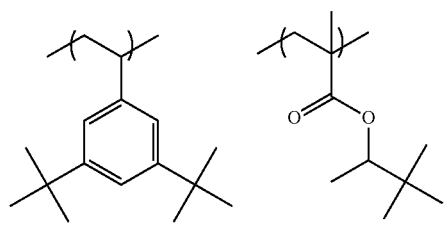
(C-4) 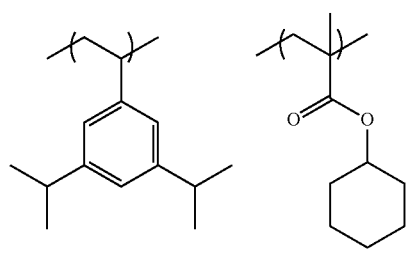
(C-5) 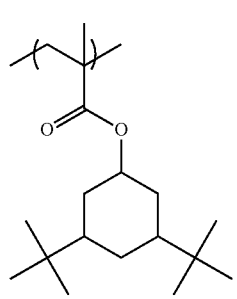
(C-6) 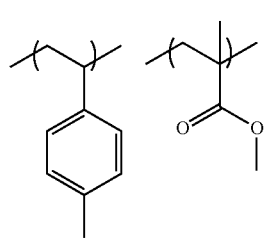
(C-7) 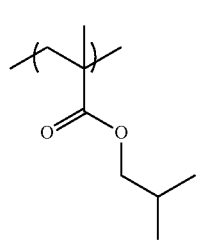
(C-8) 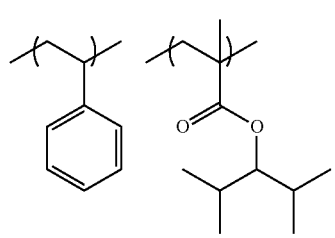
(C-9) 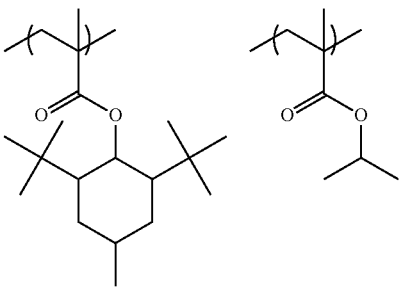
(C-10) 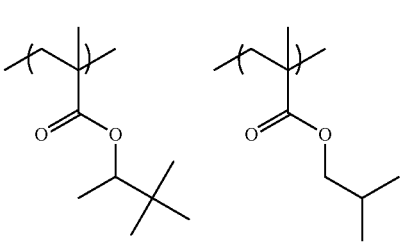
(C-11) 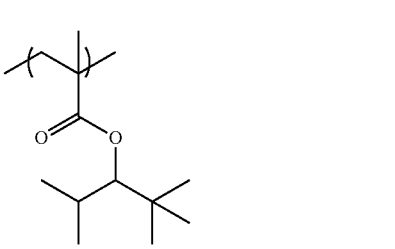
(C-12) 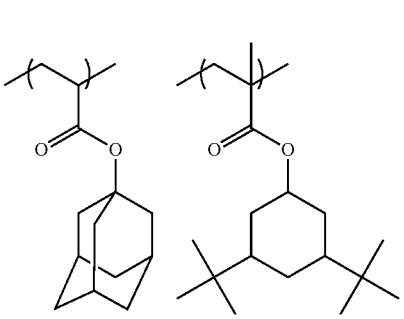
(C-13) 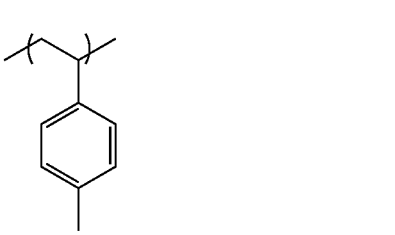
(C-14) 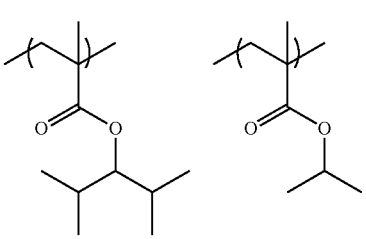

(C-15) 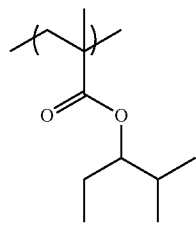
(C-16) 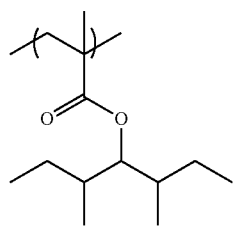
(C-17) 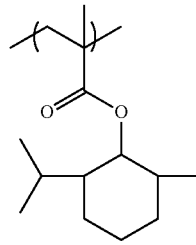
(C-18) 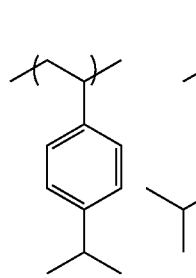
(C-19) 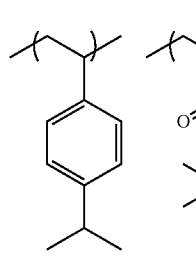
(C-20) 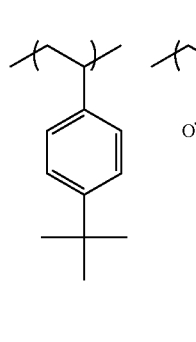
(C-21) 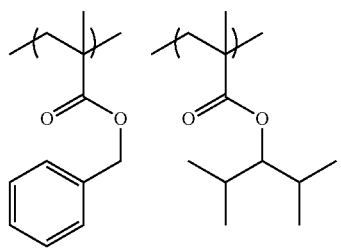
(C-22) 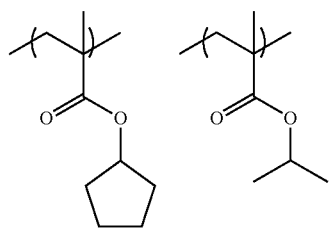
(C-23) 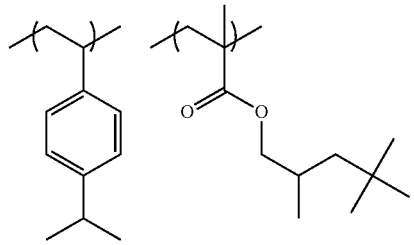
(C-24) 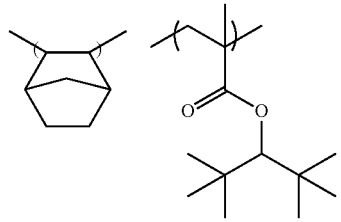
(C-25) 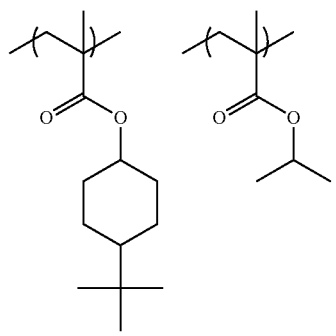
(C-26) 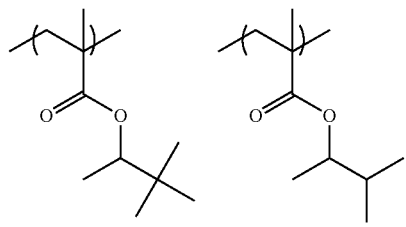

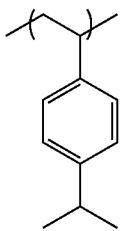

(C-27)

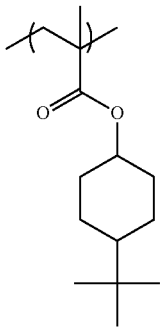 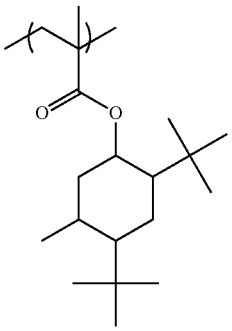

(C-28)

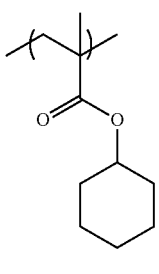 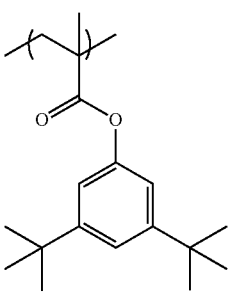

TABLE 2

| Resin | Composition | Mw | Mw/Mn |
|---|---|---|---|
| C-1 | 50/50 | 9600 | 1.74 |
| C-2 | 60/40 | 34500 | 1.43 |
| C-3 | 30/70 | 19300 | 1.69 |
| C-4 | 90/10 | 26400 | 1.41 |
| C-5 | 100 | 27600 | 1.87 |
| C-6 | 80/20 | 4400 | 1.96 |
| C-7 | 100 | 16300 | 1.83 |
| C-8 | 5/95 | 24500 | 1.79 |
| C-9 | 20/80 | 15400 | 1.68 |
| C-10 | 50/50 | 23800 | 1.46 |
| C-11 | 100 | 22400 | 1.57 |
| C-12 | 10/90 | 21600 | 1.52 |
| C-13 | 100 | 28400 | 1.58 |
| C-14 | 50/50 | 16700 | 1.82 |
| C-15 | 100 | 23400 | 1.73 |
| C-16 | 60/40 | 18600 | 1.44 |
| C-17 | 80/20 | 12300 | 1.78 |
| C-18 | 40/60 | 18400 | 1.58 |
| C-19 | 70/30 | 12400 | 1.49 |
| C-20 | 50/50 | 23500 | 1.94 |
| C-21 | 10/90 | 7600 | 1.75 |
| C-22 | 5/95 | 14100 | 1.39 |
| C-23 | 50/50 | 17900 | 1.61 |
| C-24 | 10/90 | 24600 | 1.72 |
| C-25 | 50/40/10 | 23500 | 1.65 |
| C-26 | 60/30/10 | 13100 | 1.51 |
| C-27 | 50/50 | 21200 | 1.84 |
| C-28 | 10/90 | 19500 | 1.66 |

<Surfactant>

It is optional for the composition of the present invention to further comprise a surfactant. The surfactant is preferably a fluorinated and/or siliconized surfactant.

As such a surfactant, there can be mentioned Megafac F176 or Megafac R08 produced by DIC Corporation, PF656 or PF6320 produced by OMNOVA SOLUTIONS, INC., Troy Sol S-366 produced by Troy Chemical Co., Ltd., Florad FC430 produced by Sumitomo 3M Ltd., polysiloxane polymer KP-341 produced by Shin-Etsu Chemical Co., Ltd., or the like.

Surfactants other than these fluorinated and/or siliconized surfactants can also be used. In particular, the other surfactants include polyoxyethylene alkyl ethers, polyoxyethylene alkyl aryl ethers and the like.

Moreover, heretofore known surfactants can also be appropriately used. As useful surfactants, there can be mentioned, for example, those described in section [0273] et seq of US Patent Application Publication No. 2008/0248425 A1.

One of these surfactants may be used alone, or two or more thereof may be used in combination.

It is optional for the actinic-ray- or radiation-sensitive resin composition of the present invention to further comprise a surfactant. When a surfactant is contained, the amount of surfactant added is preferably in the range of 0.0001 to 2 mass %, more preferably 0.0001 to 1 mass % and most preferably 0.0005 to 1 mass %, based on the total solids of the composition.

It is also preferred to regulate the amount of surfactant added to 10 ppm or less, or nil. This regulation enhances the localization of the hydrophobic resin in the surface layer, thereby increasing the hydrophobicity of the resist film surface and thus enhancing the water tracking property at the time of liquid-immersion exposure.

<Solvent>

The actinic-ray- or radiation-sensitive resin composition of the present invention generally further comprises a solvent.

As the solvent, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As preferred alkylene glycol monoalkyl ether carboxylates, there can be mentioned, for example, propylene glycol monomethyl ether acetate (PGMEA, also known as 1-methoxy-2-acetoxypropane), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

As preferred alkylene glycol monoalkyl ethers, there can be mentioned, for example, propylene glycol monomethyl ether (PGME, also known as 1-methoxy-2-propanol), propylene glycol monoethyl ether, propylene glycol monopropyl ether, propylene glycol monobutyl ether, ethylene glycol monomethyl ether and ethylene glycol monoethyl ether.

As preferred alkyl lactates, there can be mentioned, for example, methyl lactate, ethyl lactate, propyl lactate and butyl lactate.

As preferred alkyl alkoxypropionates, there can be mentioned, for example, ethyl 3-ethoxypropionate, methyl 3-methoxypropionate, methyl 3-ethoxypropionate and ethyl 3-methoxypropionate.

As preferred cyclolactones, there can be mentioned, for example, β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

As preferred optionally cyclized monoketone compounds, there can be mentioned, for example, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

As preferred alkylene carbonates, there can be mentioned, for example, propylene carbonate, vinylene carbonate, ethylene carbonate and butylene carbonate.

As preferred alkyl alkoxyacetates, there can be mentioned, for example, acetic acid 2-methoxyethyl ester, acetic acid 2-ethoxyethyl ester, acetic acid 2-(2-ethoxyethoxy) ethyl ester, acetic acid 3-methoxy-3-methylbutyl ester and acetic acid 1-methoxy-2-propyl ester.

As preferred alkyl pyruvates, there can be mentioned, for example, methyl pyruvate, ethyl pyruvate and propyl pyruvate.

As a preferably employable solvent, there can be mentioned a solvent having a boiling point of 130° C. or above measured at ordinary temperature under ordinary pressure. For example, there can be mentioned cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, acetic acid 2-ethoxyethyl ester, acetic acid 2-(2-ethoxyethoxy) ethyl ester or propylene carbonate.

In the present invention, one of these solvents may be used alone, or two or more thereof may be used in combination.

In the present invention, a mixed solvent comprised of a mixture of a solvent containing a hydroxyl group in its structure and a solvent containing no hydroxyl group may be used as the organic solvent.

The solvent containing a hydroxyl group and the solvent containing no hydroxyl group can be appropriately selected from among the compounds set forth above by way of example. The solvent containing a hydroxyl group is preferably an alkylene glycol monoalkyl ether, an alkyl lactate or the like, more preferably propylene glycol monomethyl ether or ethyl lactate. The solvent containing no hydroxyl group is preferably an alkylene glycol monoalkyl ether acetate, an alkyl alkoxypropionate, an optionally cyclized monoketone compound, a cyclolactone, an alkyl acetate or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent containing a hydroxyl group and a solvent containing no hydroxyl group is in the range of 1/99 to 99/1, preferably 10/90 to 90/10 and more preferably 20/80 to 60/40. The mixed solvent containing a solvent containing no hydroxyl group in an amount of 50 mass % or more is especially preferred from the viewpoint of uniform applicability.

It is preferred for the solvent to be a mixed solvent comprised of two or more solvents containing propylene glycol monomethyl ether acetate.

<Dissolution Inhibiting Compound of 3000 or Less Molecular Weight Decomposed Under the Action of an Acid to Thereby Increase its Solubility in an Alkali Developer>

From the viewpoint of not lowering the transmission of light of 220 nm or shorter wavelength, it is preferred for the dissolution inhibiting compound (hereinafter also referred to as "dissolution inhibiting compound") of 3000 or less molecular weight decomposed under the action of an acid to thereby increase its solubility in an alkali developer to be an alicyclic or aliphatic compound containing an acid-decomposable group, such as any of cholic acid derivatives containing an acid-decomposable group described in Proceeding of SPIE, 2724, 355 (1996). The acid-decomposable group and alicyclic structure can be the same as described above in connection with the resin (A).

When the actinic-ray- or radiation-sensitive resin composition of the present invention is exposed to a KrF excimer laser or irradiated with electron beams, a compound with a structure resulting from the replacement of the phenolic hydroxyl group of a phenol compound with an acid-decomposable group is preferably used as the dissolution inhibiting compound. The phenol compound preferably contains 1 to 9 phenol skeletons, more preferably 2 to 6 phenol skeletons.

The amount of dissolution inhibiting compound added, based on the total solids of the actinic-ray- or radiation-sensitive resin composition, is preferably in the range of 0.5 to 50 mass %, more preferably 0.5 to 40 mass %.

Specific examples of the dissolution inhibiting compounds are shown below, which in no way limit the scope of the present invention.

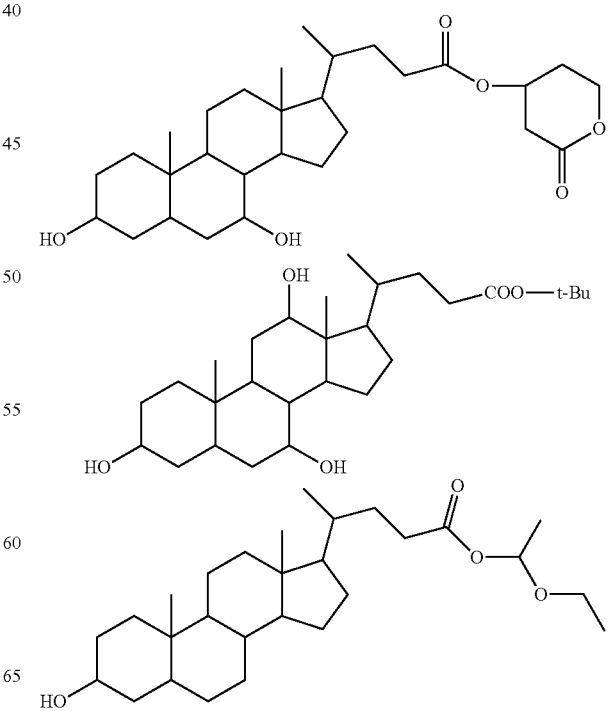

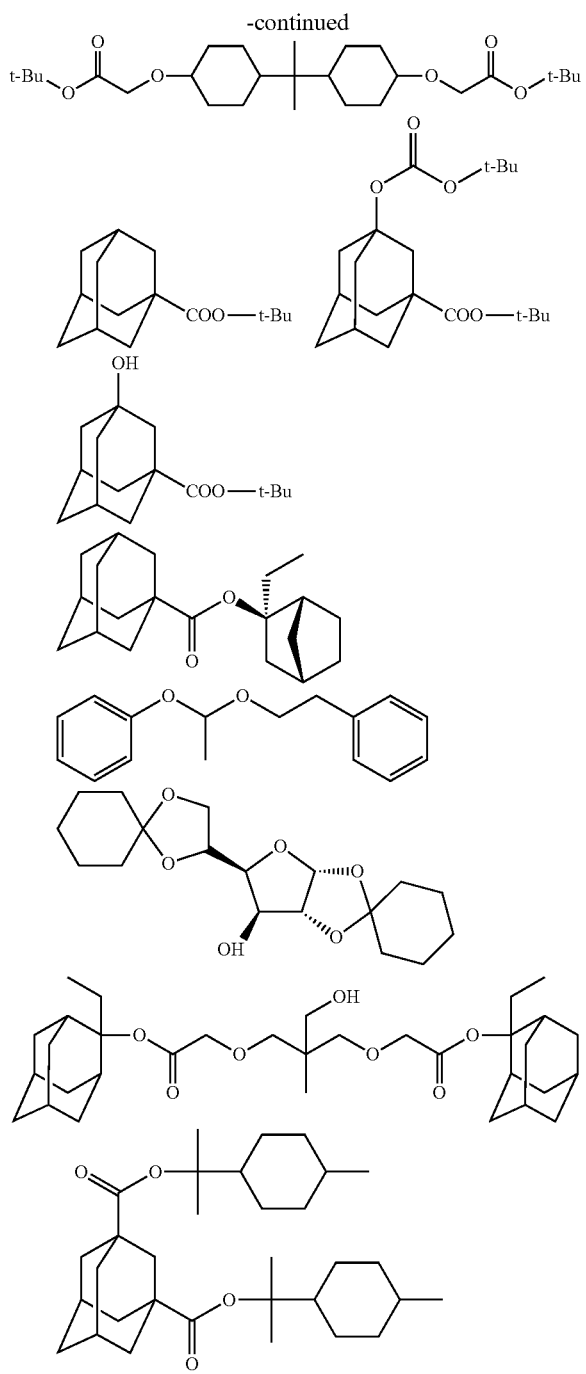

<Other Component>

The composition of the present invention may be loaded with, other than the foregoing components, a carboxylic acid onium salt, a dye, a plasticizer, a photosensitizer, a light absorbing agent, etc.

<Method of Forming Pattern>

The method of forming a pattern according to the present invention comprises the operations of exposing an actinic-ray- or radiation-sensitive film to light and developing the exposed film.

The actinic-ray- or radiation-sensitive film is formed from the foregoing composition of the present invention. In particular, the film is preferably formed on a substrate. In the method of forming a pattern according to the present invention, all the operations of forming an actinic-ray- or radiation-sensitive film from the composition of the present invention on a substrate, exposing the actinic-ray- or radiation-sensitive film to light and developing the exposed film can be performed through generally known procedures.

From the viewpoint of enhancement of resolving power, it is preferred to use the actinic-ray- or radiation-sensitive resin composition of the present invention in a film thickness of 30 to 250 nm. More preferably, the composition is used in a film thickness of 30 to 200 nm. This film thickness can be attained by setting the solid content of the actinic-ray- or radiation-sensitive resin composition within an appropriate range so as to cause the composition to have an appropriate viscosity, thereby improving the applicability and film forming property.

The total solid content of the actinic-ray- or radiation-sensitive resin composition of the present invention is generally in the range of 1 to 10 mass %, preferably 1 to 8.0 mass % and more preferably 1.0 to 6.0 mass %.

The actinic-ray- or radiation-sensitive resin composition of the present invention is used in such a manner that the above-described components are dissolved in a given solvent, filtered and applied onto a given support. The filter is preferably prepared of a polytetrafluoroethylene, polyethylene or nylon having a pore size of 0.1 µm or less, preferably 0.05 µm or less and more preferably 0.03 µm or less. In the filtration, two or more types of filters may be connected in series or parallel. Moreover, the composition may be filtered two or more times. Further, deaeration or the like of the composition may be performed prior to and/or after the filtration.

The composition is applied onto a substrate, such as one for use in the production of integrated circuit elements (e.g., silicon/silicon dioxide coating), by appropriate application means, such as a spinner. Thereafter, the composition is dried. Thus, an actinic-ray- or radiation-sensitive film can be obtained.

The thus formed film is exposed through a given mask to actinic rays or radiation, preferably baked (heated), developed and rinsed. Thus, a desirable pattern can be obtained. In the exposure to electron beams, lithography through no mask (direct lithography) is generally carried out.

A prebake (PB) is preferably carried out after the film formation but before the exposure operation.

It is preferred to perform post-exposure bake (PEB) after the exposure operation but before the development operation.

In both PB and PEB, the baking temperature is preferably in the range of 70 to 120° C., more preferably 80 to 110° C. The baking time is preferably in the range of 30 to 300 seconds, more preferably 30 to 180 seconds and further more preferably 30 to 90 seconds.

The baking can be carried out by means provided in a conventional exposure/development apparatus and may also be carried out using a hot plate or the like.

The baking accelerates the reaction in exposed areas, thereby enhancing the sensitivity and pattern profile.

The actinic rays or radiation is not particularly limited. Examples thereof include a KrF excimer laser, an ArF excimer laser, EUV light and electron beams. An ArF excimer laser, EUV light and electron beams are preferred.

The developer for use in the operation of developing the actinic-ray- or radiation-sensitive film formed of the composition of the present invention is not particularly limited. For example, use can be made of an alkali developer or a developer comprising an organic solvent (hereinafter also referred to as an organic developer).

As the alkali developer, use can be made of, for example, an alkaline aqueous solution containing an inorganic alkali, such as sodium hydroxide, potassium hydroxide, sodium carbonate, sodium silicate, sodium metasilicate or aqueous ammonia; a primary amine, such as ethylamine or n-propylamine; a secondary amine, such as diethylamine or di-n-butylamine; a tertiary amine, such as triethylamine or methyldiethylamine; an alcoholamine, such as dimethylethanolamine or triethanolamine; a quaternary ammonium salt, such as tetramethylammonium hydroxide or tetraethylammonium hydroxide; a cycloamine, such as pyrrole or piperidine; or the like. Appropriate amounts of an alcohol and/or a surfactant may further be added to the above alkaline aqueous solution before use. The alkali concentration of the alkali developer is generally in the range of 0.1 to 20 mass %. The pH value of the alkali developer is generally in the range of 10.0 to 15.0.

As the organic developer, use can be made of a polar solvent, such as a ketone solvent, an ester solvent, an alcohol solvent, an amide solvent or an ether solvent, and a hydrocarbon solvent.

As the ketone solvent, there can be mentioned, for example, 1-octanone, 2-octanone, 1-nonanone, 2-nonanone, acetone, 2-heptanone(methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, propylene carbonate or the like.

As the ester solvent, there can be mentioned, for example, methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl 3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate or the like.

As the alcohol solvent, there can be mentioned, for example, an alcohol, such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol or n-decanol; a glycol solvent, such as ethylene glycol, diethylene glycol or triethylene glycol; a glycol ether solvent, such as ethylene glycol monomethyl ether, propylene glycol monomethyl ether, ethylene glycol monoethyl ether, propylene glycol monoethyl ether, diethylene glycol monomethyl ether, triethylene glycol monoethyl ether or methoxymethylbutanol; or the like.

As the ether solvent, there can be mentioned, for example, not only any of the above-mentioned glycol ether solvents but also dioxane, tetrahydrofuran or the like.

As the amide solvent, there can be mentioned, for example, N-methyl-2-pyrrolidone, N,N-dimethylacetamide, N,N-dimethylformamide, hexamethylphosphoric triamide, 1,3-dimethyl-2-imidazolidinone or the like.

As the hydrocarbon solvent, there can be mentioned, for example, an aromatic hydrocarbon solvent, such as toluene or xylene, or an aliphatic hydrocarbon solvent, such as pentane, hexane, octane or decane.

Any two or more of these solvents may be mixed together before use. Alternatively, any of the solvents may be mixed with a solvent other than those mentioned above or water before use. It is preferred for the content of water in the organic developer to be less than 10 mass %. More preferably, the organic developer contains substantially no trace of water.

Namely, the amount of organic solvent used in the organic developer is preferably in the range of 90 to 100 mass %, more preferably 95 to 100 mass %, based on the whole amount of the developer.

It is especially preferred for the organic developer to be a developer comprising at least one organic solvent selected from the group consisting of a ketone solvent, an ester solvent, an alcohol solvent, an amide solvent and an ether solvent.

According to necessity, an appropriate amount of surfactant can be added to the organic developer. The surfactant is not particularly limited. For example, use can be made of any of ionic and nonionic fluorinated and/or siliconized surfactants and the like. As such fluorinated and/or siliconized surfactants, there can be mentioned, for example, those described in JP-A's S62-36663, S61-226746, S61-226745, S62-170950, S63-34540, H7-230165, H8-62834, H9-54432 and H9-5988, and U.S. Pat. Nos. 5,405,720, 5,360,692, 5,529,529, 5,296,296, 5,436,436, 5,576,576, 5,294,294 and 5,824,824. Nonionic surfactants are preferred. Although nonionic surfactants are not particularly limited, using a fluorinated surfactant or siliconized surfactant is preferred. The amount of surfactant added is generally in the range of 0.001 to 5 mass %, preferably 0.005 to 2 mass % and more preferably 0.01 to 0.5 mass %, based on the whole amount of the developer.

Pure water is used as a rinse liquid. Before the use thereof, an appropriate amount of surfactant may be added thereto.

As the development method, use can be made of, for example, a method in which the substrate is dipped in a tank filled with a developer for a given period of time (dip method), a method in which a developer is puddled on the surface of the substrate by its surface tension and allowed to stand still for a given period of time to thereby effect development (puddle method), a method in which a developer is sprayed onto the surface of the substrate (spray method), or a method in which a developer is continuously discharged onto the substrate being rotated at a given speed while scanning a developer discharge nozzle at a given speed (dynamic dispense method).

Further, the development operation or rinse operation may be followed by the operation of removing any developer or rinse liquid adhering on the pattern by use of a supercritical fluid.

Prior to the formation of the actinic-ray- or radiation-sensitive film (resist film), the substrate may be coated with an antireflection film.

As the antireflection film, use can be made of not only an inorganic film of titanium, titanium dioxide, titanium nitride, chromium oxide, carbon, amorphous silicon or the like but also an organic film comprised of a light absorbing agent and a polymer material. Also, as an organic antireflection film, use can be made of any of commercially available organic antireflection films, such as DUV-30 Series and DUV-40 Series produced by Brewer Science Inc. and AR-2, AR-3 and AR-5 produced by Shipley Co., Ltd.

Exposure (liquid immersion exposure) may be carried out after filling the interstice between the film and a lens with a liquid (immersion medium) of refractive index higher than that of air at the time of exposure to actinic rays or radiation. This enhances the resolution. The useful immersion medium is preferably water. Water is preferred from the viewpoint of a low temperature coefficient of refractive index, easy procurement and easy handling.

Further, from the viewpoint of refractive index increase, use can be made of a medium of 1.5 or higher refractive index. Such a medium may be an aqueous solution or an organic solvent.

When water is used as an immersion liquid, any of additives intended for an increase of refractive index, etc. may be added to water in a slight proportion. Examples of such additives are particularized in Chapter 12 of "Process and Material of Liquid Immersion Lithography" published by CMC Publishing Co., Ltd. On the other hand, the presence of a substance being opaque in 193-nm light, or an impurity whose refractive index is greatly different from that of water, invites a distortion of optical image projected on the film. Accordingly, it is preferred to use distilled water as the immersion water. Further, use may be made of water having been purified through an ion exchange filter or the like.

Desirably, the electrical resistance of purified water is 18.3 MΩcm or higher, and the TOC (organic matter concentration) thereof is 20 ppb or below. Prior deaeration of the water is desired.

For the prevention of any direct contact of the actinic-ray- or radiation-sensitive film with the immersion liquid, a film that is highly insoluble in the immersion liquid (hereinafter also referred to as "top coat") may be provided between the actinic-ray- or radiation-sensitive film and the immersion liquid. The functions to be fulfilled by the top coat are applicability onto the resist film, transparency in radiation of especially 193 nm wavelength and high insolubility in the immersion liquid. It is preferred to use, as the top coat, one that does not mix with the resist film and is uniformly applicable onto the actinic-ray- or radiation-sensitive film.

From the viewpoint of transparency at 193 nm, the top coat is preferably comprised of a polymer containing no aromatic moiety. As such a polymer, there can be mentioned, for example, a hydrocarbon polymer, an acrylic ester polymer, polymethacrylic acid, polyacrylic acid, polyvinyl ether, a siliconized polymer or a fluoropolymer. Any of the above-mentioned hydrophobic resins finds appropriate application in the top coat. When impurities are leached from the top coat into the immersion liquid, the optical lens is stained. Therefore, it is preferred to effectively reduce the amount of residual monomer components of polymer contained in the top coat.

When the top coat is detached, use may be made of a developer, or a separate peeling agent. The peeling agent is preferably comprised of a solvent exhibiting a lower permeation into the actinic-ray- or radiation-sensitive film. Detachability by an alkali developer is preferred from the viewpoint that the detaching operation can be performed simultaneously with the development processing operation for the resist. It is preferred for the top coat to be acidic from the viewpoint of detachment with the use of an alkali developer. However, from the viewpoint of non-intermiscibility with the resist, the top coat may be neutral or alkaline.

The difference in refractive index between the top coat and the immersion liquid is preferably nil or slight. If so, the resolving power can be enhanced. When an ArF excimer laser (wavelength: 193 nm) is used as an exposure light source, water is preferably used as the immersion liquid. Accordingly, it is preferred for the top coat for ArF liquid immersion exposure to exhibit a refractive index close to that of water (1.44).

From the viewpoint of transparency and refractive index, it is preferred for the top coat to be a thin film. Preferably, the top coat does not mix with the actinic-ray- or radiation-sensitive film and also does not mix with the immersion liquid. From this viewpoint, when the immersion liquid is water, it is preferred for the solvent for use in the top coat to be highly insoluble in the solvent used in the actinic-ray- or radiation-sensitive resin composition of the present invention and to be a non-water-soluble medium. In contrast, when the immersion liquid is an organic solvent, the top coat may be soluble or insoluble in water.

Furthermore, the present invention relates to a process for manufacturing an electronic device in which the above-described pattern forming method of the present invention is included, and relates to an electronic device manufactured by the process.

The electronic device of the present invention can be appropriately mounted in electrical and electronic equipments (household electronic appliance, OA/media-related equipment, optical apparatus, telecommunication equipment and the like)

EXAMPLES

Embodiments of the present invention will be described in greater detail below by way of its examples. However, the gist of the present invention is in no way limited to these examples.

Synthetic Example 1: Synthesis of Photoacid Generator (B-1)

In a flask, 10.0 g of ethyl bromofluoroacetate, 6.8 g of sodium sulfite, 40 ml of acetonitrile and 20 ml of water were placed, and agitated at 60° C. for 5 hours. The thus obtained reaction solution was transferred into a separatory funnel, and the separated water phase was washed with hexane twice. The thus obtained aqueous solution was loaded with 18.6 g of triphenylsulfonium bromide and 20 ml of chloroform, and agitated for an hour. The resultant reaction solution was transferred into a separatory funnel, and the separated organic phase was washed with water several times. The washed organic phase was concentrated by means of an evaporator, thereby obtaining 20.2 g of desired compound (B-1) in the form of a white solid.

(B-1)

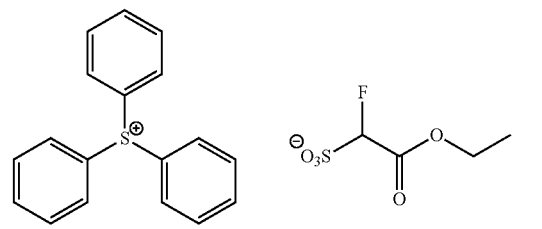

$^1$H-NMR (300 MHz, CDCl$_3$) δ=7.81-7.60 (m, 15H), 5.52 (d, 1H), 4.31 (m, 4H), 1.38 (t, 3H).

$^{19}$F-NMR (300 MHz, CDCl$_3$) δ=−182.51 (d, 1F)

The following other acid generators (B) were synthesized in the same manner as in the synthesis of compound (B-1) above.

<Acid Generator B>
(B-1)
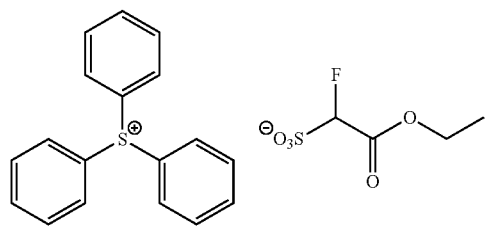
(B-2)
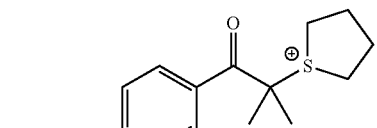
(B-3)
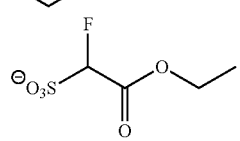
(B-4)
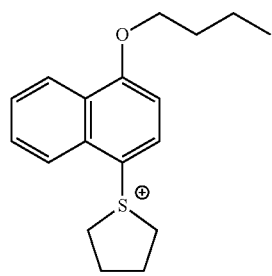
(B-5)
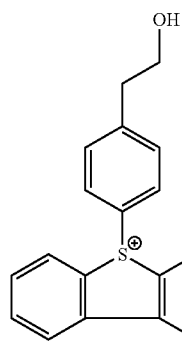
(B-6)
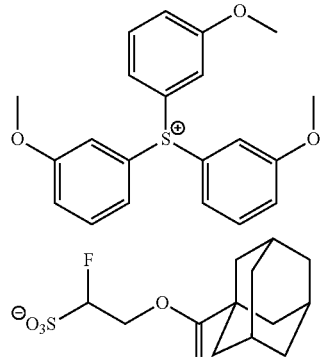
(B-7)
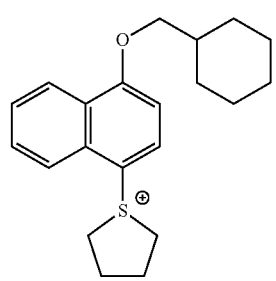
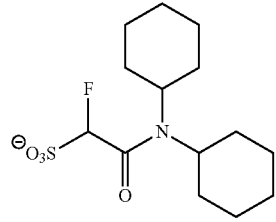
(B-8)
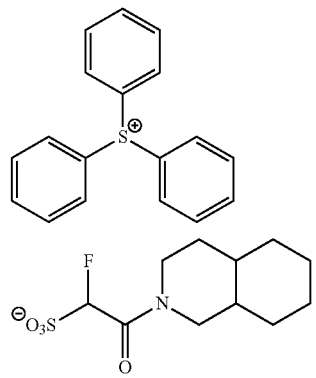
(B-9)
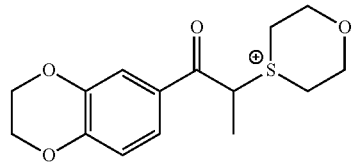
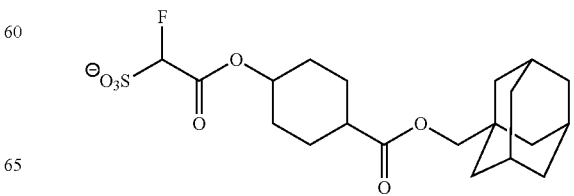

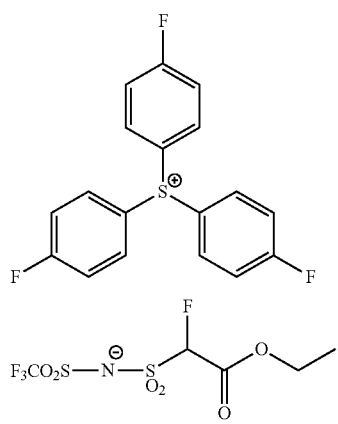
(B-10)
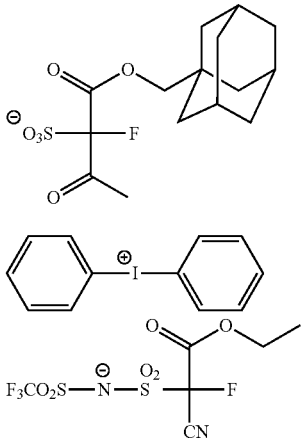
(B-11)
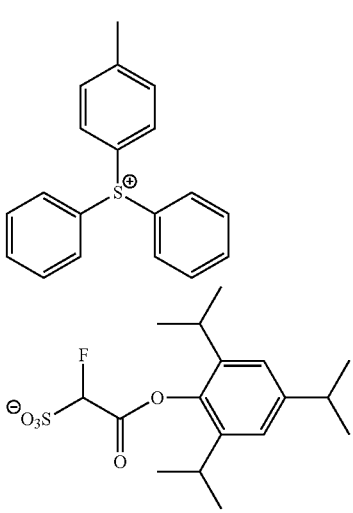
(B-12)
(B-13)
(B-14)
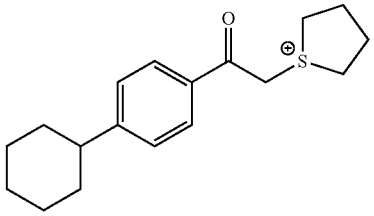
(B-15)
(B-16)
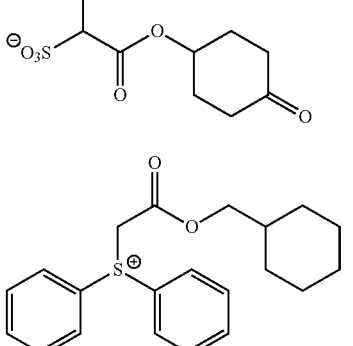
(B-17)
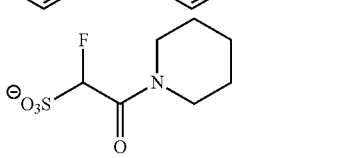
(B-18)

-continued
(B-19)
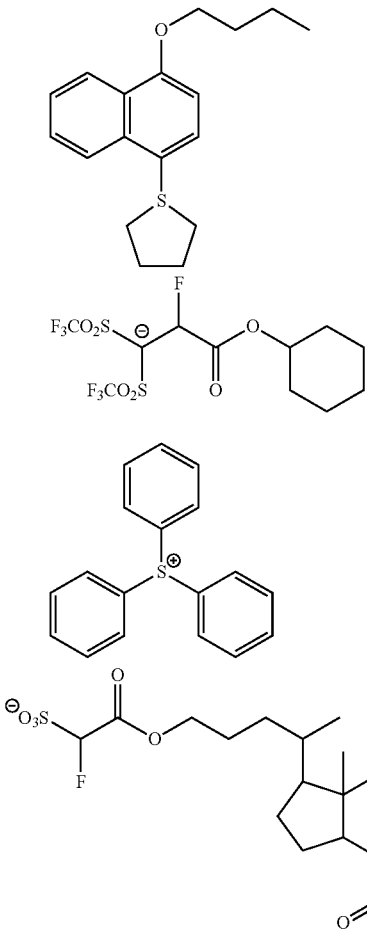
(B-20)
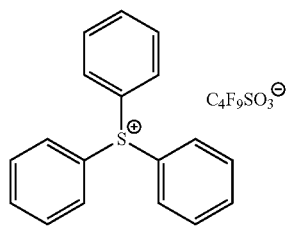
<Other Acid Generator>
Any of the following compounds as acid generators other than the compounds (B) according to the present invention was used in combination with compounds (B), or used for comparative purposes.
PAG-X
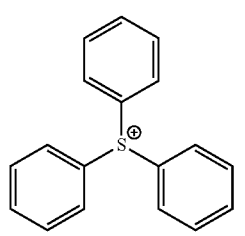
PAG-Y
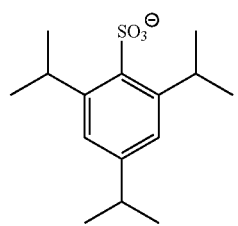
-continued
(A-X)
(A-Y)
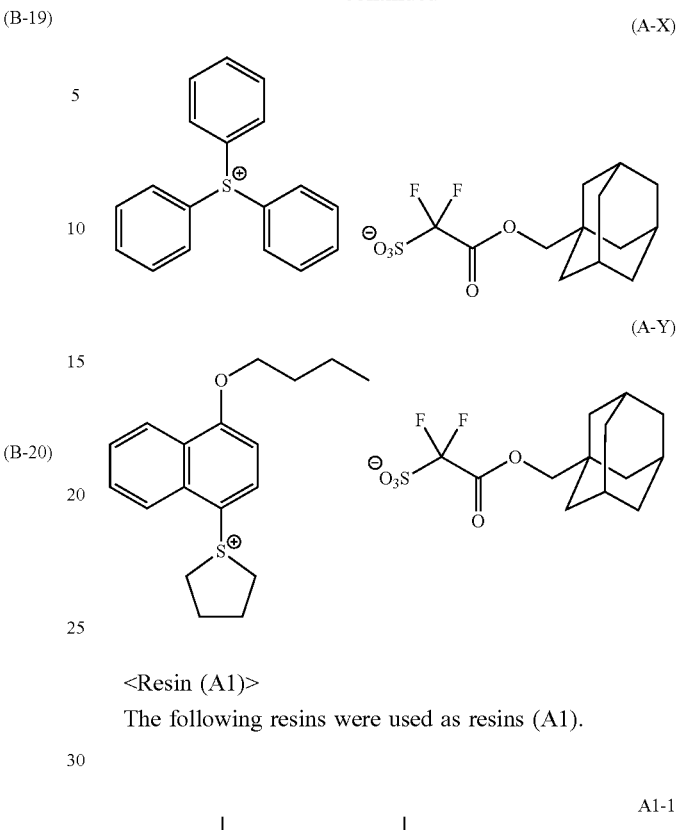
<Resin (A1)>
The following resins were used as resins (A1).
A1-1
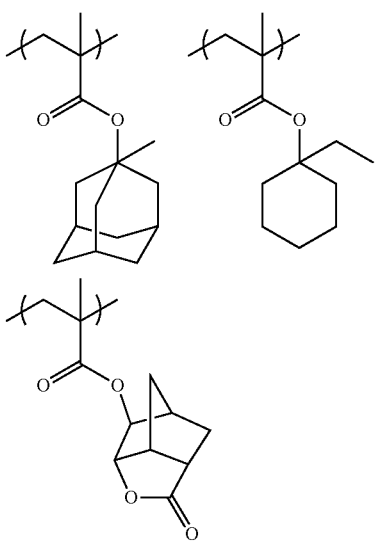
Comp. ratio: 15/45/40
Mw: 7700
Mw/Mn: 1.58
A1-2
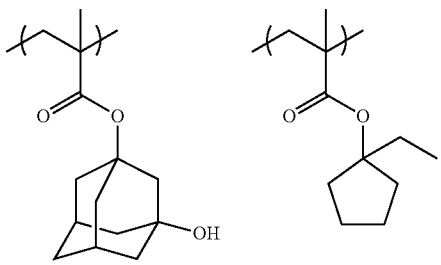

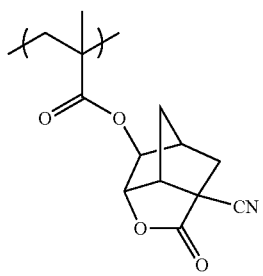
Comp. ratio: 10/50/40
Mw: 8400
Mw/Mn: 1.55
A1-3
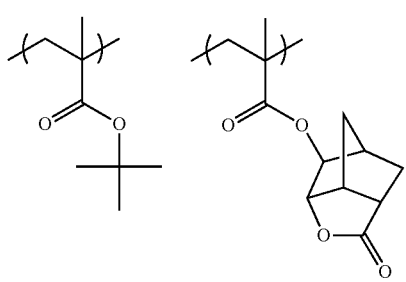
Comp. ratio: 45/55
Mw: 18000
Mw/Mn: 1.65
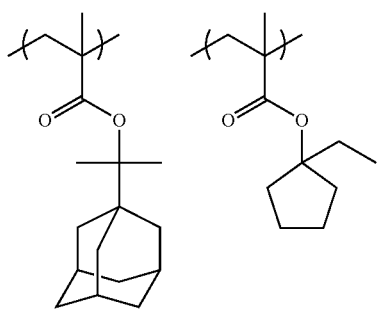
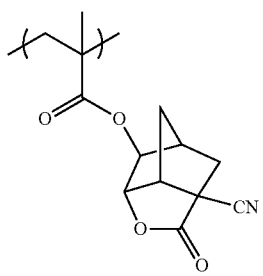
Comp. ratio: 10/50/10
Mw: 10000
Mw/Mn: 1.59
A1-5
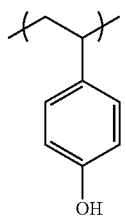 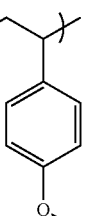
Comp. ratio: 70/30
Mw: 7500
Mw/Mn: 1.17
A1-6
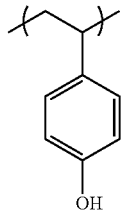 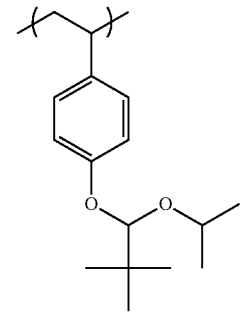
Comp. ratio: 60/40
Mw: 8900
Mw/Mn: 1.16
A1-4
A1-7
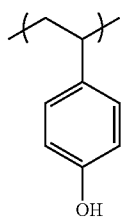 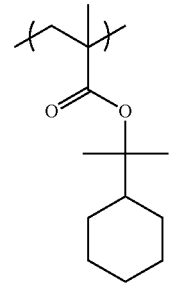 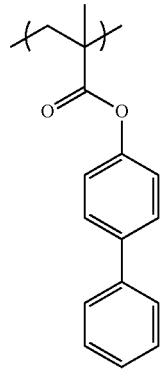
Comp. ratio: 40/50/10
Mw: 12000
Mw/Mn: 1.57
A1-8
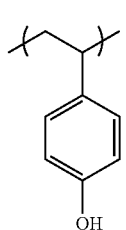 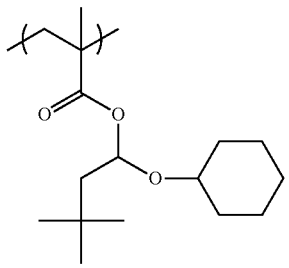

-continued
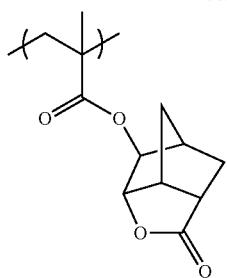
Comp. ratio: 20/50/30
Mw: 10000
Mw/Mn: 1.49
<Resin (A2)>
The following resins were used as resins (A2).
A2-1
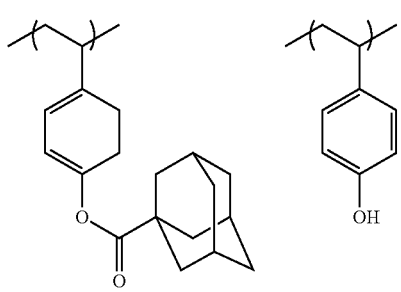
Comp. ratio: 10/90
Mw: 16000
Mw/Mn: 1.22
A2-2
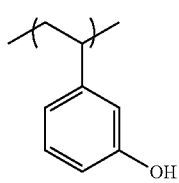
Mw: 12000
Mw/Mn: 1.35
A2-3
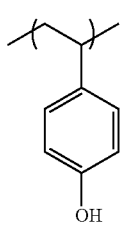
VP-5000 produced by
Nippon Soda Co., Ltd.
Mw: 6000
Mw/Mn: 1.15
<Hydrophobic Resin (HR)>
HR-1
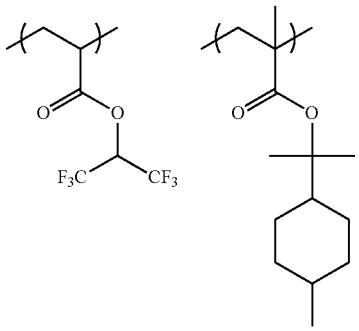
Comp. ratio: 30/70
Mw: 15000
Mw/Mn: 1.58
HR-2
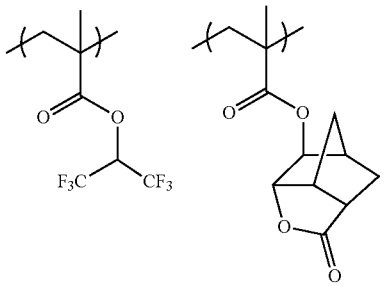
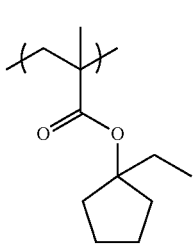
Comp. ratio: 40/40/20
Mw: 7000
Mw/Mn: 1.67
HR-3
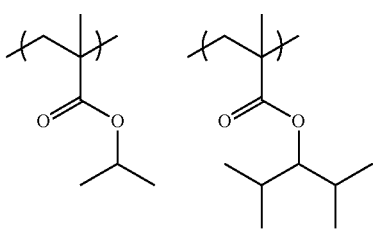
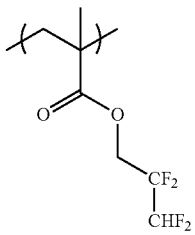
Comp. ratio: 30/65/5
Mw: 30000
Mw/Mn: 1.68

HR-4

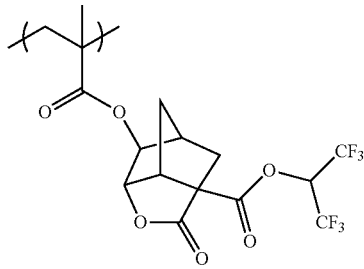

Comp. ratio: 90/10
Mw: 9000
Mw/Mn: 1.77

<Basic Compound>

DIA: 2,6-diisopropylaniline,
TEA: triethanolamine,
DBA: N,N-dibutylaniline,
PBI: 2-phenylbenzimidazole,
PEA: N-phenyldiethanolamine,
TBAH: tetrabutylammonium hydroxide,
TBAB: tetrabutylammonium benzoate,
TOA: tri(n-octyl)amine, and
TPI: 2,4,5-triphenylimidazol.

<Low-Molecular Compound (D) Containing a Nitrogen Atom and Containing a Group Leaving Under the Action of an Acid>

D-1

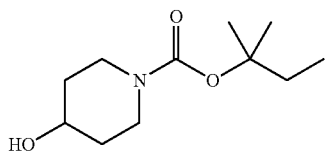

<Basic Compound (E) that when Exposed to Actinic Rays or Radiation, Lowers or Loses its Basicity>

E-1

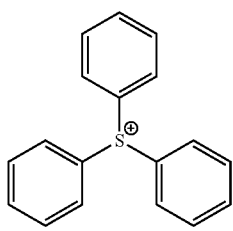

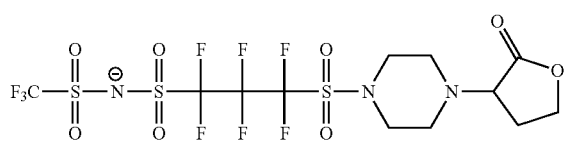

E-2

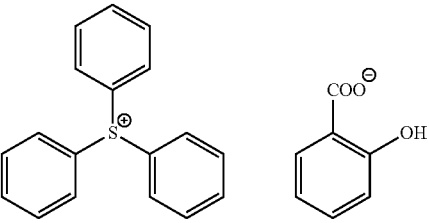

E-3

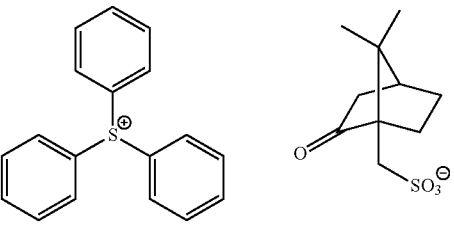

<Acid Crosslinking Agent>

CL-1

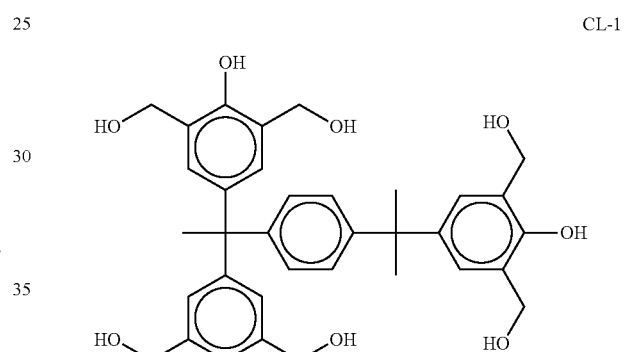

CL-2

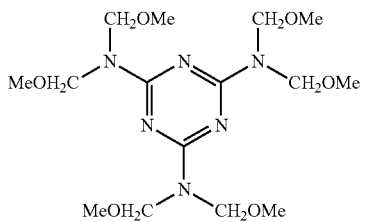

CL-3

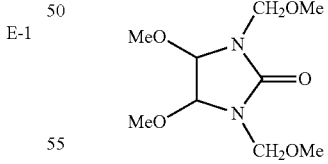

<Surfactant>

W-1: Megafac F176 (produced by DIC Corporation, fluorinated),
W-2: Megafac R08 (produced by DIC Corporation, fluorinated and siliconized),
W-3: PF6320 (produced by OMNOVA SOLUTIONS, INC., fluorinated),
W-4: Troy Sol S-366 (produced by Troy Chemical Co., Ltd.), and W-5: polysiloxane polymer KP-341 (produced by Shin-Etsu Chemical Co., Ltd., siliconized).

<Solvent>

S1: propylene glycol monomethyl ether acetate (PGMEA),

S2: cyclohexanone,

S3: γ-butyrolactone,

B1: propylene glycol monomethyl ether (PGME), and

B2: ethyl lactate.

<Preparation of Resist>

Dissolution of individual components in solvents as indicated in each of the following Tables was carried out, thereby obtaining solutions each of 4 mass % solid content. The solutions were each passed through a polytetrafluoroethylene filter of 0.05 μm pore size, thereby obtaining actinic-ray- or radiation-sensitive resin compositions (resist compositions). The actinic-ray- or radiation-sensitive resin compositions were evaluated by the following methods, and the results are listed in the Tables.

With respect to the individual components in the following Tables, when a plurality of different species thereof was used, the ratio refers to a mass ratio.

Evaluation of Resist

Examples 1A to 25A, and Comparative Examples 1A and 2A

[Exposure Condition 1: ArF Liquid Immersion Exposure, Alkali Development]

An organic antireflection film ARC29SR (produced by Nissan Chemical Industries, Ltd.) was applied onto a 12-inch silicon wafer and baked at 205° C. for 60 seconds, thereby forming a 98 nm-thick antireflection film. Each of the prepared actinic-ray- or radiation-sensitive resin compositions was applied thereonto and baked at 130° C. for 60 seconds, thereby forming a 120 nm-thick resist film. When use was made of a top coat, a 3 mass % solution obtained by dissolving a top coat resin in decane/octanol (mass ratio 9/1) was applied onto the resist film and baked at 85° C. for 60 seconds, thereby forming a 50 nm-thick top coat layer. The resultant wafer was exposed through a 6% half-tone mask of 48 nm line width 1:1 line and space pattern to light by means of an ArF excimer laser liquid immersion scanner (manufactured by ASML, XT-1700i, NA 1.20, C-Quad, outer sigma 0.981, inner sigma 0.895, XY deflection). Ultrapure water was used as the immersion liquid. Thereafter, the exposed wafer was baked at 100° C. for 60 seconds, developed by puddling with an aqueous solution of tetramethylammonium hydroxide (2.38 mass %) for 30 seconds, rinsed by puddling with pure water and spin dried, thereby obtaining a positive resist pattern.

(Evaluation of Sensitivity)

Each of the above obtained line/space=1/1 line patterns (ArF liquid immersion exposure, 48 nm line width) was observed by means of a scanning electron microscope (model S9380, manufactured by Hitachi, Ltd.). The sensitivity was defined as the minimum exposure energy at which a 48 nm line width line and space pattern (line:space=1:1) could be resolved.

(Evaluation of Resolving Power)

The resolving power was defined as a limiting resolving power (minimum line width at which a line and a space could be separated and resolved from each other) under the amount of exposure exhibiting the above sensitivity.

(Evaluation of LWR)

Each of the above obtained line patterns of line/space=1/1 (ArF liquid immersion exposure: 48 nm line width) was observed by means of a scanning electron microscope (model S9380 manufactured by Hitachi, Ltd.). In an edge 2 μm region along the longitudinal direction of the line pattern, the line width was measured at 50 points. With respect to the dispersion of measurements, the standard deviation was determined, and 3σ was computed therefrom. The smaller the value thereof, the more favorable the performance exhibited.

(Evaluation of Pattern Shape)

The shape of a cross section of each 48 nm line width line and space pattern (line:space=1:1) formed in the amount of exposure exhibiting the above sensitivity was observed by means of a scanning electron microscope (model S-4300, manufactured by Hitachi, Ltd.) The pattern shape was graded into rectangle, taper and T-top on a 3-point scale.

The obtained evaluation results are listed in Table 3 below.

TABLE 3

| | ArF liquid immersion exposure/alkali development/positive | | | | | | | | | |
|---|---|---|---|---|---|---|---|---|---|---|
| | Acid generator 2.0 g | Resin(A) 10 g | Basic comp., Comp.(D) or Comp.(E) 0.3 g | Hydrophobic resin(HR) or TC 35 mg | Solvent (mass ratio) | Surfactant 10 mg | Sensitivity (mJ/cm$^2$) | Resolving power (nm) | LWR (nm) | Pattern shape |
| Ex. 1A | B-1 | A1-1 | PBI | HR-1 | S1/S2 (7/3) | W-1 | 27.5 | 35.8 | 5.0 | Rectangle |
| Ex. 2A | B-1 | A1-2 | TEA | HR-2 | S1/S2 (7/3) | W-2 | 28.5 | 35.6 | 4.8 | Rectangle |
| Ex. 3A | B-1/B-2 (4/1) | A1-2 | DBA | — | S1/S2 (7/3) | W-1 | 27.0 | 36.2 | 5.0 | Rectangle |
| Ex. 4A | B-2 | A1-1 | D-1 | HR-1 | S1/S2/S3 (7/2/1) | W-1 | 28.0 | 36.8 | 5.5 | Rectangle |
| Ex. 5A | B-2 | A1-2 | DBA | — | S1/S3 (7/3) | W-2 | 29.0 | 37.1 | 5.2 | Rectangle |
| Ex. 6A | B-2 | A1-2 | PBI | HR-2 | S1/S2 (7/3) | W-1 | 28.0 | 37.2 | 4.8 | Rectangle |
| Ex. 7A | B-3 | A1-1/A1-2 (5 g/5 g) | DIA | HR-1 (TC) | S1/S2 (7/3) | W-1 | 28.5 | 40.2 | 6.1 | Rectangle |
| Ex. 8A | B-4 | A1-2 | E-1 | HR-1 | S1/B2 (6/4) | — | 28.5 | 38.1 | 5.8 | Rectangle |
| Ex. 9A | B-5 | A1-2 | E-3 | HR-1 | S1/S2 (7/3) | W-2 | 28.0 | 36.3 | 5.0 | Rectangle |

TABLE 3-continued

ArF liquid immersion exposure/alkali development/positive

| | Acid generator 2.0 g | Resin(A) 10 g | Basic comp., Comp.(D) or Comp.(E) 0.3 g | Hydrophobic resin(HR) or TC 35 mg | Solvent (mass ratio) | Surfactant 10 mg | Sensitivity (mJ/cm$^2$) | Resolving power (nm) | LWR (nm) | Pattern shape |
|---|---|---|---|---|---|---|---|---|---|---|
| Ex. 10A | B-5/B-10 (1/1) | A1-2 | PBI | HR-2 | S1/S2 (7/3) | W-4 | 29.0 | 35.6 | 4.8 | Rectangle |
| Ex. 11A | B-6 | A1-1 | PEA | HR-1 | S1/S2 (7/3) | W-2 | 28.5 | 38.3 | 5.5 | Rectangle |
| Ex. 12A | B-6/B-2 (3/1) | A1-1 | PBI | HR-2 | S1/S2 (7/3) | W-1 | 28.5 | 37.2 | 5.1 | Rectangle |
| Ex. 13A | B-7 | A1-2 | TEA | — | S1/B1 (7/3) | W-3 | 29.0 | 37.5 | 4.9 | Rectangle |
| Ex. 14A | B-8 | A1-1 | TEA | — | S1/S2 (7/3) | W-1 | 29.0 | 36.8 | 4.8 | Rectangle |
| Ex. 15A | B-8/B-7 (2/1) | A1-1 | PBI | HR-1 | S1/S2 (7/3) | W-1 | 28.0 | 36.5 | 4.5 | Rectangle |
| Ex. 16A | B-9 | A1-2 | DIA | — | S1/S2 (7/3) | W-2 | 28.5 | 35.0 | 5.1 | Rectangle |
| Ex. 17A | B-10 | A1-3 | DBA | HR-2 | S1/S2/B2 (5/4/1) | — | 27.5 | 39.0 | 5.0 | Rectangle |
| Ex. 18A | B-11 | A1-2 | E-2 | — | S1/S2 (7/3) | W-1 | 27.0 | 36.0 | 4.5 | Rectangle |
| Ex. 19A | B-12 | A1-1 | TEA | HR-1 | S1/S2 (6/4) | W-5 | 27.5 | 39.0 | 6.2 | Rectangle |
| Ex. 20A | B-13 | A1-2 | PBI | HR-1 | S1/S2 (7/3) | W-1 | 29.0 | 39.2 | 5.2 | Rectangle |
| Ex. 21A | B-14 | A1-1 | TEA | HR-3 | S1/B1 (7/3) | W-1 | 29.5 | 40.2 | 6.0 | Rectangle |
| Ex. 22A | B-15/PAG-Y (1/1) | A1-2 | D-1 | — | S1/S2 (7/3) | W-4 | 28.0 | 41.5 | 6.2 | Rectangle |
| Ex. 23A | B-16/PAG-X (3/1) | A1-2 | PBI | HR-4 | S1/S2 (7/3) | W-1 | 28.0 | 36.9 | 4.9 | Rectangle |
| Ex. 24A | B-17 | A1-2 | DBA | HR-1 | S1 | W-1 | 27.5 | 37.5 | 5.1 | Rectangle |
| Ex. 25A | B-18 | A1-1 | TEA | — | S1/S2 (7/3) | W-3 | 28.5 | 37.8 | 5.2 | Rectangle |
| Ex. 26A | B-19 | A1-1 | E-3 | HR-1 (TC) | S1/S2 (7/3) | W-1 | 29.0 | 40.5 | 6.1 | Rectangle |
| Ex. 27A | B-20 | A1-2 | E-1 | HR-1 (TC) | S1/S2 (7/3) | W-1 | 28.5 | 41.5 | 6.2 | Rectangle |
| Comp. Ex. 1A | A-X | A1-1 | PBI | HR-1 | S1/S2 (7/3) | W-1 | 30.0 | 44.2 | 6.5 | Taper |
| Comp. Ex. 2A | A-Y | A1-2 | PBI | — | S1/S2 (7/3) | W-1 | 31.5 | 42.3 | 6.8 | Taper |

Examples 1B to 25B, and Comparative Examples 1B and 2B

[Exposure Condition 2: ArF Liquid Immersion Exposure, Organic Solvent Development]

An organic antireflection film ARC29SR (produced by Nissan Chemical Industries, Ltd.) was applied onto a 12-inch silicon wafer and baked at 205° C. for 60 seconds, thereby forming a 95 nm-thick antireflection film. Each of the prepared actinic-ray- or radiation-sensitive resin compositions was applied thereonto and baked (prebaked: PB) at 100° C. for 60 seconds, thereby forming a 100 nm-thick resist film.

The resultant wafer was exposed through a 6% half-tone mask of 48 nm line width 1:1 line and space pattern to light by means of an ArF excimer laser liquid immersion scanner (manufactured by ASML, XT1700i, NA1.20, C-Quad, outer sigma 0.900, inner sigma 0.812, XY deflection). Ultrapure water was used as the immersion liquid. Thereafter, the exposed wafer was baked (post-exposure baked: PEB) at 105° C. for 60 seconds. The wafer after PEB was developed by puddling with a negative developer (butyl acetate) for 30 seconds, and rinsed by puddling with a rinse liquid [methyl isobutyl carbinol (MIBC)] for 30 seconds. Thereafter, the wafer was rotated at a rotating speed of 4000 rpm for 30 seconds, thereby obtaining a 48 nm line width 1:1 line and space negative resist pattern.

The evaluation of sensitivity, evaluation of resolving power, evaluation of LWR and evaluation of pattern shape were performed in the same manner as described above.

The evaluation results are listed in Table 4 below.

TABLE 4

ArF liquid immersion exposure/organic solvent development/negative

| | Acid generator 2.0 g | Resin (A) 10 g | Basic comp., Comp.(D) or Comp.(E) 0.3 g | Hydrophobic resin (HR) or TC 35 mg | Solvent (mass ratio) | Surfactant 10 mg | Sensitivity (mJ/cm$^2$) | Resolving power (nm) | LWR (nm) | Pattern shape |
|---|---|---|---|---|---|---|---|---|---|---|
| Ex. 1B | B-1 | A1-3 | PBI | HR-1 | S1/S2 (7/3) | W-1 | 33.0 | 31.8 | 4.7 | Rectangle |

TABLE 4-continued

| | Acid generator 2.0 g | Resin (A) 10 g | Basic comp., Comp.(D) or Comp.(E) 0.3 g | Hydrophobic resin (HR) or TC 35 mg | Solvent (mass ratio) | Surfactant 10 mg | Sensitivity (mJ/cm$^2$) | Resolving power (nm) | LWR (nm) | Pattern shape |
|---|---|---|---|---|---|---|---|---|---|---|
| Ex. 2B | B-1 | A1-4 | TEA | HR-2 | S1/S2 (7/3) | W-2 | 34.0 | 31.5 | 4.5 | Rectangle |
| Ex. 3B | B-1/B-2 (4/1) | A1-3 | DBA | — | S1/S2 (7/3) | W-1 | 32.5 | 36.5 | 4.7 | Rectangle |
| Ex. 4B | B-2 | A1-1 | D-1 | HR-1 | S1/S2/S3 (7/2/1) | W-1 | 33.5 | 32.8 | 5.2 | Rectangle |
| Ex. 5B | B-2 | A1-3 | DBA | — | S1/S3 (7/3) | W-2 | 34.5 | 33.1 | 4.9 | Rectangle |
| Ex. 6B | B-2 | A1-3/A1-4 (5 g/5 g) | PBI | HR-2 | S1/S2 (7/3) | W-1 | 33.5 | 33.2 | 4.5 | Rectangle |
| Ex. 7B | B-3 | A1-4 | DIA | HR-1 (TC) | S1/S2 (7/3) | W-1 | 34.0 | 36.2 | 5.8 | Rectangle |
| Ex. 8B | B-4 | A1-3 | E-1 | HR-1 | S1/B2 (6/4) | — | 34.0 | 34.0 | 5.5 | Rectangle |
| Ex. 9B | B-5 | A1-3 | E-3 | HR-1 | S1/S2 (7/3) | W-2 | 33.5 | 32.3 | 4.7 | Rectangle |
| Ex. 10B | B-5/B-10 (1/1) | A1-3 | PBI | HR-2 | S1/S2 (7/3) | W-4 | 34.5 | 31.6 | 4.5 | Rectangle |
| Ex. 11B | B-6 | A1-4 | PEA | HR-1 | S1/S2 (7/3) | W-2 | 34.0 | 34.3 | 5.2 | Rectangle |
| Ex. 12B | B-6/B-2 (3/1) | A1-4 | PBI | HR-2 | S1/S2 (7/3) | W-1 | 34.0 | 33.1 | 4.8 | Rectangle |
| Ex. 13B | B-7 | A1-3 | TEA | — | S1/B1 (7/3) | W-3 | 34.5 | 33.5 | 4.6 | Rectangle |
| Ex. 14B | B-8 | A1-4 | TEA | — | S1/S2 (7/3) | W-1 | 34.5 | 32.8 | 4.5 | Rectangle |
| Ex. 15B | B-8/B-7 (2/1) | A1-4 | PBI | HR-1 | S1/S2 (7/3) | W-1 | 33.5 | 32.5 | 4.2 | Rectangle |
| Ex. 16B | B-9 | A1-3 | DIA | — | S1/S2 (7/3) | W-2 | 34.0 | 31.2 | 4.8 | Rectangle |
| Ex. 17B | B-10 | A1-3 | DBA | HR-2 | S1/S2/B2 (5/4/1) | — | 33.0 | 35.5 | 4.7 | Rectangle |
| Ex. 18B | B-11 | A1-3 | E-2 | — | S1/S2 (7/3) | W-1 | 32.5 | 32.0 | 4.2 | Rectangle |
| Ex. 19B | B-12 | A1-4 | TEA | HR-1 | S1/S2 (6/4) | W-5 | 33.0 | 35.0 | 5.9 | Rectangle |
| Ex. 20B | B-13 | A1-1 | PBI | HR-1 | S1/S2 (7/3) | W-1 | 34.5 | 35.2 | 4.9 | Rectangle |
| Ex. 21B | B-14 | A1-4 | TEA | HR-3 | S1/B1 (7/3) | W-1 | 35.0 | 37.0 | 5.7 | Rectangle |
| Ex. 22B | B-15/PAG-Y (1/1) | A1-3 | D-1 | — | S1/S2 (7/3) | W-4 | 33.5 | 38.5 | 5.9 | Rectangle |
| Ex. 23B | B-16/PAG-X (3/1) | A1-3 | PBI | HR-4 | S1/S2 (7/3) | W-1 | 33.5 | 32.9 | 4.6 | Rectangle |
| Ex. 24B | B-17 | A1-3 | DBA | HR-1 | S1 | W-1 | 33.0 | 33.5 | 4.8 | Rectangle |
| Ex. 25B | B-18 | A1-4 | TEA | — | S1/S2 (7/3) | W-3 | 34.0 | 33.9 | 4.9 | Rectangle |
| Ex. 26B | B-19 | A1-3 | E-3 | HR-1 (TC) | S1/S2 (7/3) | W-1 | 35.0 | 38.5 | 6.0 | Rectangle |
| Ex. 27B | B-20 | A1-4 | E-1 | HR-1 (TC) | S1/S2 (7/3) | W-1 | 34.5 | 39.0 | 5.8 | Rectangle |
| Comp. Ex. 1B | A-X | A1-4 | PBI | HR-1 | S1/S2 (7/3) | W-1 | 35.5 | 40.2 | 6.5 | T-Top |
| Comp. Ex. 2B | A-Y | A1-4 | PBI | — | S1/S2 (7/3) | W-1 | 36.5 | 41.3 | 6.5 | T-Top |

Examples 1C to 25C and Comparative Examples 1C and 2C

[Exposure Condition 3: Exposure to EB (Electron Beams), Alkali Development, Positive Pattern]

Each of the prepared actinic-ray- or radiation-sensitive resin compositions was uniformly applied onto a silicon substrate having undergone hexamethyldisilazane treatment by means of a spin coater, and dried by baking on a hot plate at 120° C. for 90 seconds. Thus, actinic-ray- or radiation-sensitive films (resist films) each having a thickness of 100 nm were formed. Each of the formed actinic-ray- or radiation-sensitive films was exposed to electron beams by means of an electron beam irradiating apparatus (HL750 manufactured by Hitachi, Ltd., acceleration voltage 50 KeV). The exposed film was immediately baked on a hot plate at 110° C. for 90 seconds. The baked film was developed with a 2.38 mass % aqueous tetramethylammonium hydroxide solution at 23° C. for 60 seconds, rinsed with pure water for 30 seconds and spin dried. Thus, positive resist patterns were obtained.

The evaluation of sensitivity, evaluation of resolving power, evaluation of LWR and evaluation of pattern shape were performed in the same manner as described above.

The evaluation results are listed in Table 5 below.

TABLE 5

EB exposure/alkali development/positive

| | Acid generator 2.0 g | Resin (A) 10 g | Basic comp., Comp.(D) or Comp.(E) 0.3 g | Hydrophobic resin (HR) or TC 35 mg | Solvent (mass ratio) | Surfactant 10 mg | Sensitivity ($\mu C/cm^2$) | Resolving power (nm) | LWR (nm) | Pattern shape |
|---|---|---|---|---|---|---|---|---|---|---|
| Ex. 1C | B-1 | A1-5 | TBAH | HR-1 | S1/S2 (7/3) | W-1 | 32.0 | 32.4 | 4.2 | Rectangle |
| Ex. 2C | B-1 | A1-6 | E-1 | HR-2 | S1/S2 (7/3) | W-2 | 33.0 | 32.5 | 4.1 | Rectangle |
| Ex. 3C | B-1/B-2 (4/1) | A1-5 | TBAH | — | S1/S2 (7/3) | W-1 | 31.5 | 36.1 | 4.2 | Rectangle |
| Ex. 4C | B-2 | A1-6 | D-1 | HR-1 | S1/S2/S3 (7/2/1) | W-1 | 32.5 | 33.7 | 4.8 | Rectangle |
| Ex. 5C | B-2 | A1-5 | TBAB | — | S1/S3 (7/3) | W-2 | 33.5 | 34.0 | 4.5 | Rectangle |
| Ex. 6C | B-2 | A1-5 | TOA | HR-2 | S1/S2 (7/3) | W-1 | 32.5 | 34.1 | 4.1 | Rectangle |
| Ex. 7C | B-3 | A1-6 | TBAH | — | S1/S2 (7/3) | W-1 | 33.0 | 38.1 | 5.4 | Rectangle |
| Ex. 8C | B-4 | A1-5 | TBAH | HR-1 | S1/B2 (6/4) | — | 33.0 | 35.0 | 5.1 | Rectangle |
| Ex. 9C | B-5 | A1-5 | TBAH | — | S1/S2 (7/3) | W-2 | 32.5 | 33.2 | 4.3 | Rectangle |
| Ex. 10C | B-5/B-10 (1/1) | A1-5/A1-6 (5 g/5 g) | E-3 | HR-2 | S1/S2 (7/3) | W-4 | 33.5 | 32.5 | 4.1 | Rectangle |
| Ex. 11C | B-6 | A1-6 | TBAH | HR-1 | S1/S2 (7/3) | W-2 | 33.0 | 35.2 | 4.8 | Rectangle |
| Ex. 12C | B-6/B-2 (3/1) | A1-6 | TPI | HR-2 | S1/S2 (7/3) | W-1 | 33.0 | 34.0 | 4.3 | Rectangle |
| Ex. 13C | B-7 | A1-5 | TBAB | — | S1/B1 (7/3) | W-3 | 33.5 | 34.4 | 4.2 | Rectangle |
| Ex. 14C | B-8 | A1-6 | TBAH | — | S1/S2 (7/3) | W-1 | 33.5 | 33.7 | 4.1 | Rectangle |
| Ex. 15C | B-8/B-7 (2/1) | A1-6 | TBAH | HR-1 | S1/S2 (7/3) | W-1 | 32.5 | 33.4 | 3.9 | Rectangle |
| Ex. 16C | B-9 | A1-5 | TOA | — | S1/S2 (7/3) | W-2 | 33.0 | 31.9 | 4.4 | Rectangle |
| Ex. 17C | B-10 | A1-5 | DBA | HR-2 | S1/S2/B2 (5/4/1) | — | 32.0 | 34.8 | 4.3 | Rectangle |
| Ex. 18C | B-11 | A1-5 | TPI | — | S1/S2 (7/3) | W-1 | 31.5 | 32.9 | 3.8 | Rectangle |
| Ex. 19C | B-12 | A1-7 | TBAB | HR-1 | S1/S2 (6/4) | W-5 | 32.0 | 36.2 | 5.5 | Rectangle |
| Ex. 20C | B-13 | A1-5 | TBAH | HR-1 | S1/S2 (7/3) | W-1 | 33.5 | 36.5 | 4.5 | Rectangle |
| Ex. 21C | B-14 | A1-6 | TEA | HR-3 | S1/B1 (7/3) | W-1 | 34.0 | 37.8 | 5.2 | Rectangle |
| Ex. 22C | B-15/PAG-Y (1/1) | A1-5 | TBAH | — | S1/S2 (7/3) | W-4 | 32.5 | 39.0 | 5.5 | Rectangle |
| Ex. 23C | B-16/PAG-X (3/1) | A1-5 | TPI | HR-4 | S1/S2 (7/3) | W-1 | 32.5 | 33.8 | 4.2 | Rectangle |
| Ex. 24C | B-17 | A1-5 | TBAH | HR-1 | S1 | W-1 | 32.0 | 34.4 | 4.4 | Rectangle |
| Ex. 25C | B-18 | A1-6 | TEA | — | S1/S2 (7/3) | W-3 | 33.0 | 34.7 | 4.5 | Rectangle |
| Ex. 26C | B-19 | A1-5 | E-3 | — | S1/S2 (7/3) | W-1 | 34.0 | 38.5 | 5.5 | Rectangle |
| Ex. 27C | B-20 | A1-6 | TBAH | — | S1/S2 (7/3) | W-3 | 33.5 | 37.5 | 5.2 | Rectangle |
| Comp. Ex. 1C | A-X | A1-5 | TBAH | HR-1 | S1/S2 (7/3) | W-1 | 35.0 | 40.5 | 5.8 | Taper |
| Comp. Ex. 2C | A-Y | A1-6 | TBAB | — | S1/S2 (7/3) | W-1 | 36.0 | 42.0 | 5.5 | Taper |

Examples 1D to 25D and Comparative Examples 1D and 2D

[Exposure Condition 4: Exposure to EB (Electron Beams), Alkali Development, Negative Pattern]

Each of the prepared actinic-ray- or radiation-sensitive resin compositions was uniformly applied onto a silicon substrate having undergone hexamethyldisilazane treatment by means of a spin coater, and dried by baking on a hot plate at 120° C. for 90 seconds. Thus, actinic-ray- or radiation-sensitive films (resist films) each having a thickness of 100 nm were formed. Each of the formed actinic-ray- or radiation-sensitive films was exposed to electron beams by means of an electron beam irradiating apparatus (HL750 manufactured by Hitachi, Ltd., acceleration voltage 50 KeV). The exposed film was immediately baked on a hot plate at 110° C. for 60 seconds. The baked film was developed with a 2.38 mass % aqueous tetramethylammonium hydroxide solution at 23° C. for 60 seconds, rinsed with pure water for 30 seconds and spin dried. Thus, negative resist patterns were obtained.

The evaluation of sensitivity, evaluation of resolving power, evaluation of LWR and evaluation of pattern shape were performed in the same manner as described above.

The evaluation results are listed in Table 6 below.

TABLE 6

EB exposure/alkali development/negative

| | Acid generator 1 g | Resin (A) 10 g | Basic comp., Comp.(D) or Comp.(E) 0.2 g | cross-linking agent 3.0 g | Solvent (mass ratio) | Surfactant 10 mg | Sensitivity (μC/cm²) | Resolving power (nm) | LWR (nm) | Pattern shape |
|---|---|---|---|---|---|---|---|---|---|---|
| Ex. 1D | B-1 | A2-1 | TBAH | CL-1 | S1/S2 (7/3) | W-1 | 35.5 | 33.7 | 3.9 | Rectangle |
| Ex. 2D | B-1 | A2-2 | E-1 | CL-2 | S1/S2 (7/3) | W-2 | 36.0 | 34.3 | 3.7 | Rectangle |
| Ex. 3D | B-1/B-2 (4/1) | A2-3 | TBAH | CL-1 | S1/S2 (7/3) | W-1 | 34.5 | 35.0 | 3.9 | Rectangle |
| Ex. 4D | B-2 | A2-1/A2-3 (5 g/5 g) | D-1 | CL-1 | S1/S2/S3 (7/2/1) | W-1 | 35.5 | 35.2 | 4.5 | Rectangle |
| Ex. 5D | B-2 | A2-1 | TBAB | CL-2 | S1/S3 (7/3) | W-2 | 36.5 | 35.5 | 4.2 | Rectangle |
| Ex. 6D | B-2 | A2-3 | TOA | CL-1/CL-3 (1/1) | S1/S2 (7/3) | W-1 | 36.0 | 35.6 | 3.8 | Rectangle |
| Ex. 7D | B-3 | A2-1 | TBAH | CL-1 | S1/S2 (7/3) | W-1 | 36.0 | 38.8 | 5.3 | Rectangle |
| Ex. 8D | B-4 | A2-3 | TBAH | CL-1 | S1/B2 (6/4) | — | 36.0 | 36.4 | 4.8 | Rectangle |
| Ex. 9D | B-5 | A2-3 | TBAH | CL-1 | S1/S2 (7/3) | W-2 | 35.5 | 34.7 | 4.1 | Rectangle |
| Ex. 10D | B-5/B-10 (1/1) | A2-1 | E-3 | CL-1 | S1/S2 (7/3) | W-4 | 36.5 | 34.0 | 3.8 | Rectangle |
| Ex. 11D | B-6 | A2-2 | TBAH | CL-1 | S1/S2 (7/3) | W-2 | 36.0 | 36.7 | 4.5 | Rectangle |
| Ex. 12D | B-6/B-2 (3/1) | A2-1 | TPI | CL-1 | S1/S2 (7/3) | W-1 | 36.0 | 35.3 | 4.0 | Rectangle |
| Ex. 13D | B-7 | A2-3 | TBAB | CL-2 | S1/B1 (7/3) | W-3 | 36.0 | 35.9 | 3.9 | Rectangle |
| Ex. 14D | B-8 | A2-3 | TBAH | CL-3 | S1/S2 (7/3) | W-1 | 36.5 | 35.2 | 3.6 | Rectangle |
| Ex. 15D | B-8/B-7 (2/1) | A2-1 | TBAH | CL-1 | S1/S2 (7/3) | W-1 | 35.5 | 34.9 | 3.6 | Rectangle |
| Ex. 16D | B-9 | A2-3 | TOA | CL-2 | S1/S2 (7/3) | W-2 | 36.0 | 33.4 | 4.1 | Rectangle |
| Ex. 17D | B-10 | A2-3 | DBA | CL-1 | S1/S2/B2 (5/4/1) | — | 35.0 | 37.5 | 4.0 | Rectangle |
| Ex. 18D | B-11 | A2-1 | TPI | CL-1 | S1/S2 (7/3) | W-1 | 34.5 | 34.4 | 3.3 | Rectangle |
| Ex. 19D | B-12 | A2-1 | TBAB | CL-2 | S1/S2 (6/4) | W-5 | 35.5 | 37.4 | 5.2 | Rectangle |
| Ex. 20D | B-13 | A2-3 | TBAH | CL-1 | S1/S2 (7/3) | W-1 | 36.5 | 38.0 | 4.2 | Rectangle |
| Ex. 21D | B-14 | A2-2 | TEA | CL-1 | S1/B1 (7/3) | W-1 | 37.0 | 39.3 | 4.9 | Rectangle |
| Ex. 22D | B-15/PAG-Y (1/1) | A2-1 | TBAH | CL-1 | S1/S2 (7/3) | W-4 | 35.5 | 38.5 | 5.2 | Rectangle |
| Ex. 23D | B-16/PAG-X (3/1) | A2-1 | TPI | CL-1 | S1/S2 (7/3) | W-1 | 35.5 | 35.3 | 3.8 | Rectangle |
| Ex. 24D | B-17 | A2-1 | TBAH | CL-1 | S1 | W-1 | 35.0 | 35.9 | 4.1 | Rectangle |
| Ex. 25D | B-18 | A2-1 | TEA | CL-2 | S1/S2 (7/3) | W-3 | 36.0 | 36.1 | 4.2 | Rectangle |
| Ex. 26D | B-19 | A2-1 | E-3 | CL-1 | S1/S2 (7/3) | W-1 | 37.0 | 40.1 | 5.0 | Rectangle |
| Ex. 27D | B-20 | A2-3 | TBAH | CL-2 | S1/S2 (7/3) | W-3 | 36.5 | 39.5 | 4.8 | Rectangle |
| Comp. Ex. 1D | A-X | A2-1 | TBAH | CL-1 | S1/S2 (7/3) | W-1 | 38.0 | 42.0 | 5.5 | T-Top |
| Comp. Ex. 2D | A-Y | A2-3 | TBAB | CL-1 | S1/S2 (7/3) | W-1 | 37.5 | 41.0 | 5.2 | T-Top |

Examples 1E to 25E, and Comparative Examples 1E and 2E

[Exposure Condition 5: Exposure to EUV (Extreme Ultraviolet), Alkali Development]

Each of the prepared actinic-ray- or radiation-sensitive resin compositions was uniformly applied onto a silicon substrate having undergone hexamethyldisilazane treatment by means of a spin coater, and dried by baking on a hot plate at 120° C. for 90 seconds. Thus, actinic-ray- or radiation-sensitive films (resist films) each having a thickness of 50 nm were formed. Each of the formed actinic-ray- or radiation-sensitive films was exposed through a reflective mask of 40 nm line width 1:1 line and space pattern to EUV by means of an EUV exposure apparatus. The exposed film was immediately baked on a hot plate at 110° C. for 60 seconds. The baked film was developed with a 2.38 mass % aqueous tetramethylammonium hydroxide solution at 23° C. for 60 seconds, rinsed with pure water for 30 seconds and spin dried. Thus, positive resist patterns were obtained.

The evaluation of sensitivity, evaluation of resolving power, evaluation of LWR and evaluation of pattern shape were performed in the same manner as described above.

The evaluation results are listed in Table 7 below.

TABLE 7

EUV exposure/alkali development/positive

| | Acid generator 2.0 g | Resin (A) 10 g | Basic comp., Comp.(D) or Comp.(E) 0.3 g | Hydrophobic resin (HR) or TC 35 mg | Solvent (mass ratio) | Surfactant 10 mg | Sensitivity (mJ/cm$^2$) | Resolving power (nm) | LWR (nm) | Pattern shape |
|---|---|---|---|---|---|---|---|---|---|---|
| Ex. 1E | B-1 | A1-5 | TBAH | HR-1 | S1/S2 (7/3) | W-1 | 25.0 | 22.2 | 4.8 | Rectangle |
| Ex. 2E | B-1 | A1-6 | E-1 | HR-2 | S1/S2 (7/3) | W-2 | 26.5 | 22.1 | 4.5 | Rectangle |
| Ex. 3E | B-1/B-2 (4/1) | A1-5 | TBAH | — | S1/S2 (7/3) | W-1 | 25.0 | 23.3 | 4.6 | Rectangle |
| Ex. 4E | B-2 | A1-6 | D-1 | HR-1 | S1/S2/S3 (7/2/1) | W-1 | 26.0 | 23.5 | 5.2 | Rectangle |
| Ex. 5E | B-2 | A1-5 | TBAB | HR-1 (TC) | S1/S3 (7/3) | W-2 | 27.0 | 23.4 | 4.9 | Rectangle |
| Ex. 6E | B-2 | A1-8 | TOA | HR-2 | S1/S2 (7/3) | W-1 | 26.0 | 23.9 | 4.5 | Rectangle |
| Ex. 7E | B-3 | A1-6 | TBAH | — | S1/S2 (7/3) | W-1 | 26.5 | 27.8 | 5.8 | Rectangle |
| Ex. 8E | B-4 | A1-5/A1-6 (5 g/5 g) | TBAH | HR-1 | S1/B2 (6/4) | — | 26.5 | 24.8 | 5.5 | Rectangle |
| Ex. 9E | B-5 | A1-5 | TBAH | — | S1/S2 (7/3) | W-2 | 26.0 | 23.1 | 4.7 | Rectangle |
| Ex. 10E | B-5/B-10 (1/1) | A1-5 | E-3 | HR-2 | S1/S2 (7/3) | W-4 | 27.0 | 22.3 | 4.5 | Rectangle |
| Ex. 11E | B-6 | A1-6 | TBAH | HR-1 | S1/S2 (7/3) | W-2 | 26.0 | 25.0 | 5.2 | Rectangle |
| Ex. 12E | B-6/B-2 (3/1) | A1-6 | TPI | HR-2 | S1/S2 (7/3) | W-1 | 26.5 | 23.6 | 4.7 | Rectangle |
| Ex. 13E | B-7 | A1-7 | TBAB | — | S1/B1 (7/3) | W-3 | 27.0 | 24.2 | 4.6 | Rectangle |
| Ex. 14E | B-8 | A1-6 | TBAH | — | S1/S2 (7/3) | W-1 | 27.5 | 23.4 | 4.5 | Rectangle |
| Ex. 15E | B-8/B-7 (2/1) | A1-6 | E-2 | HR-1 | S1/S2 (7/3) | W-1 | 26.0 | 23.2 | 4.3 | Rectangle |
| Ex. 16E | B-9 | A1-5 | TOA | — | S1/S2 (7/3) | W-2 | 26.5 | 21.7 | 4.8 | Rectangle |
| Ex. 17E | B-10 | A1-8 | DBA | HR-2 | S1/S2/B2 (5/4/1) | — | 25.5 | 26.8 | 5.8 | Rectangle |
| Ex. 18E | B-11 | A1-5 | TPI | — | S1/S2 (7/3) | W-1 | 25.5 | 22.7 | 4.2 | Rectangle |
| Ex. 19E | B-12 | A1-7 | TBAB | HR-1 | S1/S2 (6/4) | W-5 | 25.5 | 25.5 | 5.9 | Rectangle |
| Ex. 20E | B-13 | A1-5 | E-1 | HR-1 | S1/S2 (7/3) | W-1 | 27.0 | 26.3 | 4.9 | Rectangle |
| Ex. 21E | B-14 | A1-6 | TEA | HR-3 | S1/B1 (7/3) | W-1 | 27.5 | 27.6 | 5.6 | Rectangle |
| Ex. 22E | B-15/PAG-Y (1/1) | A1-5 | TBAH | — | S1/S2 (7/3) | W-4 | 26.0 | 28.0 | 6.2 | Rectangle |
| Ex. 23E | B-16/PAG-X (3/1) | A1-5 | TPI | HR-4 | S1/S2 (7/3) | W-1 | 26.0 | 23.4 | 4.6 | Rectangle |
| Ex. 24E | B-17 | A1-5 | TBAH | HR-1 | S1 | W-1 | 25.0 | 24.2 | 4.8 | Rectangle |
| Ex. 25E | B-18 | A1-6 | TEA | — | S1/S2 (7/3) | W-3 | 26.5 | 24.5 | 4.9 | Rectangle |
| Ex. 26E | B-19 | A1-5 | E-3 | HR-1 | S1/S2 (7/3) | W-1 | 29.5 | 28.5 | 6.1 | Rectangle |
| Ex. 27E | B-20 | A1-6 | TBAH | HR-1 (TC) | S1/S2 (7/3) | W-3 | 28.5 | 29.0 | 6.0 | Rectangle |
| Comp. Ex. 1E | A-X | A1-5 | TBAH | HR-1 | S1/S2 (7/3) | W-1 | 30.0 | 30.2 | 6.5 | Taper |
| Comp. Ex. 2E | A-Y | A1-6 | TBAB | — | S1/S2 (7/3) | W-1 | 32.5 | 32.2 | 6.7 | Taper |

Examples 1F to 25F, and Comparative Examples 1F and 2F

[Exposure Condition 6: Exposure to EUV (Extreme Ultraviolet), Organic Solvent Development]

Each of the prepared actinic-ray- or radiation-sensitive resin compositions was uniformly applied onto a silicon substrate having undergone hexamethyldisilazane treatment by means of a spin coater, and dried by baking on a hot plate at 120° C. for 90 seconds. Thus, actinic-ray- or radiation-sensitive films (resist films) each having a thickness of 50 nm were formed. Each of the formed actinic-ray- or radiation-sensitive films was exposed through a reflective mask of 40 nm line width 1:1 line and space pattern to EUV by means of an EUV exposure apparatus. The exposed film was immediately baked on a hot plate at 110° C. for 60 seconds. The baked film was developed by puddling with butyl acetate for 30 seconds, baked at 90° C. for 60 seconds and spin dried. Thus, negative resist patterns were obtained.

The evaluation of sensitivity, evaluation of resolving power, evaluation of LWR and evaluation of pattern shape were performed in the same manner as described above.

The evaluation results are listed in Table 8 below.

TABLE 8

EUV exposure/organic solvent development/negative

| | Acid generator 2.0 g | Resin (A) 10 g | Basic comp., Comp.(D) or Comp.(E) 0.3 g | Hydrophobic resin (HR) or TC 35 mg | Solvent (mass ratio) | Surfactant 10 mg | Sensitivity (mJ/cm$^2$) | Resolving power (nm) | LWR (nm) | Pattern shape |
|---|---|---|---|---|---|---|---|---|---|---|
| Ex. 1F | B-1 | A1-7 | TBAH | HR-1 | S1/S2 (7/3) | W-1 | 20.0 | 24.5 | 5.8 | Rectangle |
| Ex. 2F | B-1 | A1-7 | E-1 | HR-2 | S1/S2 (7/3) | W-2 | 22.0 | 24.7 | 5.6 | Rectangle |
| Ex. 3F | B-1/B-2 (4/1) | A1-7 | TBAH | — | S1/S2 (7/3) | W-1 | 20.5 | 25.9 | 5.5 | Rectangle |
| Ex. 4F | B-2 | A1-7 | D-1 | HR-1 | S1/S2/S3 (7/2/1) | W-1 | 21.5 | 26.1 | 6.3 | Rectangle |
| Ex. 5F | B-2 | A1-8 | TBAB | HR-1 | S1/S3 (7/3) | W-2 | 22.5 | 26.2 | 6.0 | Rectangle |
| Ex. 6F | B-2 | A1-8 | TOA | HR-2 | S1/S2 (7/3) | W-1 | 21.5 | 26.5 | 5.6 | Rectangle |
| Ex. 7F | B-3 | A1-7/A1-8 (5 g/5 g) | TBAH | — | S1/S2 (7/3) | W-1 | 22.0 | 29.5 | 6.9 | Rectangle |
| Ex. 8F | B-4 | A1-7 | TBAH | HR-1 | S1/B2 (6/4) | — | 22.5 | 27.4 | 6.6 | Rectangle |
| Ex. 9F | B-5 | A1-5 | TBAH | — | S1/S2 (7/3) | W-2 | 21.0 | 25.7 | 5.8 | Rectangle |
| Ex. 10F | B-5/B-10 (1/1) | A1-8 | E-3 | HR-2 | S1/S2 (7/3) | W-4 | 22.5 | 24.8 | 5.9 | Rectangle |
| Ex. 11F | B-6 | A1-6 | TBAH | HR-1 | S1/S2 (7/3) | W-2 | 21.5 | 27.5 | 6.3 | Rectangle |
| Ex. 12F | B-6/B-2 (3/1) | A1-8 | TPI | HR-2 | S1/S2 (7/3) | W-1 | 22.5 | 26.2 | 5.7 | Rectangle |
| Ex. 13F | B-7 | A1-7 | TBAB | — | S1/B1 (7/3) | W-3 | 22.5 | 26.8 | 5.7 | Rectangle |
| Ex. 14F | B-8 | A1-6 | TBAH | — | S1/S2 (7/3) | W-1 | 23.0 | 26.0 | 5.6 | Rectangle |
| Ex. 15F | B-8/B-7 (2/1) | A1-8 | E-2 | HR-1 | S1/S2 (7/3) | W-1 | 21.5 | 25.8 | 5.4 | Rectangle |
| Ex. 16F | B-9 | A1-5 | TOA | — | S1/S2 (7/3) | W-2 | 22.0 | 24.3 | 5.9 | Rectangle |
| Ex. 17F | B-10 | A1-8 | DBA | HR-2 | S1/S2/B2 (5/4/1) | — | 21.0 | 28.5 | 5.8 | Rectangle |
| Ex. 18F | B-11 | A1-8 | TPI | — | S1/S2 (7/3) | W-1 | 21.0 | 25.1 | 5.3 | Rectangle |
| Ex. 19F | B-12 | A1-8 | TBAB | HR-1 | S1/S2 (6/4) | W-5 | 21.5 | 28.1 | 7.1 | Rectangle |
| Ex. 20F | B-13 | A1-5 | E-1 | HR-1 | S1/S2 (7/3) | W-1 | 22.5 | 28.9 | 6.0 | Rectangle |
| Ex. 21F | B-14 | A1-6 | TEA | HR-3 | S1/B1 (7/3) | W-1 | 23.0 | 30.2 | 6.8 | Rectangle |
| Ex. 22F | B-15/PAG-Y (1/1) | A1-8 | TBAH | — | S1/S2 (7/3) | W-4 | 21.5 | 29.6 | 7.0 | Rectangle |
| Ex. 23F | B-16/PAG-X (3/1) | A1-8 | TPI | HR-4 | S1/S2 (7/3) | W-1 | 21.5 | 26.0 | 5.7 | Rectangle |
| Ex. 24F | B-17 | A1-5 | TBAH | HR-1 | S1 | W-1 | 20.5 | 26.8 | 5.9 | Rectangle |
| Ex. 25F | B-18 | A1-6 | TEA | — | S1/S2 (7/3) | W-3 | 22.0 | 27.0 | 6.5 | Rectangle |
| Ex. 26F | B-19 | A1-7 | E-3 | HR-1 | S1/S2 (7/3) | W-1 | 25.8 | 30.1 | 7.0 | Rectangle |
| Ex. 27F | B-20 | A1-8 | TBAH | HR-1 | S1/S2 (7/3) | W-3 | 26.8 | 30.5 | 7.1 | Rectangle |
| Comp. Ex. 1F | A-X | A1-7 | TBAH | HR-1 | S1/S2 (7/3) | W-1 | 27.5 | 32.8 | 7.6 | T-Top |
| Comp. Ex. 2F | A-Y | A1-8 | TBAB | — | S1/S2 (7/3) | W-1 | 28.0 | 34.8 | 7.8 | T-Top |

The invention claimed is:

1. An actinic-ray- or radiation-sensitive resin composition comprising a resin (A) and any of compounds (B) of general formula (I) below,

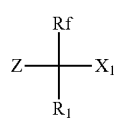

(I)

in which

Rf represents a fluorine atom $R_1$ represents a hydrogen atom;

$X_1$ represents an organic group of general formula (Ia) below, provided that $X_1$ may be bonded to $R_1$ to thereby form a ring; and Z represents a moiety which, when exposed to actinic rays or radiation, is converted to a sulfonic acid group, an imidic acid group or a methide acid group, $-L_{11}-X_{11}$ (Ia)

in which

L$_{11}$ represents a bivalent connecting group having at least one —CH$_2$— group and only one —C(=O)— group, provided that the connecting group represented by L$_{11}$ contains no fluorine atom, and X$_{11}$ represents an alicyclic group, or a heterocyclic group, provided that the any of organic groups of general formula (Ia) as a whole contains at least five carbon atoms.

2. The actinic-ray- or radiation-sensitive resin composition according to claim 1, wherein Z in the general formula (I) represents the moiety which, when exposed to actinic rays or radiation, is converted to the sulfonic acid.

3. The actinic-ray- or radiation-sensitive resin composition according to claim 1, wherein X$_{11}$ in the general formula (Ia) is a polycyclic alicyclic group.

4. The actinic-ray- or radiation-sensitive resin composition according to claim 1, wherein L$_{11}$ in the general formula (Ia) is a bivalent connecting group comprising —CH$_2$—, —CO— and —O— groups.

5. The actinic-ray- or radiation-sensitive resin composition according to claim 1, wherein L$_{11}$ in the general formula (Ia) is a bivalent connecting group comprising at least two —CH$_2$— groups.

6. The actinic-ray- or radiation-sensitive resin composition according to claim 1, wherein L$_{11}$ in the general formula (Ia) is a bivalent connecting group selected from —C(=O)—O—CH$_2$—, —CH$_2$—O—C(=O)—, and —C(=O)—O—CH$_2$—CH$_2$—CH$_2$—CH(CH$_3$)— groups.

7. An actinic-ray- or radiation-sensitive resin composition comprising a resin (A) and any of compounds (B) of general formula (I) below,

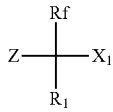
(I)

in which

Rf represents a fluorine atom;

R$_1$ represents a hydrogen atom;

X$_1$ represents an organic group of general formula (Ia) below, provided that X$_1$ may be bonded to R$_1$ to thereby form a ring;

Z represents a moiety which, when exposed to actinic rays or radiation, is converted to a sulfonic acid group, an imidic acid group or a methide acid group, -L$_{11}$-X$_{11}$ (Ia)

in which

L$_{11}$ represents a bivalent connecting group having at least one —CH$_2$— group and only one of either —C(=O)— O— or —O—C(=O)— group, provided that the connecting group represented by L$_{11}$ contains no fluorine atom, and X$_{11}$ represents an alicyclic group, or a heterocyclic group, provided that the any of organic groups of general formula (Ia) as a whole contains at least five carbon atoms.

8. The actinic-ray- or radiation-sensitive resin composition according to claim 7, wherein Z in the general formula (I) represents the moiety which, when exposed to actinic rays or radiation, is converted to the sulfonic acid.

9. The actinic-ray- or radiation-sensitive resin composition according to claim 7, wherein X$_{11}$ in the general formula (Ia) is a polycyclic alicyclic group.

10. The actinic-ray- or radiation-sensitive resin composition according to claim 7, wherein L$_{11}$ in the general formula (Ia) is a bivalent connecting group comprising at least two —CH$_2$— groups.

11. The actinic-ray- or radiation-sensitive resin composition according to claim 7, wherein L$_{11}$ in the general formula (Ia) is a bivalent connecting group selected from —C(=O)—O—CH$_2$—, —CH$_2$—O—C(=O)—, and —C(=O)—O—CH$_2$—CH$_2$—CH$_2$—CH(CH$_3$)— groups.

12. An actinic-ray- or radiation-sensitive resin composition comprising a resin (A) and any of compounds (B) of general formula (I) below,

(I)

in which

Rf represents a fluorine atom;

R$_1$ represents —C(CH$_3$)$_3$, —CN, —C(=O)CH$_3$, or —CH$_3$ group;

X$_1$ represents an organic group of general formula (Ia) below, provided that X$_1$ may be bonded to R$_1$ to thereby form a ring;

Z represents a moiety which, when exposed to actinic rays or radiation, is converted to a sulfonic acid group, an imidic acid group or a methide acid group, -L$_{11}$-X$_{11}$ (Ia)

in which

L$_{11}$ represents a bivalent connecting group having at least one —CH$_2$— group, provided that the connecting group represented by L$_{11}$ contains no fluorine atom, and X$_{11}$ represents an alicyclic group, or a heterocyclic group, provided that the any of organic groups of general formula (Ia) as a whole contains at least four carbon atoms.

* * * * *